United States Patent
Hummersone et al.

(10) Patent No.: US 9,024,018 B2
(45) Date of Patent: May 5, 2015

(54) 3-SUBSTITUTED-8-SUBSTITUTED-3H-IMIDAZO[5,1-D][1,2,3,5]TETRAZIN-4-ONE COMPOUNDS AND THEIR USE

(75) Inventors: Marc Geoffery Hummersone, Nottingham (GB); Malcolm Francis Graham Stevens, Nottingham (GB); David Cousin, Nottingham (GB)

(73) Assignee: Pharminox Limited, Nottingham (GB)

( * ) Notice: Subject to any disclaimer, the term of this patent is extended or adjusted under 35 U.S.C. 154(b) by 298 days.

(21) Appl. No.: 13/376,945

(22) PCT Filed: Jun. 23, 2010

(86) PCT No.: PCT/GB2010/001233
§ 371 (c)(1),
(2), (4) Date: Dec. 8, 2011

(87) PCT Pub. No.: WO2010/149968
PCT Pub. Date: Dec. 29, 2010

(65) Prior Publication Data
US 2012/0083513 A1    Apr. 5, 2012

Related U.S. Application Data

(60) Provisional application No. 61/219,575, filed on Jun. 23, 2009.

(51) Int. Cl.
| | | |
|---|---|---|
| *C07D 487/04* | (2006.01) | |
| *C07D 401/14* | (2006.01) | |
| *C07D 403/14* | (2006.01) | |
| *A61K 31/4188* | (2006.01) | |
| *A61K 31/427* | (2006.01) | |
| *A61P 35/00* | (2006.01) | |
| *C07D 417/04* | (2006.01) | |
| *C07D 417/14* | (2006.01) | |
| *C07D 413/04* | (2006.01) | |

(52) U.S. Cl.
CPC .......... *C07D 487/04* (2013.01); *C07C 2101/02* (2013.01)

(58) Field of Classification Search
CPC .. C07D 487/04; C07D 401/14; C07D 403/14; C07D 417/04; C07D 417/14; C07D 413/04; A61K 31/4188; A61K 31/427
USPC ........................................... 544/179; 514/183
See application file for complete search history.

(56) References Cited

U.S. PATENT DOCUMENTS

| | | | |
|---|---|---|---|
| 4,504,475 | A | 3/1985 | Cheng |
| 5,260,291 | A | 11/1993 | Lunt et al. |
| 7,087,751 | B2 | 8/2006 | Kuo et al. |
| 7,173,021 | B2 | 2/2007 | Wang et al. |
| 8,450,479 | B2 * | 5/2013 | Stevens et al. ................. 544/179 |
| 2010/0286088 | A1 | 11/2010 | Stevens et al. |
| 2013/0338104 | A1 | 12/2013 | Stevens et al. |

FOREIGN PATENT DOCUMENTS

| | | | |
|---|---|---|---|
| EP | 0252682 A2 * | 7/1987 | |
| FR | 2 511 679 A | 2/1983 | |
| GB | 2 125 402 | 3/1984 | |
| WO | WO 96/27588 | 9/1996 | |
| WO | WO2006/024238 | 3/2006 | |
| WO | WO2009/077741 A2 | 6/2009 | |
| WO | WO2009/127815 | 10/2009 | |
| WO | WO2010/149968 | 12/2010 | |
| WO | WO2011/107726 | 9/2011 | |

OTHER PUBLICATIONS

Arrowsmith et al. (1999) "Antitumour imidazotetrazines Part 37", Anti-Cancer Drug Design, 14(3):205-217.
Arrowsmith et al. (2000) "Antitumour imidazotetrazines. Part 39.1 Synthesis of bis(imidazotetrazine)s with saturated spacer groups", J. Chem. Soc. Perkin Trans. 1, 24:4432-4438.
Arrowsmith et al. (2002) "Antitumor Imidazotetrazines. 41. Conjugation of the Antitumor Agents mitozolomide and Temozolomide to Peptides and Leitropsins Bearing DNA Major and Minor Groove-Binding Structural motifs", J. Med. Chem., 45:5458-5470.
Balba et al. (1968) "Synthesis of Possible Metabolites of Methylcarbamate Insecticide Chemicals", J. Agric. Food Chem., 16(5):821-825.
Bennett et al. (1957) "Synthesis of Potential Anticancer Agents. IV. 4-Nitro- and 4-Amino-5-imidazole Sulfones", J. Am. Chem. Soc., 79:2188-2191.
Berge et al. (1977) "Pharmaceutically Acceptable Salts", J. Pharm. Sci., 66:1-19.
Blain (2008) "Switching cyclin D-cdk4 on and off" Cell Cycle 7(7):892-898.
Brown et al. (1999) "Apoptosis, p53 and tumor cell sensitivity to anticancer agents", Cancer Research, 59(7):1391-1399.

(Continued)

*Primary Examiner* — Venkataraman Balasubramanian
(74) *Attorney, Agent, or Firm* — Swanson & Bratschun, L.L.C.

(57) ABSTRACT

The present invention pertains generally to the field of therapeutic compounds, and more specifically to 3-substituted-8-substituted-3H-imidazo[5,1-d][1,2,3,5]tetrazin-4-one compounds of the following formula, wherein -A and —B are as defined herein (collectively referred to herein as 3STM compounds):

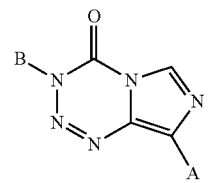

The present invention also pertains to pharmaceutical compositions comprising such compounds, and the use of such compounds and compositions, both in vitro and in vivo, to inhibit cell proliferation, and in the treatment of proliferative disorders such as cancer, etc., and methods of preparing such compounds.

39 Claims, No Drawings

(56) References Cited

OTHER PUBLICATIONS

Brown et al. (2002) "Antitumor Imidazotetrazines. 40. Radiosyntheses of [4-llC-Carbonyl]- and [3-N-llC-Methyl]-8-carbamoyl-3-methylimidazo[5,1-d]-1,2,3,5-tetrazi n-4(3H)-one (Temozolomide) for Positron Emission Tomography (PET) Studies", J. Med. Chem., 45(25):5448-5457.
Cecil Textbook of Medicine (1996) edited by Bennet and Plum, 20th edition, 1:1004-1010.
Clark et al. (1995) "Antitumor Imidazotetrazines. 32. Synthesis of Novel Imidazotetrazinones and Related Bicyclic Heterocycles to Probe the Mode of Action of the Antitumor Drug Temozolomide", J. Med. Chem., 38(9):1493-1504.
Collins et al. (2005) Curr. Opin. Pharmacol. 5(4):366-373.
Dermer et al. (1994) Bio/Technology 12:320.
Diana et al. (2009) "Pyrido[2',3':4,5]pyrrolo[2,1-d][1,2,3,5]tetrazine-4(3H)-ones, a new class of temozolomide heteroanalogues", ARKIVOC, (viii):177-186.
Diana et al. (2009) "Pyrido[4',3':4,5]pyrrolo[2,1-d][1,2,3,5]tetrazine a new class of Temozolomide heteroanalogues", ARKIVOC, (x):1-11.
Fisher et al. (1961) "Nitro- and amino-imidazolesulphonamides", Can. J. Chem., 39:501-504.
Freshney et al. (1983) Culture of Animal Cells, A Manual of Basic Technique, Alan R. Liss, Inc. New York, 4.
Gao et al. (2010) "Synthesis of Pyrazolo[5,1-d][1,2,3,5]tetrazine-4(3H)-ones", J. Comb. Chem., 12:69-74.
Golub et al. (1999) Science 286:531-537.
Hartley et al. (1988) "DNA sequence specificity of guanine N7-alkylations for a series of structurally related triazenes", Carcinogenesis, 9:669-674.
Hegi et al. (2004) "Clinical trial substantiates the predictive value of O-6-Methylguanin-DNA-Methyltransferase promoter methylation in glioblastmoa patients treated with temozolomide", Clin. Cancer Res., 10:1871-1874.
Hegi et al. (2005) "MGMT Gene Silencing and Benefit from Temozolomide in Glioblastoma", New England J. Med., 352:997-1003.
Horspool et al. (1990) "Antitumor Imidazotetrazines. 20. Preparation of the 8-Acid Derivatives of Mitozolomide and Its Utility in the Preparation of Active Antitumor Agents", J. Med. Chem. 33(5):1393-1399.
International Preliminary Report on Patentability dated Jun. 22, 2010 from PCT/GB2008/004140.
International Search Report dated Oct. 19, 2009 from PCT/GB2008/004140.
Jones et al. (1924) "A study of some new hydroxamic acids of hydroxyl and alkoxy fatty acids", J. Am. Chem. Soc., 46:2518.
Langnel et al. (2000) "Anti-tumor imidazotetrazines. 38. New 8-substituted derivatives of the imidazo[5,1-d]-1,2,3,5-tetrazines temozolomide and mitozolomide", ARKIVOC, (iii):421-437.
Lee et al. (1994) "Inactivation of O6-alkylguanine-DNA alkyltransferase in human peripeheral blood mononuclear cells by temozolomide", Br. J. Cancer, 69:452-456.
Lowe et al. (1992) "Antitumor imidazotetrazines. 25. Crystal structure of 8-carbamoyl-3-methylimidazo[5,1-d]-1,2,3,5 -tetrazin-4(3H)-one (temozolomide) and structural comparisons with the related drugs mitozolomide and DTIC", J. Med. Chem., 35(18):3377-3382.
Lowe et al. (1994) "DCMCIT, an Analogue of the Antitumour Drugs Mitozolomide and Temozolomide", Acta Crystallographica Sect. C, 50:1629-1631.
Lunt et al. (1987) "Antitumor Imidazotetrazines. 14. Synthesis and Antitumor Activity of 6- and 8-Substituted Imidazo Not 5,1-D 3/4 -1,2,3,5-Tetrazinones and 8-Substituted Pyrazolo Not 5,1-D 3/4-1,2,3,5-Tetrazinones", J. Med. Chem., 30(2):357-366.
Mosmann (1983) "Rapid colorimetric assay for cellular growth and survival: Application to proliferation and cytotoxicity assays", Journal of Immunological Methods, 65(1-2):55-63.
Newlands et al. (1997) "Temozolomide: a review of its discovery, chemical properties, pre-clinical development and clinical trials", Cancer Treat. Rev., 23:35-61.
Ozaki (1972) "Recent Advances in isocyanate chemistry", Chem. Rev., 72:457-496.
Ruchelman et al. (2004) Biorganic & Medicinal Chemistry 12:795-806.
Saunders et al. (1948) "The chemistry of organic isocyanates", Chem. Rev., 43:203-218.
Shioiri et al. (1972) "Diphenylphosphoryl Azide. A New Convenient Reagent for a Modified Curtius Reaction and for the Peptide Synthesis", J. Am. Chem. Soc., 94:6203-6205.
Stevens and Newlands (1993) "From Triazines and Triazenes to Temozolomide", Eur. J. Cancer, 29A:1045-1047.
Stevens et al. (1984) "Antitumour imidazotetrazines. Part 1. Synthesis and chemistry of 8-carbamoyl-3-(2-chloroethyl)imidazo[1,5-d]-1,2,3,5-tetrazin-4(3H)-one, a novel broad spectrum antitumour agent", J. Med. Chem., 27:196-201.
Suresh Babu et al. (2000) "(Fluoren-9-ylmethoxy)carbonyl (Fmoc) amino acid azides: Synthesis, isolation, characterisation, stability and application to synthesis of peptides", J. Chem. Soc. Perkin Trans. 1, 4328-4331.
Tisdale et al. (1985) "Induction of Haemoglobin Synthesis in the Human leukaemia Cell line K562 by Monomethyltriazenes and Imidazotetrazinones", Biochem. Pharmacol., 34(12):2077-2082.
Viola et al. (2009) "Pyrrolotetrazinones deazaanalogues of temozolomide induce apoptosis in Jurkat cell line: involvement of tubulin polymerization inhibition", Cancer Chemother. Pharmacol., 64:1235-1251.
Vippagunta et al. (2001) Advanced Drug Delivery Reviews 48:3-26.
Walsh et al. (1996) "Solid phase synthesis of a mitozolomide-oligonucleotide conjugate using a novel silyl-linked solid support", Pharmaceutical Sciences, 2(1):33-38.
Wang et al. (1996) "Synthetic studies of 8-carbamoylimidazo-[5,1-D]-1,2,3,5-tetrazin-4(3H)-one: a key derivative of antitumour drug temozolomide", Bioorg. Med. Chem. Lett., 6(2):185-188.
Wang et al. (2002) "Synthesis and antibacterial activity of dual-action agents of a b-lactam antibiotic with cytotoxic agent mitozolomide or temozolomide", Eur. J. Med. Chem., 37:323-332.
Wang et al. (1998) "Antitumour imidazotetrazines. Part 36. Conversion of 5-amino-imidazole-4-carboxamide to imidazo[5,1-d][1,2,3,5]tetrazin-4(3H)-ones and imidazo[1,5-a][1,3,5]triazin-4(3H)-ones related in structure to the antitumour agents temozolomide and mitozolomide", J. Chem. Soc. Perkin Trans. 1, 10:1669-1675.
Wang et al. (1995) "Antitumour imidazotetrazines. Part 33. New syntheses of the antitumour drug temozolomide using 'masked' methyl isocyanates", J. Chem. Soc. Perkin Trans. 1, 21:2783-2787.
Wanner et al. (2002) "A new synthesis of temozolomide", J. Chem. Soc. Perkin Trans. 1, 1877-1880.
Wedge et al. (1996) "3-Aminobenzamide and/or 06-benzylguanine evaluated as an adjuvant to temozolomide or BCNU treatment in cell lines of variable mismatch repair status and 06-alkylguanine-DNA alkyltransferase activity", Br. J. Cancer, 74:1030-1036.
Wermuth (1996) "Molecular Variations Based on Isosteric Replacements", Practice of Medicinal Chemistry, 203-327.
West (1988) "Solid State Chemistry and its Applications" Wiley, New York pp. 358 & 365.
Wood et al. (2001) Current Opinion in Pharmacology 1:370-377.
Yalçin et al. (1992) "The synthesis and the structure-activity relationships of some substituted benzoxazoles, oxazolo(4,5=b)pyridines, benzothiazoles and benzimidazoles as antimicrobial agents", Eur. J. Med. Chem., 27:401-406.
Zhang et al. (2010) Oncology 78:103-114 "Acquired resistance to temozolomide in glioma cell lines: molecular mechanisms and potential translational applications".
Zhao et al. (2001) "Synthesis and Antitumour Activities of 3-Substituted 4-Oxo-3H-imidazo(5,1-d)(1,2,3,5)tetrazine- 8-carboxylic Acids and Their Derivatives", Chinese J. Med. Chem., 11(5):263-269.

(56) References Cited

OTHER PUBLICATIONS

Zhu et al. (2007) "Design, Synthesis, and Quantitative Structure-Activity Relationship Study of Herbicidal Analogues of Pyrazolo[5,1-d][1,2,3,5]tetrazin-4(3H)ones", J. Agric. Food Chem., 55:1364-1369.

Fodstad et al. (1985) Cancer Res 45:1778-1786, "Activity of Mitrozolomide (NSC 353451), a New Imidazotetrazine, against Xenografts from Human Melanomas, Sarcomas, and Lung and Colon Carcinomas".

Gibson et al. (1984) Cancer Res 44:1772-1775, DNA Cross-Linking and Cytotoxicity in Normal and Transformed Human Cells Treated in Vitro with 8-Carbamoyl-3-(2-chloroethyl)imidazo[5,1-*d*]-1,2,3,5-tetrazin-4(3 *H*)-one.

Kerr et al. (1990) Cancer Chemother Pharmacol 25:352-354, "Relationship between the pharmacokinetics and toxicity of mitozolomide".

Zhang et al. (2012) Current Molecular Pharmacology 5:102-114, "Temozolomide: Mechanisms of Action, Repair and Resistance".

\* cited by examiner

3-SUBSTITUTED-8-SUBSTITUTED-3H-IMIDAZO[5,1-D][1,2,3,5]TETRAZIN-4-ONE COMPOUNDS AND THEIR USE

RELATED APPLICATION

This application is a 35 U.S.C. §371 national phase application of PCT/GB2010/001233 (WO 2010/149968), filed on Jun. 23, 2010, entitled "Substituted-8-Substituted-3H-Imidazof[5,1-D][1,2,3,5]tetrazin-4-one Compounds and Their Use," which claims the benefit of U. S. provisional patent application number 61/219,575 filed Jun. 23, 2009, the contents of which are incorporated herein by reference in their entirety.

TECHNICAL FIELD

The present invention pertains generally to the field of therapeutic compounds, and more specifically to 3-substituted-8-substituted-3H-imidazo[5,1-d][1,2,3,5]tetrazin-4-one compounds (collectively referred to herein as 38TM compounds). The present invention also pertains to pharmaceutical compositions comprising such compounds, and the use of such compounds and compositions, both in vitro and in vivo, to inhibit cell proliferation, and in the treatment of proliferative disorders such as cancer, etc., and methods of preparing such compounds.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Temozolomide

Temozolomide (also known as 3,4-dihydro-3-methyl-4-oxoimidazo[5,1-d]-1,2,3,5-tetrazine-8-carboxamide; 8-carbamoyl-3-methylimidazo[5,1-d]-1,2,3,5-tetrazin-4(3H)-one; methazolastone; M & B 39831; CCRG-81045; NSC-362856; Temodal; Temodar) is a well known anti-neoplastic agent that acts as an alkylating agent. Its primary application is in the treatment of brain cancer (e.g., glioma).

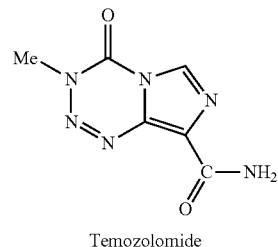 [SMILES: Cn1nnc2c(C(N)=O)ncn2c1=O]

Temozolomide

Temozolomide is a prodrug, being cleaved in a multi-step pathway firstly to liberate an unstable monomethyltriazene (MTIC), which then suffers proteolytic fragmentation to generate a highly-reactive methylating agent (methanediazonium ion) and 5-aminoimidazole-4-carboxamide (see, e.g., Arrowsmith et al., 2002, J. Med. Chem., Vol. 45, pp. 5458-5470). Support for this process comes from the isolation of MTIC from the degradation of temozolomide in aqueous sodium carbonate solution (see, e.g., Stevens et al., 1984, J. Med. Chem., Vol. 27, pp. 196-201). There is only a small pH window around physiological pH where ring-opening of temozolomide is accompanied by fragmentation of MTIC in a methylating mode.

The methanediazonium active species derived from MTIC (or temozolomide) is believed to covalently methylate guanine residues of DNA in tracts of three or more guanines (see, e.g., Hartley et al., 1988, Carcinogenesis, Vol. 9, pp. 669-674; Clark et al., 1995, J. Med. Chem., Vol. 38, pp. 1493-1504). The significant site of DNA methylation is the O-6 position of guanine residues and tumours which express high levels of the DNA repair protein O(6)-methylguanine methyltransferase (MGMT; also known as ATase) are inherently resistant to the drug (see, e.g., Wedge et al., 1996, Br. J. Cancer, Vol. 74, pp. 1030-1036; Lee et al., 1994, Br. J. Cancer, Vol. 69, pp. 452-456.) These studies have been reviewed (see, e.g., Stevens and Newlands, 1993, Eur. J. Cancer, Vol. 29A, pp. 1045-1047; Newlands et al., 1997, Cancer Treat. Rev., Vol. 23, pp. 35-61). O-6 guanine methylation is a cytotoxic (anti-tumor) lesion since it provokes base mis-pairing with thymine during DNA replication. Unless repaired by MGMT, mis-pairing on the daughter strand is recognised by mismatch repair proteins which trigger futile cycles of thymine excision and re-insertion leading to persistent DNA strand breaks.

In a significant development in our understanding of the molecular determinants influencing tumor responses to temozolomide, it is now clear that the promoter methylation status (at cytosine C-5 in CpG sequences of the MGMT gene) is a powerful predictor of clinical outcome in glioblastoma patients (see, e.g., Hegi et al., 2004, Clin. Cancer Res. Vol. 10, pp. 1871-1874; Hegi et al., 2005, New England J. Med., Vol. 352, pp. 997-1003). Tumors with the MGMT gene switched off, as in some brain tumors, are unable to repair the O-6 guanine lesions and are particularly sensitive to temozolomide. Conversely, most common tumors with the MGMT repair gene switched on, leading to high cellular levels of MGMT, can repair the O-6 guanine lesions and are resistant to the drug. This epigenetic feature considerably restricts the spectrum of action of temozolomide and its penetration of the cancer market.

A new strategy to overcome these deficiencies proposes that compounds structurally related in structure to temozolomide and retaining the drug's favourable pharmaceutical profile—such as ease of synthesis, acid stability, oral bioavailability, freedom from metabolic complications, transmission across the blood-brain barrier, and an acceptable toxicological profile—could be developed which create an alternative anti-tumor lesion at O-6 residues of guanines in DNA (i.e., not methylation) which cannot be repaired by MGMT. Such compounds would be likely to retain useful therapeutic activity against all brain tumors, but also those major killer tumor types (e.g., lung, breast, ovarian, colorectal, renal, pancreatic, melanoma) which are currently inherently resistant to temozolomide.

Temozolomide is the subject of granted claim 13 of U.S. Pat. No. 5,260,291 to Lunt et al. granted 9 Nov. 1993.

Certain 3-substituted-4-oxo-3,4-dihydro-imidazo[5,1-d][1,2,3,5]tetrazine-8-carboxylic acid amide (3™) compounds are described in international patent application number PCT/GB2008/004140 filed 16 Dec. 2008 (published as WO 2009/077741 on 25 Jun. 2009).

SUMMARY OF THE INVENTION

One aspect of the invention pertains to certain 3-substituted-8-substituted-3H-imidazo[5,1-d][1,2,3,5]tetrazin-4-one compounds (collectively referred to herein as 38TM compounds), as described herein.

Another aspect of the invention pertains to compositions (e.g., a pharmaceutical compositions) comprising a 38TM compound, as described herein, and a pharmaceutically acceptable carrier or diluent.

Another aspect of the invention pertains to methods of preparing a composition (e.g., a pharmaceutical composition) comprising the step of admixing a 38TM compound, as described herein, and a pharmaceutically acceptable carrier or diluent.

Another aspect of the present invention pertains to methods of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a 38TM compound, as described herein.

Another aspect of the present invention pertains to methods of treatment comprising administering to a subject in need of treatment a therapeutically-effective amount of a 38TM compound, as described herein, preferably in the form of a pharmaceutical composition.

Another aspect of the present invention pertains to a 38TM compound as described herein for use in a method of treatment of the human or animal body by therapy.

Another aspect of the present invention pertains to use of a 38TM compound, as described herein, in the manufacture of a medicament for use in treatment.

In one embodiment, the treatment is treatment of a proliferative disorder.

In one embodiment, the treatment is treatment of cancer.

In one embodiment, the treatment is treatment of: lung cancer, breast cancer, ovarian cancer, colorectal cancer, melanoma, renal cancer, prostate cancer, esophageal cancer, squamous carcinoma of the head or neck, or glioma.

In one embodiment, the treatment is treatment of: glioma.

Another aspect of the present invention pertains to a kit comprising (a) a 38TM compound, as described herein, preferably provided as a pharmaceutical composition and in a suitable container and/or with suitable packaging; and (b) instructions for use, for example, written instructions on how to administer the compound.

Another aspect of the present invention pertains to certain methods of synthesis, as described herein.

Another aspect of the present invention pertains to a compound (e.g., a 38TM compound) obtainable by a method of synthesis as described herein, or a method comprising a method of synthesis as described herein.

Another aspect of the present invention pertains to a compound (e.g., a 38TM compound) obtained by a method of synthesis as described herein, or by a method comprising a method of synthesis as described herein.

Another aspect of the present invention pertains to certain novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

One aspect of the present invention pertains to certain compounds that may be considered to be derivatives of Temozolomide (also known as 3-methyl-4-oxo-3,4-dihydro-imidazo[5,1-d][1,2,3,5]tetrazine-8-carboxylic acid amide):

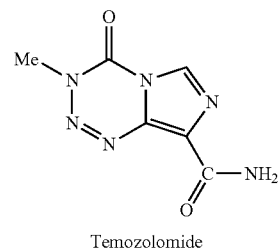 [SMILES: Cn1nnc2c(C(N)=O)ncn2c1=O]

Temozolomide

The compounds may conveniently be described as 3-substituted-8-substituted-3H-imidazo[5,1-d][1,2,3,5]tetrazin-4-one compounds.

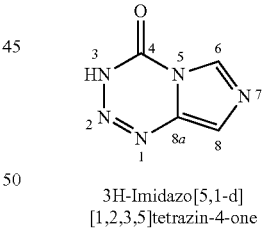

3H-Imidazo[5,1-d]
[1,2,3,5]tetrazin-4-one

In all embodiments, the compounds have an 8-substituent that is different from that found in Temozolomide, i.e., is different from —C(=O)NH$_2$.

In some embodiments, the compounds have a 3-substituent that is different from that found in Temozolomide, i.e., is different from -Me.

In some embodiments, the compounds have a 3-substituent that is the same as that found in Temozolomide, i.e., is -Me.

Thus, one aspect of the present invention pertains to compounds selected from compounds of the following formula and salts, hydrates, and solvates thereof (e.g., pharmaceutically acceptable salts, hydrates, and solvates thereof), wherein -A and —B are as defined herein (collectively denoted herein as "38TM compounds"):

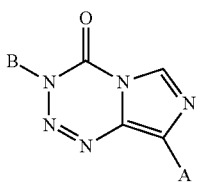

Some embodiments of the invention include the following:

(1) A compound selected from compounds of the following formula and pharmaceutically acceptable salts, hydrates, and solvates thereof:

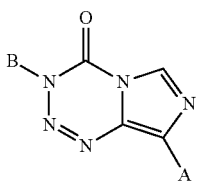

wherein:
-A is independently -$A^1$, -$A^2$, -$A^3$, -$A^4$, -$A^5$, or -$A^6$; and
—B is independently —$B^1$, —$B^2$, —$B^3$, $B^4$, $B^5$, $B^6$, —$B^7$, —$B^8$, —$B^9$, —$B^{10}$, —$B^{11}$, $B^{12}$, —$B^{13}$, or —$B^{14}$;

wherein:
-$A^1$ is independently $C_{5-12}$heteroaryl, and is optionally substituted;
-$A^2$ is independently thioamido or substituted thioamido;
-$A^3$ is independently imidamido or substituted imidamido;
-$A^4$ is independently hydroxamic acid or hydroxamate;
-$A^5$ is independently substituted carboxamide;
-$A^6$ is independently aliphatic $C_{2-6}$alkenyl, and is optionally substituted;

and wherein:
—$B^1$ is independently saturated aliphatic $C_{1-6}$alkyl;
—$B^2$ is independently aliphatic $C_{2-6}$alkynyl;
—$B^3$ is independently mercapto-$C_{1-4}$alkyl, sulfanyl-$C_{1-4}$alkyl, sulfinyl-$C_{1-4}$alkyl, or sulfonyl-$C_{1-4}$alkyl;
—$B^4$ is independently hydroxy-$C_{1-4}$alkyl or ether-$C_{1-4}$alkyl;
—$B^5$ is independently phenyl-$C_{1-6}$alkyl or $C_{5-6}$heteroaryl-$C_{1-6}$alkyl, and is optionally substituted;
—$B^6$ is independently acyl-$C_{1-6}$alkyl, carboxy-$C_{1-6}$alkyl, oxyacyl-$C_{1-6}$alkyl, or acyloxy-$C_{1-6}$alkyl;
—$B^7$ is independently amido-$C_{1-4}$alkyl or substituted amido-$C_{1-4}$alkyl;
—$B^8$ is independently $C_{3-6}$cycloalkyl, $C_{3-6}$cycloalkyl-$C_{1-4}$alkyl, $C_{3-6}$heterocyclyl, or $C_{3-6}$heterocyclyl-$C_{1-4}$alkyl, and is optionally substituted;
—$B^9$ is independently halo-$C_{1-6}$alkyl;
—$B^{19}$ is independently nitro-$C_{1-6}$alkyl;
—$B^{11}$ is independently cyano-$C_{1-6}$alkyl;
—$B^{12}$ is independently phosphate-$C_{1-6}$alkyl;
—$B^{13}$ is independently carbamate-$C_{1-6}$alkyl; and
—$B^{14}$ is independently oxime-$C_{1-6}$alkyl.

A1. 8-Heteroaryl Compounds (A1-1) A compound according to (1), wherein -A is independently -$A^1$.

(A1-2) A compound according to (A1-1), wherein -$A^1$ is independently $C_{5-12}$heteroaryl, and is optionally substituted.

(A1-3) A compound according to (A1-1), wherein -$A^1$ is independently furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, indolyl, isoindolyl, benzofuranyl, isobenzofuranyl, benzothienyl, isobenzothienyl, indazolyl, benzimidazolyl, benzothiazolyl, benzoisothiazolyl, benzoxazolyl, benzoisoxazolyl, quinolinyl, isoquinolinyl, cinnolinyl, or quinazolinyl, and is optionally substituted.

(A1-4) A compound according to (A1-1), wherein -$A^1$ is independently $C_{5-6}$heteroaryl, and is optionally substituted.

(A1-5) A compound according to (A1-1), wherein -$A^1$ is independently furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, or pyridazinyl, and is optionally substituted.

(A1-6) A compound according to (A1-1), wherein -$A^1$ is independently $C_5$heteroaryl, and is optionally substituted.

(A1-7) A compound according to (A1-1), wherein -$A^1$ is independently furanyl, thienyl, pyrrolyl, oxazolyl, isoxazolyl, thiazolyl, isothiazolyl, imidazolyl, pyrazolyl, oxadiazolyl, thiadiazolyl, or triazolyl, and is optionally substituted.

(A1-8) A compound according to (A1-1), wherein -$A^1$ is independently pyrrolyl, oxazolyl, isoxazolyl, thiazolyl, isothiazolyl, imidazolyl, pyrazolyl, oxadiazolyl, thiadiazolyl, or triazolyl, and is optionally substituted.

(A1-9) A compound according to (A1-1), wherein -$A^1$ is independently oxazolyl, thiazolyl, imidazolyl, pyrazolyl, oxadiazolyl, or thiadiazolyl, and is optionally substituted.

(A1-10) A compound according to (A1-1), wherein -$A^1$ is independently oxazol-2-yl, thiazol-2-yl, imidazol-2-yl, pyrazol-2-yl, oxadiazol-2-yl, or thiadiazol-2-yl, and is optionally substituted.

(A1-11) A compound according to (A1-1), wherein -$A^1$ is independently oxazolyl, thiazolyl, imidazolyl, or oxadiazolyl, and is optionally substituted.

(A1-12) A compound according to (A1-1), wherein -$A^1$ is independently oxazol-2-yl, thiazol-2-yl, imidazol-2-yl, or oxadiazol-2-yl, and is optionally substituted.

(A1-13) A compound according to (A1-1), wherein -$A^1$ is independently thiazolyl, and is optionally substituted.

(A1-14) A compound according to (A1-1), wherein -$A^1$ is independently thiazol-2-yl, and is optionally substituted.

(A1-15) A compound according to (A1-1), wherein -$A^1$ is independently thiazol-2-yl, and is optionally substituted at the 4-position.

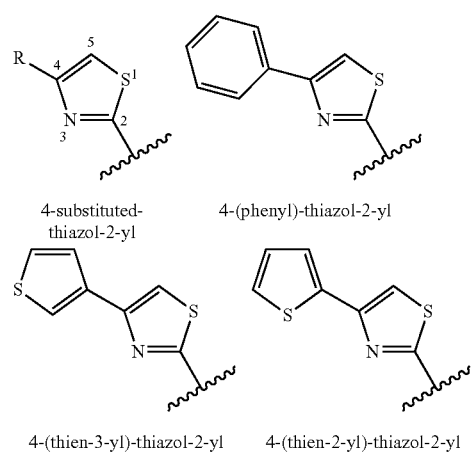

4-substituted-thiazol-2-yl    4-(phenyl)-thiazol-2-yl 4-(thien-3-yl)-thiazol-2-yl    4-(thien-2-yl)-thiazol-2-yl -continued

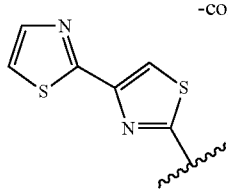

4-(thiazol-2-yl)-thiazol-2-yl (A1-16) A compound according to (A1-1), wherein -A¹ is independently thiazol-2-yl, and is optionally substituted at the 5-position.

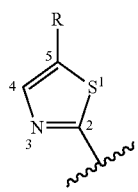

5-substituted-thiazol-2-yl (A1-17) A compound according to (A1-1), wherein -A¹ is independently oxazolyl, and is optionally substituted.
(A1-18) A compound according to (A1-1), wherein -A¹ is independently oxazol-2-yl, and is optionally substituted.
(A1-19) A compound according to (A1-1), wherein -A¹ is independently oxazol-2-yl, and is optionally substituted at the 4-position.

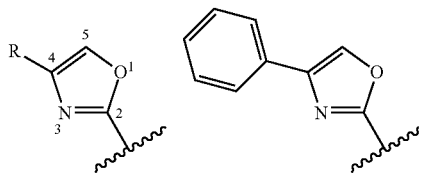

4-substituted-oxazol-2-yl        4-(phenyl)-oxazol-2-yl (A1-20) A compound according to (A1-1), wherein -A¹ is independently oxazol-2-yl, and is optionally substituted at the 5-position.

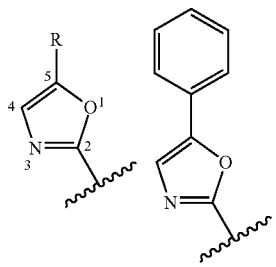

5-substituted-oxazol-2-yl        5-(phenyl)-oxazol-2-yl (A1-21) A compound according to (A1-1), wherein -A¹ is independently imidazolyl, and is optionally substituted.
(A1-22) A compound according to (A1-1), wherein -A¹ is independently imidazol-2-yl, and is optionally substituted.
(A1-23) A compound according to (A1-1), wherein -A¹ is independently imidazol-2-yl or N—(C$_{1-4}$alkyl)-imidazol-2-yl, and is optionally substituted.

(A1-24) A compound according to (A1-1), wherein -A¹ is independently imidazol-2-yl, and is optionally substituted at the 4-position.

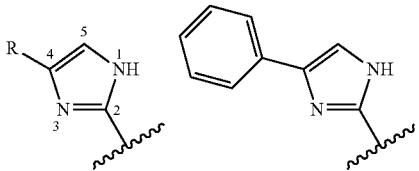

4-substituted-imidazol-2-yl        4-phenyl-imidazol-2-yl

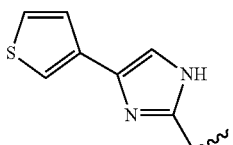

4-(thien-2-yl)-imidazol-2-yl (A1-25) A compound according to (A1-1), wherein -A¹ is independently imidazol-2-yl or N—(C$_{1-4}$alkyl)-imidazol-2-yl, and is optionally substituted at the 4-position.

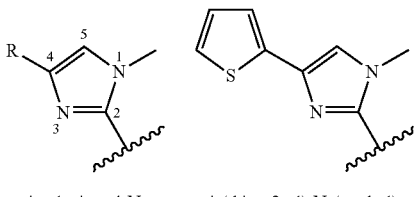

4-substituted-N-(methyl)-imidazol-2-yl        4-(thien-2-yl)-N-(methyl)-imidazol-2-yl

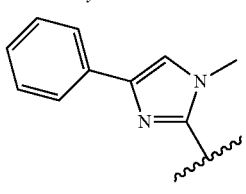

4-(phenyl)-N-(methyl)-imidazol-2-yl (A1-26) A compound according to (A1-1), wherein -A¹ is independently imidazol-2-yl, and is optionally substituted at the 5-position.

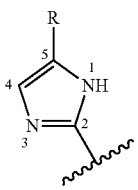

5-substituted-imidazol-2-yl (A1-27) A compound according to (A1-1), wherein -A¹ is independently imidazol-2-yl or N—(C$_{1-4}$alkyl)-imidazol-2-yl, and is optionally substituted at the 5-position.

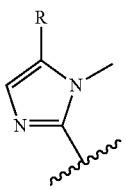

5-substituted-N-
(methyl)-
imidazol-2-yl (A1-28) A compound according to (A1-1), wherein -A¹ is independently oxadiazolyl, and is optionally substituted.
(A1-29) A compound according to (A1-1), wherein -A¹ is independently oxadiazol-2-yl, and is optionally substituted.
(A1-30) A compound according to (A1-1), wherein -A¹ is independently oxadiazol-2-yl, and is optionally substituted at the 5-positon.

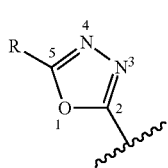 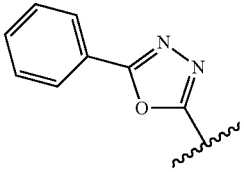

5-substituted-   5-phenyl-oxadiazol-2-yl
oxadiazol-2-yl (A1-31) A compound according to (A1-1), wherein -A¹ is independently $C_{9-12}$heteroaryl, and is optionally substituted.
(A1-32) A compound according to (A1-1), wherein -A¹ is independently $C_{9-10}$heteroaryl, and is optionally substituted.
(A1-33) A compound according to (A1-1), wherein -A¹ is independently indolyl, isoindolyl, benzofuranyl, isobenzofuranyl, benzothienyl, isobenzothienyl, indazolyl, benzimidazolyl, benzothiazolyl, benzoisothiazolyl, benzoxazolyl, benzoisoxazolyl, quinolinyl, isoquinolinyl, cinnolinyl, or quinazolinyl, and is optionally substituted.
(A1-34) A compound according to (A1-1), wherein -A¹ is independently $C_9$heteroaryl, and is optionally substituted.
(A1-35) A compound according to (A1-1), wherein -A¹ is independently indolyl, isoindolyl, benzofuranyl, isobenzofuranyl, benzothienyl, isobenzothienyl, indazolyl, benzimidazolyl, benzothiazolyl, benzoisothiazolyl, benzoxazolyl, or benzoisoxazolyl, and is optionally substituted.
(A1-36) A compound according to (A1-1), wherein -A¹ is independently indolyl, benzofuranyl, benzothienyl, benzimidazolyl, benzothiazolyl, or benzoxazolyl, and is optionally substituted.
(A1-37) A compound according to (A1-1), wherein -A¹ is independently benzimidazolyl, benzothiazolyl, or benzoxazolyl, and is optionally substituted.
(A1-38) A compound according to (A1-1), wherein -A¹ is independently benzimidazol-2-yl, benzothiazol-2-yl, or benzoxazol-2-yl, and is optionally substituted.
(A1-39) A compound according to (A1-1), wherein -A¹ is independently benzimidazolyl, and is optionally substituted.
(A1-40) A compound according to (A1-1), wherein -A¹ is independently benzimidazol-2-yl, and is optionally substituted.

(A1-41) A compound according to (A1-1), wherein -A¹ is independently benzimidazol-2-yl or N—($C_{1-4}$alkyl)-benzimidazol-2-yl, and is optionally substituted.

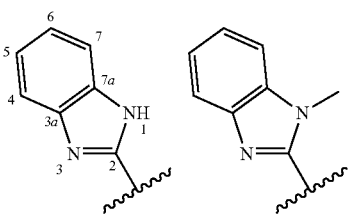

benzimidazol-2-yl    N-(methyl)-
                     benzimidazol-2-yl (A1-42) A compound according to (A1-1), wherein -A¹ is independently benzimidazol-2-yl, and is optionally substituted at the 1-position.

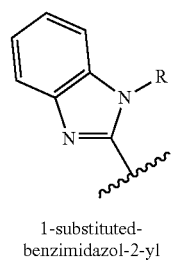

1-substituted-
benzimidazol-2-yl (A1-43) A compound according to (A1-1), wherein -A¹ is independently benzothiazolyl, and is optionally substituted.
(A1-44) A compound according to (A1-1), wherein -A¹ is independently benzothiazol-2-yl, and is optionally substituted.

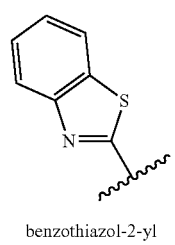 [SMILES: *c1nc2ccccc2s1]

benzothiazol-2-yl (A1-45) A compound according to (A1-1), wherein -A¹ is independently benzoxazolyl, and is optionally substituted.
(A1-46) A compound according to (A1-1), wherein -A¹ is independently benzoxazol-2-yl, and is optionally substituted.

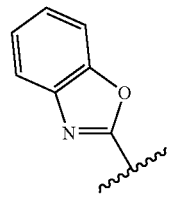

benzoxazol-2-yl (A1-47) A compound according to any one of (A1-1) to (A1-46), wherein -A¹ is independently unsubstituted or substituted with one or more groups selected from:

—F, —Cl, —Br, —I,
—$R^{Z1}$, —$CF_3$,
—OH, —$OR^{Z1}$, —$OCF_3$,
—$SR^{Z1}$,
—$NH_2$, —$NHR^{Z1}$, —$NR^{Z1}{}_2$, pyrrolidino, piperidino, morpholino, piperizino, (N—$C_{1-4}$alkyl)-piperizino,
—C(=O)OH, —C(=O)$OR^{Z1}$,
—C(=O)$R^{Z1}$,
—OC(=O)$R^{Z1}$,
—C(=O)$NH_2$, —C(=O)$NHR^{Z1}$, —C(=O)$NR^{Z1}{}_2$, —C(=O)-pyrrolidino, —C(=O)-piperidino, —C(=O)-morpholino, —C(=O)-piperizino, —C(=O)—(N—$C_{1-4}$alkyl)-piperizino,
—NHC(=O)$R^{Z1}$, —$NR^{Z1}$C(=O)$R^{Z1}$,
—OC(=O)$NH_2$, —OC(=O)$NHR^{Z1}$, —OC(=O)$NR^{Z1}{}_2$, —OC(=O)-pyrrolidino, —OC(=O)-piperidino, —OC(=O)-morpholino, —OC(=O)-piperizino, (N—$C_{1-4}$alkyl)-piperizino,
—NHC(=O)OH, —NHC(=O)$OR^{Z1}$, —$NR^{Z1}$C(=O)$OR^{Z1}$,
—NHC(=O)$NH_2$, —NHC(=O)$NHR^{Z1}$, —NHC(=O)$NR^{Z1}{}_2$, —NHC(=O)-pyrrolidino, —NHC(=O)-piperidino, —NHC(=O)-morpholino, —NHC(=O)-piperizino, —NHC(=O)—(N—$C_{1-4}$alkyl)-piperizino,
—$NO_2$, and —CN,
wherein each —$R^{Z1}$ is independently saturated aliphatic $C_{1-4}$alkyl, aliphatic $C_{3-6}$alkynyl, saturated $C_{3-6}$cycloalkyl, $C_{5-6}$heteroaryl, -Ph, or —$CH_2$-Ph,
wherein each of said $C_{3-6}$cycloalkyl, $C_{5-6}$heteroaryl, and -Ph is optionally substituted, for example, with one or more substituents selected from —F, —Cl, —Br, —I, —$R^{Z1A}$, —$CF_3$, —OH, —$OR^{Z1A}$, and —$OCF_3$,
wherein each —$R^{Z1A}$ is independently saturated aliphatic $C_{1-4}$alkyl,
and additionally wherein two adjacent substituents may together form —O—$CH_2$—O— or —O—$CH_2CH_2$—O—.

(A1-48) A compound according to any one of (A1-1) to (A1-46), wherein -$A^1$ is independently unsubstituted or substituted with one or more groups selected from:
—F, —Cl, —Br, —I,
—$R^{Z1}$, —$CF_3$,
—OH, —$OR^{Z1}$, —$OCF_3$,
—$NH_2$, —$NHR^{Z1}$, —$NR^{Z1}{}_2$, pyrrolidino piperidino, morpholino, piperizino, (N—$C_{1-4}$alkyl)-piperizino,
—C(=O)OH, —C(=O)$OR^{Z1}$,
—C(=O)$R^{Z1}$,
—OC(=O)$R^{Z1}$,
—C(=O)$NH_2$, —C(=O)$NHR^{Z1}$, —C(=O)$NR^{Z1}{}_2$, —C(=O)-pyrrolidino, —C(=O)-piperidino, —C(=O)-morpholino, —C(=O)-piperizino, —C(=O)—(N—$C_{1-4}$alkyl)-piperizino,
—NHC(=O)$R^{Z1}$, —$NR^{Z1}$C(=O)$R^{Z1}$, and
—CN,
and additionally wherein two adjacent substituents may together form —O—$CH_2$—O— or —O—$CH_2CH_2$—O—.

(A1-49) A compound according to any one of (A1-1) to (A1-46), wherein -$A^1$ is independently unsubstituted or substituted with one or more groups selected from:
—F, —Cl, —Br, —I,
—$R^{Z1}$, —$CF_3$,
—OH, —$OR^{Z1}$, —$OCF_3$,
—$NH_2$, —$NHR^{Z1}$, —$NR^{Z1}{}_2$, pyrrolidino piperidino, morpholino, piperizino, (N—$C_{1-4}$alkyl)-piperizino,
—C(=O)$NH_2$, —C(=O)$NHR^{Z1}$, —C(=O)$NR^{Z1}{}_2$, —C(=O)-pyrrolidino, —C(=O)-piperidino, —C(=O)-morpholino, —C(=O)-piperizino, —C(=O)—(N—$C_{1-4}$alkyl)-piperizino,
—NHC(=O)$R^{Z1}$, —$NR^{Z1}$C(=O)$R^{Z1}$, and
—CN,
and additionally wherein two adjacent substituents may together form —O—$CH_2$—O— or —O—$CH_2CH_2$—O—.

(A1-50) A compound according to any one of (A1-1) to (A1-46), wherein -$A^1$ is independently unsubstituted or substituted with one or more groups selected from:
—$R^{Z1}$,
—$NH_2$, —$NHR^{Z1}$, —$NR^{Z1}{}_2$, pyrrolidino piperidino, morpholino, piperizino, (N—$C_{1-4}$alkyl)-piperizino,
—C(=O)$NH_2$, —C(=O)$NHR^{Z1}$, —C(=O)$NR^{Z1}{}_2$, —C(=O)-pyrrolidino, —C(=O)-piperidino, —C(=O)-morpholino, —C(=O)-piperizino, —C(=O)—(N—$C_{1-4}$alkyl)-piperizino, and
—CN.

(A1-51) A compound according to any one of (A1-1) to (A1-46), wherein -$A^1$ is independently unsubstituted or substituted with one or more groups selected from: —$R^{Z1}$.

(A1-52) A compound according to any one of (A1-47) to (A1-51), wherein each —$R^{Z1}$, if present, is independently saturated aliphatic $C_{1-4}$ alkyl, aliphatic $C_{3-6}$alkynyl, saturated $C_{3-6}$cycloalkyl, furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, -Ph, or —$CH_2$-Ph,
wherein each of said $C_{3-6}$cycloalkyl, furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, and -Ph is optionally substituted.

(A1-53) A compound according to any one of (A1-47) to (A1-51), wherein each —$R^{Z1}$ if present, is independently saturated aliphatic $C_{1-4}$alkyl, aliphatic $C_{3-6}$alkynyl, saturated $C_{3-6}$cycloalkyl, thienyl, thiazolyl, pyridinyl, -Ph, or —$CH_2$-Ph, wherein each of said $C_{3-6}$cycloalkyl, thienyl, thiazolyl, pyridinyl, and -Ph is optionally substituted.

(A1-54) A compound according to any one of (A1-47) to (A1-51), wherein each —$R^{Z1}$ if present, is independently $C_{5-6}$heteroaryl, -Ph, or —$CH_2$-Ph, wherein each of said $C_{5-6}$heteroaryl and -Ph is optionally substituted.

(A1-55) A compound according to any one of (A1-47) to (A1-51), wherein each —$R^{Z1}$ if present, is independently furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, -Ph, or —$CH_2$-Ph,
wherein each of said $C_{3-6}$cycloalkyl, furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, and -Ph is optionally substituted.

(A1-56) A compound according to any one of (A1-47) to (A1-51), wherein each —$R^{Z1}$ if present, is independently furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, or -Ph,
wherein each of said $C_{3-6}$cycloalkyl, furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, and -Ph is optionally substituted.

(A1-57) A compound according to any one of (A1-47) to (A1-51), wherein each —$R^{Z1}$ if present, is independently thienyl, thiazolyl, pyridinyl, -Ph, or —CH$_2$-Ph, wherein each of said thienyl, thiazolyl, pyridinyl, and -Ph is optionally substituted.

(A1-58) A compound according to any one of (A1-47) to (A1-51), wherein each —R$^{Z1}$ if present, is independently thienyl, thiazolyl, pyridinyl, or -Ph, wherein each of said thienyl, thiazolyl, pyridinyl, and -Ph is optionally substituted.

(A1-59) A compound according to any one of (A1-47) to (A1-51), wherein each —R$^{Z1}$ if present, is independently thienyl, wherein said thienyl is optionally substituted.

(A1-60) A compound according to any one of (A1-47) to (A1-51), wherein each —R$^{Z1}$ if present, is independently thiazolyl, wherein said thiazolyl is optionally substituted.

(A1-61) A compound according to any one of (A1-47) to (A1-51), wherein each —R$^{Z1}$ if present, is independently pyridinyl, wherein said pyridinyl is optionally substituted.

(A1-62) A compound according to any one of (A1-47) to (A1-51), wherein each —R" if present, is independently -Ph, wherein said -Ph is optionally substituted.

(A1-63) A compound according to any one of (A1-47) to (A1-51), wherein each —R$^{Z1}$ if present, is independently thienyl, thiazolyl, pyridinyl, -Ph, or —CH$_2$-Ph.

(A1-64) A compound according to any one of (A1-47) to (A1-51), wherein each —R$^{Z1}$ if present, is independently thienyl, thiazolyl, pyridinyl, or -Ph.

(A1-65) A compound according to any one of (A1-47) to (A1-51), wherein each —R$^{Z1}$ if present, is independently thienyl.

(A1-66) A compound according to any one of (A1-47) to (A1-51), wherein each —R$^{Z1}$ if present, is independently thiazolyl.

(A1-67) A compound according to any one of (A1-47) to (A1-51), wherein each —R$^{Z1}$ if present, is independently pyridinyl.

(A1-68) A compound according to any one of (A1-47) to (A1-51), wherein each —R$^{Z1}$ if present, is independently -Ph.

(A1-69) A compound according to any one of (A1-47) to (A1-51), wherein each —R$^{Z1}$ if present, is independently saturated aliphatic C$_{1-4}$alkyl, aliphatic C$_{3-6}$alkynyl, saturated C$_{3-6}$cycloalkyl, -Ph, or —CH$_2$-Ph, wherein each of said C$_{3-6}$cycloalkyl and -Ph is optionally substituted.

(A1-70) A compound according to any one of (A1-47) to (A1-51), wherein each —R$^{Z1}$ if present, is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted.

(A1-71) A compound according to any one of (A1-47) to (A1-51), wherein each —R$^{Z1}$ if present, is independently saturated aliphatic C$_{1-4}$alkyl, saturated C$_{3-6}$cycloalkyl, -Ph, or —CH$_2$-Ph.

(A1-72) A compound according to any one of (A1-47) to (A1-51), wherein each —R$^{Z1}$ if present, is independently saturated aliphatic C$_{1-4}$alkyl or saturated C$_{3-6}$cycloalkyl.

(A1-73) A compound according to any one of (A1-47) to (A1-51), wherein each —R$^{Z1}$ if present, is independently saturated aliphatic C$_{1-4}$alkyl.

(A1-74) A compound according to any one of (A1-47) to (A1-51), wherein each —R$^{Z1}$ if present, is independently -Me, -Et, -nPr, -iPr, -nBu, -sBu, -iBu, or -tBu.

(A1-75) A compound according to (A1-1) selected from the following compounds and pharmaceutically acceptable salts, hydrates, and solvates thereof:

| Code No. | Structure |
|---|---|
| WW-001 | 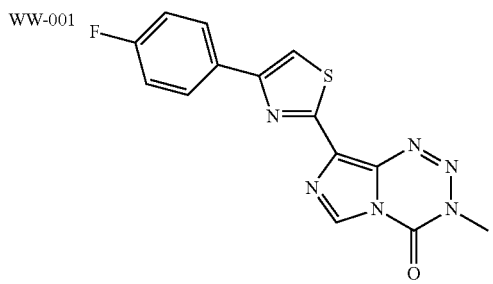 |
| WW-002 | 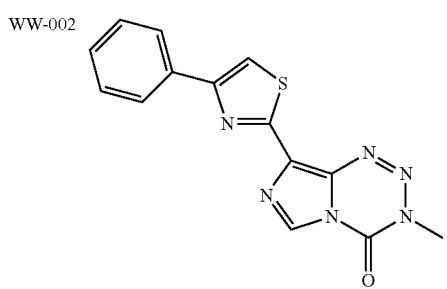 |
| WW-003 | 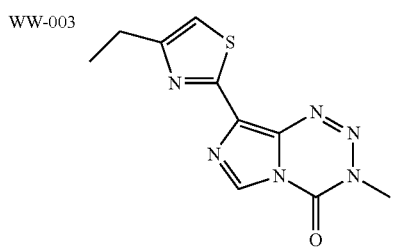 |
| WW-004 | 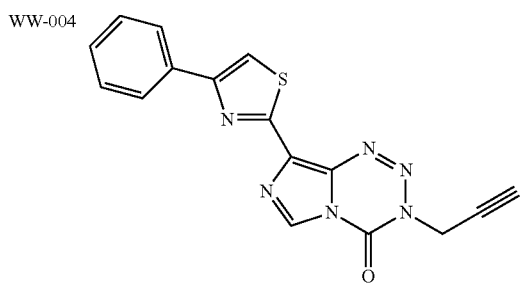 |
| WW-005 | 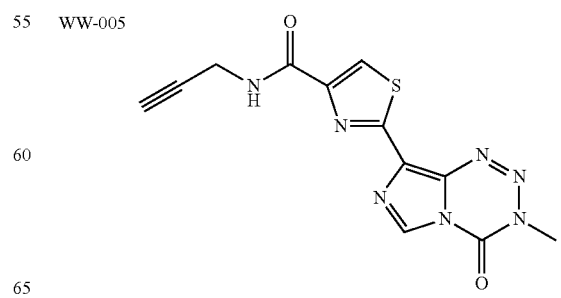 |

| Code No. | Structure |
|---|---|
| WW-006 | 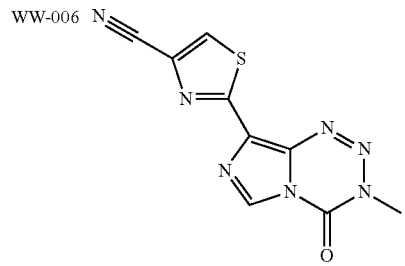 |
| WW-007 | 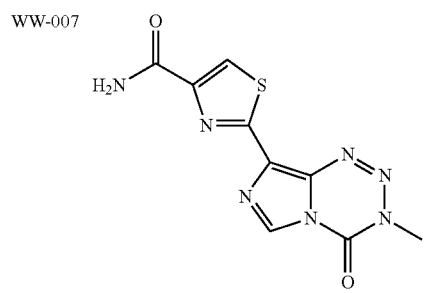 |
| WW-008 | 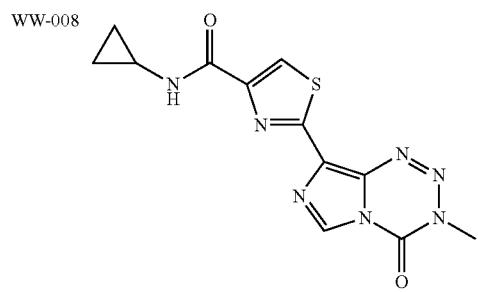 |
| WW-009 | 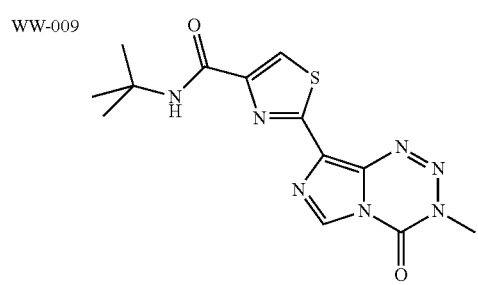 |
| WW-010 | 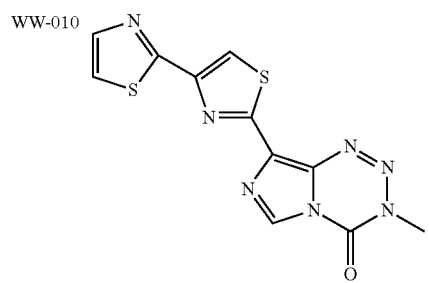 |
| Code No. | Structure |
|---|---|
| WW-011 | 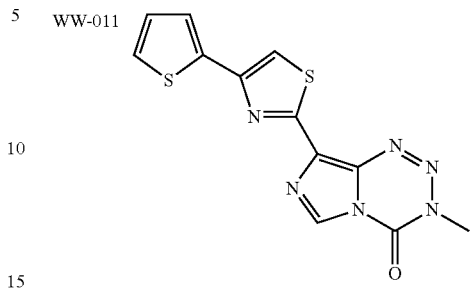 |
| WW-012 | 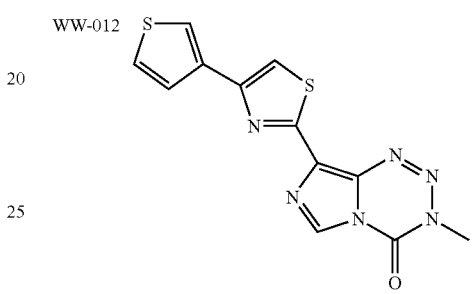 |
| WW-013 | 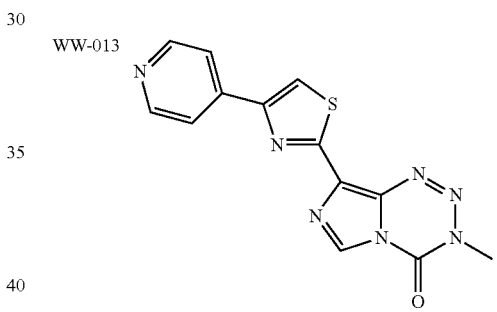 |
| WW-014 | 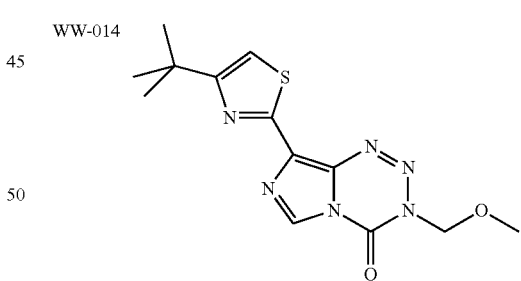 |
| WW-015 | 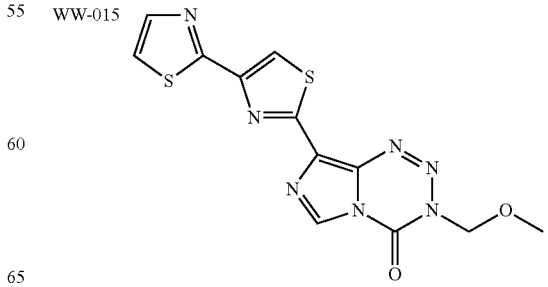 |

-continued
| Code No. | Structure |
|---|---|
| WW-016 | 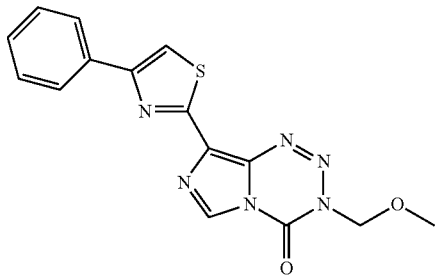 |
| WW-017 | 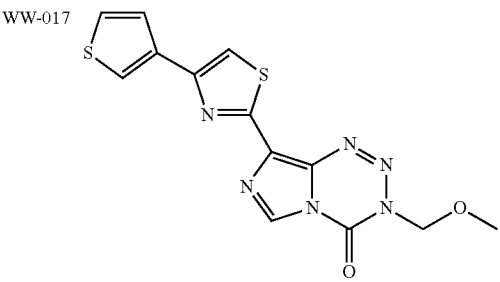 |
| WW-018 | 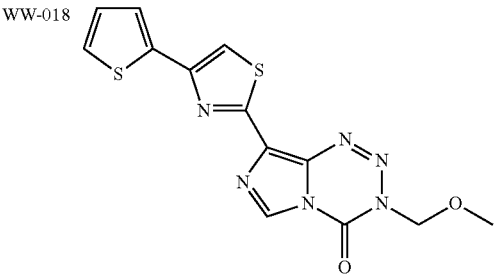 |
| WW-019 | 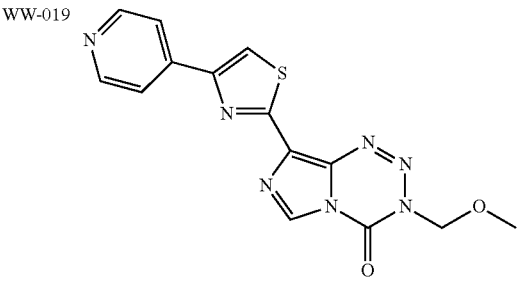 |
| WW-020 | 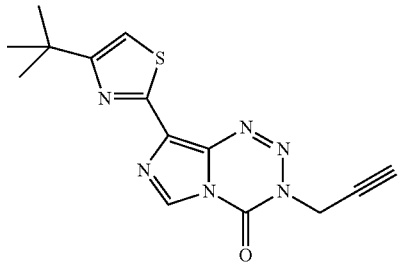 [SMILES: C#CCn1nnc2c(-c3nc(C(C)(C)C)cs3)ncn2c1=O] |
-continued
| Code No. | Structure |
|---|---|
| WW-021 | 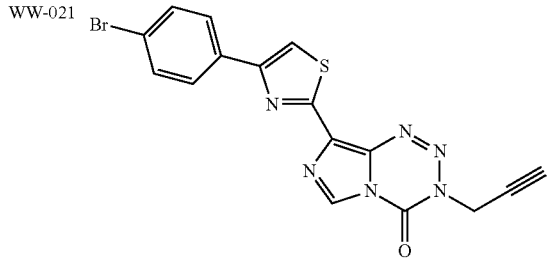 |
| WW-022 | 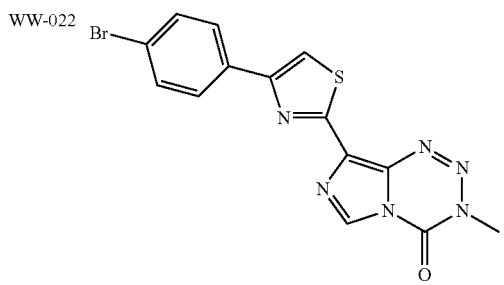 |
| WW-023 | 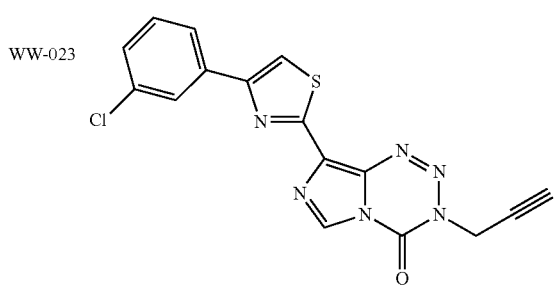 |
| WW-024 | 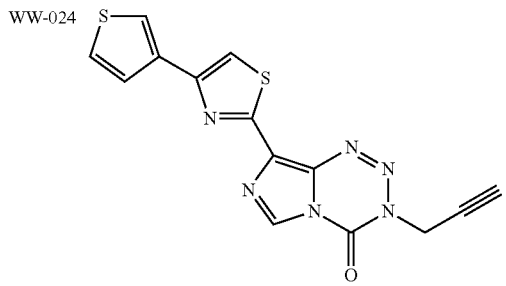 |
| WW-025 | 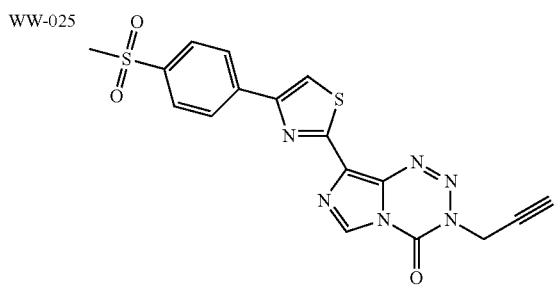 |

| Code No. | Structure |
|---|---|
| WW-026 | 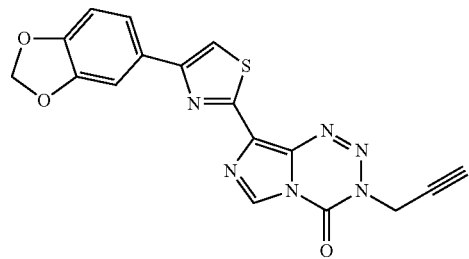 [SMILES: C#CCn1nnc2c(-c3nc(-c4ccc5c(c4)OCO5)cs3)ncn2c1=O] |
| WW-027 | 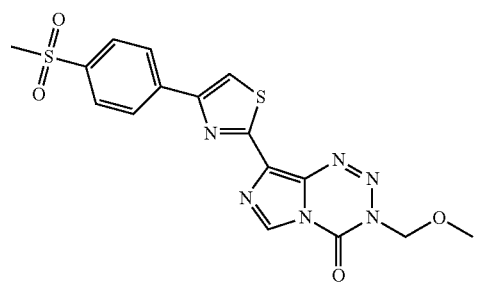 |
| WW-028 | 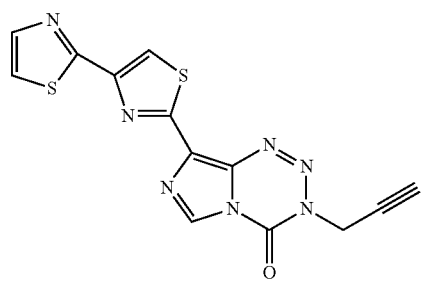 [SMILES: C#CCn1nnc2c(-c3nc(-c4nccs4)cs3)ncn2c1=O] |
| WW-029 | 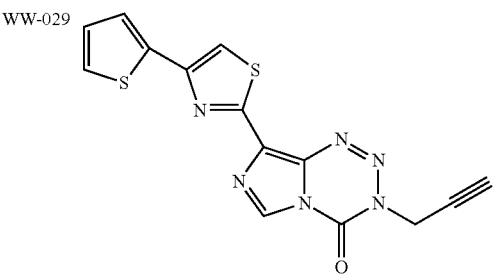 |
| WW-030 | 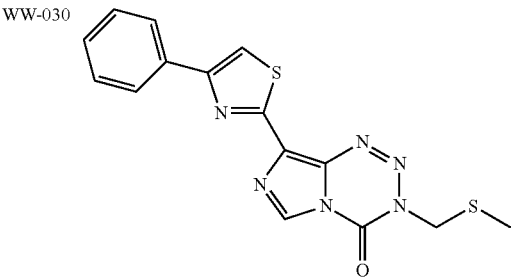 |
| Code No. | Structure |
|---|---|
| WW-031 | 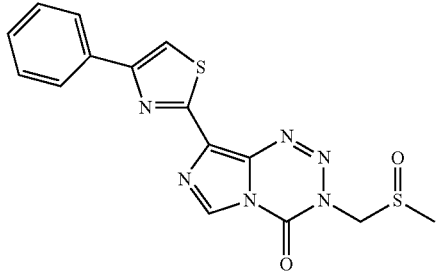 [SMILES: CS(=O)Cn1nnc2c(-c3nc(-c4ccccc4)cs3)ncn2c1=O] |
| WW-032 | 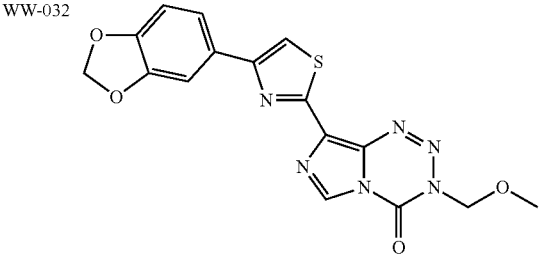 |
| WW-033 | 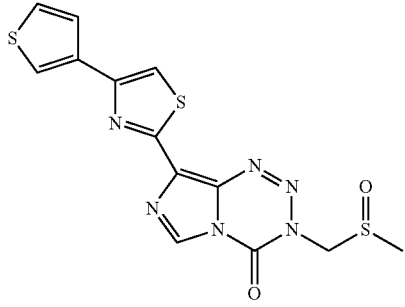 [SMILES: CS(=O)Cn1nnc2c(-c3nc(-c4ccsc4)cs3)ncn2c1=O] |
| WW-034 | 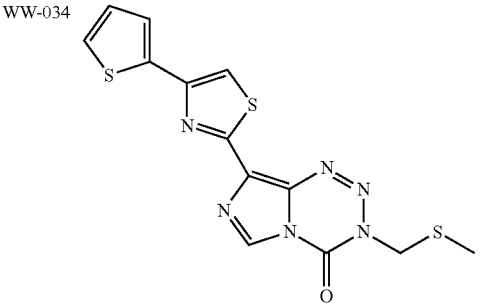 |
| WW-035 | 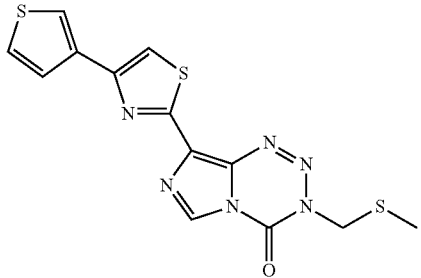 [SMILES: CSCn1nnc2c(-c3nc(-c4ccsc4)cs3)ncn2c1=O] |

-continued
| Code No. | Structure |
|---|---|
| WW-036 | 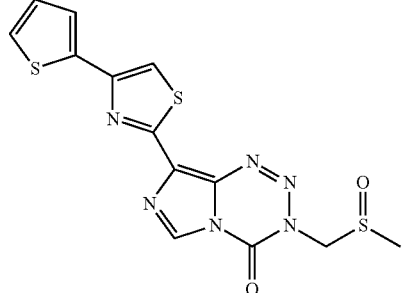 [SMILES: CS(=O)Cn1nnc2c(-c3nc(-c4cccs4)cs3)ncn2c1=O] |
| WW-037 | 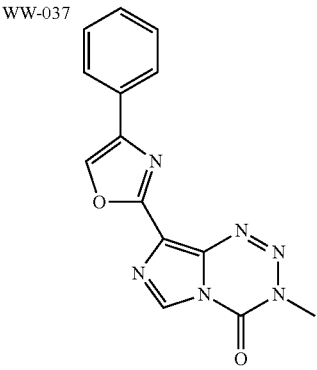 |
| WW-038 | 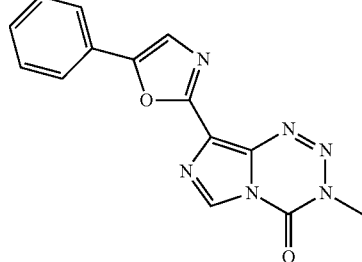 |
| WW-039 | 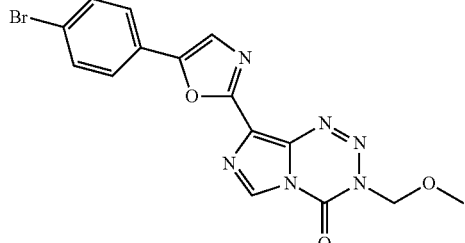 |
| WW-040 | 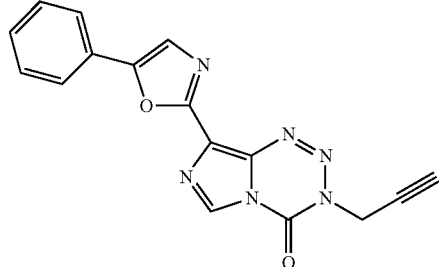 |
-continued
| Code No. | Structure |
|---|---|
| WW-041 | 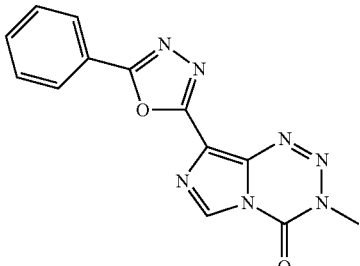 |
| WW-042 | 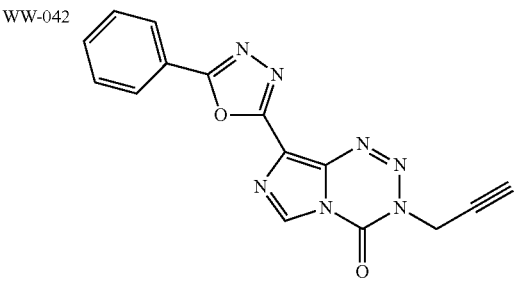 |
| WW-043 | 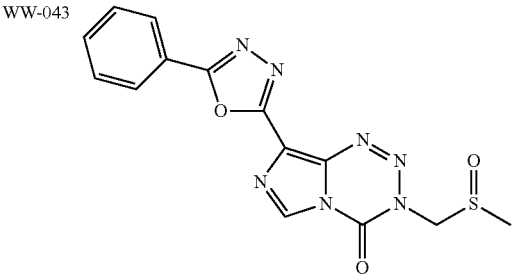 |
| WW-044 | 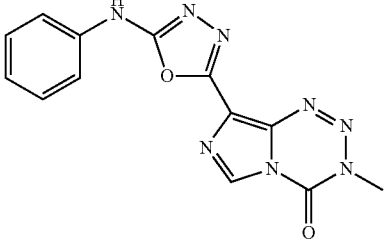 |
| WW-045 | 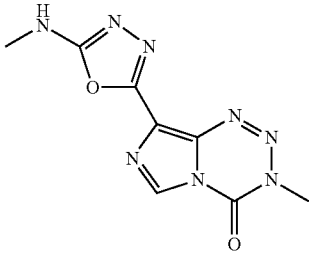 |

| Code No. | Structure |
|---|---|
| WW-046 | 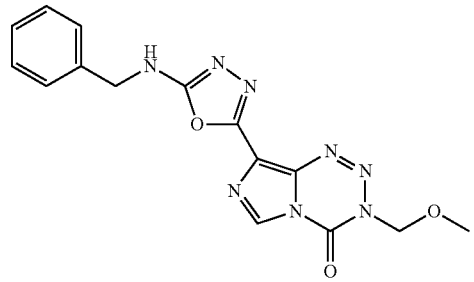 [SMILES: COCn1nnc2c(-c3nnc(NCc4ccccc4)o3)ncn2c1=O] |
| WW-047 | 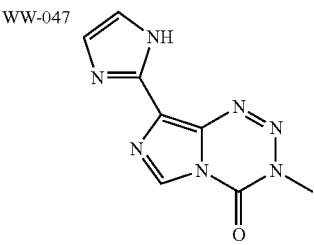 |
| WW-048 | 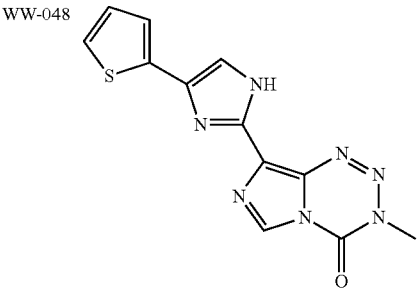 |
| WW-049 | 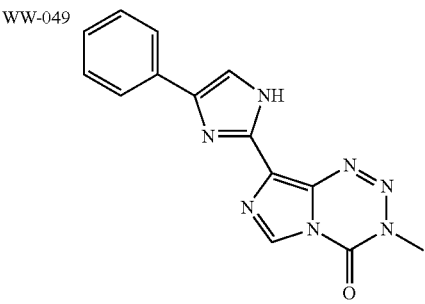 |
| WW-050 | 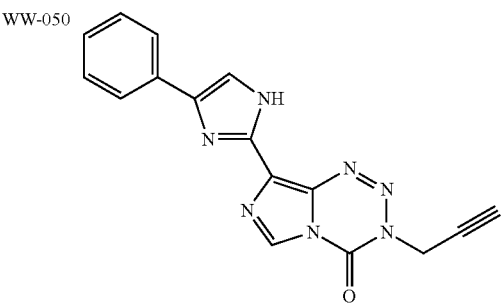 |
| WW-051 | 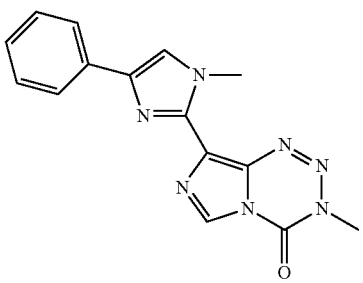 [SMILES: Cn1cc(-c2ccccc2)nc1-c1ncn2c(=O)n(C)nnc12] |
| WW-052 | 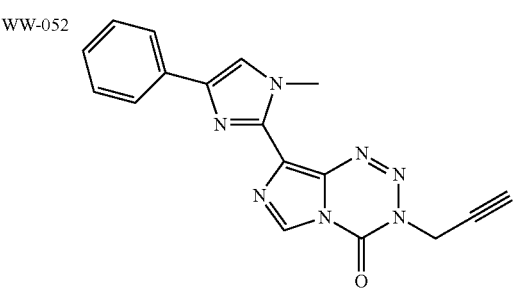 |
| WW-053 | 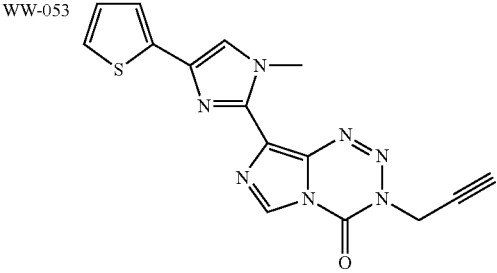 |
| WW-054 | 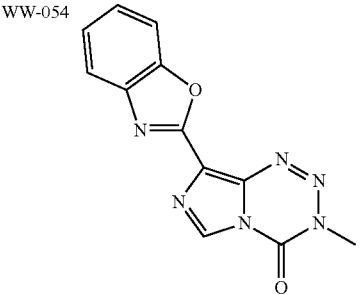 |
| WW-055 | 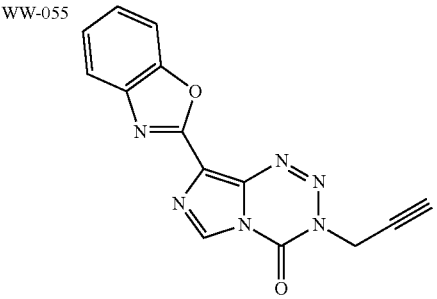 |

| Code No. | Structure |
|---|---|
| WW-056 | 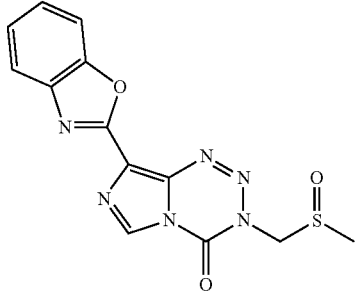 [SMILES: CS(=O)Cn1nnc2c(-c3nc4ccccc4o3)ncn2c1=O] |
| WW-057 | 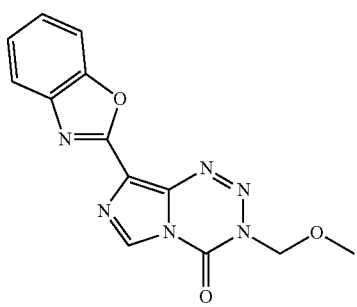 [SMILES: COCn1nnc2c(-c3nc4ccccc4o3)ncn2c1=O] |
| WW-058 | 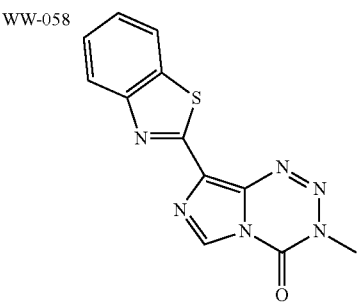 |
| WW-059 | 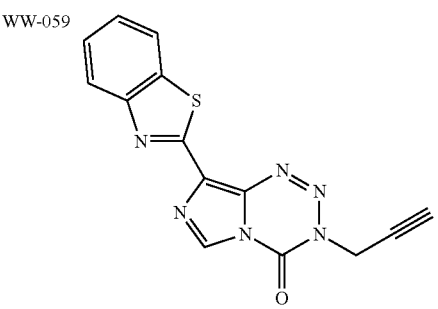 |
| WW-060 | 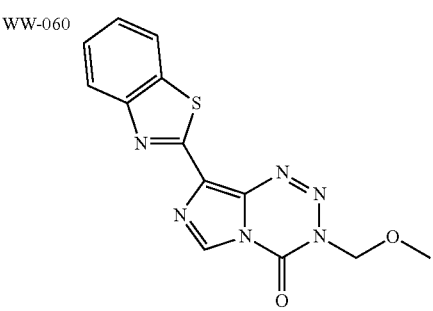 |
| Code No. | Structure |
|---|---|
| WW-061 | 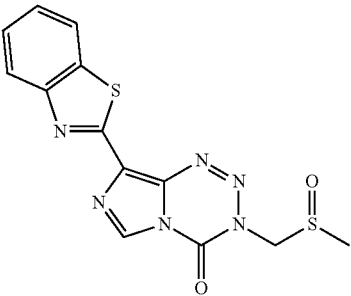 [SMILES: CS(=O)Cn1nnc2c(-c3nc4ccccc4s3)ncn2c1=O] |
| WW-062 | 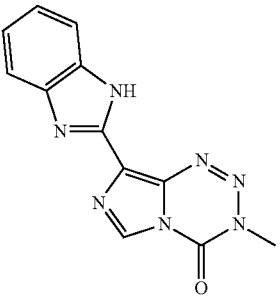 |
| WW-063 | 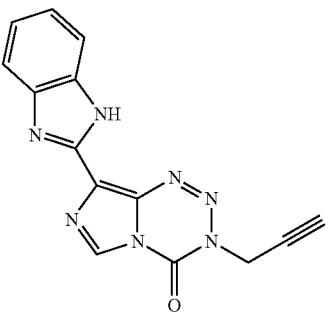 [SMILES: C#CCn1nnc2c(-c3nc4ccccc4[nH]3)ncn2c1=O] |
| WW-064 | 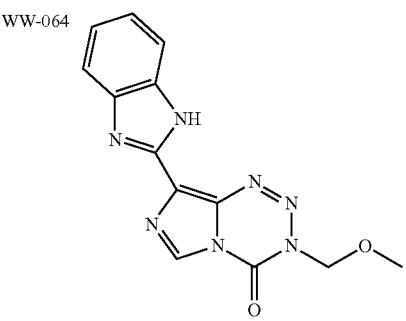 |
| WW-065 | 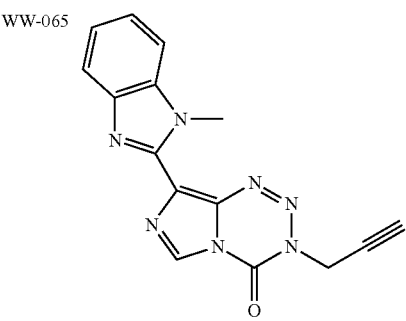 |

| Code No. | Structure |
|---|---|
| WW-066 | 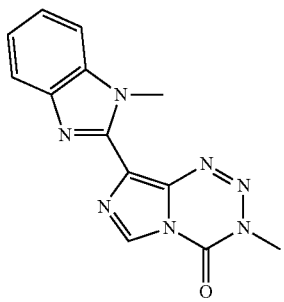 [SMILES: Cn1nnc2c(-c3nc4ccccc4n3C)ncn2c1=O] |

A2. 8-Thioamide Compounds (A2-1) A compound according to (1), wherein -A is independently -A².

(A2-2) A compound according to (A2-1), wherein -A² is independently thioamido or substituted thioamido.

(A2-3) A compound according to (A2-1), wherein -A² is independently:
—C(=S)NH$_2$, —C(=S)NHR$^{Z2}$, —C(=S)NR$^{Z2}$$_2$, —C(=S)-pyrrolidino, —C(=S)-piperidino, —C(=S)-morpholino, —C(=S)-piperizino, or —C(=S(N—C$_{1-4}$alkyl)-piperizino,
wherein:
—R$^{Z2}$ is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph,
wherein each of said C$_{3-6}$cycloalkyl, C$_{5-6}$heteroaryl, and -Ph is optionally substituted, for example, with one or more groups selected from:
—F, —Cl, —Br, —I,
—R$^{Z2A}$, —CF$_3$,
—OH, —OR$^{Z2A}$, —OCF$_3$,
SR$^{Z2A}$,
—NH$_2$, —NHR$^{Z2A}$, —NR$^{Z2A}$$_2$, pyrrolidino, piperidino, morpholino, piperizino, (N—C$_{1-4}$alkyl)-piperizino,
—C(=O)OH, —C(=O)OR$^{Z2A}$,
—C(=O)R$^{Z2A}$,
—OC(=O)R$^{Z2A}$,
—C(=O)NH$_2$, —C(=O)NHR$^{Z2A}$, —C(=O)NR$^{Z2A}$$_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Z2A}$, —NR$^{Z2A}$C(=O)R$^{Z2A}$,
—OC(=O)NH$_2$, —OC(=O)NHR$^{Z2A}$, —OC(=O)NR$^{Z2A}$$_2$, —OC(=O)-pyrrolidino, —OC(=O)-piperidino, —OC(=O)-morpholino, —OC(=O)-piperizino, (N—C$_{1-4}$alkyl)-piperizino,
—NHC(=O)OH, —NHC(=O)OR$^{Z2A}$, —NR$^{Z2A}$C(=O)OR$^{Z2A}$,
—NHC(=O)NH$_2$, —NHC(=O)NHR$^{Z2A}$, —NHC(=O)NR$^{Z2A}$$_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino,
—NO$_2$, and —CN,
wherein each —R$^{Z2A}$ is independently saturated aliphatic C$_{1-4}$alkyl, saturated C$_{3-6}$cycloalkyl, -Ph, or —CH$_2$-Ph,
wherein each C$_{3-6}$cycloalkyl and -Ph is optionally substituted with one or more substituents selected from —F, —Cl, —Br, —I, —R$^{Z2B}$, —CF$_3$, —OH, —OR$^{Z2B}$, and —OCF$_3$, wherein each —R$^{Z2B}$ is independently saturated aliphatic C$_{1-4}$alkyl.

(A2-4) A compound according to (A2-3), wherein -A² is independently —C(=S)NH$_2$, —C(=S)NHR$^{Z2}$, or —C(=S)NR$^{Z2}$$_2$.

(A2-5) A compound according to (A2-3), wherein -A² is independently —C(=S)NH$_2$ or —C(=S)NHR$^{Z2}$.

(A2-6) A compound according to (A2-3), wherein -A² is independently —C(=S)NHR$^{Z2}$.

(A2-7) A compound according to any one of (A2-3) to (A2-6), wherein —R$^{Z2}$, if present, is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph, wherein each of said C$_{3-6}$cycloalkyl, C$_{5-6}$heteroaryl, and -Ph is optionally substituted with one or more groups selected from:
—F, —Cl, —Br, —I,
—R$^{Z2A}$, —CF$_3$,
—OH, —OR$^{Z2A}$, —OCF$_3$,
—NH$_2$, —NHR$^{Z2A}$, —NR$^{Z2A}$$_2$, pyrrolidino piperidino, morpholino, piperizino, (N—C$_{1-4}$alkyl)-piperizino,
—C(=O)OH, —C(=O)OR$^{Z2A}$,
—C(=O)R$^{Z2A}$,
—OC(=O)R$^{Z2A}$,
—C(=O)NH$_2$, —C(=O)NHR$^{Z2A}$, —C(=O)NR$^{Z2A}$$_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Z2A}$, —NR$^{Z2A}$C(=O)R$^{Z2A}$, and
—CN.

(A2-8) A compound according to any one of (A2-3) to (A2-6), wherein —R$^{Z2}$, if present, is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more groups selected from:
—F, —Cl, —Br, —I,
—R$^{Z2A}$, —CF$_3$,
—OH, —OR$^{Z2A}$, —OCF$_3$,
—NH$_2$, —NHR$^{Z2A}$, —NR$^{Z2A}$$_2$, pyrrolidino piperidino, morpholino, piperizino, (N—C$_{1-4}$alkyl)-piperizino,
—C(=O)OH, —C(=O)OR$^{Z2A}$,
—C(=O)R$^{Z2A}$,
—OC(=O)R$^{Z2A}$,
—C(=O)NH$_2$, —C(=O)NHR$^{Z2A}$, —C(=O)NR$^{Z2A}$$_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Z2A}$, —NR$^{Z2A}$C(=O)R$^{Z2A}$, and
—CN.

(A2-9) A compound according to any one of (A2-3) to (A2-6), wherein —R$^{Z2}$, if present, is independently saturated aliphatic C$_{1-4}$alkyl, -Ph, or —CH$_2$-Ph, wherein said -Ph is optionally substituted with one or more groups selected from:
—F, —Cl, —Br, —I,
—R$^{Z2A}$, —CF$_3$,
—OH, —OR$^{Z2A}$, —OCF$_3$,
—NH$_2$, —NHR$^{Z2A}$, —NR$^{Z2A}$$_2$, pyrrolidino piperidino, morpholino, piperizino, (N—C$_{1-4}$alkyl)-piperizino,
—C(=O)OH, —C(=O)OR$^{Z2A}$,
—C(=O)R$^{Z2A}$,
—OC(=O)R$^{Z2A}$,
—C(=O)NH$_2$, —C(=O)NHR$^{Z2A}$, —C(=O)NR$^{Z2A}$$_2$, —C(=O)-pyrrolidino, —C(=O)-piperidino, —C(=O)-morpholino, —C(=O)-piperizino, —C(=O)—(N—C$_{1-4}$alkyl)-piperizino, —NHC(=O)R$^{Z2A}$, —NR$^{Z2A}$C(=O)R$^{Z2A}$, and —CN.

(A2-10) A compound according to any one of (A2-3) to (A2-6), wherein —R$^{Z2}$, if present, is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph, wherein each of said C$_{3-6}$cycloalkyl, C$_{5-6}$heteroaryl, and -Ph is optionally substituted with one or more groups selected from: —F, —Cl, —Br, —I, —R$^{Z2A}$, —CF$_3$, —OH, —OR$^{Z2A}$, and —OCF$_3$.

(A2-11) A compound according to any one of (A2-3) to (A2-6), wherein —R$^{Z2}$, if present, is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more groups selected from: —F, —Cl, —Br, —I, —R$^{Z2A}$, —CF$_3$, —OH, —OR$^{Z2A}$, and —OCF$_3$.

(A2-12) A compound according to any one of (A2-3) to (A2-6), wherein —R$^{Z2}$, if present, is independently saturated aliphatic C$_{1-4}$alkyl, -Ph, or —CH$_2$-Ph, wherein said -Ph is optionally substituted with one or more groups selected from: —F, —Cl, —Br, —I, —R$^{Z2A}$, —CF$_3$, —OH, —OR$^{Z2A}$, and —OCF$_3$.

(A2-13) A compound according to any one of (A2-3) to (A2-6), wherein —R$^{Z2}$, if present, is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph.

(A2-14) A compound according to any one of (A2-3) to (A2-6), wherein —R$^{Z2}$, if present, is independently saturated aliphatic C$_{1-4}$alkyl, saturated C$_{3-6}$cycloalkyl, -Ph, or —CH$_2$-Ph.

(A2-15) A compound according to any one of (A2-3) to (A2-6), wherein —R$^{Z2}$, if present, is independently saturated aliphatic C$_{1-4}$alkyl, -Ph, or —CH$_2$-Ph.

(A2-16) A compound according to any one of (A2-3) to (A2-6), wherein —R$^{Z2}$, if present, is independently saturated aliphatic C$_{1-4}$alkyl.

(A2-17) A compound according to any one of (A2-3) to (A2-6), wherein —Rn, if present, is independently -Me or -Et.

(A2-18) A compound according to (A2-3), wherein -A$^2$ is independently —C(=S)NH$_2$.

(A2-19) A compound according to (A2-3) selected from the following compound and pharmaceutically acceptable salts, hydrates, and solvates thereof:

| Code No. | Structure |
| --- | --- |
| TT-001 | 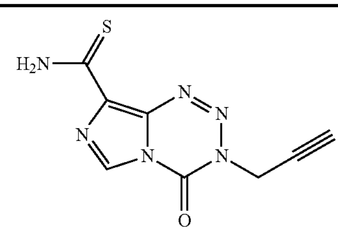 |

A3. 8-Imidamide Compounds (A3-1) A compound according to (1), wherein -A is independently -A$^3$.

(A3-2) A compound according to (A3-1), wherein -A$^3$ is independently imidamido or substituted imidamido.

(A3-3) A compound according to (A3-1), wherein -A$^3$ is independently:

—C(=NH)NH$_2$, —C(=NH)NHR$^{Z3}$, or —C(=NH)NR$^{Z3}_2$, —C(=NH)-pyrrolidino, —C(=NH)-piperidino, —C(=NH)-morpholino, —C(=NH)-piperizino, or —C(=NH)—N—C$_{1-4}$alkyl)-piperizino, wherein:
—R$^{Z3}$ is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph, wherein each of said C$_{1-4}$alkyl, C$_{3-6}$cycloalkyl, C$_{6-6}$heteroaryl, and -Ph is optionally substituted, for example, with one or more groups selected from:
—F, —Cl, —Br, —I,
—R$^{Z3A}$, —CF$_3$,
—OH, —OR$^{Z3A}$, —OCF$_3$,
—SR$^{Z3A}$,
—NH$_2$, —NHR$^{Z3A}$, —NR$^{Z3A}_2$, pyrrolidino, piperidino, morpholino, piperizino, (N—C$_{1-4}$alkyl)-piperizino,
—C(=O)OH, —C(=O)OR$^{Z3A}$,
—C(=O)R$^{Z3A}$,
—OC(=O)R$^{Z3A}$,
—C(=O)NH$_2$, —C(=O)NHR$^{Z3A}$, —C(=O)NR$^{Z3A}_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Z3A}$, —NR$^{Z3A}$C(=O)R$^{Z3A}$,
—OC(=O)NH$_2$, —OC(=O)NHR$^{Z3A}$, —OC(=O)NR$^{Z3A}_2$, —OC(=O)-pyrrolidino,
—OC(=O)-piperidino, —OC(=O)-morpholino, —OC(=O)-piperizino, (N—C$_{1-4}$alkyl)-piperizino,
—NHC(=O)OH, —NHC(=O)OR$^{Z3A}$, —NR$^{Z3A}$C(=O)OR$^{Z3A}$,
—NHC(=O)NH$_2$, —NHC(=O)NHR$^{Z3A}$, —NHC(=O)NR$^{Z3A}_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino,
—NO$_2$, and —CN, wherein each —R$^{Z3A}$ is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more substituents selected from —F, —Cl, —Br, —I, —R$^{Z3B}$, —CF$_3$, —OH, —OR$^{Z3B}$, and —OCF$_3$, wherein each —R$^{Z3B}$ is independently saturated aliphatic C$_{1-4}$alkyl.

(A3-4) A compound according to (A3-3), wherein -A$^3$ is independently —C(=NH)NH$_2$, —C(=NH)NHR$^{Z3}$, or —C(=NH)NR$^{Z3}_2$.

(A3-5) A compound according to (A3-3), wherein -A$^3$ is independently —C(=NH)NH$_2$ or —C(=NH)NHR$^{Z3}$.

(A3-6) A compound according to (A3-3), wherein -A$^3$ is independently —C(=NH)NHR$^{Z3}$.

(A3-7) A compound according to any one of (A3-3) to (A3-6), wherein —R$^{Z3}$, if present, is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph, wherein each of said C$_{1-4}$alkyl, C$_{3-6}$cycloalkyl, C$_{5-6}$heteroaryl, and -Ph is optionally substituted with one or more groups selected from:
—F, —Cl, —Br, —I,
—R$^{Z3A}$, —CF$_3$,
—OH, —OR$^{Z3A}$,
—NH$_2$, —NHR$^{Z3A}$, —NR$^{Z3A}_2$, pyrrolidino piperidino, morpholino, piperizino, (N—C$_{1-4}$alkyl)-piperizino,
—C(=O)OH, —C(=O)OR$^{Z3A}$,
—C(=O)R$^{Z3A}$,
—OC(=O)R$^{Z3A}$,
—C(=O)NH$_2$, —C(=O)NHR$^{Z3A}$, —C(=O)NR$^{Z3A}_2$, —C(=O)-pyrrolidino, —C(=O)-piperidino, —C(=O)-morpholino, —C(=O)-piperizino,
—C(=O)—(N—C$_{1-4}$alkyl)-piperizino,
—NHC(=O)R$^{Z3A}$, —NR$^{Z3A}$C(=O)R$^{Z3A}$, and
—CN.

(A3-8) A compound according to any one of (A3-3) to (A3-6), wherein —R$^{Z3}$, if present, is independently saturated aliphatic C$_{1-4}$alkyl, saturated C$_{3-6}$cycloalkyl, -Ph, or —CH$_2$-Ph, wherein each of said C$_{1-4}$alkyl, C$_{3-6}$cycloalkyl and -Ph is optionally substituted with one or more groups selected from:
—F, —Cl, —Br, —I,
—R$^{Z3A}$, —CF$_3$,
—OH, —OR$^{Z3A}$, —OCF$_3$,
—NH$_2$, —NHR$^{Z3A}$, —NR$^{Z3A}$$_2$, pyrrolidino piperidino, morpholino, piperizino, (N—C$_{1-4}$alkyl)-piperizino,
—C(=O)OH, —C(=O)OR$^{Z3A}$,
—C(=O)R$^{Z3A}$,
—OC(=O)R$^{Z3A}$,
—C(=O)NH$_2$, —C(=O)NHR$^{Z3A}$, —C(=O)NR$^{Z3A}$$_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Z3A}$, —NR$^{Z3A}$C(=O)R$^{Z3A}$, and
—CN.

(A3-9) A compound according to any one of (A3-3) to (A3-6), wherein —R$^{Z3}$, if present, is independently saturated aliphatic C$_{1-4}$alkyl, -Ph, or —CH$_2$-Ph, wherein said each of said C$_{1-4}$alkyl and -Ph is optionally substituted with one or more groups selected from:
—F, —Cl, —Br, —I,
—R$^{Z3A}$, —CF$_3$,
—OH, —OR$^{Z3A}$, —OCF$_3$,
—NH$_2$, —NHR$^{Z3A}$, —NR$^{Z3A}$$_2$, pyrrolidino piperidino, morpholino, piperizino, (N—C$_1$alkyl)-piperizino,
—C(=O)OH, —C(=O)OR$^{Z3A}$,
—C(=O)R$^{Z3A}$,
—OC(=O)R$^{Z3A}$,
—C(=O)NH$_2$, —C(=O)NHR$^{Z3A}$, —C(=O)NR$^{Z3A}$$_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Z3A}$, —NR$^{Z3A}$C(=O)R$^{Z3A}$, and
—CN.

(A3-10) A compound according to any one of (A3-3) to (A3-6), wherein —R$^{Z3}$, if present, is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph, wherein each of said C$_{1-4}$alkyl, C$_{3-6}$cycloalkyl, C$_{5-6}$heteroaryl, and -Ph is optionally substituted with one or more groups selected from: —F, —Cl, —Br, —I, —R$^{Z3A}$, —CF$_3$, —OH, —OR$^{Z3A}$, —OCF$_3$, —C(=O)OH, and —C(=O)OR$^{Z3A}$.

(A3-11) A compound according to any one of (A3-3) to (A3-6), wherein —R$^{Z3}$, if present, is independently saturated aliphatic C$_{1-4}$alkyl, saturated C$_{3-6}$cycloalkyl, -Ph, or —CH$_2$-Ph, wherein each of said C$_{1-4}$alkyl, C$_{3-6}$cycloalkyl and -Ph is optionally substituted, for example, with one or more groups selected from: —F, —Cl, —Br, —I, —R$^{Z3A}$, —CF$_3$, —OH, —OR$^{Z3A}$, —OCF$_3$, —C(=O)OH, and —C(=O)OR$^{Z3A}$.

(A3-12) A compound according to any one of (A3-3) to (A3-6), wherein —R$^{Z3}$, if present, is independently saturated aliphatic C$_{1-4}$alkyl, -Ph, or —CH$_2$-Ph, wherein each of said C$_{1-4}$alkyl and -Ph is optionally substituted with one or more groups selected from: —F, —Cl, —Br, —I, —R$^{Z3A}$, —CF$_3$, —OH, —OR$^{Z3A}$, —OCF$_3$, —C(=O)OH, and —C(=O)OR$^{Z3A}$.

(A3-13) A compound according to any one of (A3-3) to (A3-6), wherein —R$^{Z3}$, if present, is independently saturated aliphatic C$_{1-4}$alkyl, saturated C$_{3-6}$cycloalkyl, -Ph, or —CH$_2$-Ph.

(A3-14) A compound according to any one of (A3-3) to (A3-6), wherein each —R$^{Z3}$, if present, is independently saturated aliphatic C$_{1-4}$alkyl or saturated C$_{3-6}$cycloalkyl.

(A3-15) A compound according to any one of (A3-3) to (A3-6), wherein each —R$^{Z3}$, if present, is independently saturated C$_{3-6}$cycloalkyl.

(A3-16) A compound according to any one of (A3-3) to (A3-6), wherein each —R$^{Z3}$, if present, is independently saturated aliphatic C$_{1-4}$alkyl.

(A3-17) A compound according to (A3-3) wherein -A$^3$ is independently —C(=NH)—NH—CH$_2$—C(=O)OMe.

(A3-18) A compound according to (A3-3) selected from the following compound and pharmaceutically acceptable salts, hydrates, and solvates thereof:

| Code No. | Structure |
|---|---|
| SS-001 | 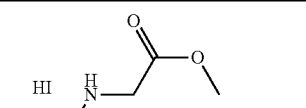 |

A4. 8-Hydroxamate Compounds (A4-1) A compound according to (1), wherein -A is independently -A$^4$.

(A4-2) A compound according to (A4-1), wherein -A$^4$ is independently hydroxamic acid or hydroxamate.

(A4-3) A compound according to (A4-1), wherein -A$^4$ is independently:
—C(=O)—NH—OH, —C(=O)—NR$^{Z4}$—OH,
—C(=O)—NH—OR$^{Z4}$, —C(=O)—NR$^{Z4}$—OR$^{Z4}$,
wherein:
—R$^{Z4}$ is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph,
wherein each of said C$_{3-6}$cycloalkyl, C$_{5-6}$heteroaryl, and -Ph is optionally substituted, for example, with one or more groups selected from:
—F, —Cl, —Br, —I,
—R$^{Z4A}$, —CF$_3$,
—OH, —OR$^{Z4A}$, —OCF$_3$,
—SR$^{Z4A}$,
—NH$_2$, —NHR$^{Z4A}$, —NR$^{Z4A}$$_2$, pyrrolidino, piperidino, morpholino, piperizino, (N—C$_{1-4}$alkyl)-piperizino,
—C(=O)OH, —C(=O)OR$^{Z4A}$,
—C(=O)R$^{Z4A}$,
—OC(=O)R$^{Z4A}$,
—C(=O)NH$_2$, —C(=O)NHR$^{Z4A}$, —C(=O)NR$^{Z4A}$$_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Z4A}$, —NR$^{Z4A}$C(=O)R$^{Z4A}$,
—OC(=O)NH$_2$, —OC(=O)NHR$^{Z4A}$, —OC(=O)NR$^{Z4A}$$_2$, —OC(=O)-pyrrolidino, —OC(=O)-piperidino, —OC(=O)-morpholino, —OC(=O)-piperizino, (N—C$_{1-4}$alkyl)-piperizino, —NHC(=O)OH, —NHC(=O)OR$^{Z4A}$, —NR$^{Z4A}$C(=O)OR$^{Z4A}$,
—NHC(=O)NH$_2$, —NHC(=O)NHR$^{Z4A}$, —NHC(=O)NR$^{Z4A}$$_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino,
—NO$_2$, and —CN,
wherein each —R$^{Z4A}$ is independently saturated aliphatic C$_{1-4}$alkyl, saturated C$_{3-6}$cycloalkyl, -Ph, or —CH$_2$-Ph,
wherein each of said C$_{3-6}$cycloalkyl and -Ph is optionally substituted with one or more substituents selected from —F, —Cl, —Br, —I, —R$^{Z4B}$, —CF$_3$, —OH, —OR$^{Z4B}$, and —OCF$_3$,
wherein each —R$^{Z4B}$ is independently saturated aliphatic C$_{1-4}$alkyl.

(A4-4) A compound according to (A4-3), wherein -A$^4$ is independently —C(=O)—NH—OH or —C(=O)—NH—OR$^{Z4}$.

(A4-5) A compound according to (A4-3), wherein -A$^4$ is independently —C(=O)—NH—OR$^{Z4}$.

(A4-6) A compound according to any one of (A4-3) to (A4-5), wherein —R$^{Z4}$, if present, is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph, wherein each of said C$_{3-6}$cycloalkyl, C$_{5-6}$heteroaryl, and -Ph is optionally substituted with one or more groups selected from:
—F, —Cl, —Br, —I,
—R$^{Z4A}$, —CF$_3$,
—OH, —OR$^{Z4A}$, —OCF$_3$,
—NH$_2$, —NHR$^{Z4A}$, —NR$^{NA}$$_2$, pyrrolidino piperidino, morpholino, piperizino, (N—C$_{1-4}$alkyl)-piperizino,
—C(=O)OH, —C(=O)OR$^{Z4A}$,
—C(=O)R$^{Z4A}$;
—OC(=O)R$^{Z4A}$,
—C(=O)NH$_2$, —C(=O)NHR$^{Z4A}$, —C(=O)NR$^{Z4A}$$_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Z4A}$, —NR$^{Z4A}$C(=O)R$^{Z4A}$, and
—CN.

(A4-7) A compound according to any one of (A4-3) to (A4-5), wherein —R$^{Z4}$, if present, is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more groups selected from:
—F, —Cl, —Br, —I,
—R$^{Z4A}$, —CF$_3$,
—OH, —OR$^{Z4A}$, —OCF$_3$,
—NH$_2$, —NHR$^{Z4A}$, —NR$^{NA}$$_2$, pyrrolidino piperidino, morpholino, piperizino, (N—C$_{1-4}$alkyl)-piperizino,
—C(=O)OH, —C(=O)OR$^{Z4A}$,
—C(=O)R$^{Z4A}$;
—OC(=O)R$^{Z4A}$,
—C(=O)NH$_2$, —C(=O)NHR$^{Z4A}$, —C(=O)NR$^{Z4A}$$_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Z4A}$, —NR$^{Z4A}$C(=O)R$^{Z4A}$, and
—CN.

(A4-8) A compound according to any one of (A4-3) to (A4-5), wherein —R$^{Z4}$, if present, is independently saturated aliphatic C$_{1-4}$alkyl, -Ph, or —CH$_2$-Ph, wherein said -Ph is optionally substituted with one or more groups selected from:
—F, —Cl, —Br, —I,
—R$^{Z4A}$, —CF$_3$,
—OH, —OR$^{Z4A}$, —OCF$_3$,
—NH$_2$, —NHR$^{Z4A}$, —NR$^{Z4A}$$_2$, pyrrolidino piperidino, morpholino, piperizino, (N—C$_1$alkyl)-piperizino,
—C(=O)OH, —C(=O)OR$^{Z4A}$,
—C(=O)R$^{Z4A}$,
—OC(=O)R$^{Z4A}$,
C(=O)R$^{Z4A}$, —C(=O)NH$_2$, —C(=O)NHR$^{Z4A}$, —C(=O)NR$^{Z4A}$$_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Z4A}$, —NR$^{Z4A}$C(=O)R$^{Z4A}$, and
—CN.

(A4-9) A compound according to any one of (A4-3) to (A4-5), wherein —R$^{Z4}$, if present, is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph, wherein each of said C$_{3-6}$cycloalkyl, C$_{5-6}$heteroaryl, and -Ph is optionally substituted with one or more groups selected from: —F, —Cl, —Br, —I, —R$^{Z4A}$, —CF$_3$, —OH, —OR$^{Z4A}$, and —OCF$_3$.

(A4-10) A compound according to any one of (A4-3) to (A4-5), wherein —R$^{Z4}$, if present, is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more groups selected from: —F, —Cl, —Br, —I, —R$^{Z4A}$, —CF$_3$, —OH, —OR$^{Z4A}$, and —OCF$_3$.

(A4-11) A compound according to any one of (A4-3) to (A4-5), wherein —R$^{Z4}$, if present, is independently saturated aliphatic C$_{1-4}$alkyl, -Ph, or —CH$_2$-Ph, wherein said -Ph is optionally substituted with one or more groups selected from: —F, —Cl, —Br, —I, —R$^{Z4A}$, —CF$_3$, —OH, —OR$^{Z4A}$, and —OCF$_3$.

(A4-12) A compound according to any one of (A4-3) to (A4-5), wherein —R$^{Z4}$, if present, is independently saturated aliphatic C$_{1-4}$alkyl, saturated C$_{3-6}$cycloalkyl, -Ph, or —CH$_2$-Ph.

(A4-13) A compound according to any one of (A4-3) to (A4-5), wherein —R$^{Z4}$, if present, is independently saturated aliphatic C$_{1-4}$alkyl, -Ph, or —CH$_2$-Ph.

(A4-14) A compound according to any one of (A4-3) to (A4-5), wherein —R$^{Z4}$, if present, is independently -Ph or —CH$_2$-Ph.

(A4-15) A compound according to (A4-3), wherein -A$^4$ is independently —C(=O)—NH—OH.

(A4-16) A compound according to (A4-3), wherein -A$^4$ is independently —C(=O)—NH—O—CH$_2$-Ph.

(A4-17) A compound according to (A4-3) selected from the following compounds and pharmaceutically acceptable salts, hydrates, and solvates thereof:

| Code No. | Structure |
|---|---|
| RR-001 | 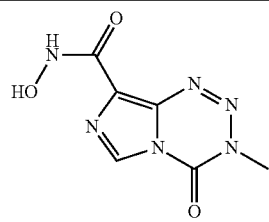 |

| Code No. | Structure |
|---|---|
| RR-002 | 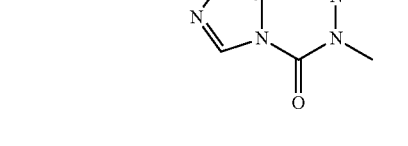 |
| RR-003 | 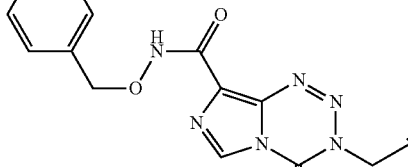 |

A5. 8-Substituted Carboxamide Compounds (A5-1) A compound according to (1), wherein -A is independently -$A^5$.

(A5-2) A compound according to (A5-1), wherein -$A^5$ is independently substituted carboxamide.

(A5-3) A compound according to (A5-1), wherein -$A^5$ is independently:
—C(=O)—NHR$^{Z5}$, —C(=O)—NR$^{Z5}{}_2$, —C(=O)-pyrrolidino, —C(=O)-piperidino, —C(=O)-morpholino, —C(=O)-piperizino, or —C(=O)—(N—C$_{1-4}$alkyl)-piperizino,
wherein:
—R$^{Z5}$ is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph,
wherein each of said C$_{3-6}$cycloalkyl, C$_{5-6}$heteroaryl, and -Ph is optionally substituted, for example, with one or more groups selected from:
—F, —Cl, —Br, —I,
—R$^{Z5A}$, —CF$_3$,
—OH, —OR$^{Z5A}$, —OCF$_3$,
—SR$^{Z5A}$,
—NH$_2$, —NHR$^{Z5A}$, —NR$^{Z5A}{}_2$, pyrrolidino, piperidino, morpholino, piperizino, (N—C$_{1-4}$alkyl)-piperizino,
—C(=O)OH, —C(=O)OR$^{Z5A}$,
—C(=O)R$^{Z5A}$,
—OC(=O)R$^{Z5A}$,
—C(=O)NH$_2$, —C(=O)NHR$^{Z5A}$, —C(=O)NR$^{Z5A}{}_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Z5A}$, —NR$^{Z5A}$C(=O)R$^{Z5A}$,
—OC(=O)NH$_2$, —OC(=O)NHR$^{Z5A}$, —OC(=O)NR$^{Z5A}{}_2$, —OC(=O)-pyrrolidino, —OC(=O)-piperidino, —OC(=O)-morpholino, —OC(=O)-piperizino, (N—C$_{1-4}$alkyl)-piperizino,
—NHC(=O)OH, —NHC(=O)OR$^{Z5A}$, —NR$^{Z5A}$C(=O)OR$^{Z5A}$,
—NHC(=O)NH$_2$, —NHC(=O)NHR$^{Z5A}$, —NHC(=O)NR$^{Z5A}{}_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino,
—NO$_2$, and —CN,
wherein each —R$^{Z5A}$ is independently saturated aliphatic C$_{1-4}$alkyl, saturated C$_{3-6}$cycloalkyl, -Ph, or —CH$_2$-Ph,
wherein each of said C$_{3-6}$cycloalkyl and -Ph is optionally substituted with one or more substituents selected from —F, —Cl, —Br, —I, —R$^{Z5B}$, —CF$_3$, —OH, —OR$^{Z5B}$, and —OCF$_3$,
wherein each —R$^{Z5B}$ is independently saturated aliphatic C$_{1-4}$alkyl.

(A5-4) A compound according to (A5-3), wherein -$A^5$ is independently —C(=O)—NHR$^{Z5}$ or —C(=O)—NR$^{Z5}{}_2$.

(A5-5) A compound according to (A5-3), wherein -$A^5$ is independently —C(=O)—NHR$^{Z5}$.

(A5-6) A compound according to (A5-3), wherein -$A^5$ is independently —C(=O)—NR$^{Z5}{}_2$.

(A5-7) A compound according to (A5-3), wherein -$A^5$ is independently —C(=O)-pyrrolidino, —C(=O)-piperidino, —C(=O)-morpholino, —C(=O)-piperizino, or —C(=O)—(N—C$_{1-4}$alkyl)-piperizino.

(A5-8) A compound according to any one of (A5-3) to (A5-7), wherein —R$^{Z5}$, if present, is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph, wherein each of said C$_{3-6}$cycloalkyl, C$_{5-6}$heteroaryl, and -Ph is optionally substituted with one or more groups selected from:
—F, —Cl, —Br, —I,
—R$^{Z5A}$, —CF$_3$, —OH, —OR$^{Z5A}$, —OCF$_3$,
—NH$_2$, —NHR$^{Z5A}$, —NR$^{Z5A}{}_2$, pyrrolidino piperidino, morpholino, piperizino, (N—C$_{1-4}$alkyl)-piperizino,
—C(=O)OH, —C(=O)OR$^{Z5A}$,
—C(=O)R$^{Z5A}$,
—OC(=O)R$^{Z5A}$,
—C(=O)NH$_2$, —C(=O)NHR$^{Z5A}$, —C(=O)NR$^{Z5A}{}_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Z5A}$, —NR$^{Z5A}$C(=O)R$^{Z5A}$, and —CN.

(A5-9) A compound according to any one of (A5-3) to (A5-7), wherein —R$^{Z5}$, if present, is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more groups selected from:
—F, —Cl, —Br, —I,
—R$^{Z5A}$, —CF$_3$,
—OH, —OR$^{Z5A}$, —OCF$_3$,
—NH$_2$, —NHR$^{Z5A}$, —NR$^{Z5A}{}_2$, pyrrolidino piperidino, morpholino, piperizino, (N—C$_{1-4}$alkyl)-piperizino,
—C(=O)OH, —C(=O)OR$^{Z5A}$,
—C(=O)R$^{Z5A}$,
—OC(=O)R$^{Z5A}$,
—C(=O)NH$_2$, —C(=O)NHR$^{Z5A}$, —C(=O)NR$^{Z5A}{}_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Z5A}$, —NR$^{Z5A}$C(=O)R$^{Z5A}$, and —CN.

(A5-10) A compound according to any one of (A5-3) to (A5-7), wherein —R$^{Z5}$, if present, is independently saturated aliphatic C$_{1-4}$alkyl, -Ph, or —CH$_2$-Ph, wherein said -Ph is optionally substituted with one or more groups selected from:
—F, —Cl, —Br, —I,
—R$^{Z5A}$, —CF$_3$,
—OH, —OR$^{Z5A}$, —OCF$_3$, —NH$_2$, —NHR$^{Z5A}$, —NR$^{Z5A}_2$, pyrrolidino piperidino, morpholino, piperizino, (N—C$_{1-4}$alkyl)-piperizino,
—C(=O)OH, —C(=O)OR$^{Z5A}$,
—C(=O)R$^{Z5A}$,
—OC(=O)R$^{Z5A}$,
—C(=O)NH$_2$, —C(=O)NHR$^{Z5A}$, —C(=O)NR$^{Z5A}_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Z5A}$, —NR$^{Z5A}$C(=O)R$^{Z5A}$, and
—CN.

(A5-11) A compound according to any one of (A5-3) to (A5-7), wherein —R$^{Z5}$, if present, is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph, wherein each of said C$_{3-6}$cycloalkyl, C$_{5-6}$heteroaryl, and -Ph is optionally substituted with one or more groups selected from: —F, —Cl, —Br, —I, —R$^{Z5A}$, —CF$_3$, —OH, —OR$^{Z5A}$, and —OCF$_3$.

(A5-12) A compound according to any one of (A5-3) to (A5-7), wherein —R$^{Z5}$, if present, is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more groups selected from: —F, —Cl, —Br, —I, —R$^{Z5A}$, —CF$_3$, —OH, —OR$^{Z5A}$, and —OCF$_3$.

(A5-13) A compound according to any one of (A5-3) to (A5-7), wherein —R$^{Z5}$, if present, is independently saturated aliphatic C$_{1-4}$alkyl, -Ph, or —CH$_2$-Ph, wherein said -Ph is optionally substituted with one or more groups selected from: —F, —Cl, —Br, —I, —R$^{Z5A}$, —CF$_3$, —OH, —OR$^{Z5A}$, and —OCF$_3$.

(A5-14) A compound according to any one of (A5-3) to (A5-7), wherein —R$^{Z5}$, if present, is independently saturated aliphatic C$_{1-4}$alkyl, saturated C$_{1-4}$cycloalkyl, -Ph, or —CH$_2$-Ph.

(A5-15) A compound according to any one of (A5-3) to (A5-7), wherein —R$^{Z5}$, if present, is independently saturated aliphatic C$_{1-4}$alkyl, -Ph, or —CH$_2$-Ph.

(A5-16) A compound according to any one of (A5-3) to (A5-7), wherein —R$^{Z5}$, if present, is independently -Ph or —CH$_2$-Ph.

(A5-17) A compound according to any one of (A5-3) to (A5-7), wherein —R$^{Z5}$, if present, is independently saturated aliphatic C$_{1-4}$alkyl.

(A5-18) A compound according to (A5-3), wherein -A$^5$ is independently —C(=O)—NHPh.

(A5-19) A compound according to (A5-3) selected from the following compounds and pharmaceutically acceptable salts, hydrates, and solvates thereof:

| Code No. | Structure |
|---|---|
| LL-001 | 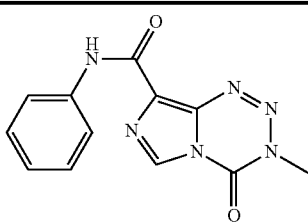 |
| LL-002 | 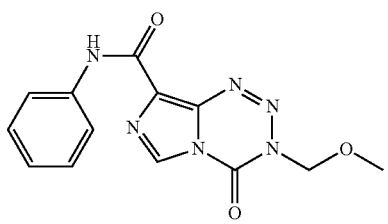 [SMILES: COCn1nnc2c(C(=O)Nc3ccccc3)ncn2c1=O] |

A6. C-8 Alkene Compounds (A6-1) A compound according to (1), wherein -A is independently -A$^6$.

(A6-2) A compound according to (A6-1), wherein -A$^6$ is independently aliphatic C$_{2-6}$alkenyl, and is optionally substituted.

(A6-3) A compound according to (A6-1), wherein -A$^6$ is independently -L$^6$-R$^{Z6}$,
wherein:
-L$^6$- is independently aliphatic C$_{2-6}$alkenyl, and
—R$^{Z6}$ is independently C$_{5-6}$heteroaryl or -Ph,
wherein each of said C$_{5-6}$heteroaryl and -Ph is optionally substituted, for example, with one or more groups selected from:
—F, —Cl, —Br, —I,
—R$^{Z6A}$, —CF$_3$,
—OH, —OR$^{Z6A}$, —OCF$_3$,
—SR$^{Z6A}$,
—NH$_2$, —NHR$^{Z6A}$, —NR$^{Z6A}_2$, pyrrolidino, piperidino, morpholino, piperizino, (N—C$_{1-4}$alkyl)-piperizino,
—C(=O)OH, —C(=O)OR$^{Z6A}$,
—C(=O)R$^{Z6A}$,
—OC(=O)R$^{Z6A}$,
—C(=O)NH$_2$, —C(=O)NHR$^{Z6A}$, —C(=O)NR$^{Z6A}_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Z6A}$, —NR$^{Z6A}$C(=O)R$^{Z6A}$,
—OC(=O)NH$_2$, —OC(=O)NHR$^{Z6A}$, —OC(=O)NR$^{Z6A}_2$, —OC(=O)-pyrrolidino, —OC(=O)-piperidino, —OC(=O)-morpholino, —OC(=O)-piperizino, (N—C$_{1-4}$alkyl)-piperizino,
—NHC(=O)OH, —NHC(=O)OR$^{Z6A}$, NR$^{Z6A}$C(=O)OR$^{Z6A}$,
—NHC(=O)NH$_2$, —NHC(=O)NHR$^{Z6A}$, —NHC(=O)NR$^{Z6A}_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino,
—NO$_2$, and —CN,
wherein each —R$^{Z6A}$ is independently saturated aliphatic C$_{1-4}$alkyl, saturated C$_{3-6}$cycloalkyl, -Ph, or —CH$_2$-Ph,
wherein each C$_{3-6}$cycloalkyl and -Ph is optionally substituted with one or more substituents selected from —F, —Cl, —Br, —I, —R$^{Z6B}$, —CF$_3$, —OH, —OR$^{Z6B}$, and —OCF$_3$,
wherein each —R$^{Z6B}$ is independently saturated aliphatic C$_{1-4}$alkyl.

(A6-4) A compound according to (A6-3), wherein —R$^{Z6}$ is independently furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, or -Ph, and each of said furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, and -Ph is optionally substituted.

(A6-5) A compound according to (A6-3), wherein —$R^{Z6}$ is independently thienyl or -Ph, and each of said thienyl and -Ph is optionally substituted.

(A6-6) A compound according to (A6-3), wherein —$R^{Z6}$ is independently -Ph, and said -Ph is optionally substituted.

(A6-7) A compound according to (A6-3), wherein —$R^{Z6}$ is independently $C_{5-6}$heteroaryl or -Ph, wherein each of said $C_{5-6}$heteroaryl and -Ph is optionally substituted with one or more groups selected from:
—F, —Cl, —Br, —I,
—$R^{Z6A}$, —$CF_3$,
—OH, —$OR^{Z6A}$, —$OCF_3$,
—$NH_2$, —$NHR^{Z6A}$, —$NR^{Z6A}_2$, pyrrolidino piperidino, morpholino, piperizino, (N—$C_{1-4}$alkyl)-piperizino,
—C(=O)OH, —C(=O)$OR^{Z6A}$,
—C(=O)$R^{Z6A}$,
—OC(=O)$R^{Z6A}$,
—C(=O)$NH_2$, —C(=O)$NHR^{Z6A}$, —C(=O)$NR^{Z6A}_2$,
—C(=O)-pyrrolidino, —C(=O)-piperidino,
—C(=O)-morpholino, —C(=O)-piperizino,
—C(=O)—(N—$C_{1-4}$alkyl)-piperizino,
—NHC(=O)$R^{Z6A}$, —$NR^{Z6A}$C(=O)$R^{Z6A}$, and
—CN.

(A6-8) A compound according to (A6-3), wherein —$R^{Z6}$ is independently furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, or -Ph,
wherein each of said furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, and -Ph is optionally substituted with one or more groups selected from:
—F, —Cl, —Br, —I,
—$R^{Z6A}$, —$CF_3$,
—OH, —$OR^{Z6A}$, —$OCF_3$,
—$NH_2$, —$NHR^{Z6A}$, —$NR^{Z6A}_2$, pyrrolidino piperidino, morpholino, piperizino, (N—$C_{1-4}$alkyl)-piperizino,
—C(=O)OH, —C(=O)$OR^{Z6A}$,
—C(=O)$R^{Z6A}$,
—OC(=O)$R^{Z6A}$,
—C(=O)$NH_2$, —C(=O)$NHR^{Z6A}$, —C(=O)$NR^{Z6A}_2$,
—C(=O)-pyrrolidino, —C(=O)-piperidino,
—C(=O)-morpholino, —C(=O)-piperizino,
—C(=O)—(N—$C_{1-4}$alkyl)-piperizino,
—NHC(=O)$R^{Z6A}$, $NR^{Z6A}$C(=O)$R^{Z6A}$, and
—CN.

(A6-9) A compound according to (A6-3), wherein —$R^{Z6}$ is independently thienyl or -Ph, wherein each of said thienyl and -Ph is optionally substituted with one or more groups selected from:
—F, —Cl, —Br, —I,
—$R^{Z6A}$, —$CF_3$,
—OH, —$OR^{Z6A}$, —$OCF_3$,
—$NH_2$, —$NHR^{Z6A}$, —$NR^{Z6A}_2$, pyrrolidino piperidino, morpholino, piperizino, (N—$C_{1-4}$alkyl)-piperizino,
—C(=O)OH, —C(=O)$OR^{Z6A}$,
—C(=O)$R^{Z6A}$,
—OC(=O)$R^{Z6A}$,
—C(=O)$NH_2$, —C(=O)$NHR^{Z6A}$, —C(=O)$NR^{Z6A}_2$,
—C(=O)-pyrrolidino, —C(=O)-piperidino,
—C(=O)-morpholino, —C(=O)-piperizino,
—C(=O)—(N—$C_{1-4}$alkyl)-piperizino,
—NHC(=O)$R^{Z6A}$, —$NR^{Z6A}$C(=O)$R^{Z6A}$, and
—CN.

(A6-10) A compound according to (A6-3), wherein —$R^{Z6}$ is independently -Ph, wherein said -Ph is optionally substituted with one or more groups selected from:
—F, —Cl, —Br, —I,
—$R^{Z6A}$, —$CF_3$,
—OH, —$OR^{Z6A}$, —$OCF_3$,
—$NH_2$, —$NHR^{Z6A}$, —$NR^{Z6A}_2$, pyrrolidino piperidino, morpholino, piperizino, (N—$C_{1-4}$alkyl)-piperizino,
—C(=O)OH, —C(=O)$OR^{Z6A}$,
—C(=O)$R^{Z6A}$,
—OC(=O)$R^{Z6A}$,
—C(=O)$NH_2$, —C(=O)$NHR^{Z6A}$, —C(=O)$NR^{Z6A}_2$,
—C(=O)-pyrrolidino, —C(=O)-piperidino,
—C(=O)-morpholino, —C(=O)-piperizino,
—C(=O)—(N—$C_{1-4}$alkyl)-piperizino,
—NHC(=O)$R^{Z6A}$, $NR^{Z6A}$C(=O)$R^{Z6A}$, and
—CN.

(A6-11) A compound according to (A6-3), wherein —$R^{Z6}$ is independently $C_{5-6}$heteroaryl or -Ph, wherein each of said $C_{5-6}$heteroaryl and -Ph is optionally substituted with one or more groups selected from: —F, —Cl, —Br, —I, —$R^{Z6A}$, —$CF_3$, —OH, $OR^{Z6A}$, —$OCF_3$, and —CN.

(A6-12) A compound according to (A6-3), wherein —$R^{Z6}$ is independently furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, or -Ph,
wherein each of said furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, and -Ph is optionally substituted with one or more groups selected from: —F, —Cl, —Br, —I, —$R^{Z6A}$, —$CF_3$, —OH, —$OR^{Z6A}$, —$OCF_3$, and —CN.

(A6-13) A compound according to (A6-3), wherein —$R^{Z6}$ is independently thienyl or -Ph, wherein each of said thienyl and -Ph is optionally substituted with one or more groups selected from: —F, —Cl, —Br, —I, —$R^{Z6A}$, —$CF_3$, —OH, —$OR^{Z6A}$, —$OCF_3$, and —CN.

(A6-14) A compound according to (A6-3), wherein —$R^{Z6}$ is independently -Ph, wherein said -Ph is optionally substituted with one or more groups selected from: —F, —Cl, —Br, —I, —$R^{Z6A}$, —$CF_3$, —OH, —$OR^{Z6A}$, —$OCF_3$, and —CN.

(A6-15) A compound according to (A6-3), wherein —$R^{Z6}$ is independently $C_{5-6}$heteroaryl or -Ph, wherein each of said $C_{5-6}$heteroaryl and -Ph is optionally substituted with —CN.

(A6-16) A compound according to (A6-3), wherein —$R^{Z6}$ is independently -Ph, wherein said -Ph is optionally substituted with —CN.

(A6-17) A compound according to any one of (A6-3) to (A6-16), wherein -$L^6$- is independently aliphatic $C_{2-4}$alkenyl.

(A6-18) A compound according to any one of (A6-3) to (A6-16), wherein -$L^6$- is independently —CH=CH—.

(A6-19) A compound according to any one of (A6-3) to (A6-16), wherein -$L^6$- is independently trans —CH=CH—.

(A6-20) A compound according to (A6-3), wherein -$A^6$ is independently —CH=CH-thienyl.

(A6-21) A compound according to (A6-3), wherein -$A^6$ is independently —CH=CH-(cyano-phenyl).

(A6-22) A compound according to (A6-3), wherein -$A^6$ is independently —CH=CH-(para-cyano-phenyl).

(A6-23) A compound according to (A6-3) selected from the following compounds and pharmaceutically acceptable salts, hydrates, and solvates thereof:

| Code No. | Structure |
|---|---|
| MM-001 | (4-cyanostyryl-imidazo-tetrazinone with N-CH2-OCH3 substituent) |
| MM-002 | (4-cyanostyryl-imidazo-tetrazinone with N-CH2-SCH3 substituent) |
| MM-003 | (4-cyanostyryl-imidazo-tetrazinone with N-CH2-S(O)2-CH3 substituent) |
| MM-004 | (thienyl-vinyl-imidazo-tetrazinone with N-CH2-OCH3 substituent) |

B1. 3-Alkyl Compounds (B1-1) A compound according to any one of (1), (A1-1) to (A1-75), (A2-1) to (A1-18), (A3-1) to (A3-18), (A4-1) to (A4-17), (A5-1) to (A5-19), and (A6-1) to (A6-23), wherein —B is independently —B$^1$.

(B1-2) A compound according to (B1-1), wherein —B$^1$ is independently saturated aliphatic $C_{1-6}$alkyl.

(B1-3) A compound according to (B1-2), wherein —B$^1$ is independently saturated aliphatic $C_{1-6}$alkyl, but is not -Me.

(B1-4) A compound according to (B1-2), wherein —B$^1$ is independently saturated aliphatic $C_{1-4}$alkyl.

(B1-5) A compound according to (B1-2), wherein —B$^1$ is independently saturated aliphatic $C_{1-4}$alkyl, but is not -Me.

(B1-6) A compound according to (B1-2), wherein —B$^1$ is independently -Me, -Et, -nPr, -iPr, -nBu, -iBu, or -tBu.

(B1-7) A compound according to (B1-2), wherein —B$^1$ is independently -Et, -nPr, -iPr, -nBu, -iBu, or -tBu.

(B1-8) A compound according to (B1-2), wherein —B$^1$ is independently -Me, -Et, -nPr, or -iPr.

(B1-9) A compound according to (B1-2), wherein —B$^1$ is independently -Et, -nPr, or -iPr.

(B1-10) A compound according to (B1-2), wherein —B$^1$ is independently -Me or -Et.

(B1-11) A compound according to (B1-2), wherein —B$^1$ is independently -Me.

(B1-12) A compound according to (B1-2), wherein —B$^1$ is independently -Et.

B2. 3-Alkynyl Compounds (B2-1) A compound according to any one of (1), (A1-1) to (A1-75), (A2-1) to (A1-18), (A3-1) to (A3-18), (A4-1) to (A4-17), (A5-1) to (A5-19), and (A6-1) to (A6-23), wherein —B is independently —B$^2$.

(B2-2) A compound according to (B2-1), wherein —B$^2$ is independently aliphatic $C_{2-6}$alkynyl.

(B2-3) A compound according to (B2-2), wherein —B$^2$ is independently aliphatic $C_{3-5}$alkynyl.

As used herein, the term "alkynyl" relates to an aliphatic hydrocarbyl group (i.e., a group having only carbon atoms and hydrogen atoms) having at least one carbon-carbon triple bond.

(B2-4) A compound according to (B2-2), wherein —B$^2$ is independently:
—C≡CH,
—C≡C—CH$_3$, —CH$_2$—C≡CH,
—C≡C—CH$_2$—CH$_3$, —C—C≡CH=CH$_2$, —C≡C—C≡CH,
—CH$_2$—CH$_2$—C≡CH, —CH=CH—C≡CH,
—C≡C—C≡CH,
—CH$_2$—C≡C—CH$_3$, or
—CH(CH$_3$)—C≡CH.

(B2-5) A compound according to (B2-2), wherein —B$^2$ is independently —CH$_2$—C≡CH.

B3. 3-Sulfur-Alkyl Compounds (B3-1) A compound according to any one of (1), (A1-1) to (A1-75), (A2-1) to (A2-19), (A3-1) to (A3-18), (A4-1) to (A4-17), (A5-1) to (A5-19), and (A6-1) to (A6-23), wherein —B is independently —B$^3$.

(B3-2) A compound according to (B3-1), wherein —B$^3$ is independently mercapto-$C_{1-4}$alkyl, sulfanyl-$C_{1-4}$alkyl, sulfinyl-$C_{1-4}$alkyl, or sulfonyl-$C_{1-4}$alkyl.

(B3-3) A compound according to (B3-1), wherein —B$^3$ is independently:
-L$^{Y3}$-SH, -L$^{Y3}$-S—R$^{Y3}$, -L$^{Y3}$-S(=O)—R$^{Y3}$, or -L$^{Y3}$-S(=O)$_2$—R$^{Y3}$,
wherein:
-L$^{Y3}$- is independently saturated aliphatic $C_{1-4}$alkylene, and
—R$^{Y3}$ is independently saturated aliphatic $C_{1-4}$alkyl, saturated $C_{3-6}$cycloalkyl, $C_{5-6}$heteroaryl, —CH$_2$—$C_{5-6}$heteroaryl, -Ph, or —CH$_2$-Ph,
wherein each of said $C_{3-6}$cycloalkyl, $C_{5-6}$heteroaryl, and -Ph is optionally substituted, for example, with one or more groups selected from:
—F, —Cl, —Br, —I,
—R$^{Y3A}$, —CF$_3$,
—OH, —OR$^{Y3A}$, —OCF$_3$, —$SR^{Y3A}$,
—$NH_2$, —$NHR^{Y3A}$, —$NR^{Y3A}{}_2$, pyrrolidino, piperidino, morpholino, piperizino, (N—$C_{1-4}$alkyl)-piperizino,
—C(=O)OH, —C(=O)$OR^{Y3A}$,
—C(=O)$R^{Y3A}$,
—OC(=O)$R^{Y3A}$,
—C(=O)$NH_2$, —C(=O)$NHR^{Y3A}$, —C(=O)$NR^{Y3A}{}_2$, —C(=O)-pyrrolidino, —C(=O)-piperidino, —C(=O)-morpholino, —C(=O)-piperizino, —C(=O)—(N—$C_{1-4}$alkyl)-piperizino,
—NHC(=O)$R^{Y3A}$, —$NR^{Y3A}$C(=O)$R^{Y3A}$,
—OC(=O)$NH_2$, —OC(=O)$NHR^{Y3A}$, —OC(=O)$NR^{Y3A}{}_2$, —OC(=O)-pyrrolidino, —OC(=O)-piperidino, —OC(=O)-morpholino, —OC(=O)-piperizino, (N—$C_{1-4}$alkyl)-piperizino,
—NHC(=O)OH, —NHC(=O)$OR^{Y3A}$, —$NR^{Y3A}$C(=O)$OR^{Y3A}$,
—NHC(=O)$NH_2$, —NHC(=O)$NHR^{Y3A}$, —NHC(=O)$NR^{Y3A}{}_2$, —NHC(=O)-pyrrolidino, —NHC(=O)-piperidino, —NHC(=O)-morpholino, —NHC(=O)-piperizino, —NHC(=O)—(N—$C_{1-4}$alkyl)-piperizino,
—$NO_2$, and —CN,
wherein each —$R^{Y3A}$ is independently saturated aliphatic $C_{1-4}$alkyl, saturated $C_{3-6}$cycloalkyl, -Ph, or —$CH_2$-Ph, wherein each of said $C_{3-6}$cycloalkyl and -Ph is optionally substituted with one or more substituents selected from —F, —Cl, —Br, —I, —$R^{Y3B}$, —$CF_3$, —OH, —$OR^{Y3B}$, and —$OCF_3$, wherein each —$R^{Y3B}$ is independently saturated aliphatic $C_{1-4}$alkyl.

(B3-4) A compound according to (B3-3), wherein —$B^3$ is independently —$C^3$—SH or -$L^{Y3}$-S—$R^{Y3}$.

(B3-5) A compound according to (B3-3), wherein —$B^3$ is independently -$L^{Y3}$-SH.

(B3-6) A compound according to (B3-3), wherein —$B^3$ is independently -$L^{Y3}$-S—$R^{Y3}$.

(B3-7) A compound according to (B3-3), wherein —$B^3$ is independently -$L^{Y3}$-6(=O)—$R^{Y3}$ or -$L^{Y3}$-S(=O)$_2$—$R^{Y3}$.

(B3-8) A compound according to (B3-3), wherein —$B^3$ is independently -$L^{Y3}$-S(=O)—$R^{Y3}$.

(B3-9) A compound according to (B3-3), wherein —$B^3$ is independently -$L^{Y3}$-S(=O)$_2$—$R^{Y3}$.

(B3-10) A compound according to any one of (B3-3) to (B3-9), wherein -$L^{Y3}$- is independently saturated aliphatic $C_{1-3}$alkylene.

(B3-11) A compound according to any one of (B3-3) to (B3-9), wherein -$L^{Y3}$- is independently —$CH_2$—, —$CH_2CH_2$—, —$CH_2CH_2CH_2$—, —CH($CH_3$)—, —CH($CH_3$)$CH_2$—, —$CH_2$CH($CH_3$)—, or —CH($CH_2CH_3$)—.

(B3-12) A compound according to any one of (B3-3) to (B3-9), wherein -$L^{Y3}$- is independently —$CH_2$—, —$CH_2CH_2$—, or —$CH_2CH_2CH_2$—.

(B3-13) A compound according to any one of (B3-3) to (B3-9), wherein -$L^{Y3}$- is independently —$CH_2$— or —$CH_2CH_2$—.

(B3-14) A compound according to any one of (B3-3) to (B3-9), wherein -$L^{Y3}$- is independently —$CH_2CH_2$—.

(B3-15) A compound according to any one of (B3-3) to (B3-9), wherein -$L^{Y3}$- is independently —$CH_2$—.

(B3-16) A compound according to any one of (B3-3) to (B3-15), wherein —R", if present, is independently saturated aliphatic $C_{1-4}$alkyl, saturated $C_{3-6}$cycloalkyl, -Ph, or —$CH_2$-Ph, wherein each of said $C_{3-6}$cycloalkyl, and -Ph is optionally substituted.

(B3-17) A compound according to any one of (B3-3) to (B3-15), wherein —$R^{Y3}$, if present, is independently saturated aliphatic $C_{1-4}$alkyl, -Ph, or —$CH_2$-Ph, wherein said -Ph is optionally substituted.

(B3-18) A compound according to any one of (B3-3) to (B3-15), wherein —$R^{Y3}$, if present, is independently saturated aliphatic $C_{1-4}$alkyl, saturated $C_{3-6}$cycloalkyl, $C_{5-6}$heteroaryl, —$CH_2$—$C_{5-6}$heteroaryl, -Ph, or —$CH_2$-Ph, wherein each of said $C_{3-6}$cycloalkyl, $C_{5-6}$heteroaryl, and -Ph is optionally substituted with one or more groups selected from:
—F, —Cl, —Br, —I,
—$R^{Y3A}$, —$CF_3$,
—OH, —$OR^{Y3A}$, —$OCF_3$,
—$NH_2$, —$NHR^{Y3A}$, —$NR^{Y3A}{}_2$, pyrrolidino piperidino, morpholino, piperizino, (N—$C_{1-4}$alkyl)-piperizino,
—C(=O)OH, —C(=O)$OR^{Y3A}$,
—C(=O)$R^{Y3A}$,
—OC(=O)$R^{Y3A}$,
—C(=O)$NH_2$, —C(=O)$NHR^{Y3A}$, —C(=O)$NR^{Y3A}{}_2$, —C(=O)-pyrrolidino, —C(=O)-piperidino, —C(=O)-morpholino, —C(=O)-piperizino, —C(=O)—(N—$C_{1-4}$alkyl)-piperizino,
—NHC(=O)$R^{Y3A}$, —$NR^{Y3A}$C(=O)$R^{Y3A}$, and
—CN.

(B3-19) A compound according to any one of (B3-3) to (B3-15), wherein —$R^{Y3}$, if present, is independently saturated aliphatic $C_{1-4}$alkyl, saturated $C_{3-6}$cycloalkyl, -Ph, or —$CH_2$-Ph, wherein each of said $C_{3-6}$cycloalkyl, and -Ph is optionally substituted with one or more groups selected from:
—F, —Cl, —Br, —I,
—$R^{Y3A}$, —$CF_3$,
—OH, —$OR^{Y3A}$, —$OCF_3$,
—$NH_2$, —$NHR^{Y3A}$, —$NR^{Y3A}{}_2$, pyrrolidino piperidino, morpholino, piperizino, (N—$C_{1-4}$alkyl)-piperizino,
—C(=O)OH, —C(=O)$OR^{Y3A}$,
—C(=O)$R^{Y3A}$,
—OC(=O)$R^{Y3A}$,
—C(=O)$NH_2$, —C(=O)$NHR^{Y3A}$, —C(=O)$NR^{Y3A}{}_2$, —C(=O)-pyrrolidino, —C(=O)-piperidino, —C(=O)-morpholino, —C(=O)-piperizino, —C(=O)—(N—$C_{1-4}$alkyl)-piperizino,
—NHC(=O)$R^{Y3A}$, —$NR^{Y3A}$C(=O)$R^{Y3A}$, and
—CN.

(B3-20) A compound according to any one of (B3-3) to (B3-15), wherein —$R^{Y3}$, if present, is independently saturated aliphatic $C_{1-4}$alkyl, -Ph, or —$CH_2$-Ph, wherein said -Ph is optionally substituted with one or more groups selected from:
—F, —Cl, —Br, —I,
—$R^{Y3A}$, —$CF_3$,
—OH, —$OR^{Y3A}$, —$OCF_3$,
—$NH_2$, —$NHR^{Y3A}$, —$NR^{Y3A}{}_2$, pyrrolidino piperidino, morpholino, piperizino, (N—$C_{1-4}$alkyl)-piperizino,
—C(=O)OH, —C(=O)$OR^{Y3A}$,
—C(=O)$R^{Y3A}$,
—OC(=O)$R^{Y3A}$,
—C(=O)$NH_2$, —C(=O)$NHR^{Y3A}$, —C(=O)$NR^{Y3A}{}_2$, —C(=O)-pyrrolidino, —C(=O)-piperidino, —C(=O)-morpholino, —C(=O)-piperizino, —C(=O)—(N—$C_{1-4}$alkyl)-piperizino,
—NHC(=O)$R^{Y3A}$, —$NR^{Y3A}$C(=O)$R^{Y3A}$, and
—CN.

(B3-21) A compound according to any one of (B3-3) to (B3-15), wherein —$R^{Y3}$, if present, is independently saturated aliphatic $C_{1-4}$alkyl, saturated $C_{3-6}$cycloalkyl, $C_{5-6}$heteroaryl, —$CH_2$—$C_{5-6}$heteroaryl, -Ph, or —$CH_2$-Ph, wherein each of said $C_{3-6}$cycloalkyl, $C_{5-6}$heteroaryl, and -Ph is optionally substituted with one or more groups selected from: —F, —Cl, —Br, —I, —R$^{Y3A}$, —CF$_3$, —OH, —OR$^{Y3A}$, and —OCF$_3$.

(B3-22) A compound according to any one of (B3-3) to (B3-15), wherein —R", if present, is independently saturated aliphatic C$_{1-4}$alkyl, saturated C$_{3-6}$cycloalkyl, -Ph, or —CH$_2$-Ph, wherein each of said C$_{3-6}$cycloalkyl, and -Ph is optionally substituted with one or more groups selected from: —F, —Cl, —Br, —I, —R$^{Y3A}$, —CF$_3$, —OH, —OR$^{Y3A}$, and —OCF$_3$.

(B3-23) A compound according to any one of (B3-3) to (B3-15), wherein —R$^{Y3}$, if present, is independently saturated aliphatic C$_{1-4}$alkyl, -Ph, or —CH$_2$-Ph, wherein said -Ph is optionally substituted with one or more groups selected from: —F, —Cl, —Br, —I, —R$^{Y3A}$, —CF$_3$, —OH, —OR$^{Y3A}$, and —OCF$_3$.

(B3-24) A compound according to any one of (B3-3) to (B3-15), wherein —R$^{Y3}$, if present, is independently saturated aliphatic C$_{1-4}$alkyl.

(B3-25) A compound according to any one of (B3-3) to (B3-15), wherein —R$^{Y3}$, if present, is independently -Me, -Et, -nPr, -iPr, -nBu, -sBu, -iBu, or -tBu.

(B3-26) A compound according to any one of (B3-3) to (B3-15), wherein —R$^{Y3}$, if present, is independently -Me, -Et, -nPr, or -iPr.

(B3-27) A compound according to any one of (B3-3) to (B3-15), wherein —R$^{Y3}$, if present, is independently -Me or -Et.

(B3-28) A compound according to any one of (B3-3) to (B3-15), wherein —R$^{Y3}$, if present, is independently -Me.

(B3-29) A compound according to (B3-3), wherein —B$^3$ is independently —CH$_2$—S-Me, —CH$_2$—S(=O)-Me, or —CH$_2$—S(=O)$_2$-Me.

(B3-30) A compound according to (B3-3), wherein —B$^3$ is independently —CH$_2$—S-Me.

(B3-31) A compound according to (B3-3), wherein —B$^3$ is independently —CH$_2$—S(=O)-Me.

(B3-32) A compound according to (B3-3), wherein —B$^3$ is independently —CH$_2$—S(=O)$_2$-Me.

B4. 3-Oxygen-Alkyl Compounds (B4-1) A compound according to any one of (1), (A1-1) to (A1-75), (A2-1) to (A2-19), (A3-1) to (A3-18), (A4-1) to (A4-17), (A5-1) to (A5-19), and (A6-1) to (A6-23), wherein —B is independently —B$^4$.

(B4-2) A compound according to (B4-1), wherein —B$^4$ is independently hydroxy-C$_{1-4}$alkyl or ether-C$_{1-4}$alkyl.

(B4-3) A compound according to (B4-1), wherein —B$^4$ is independently:
-L$^{Y4}$-OH or -L$^{Y4}$-O—R$^{Y4}$,
wherein:
-L$^{Y4}$- is independently saturated aliphatic C$_{1-4}$alkylene, and —R$^{Y4}$ is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph,
wherein each of said C$_{3-6}$cycloalkyl, C$_{5-6}$heteroaryl, and -Ph is optionally substituted, for example, with one or more groups selected from:
—F, —Cl, —Br, —I,
—R$^{Y4A}$, —CF$_3$,
—OH, —OR$^{Y4A}$, —OCF$_3$,
—SR$^{Y4A}$,
—NH$_2$, —NHR$^{Y4A}$, —NR$^{Y4A}$$_2$, pyrrolidino, piperidino, morpholino, piperizino, (N—C$_{1-4}$alkyl)-piperizino,
—C(=O)OH, —C(=O)OR$^{Y4A}$,
—C(=O)R$^{Y4A}$,
—OC(=O)R$^{Y4A}$,
—C(=O)NH$_2$, —C(=O)NHR$^{Y4A}$, —C(=O)NR$^{Y4A}$$_2$,
—C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Y4A}$, —NR$^{Y4A}$C(=O)R$^{Y4A}$,
—OC(=O)NH$_2$, —OC(=O)NHR$^{Y4A}$, —OC(=O)NR$^{Y4A}$$_2$, NHC(=O)-pyrrolidino, —OC(=O)-piperidino, —OC(=O)-morpholino, —OC(=O)-piperizino, (N—C$_{1-4}$alkyl)-piperizino,
—NHC(=O)OH, —NHC(=O)OR$^{Y4A}$, —NR$^{Y4A}$C(=O)OR$^{Y4A}$,
—NHC(=O)NH$_2$, —NHC(=O)NHR$^{Y4A}$, —NHC(=O)NR$^{Y4A}$$_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino,
—NO$_2$, and —CN,
wherein each —R$^{Y4A}$ is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more substituents selected from —F, —Cl, —Br, —I, —R$^{Y4B}$, —CF$_3$, —OH, —OR$^{Y4B}$, and —OCF$_3$, wherein each —R$^{Y4B}$ is independently saturated aliphatic C$_{1-4}$alkyl.

(B4-4) A compound according to (B4-3), wherein —B$^4$ is independently -L$^{Y4}$-OH.

(B4-5) A compound according to (B4-3), wherein —B$^4$ is independently -L$^{Y4}$-O—R$^{Y4}$.

(B4-6) A compound according to any one of (B4-3) to (B4-5), wherein -L$^{Y4}$- is independently saturated aliphatic C$_{1-3}$alkylene.

(B4-7) A compound according to any one of (B4-3) to (B4-5), wherein -L$^{Y4}$- is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

(B4-8) A compound according to any one of (B4-3) to (B4-5), wherein -L$^{Y4}$- is independently —CH$_2$—, —CH$_2$CH$_2$—, or —CH$_2$CH$_2$CH$_2$—.

(B4-9) A compound according to any one of (B4-3) to (B4-5), wherein -L$^{Y4}$- is independently —CH$_2$— or —CH$_2$CH$_2$—.

(B4-10) A compound according to any one of (B4-3) to (B4-5), wherein -L$^{Y4}$- is independently —CH$_2$CH$_2$—.

(B4-11) A compound according to any one of (B4-3) to (B4-5), wherein -L$^{Y4}$- is independently —CH$_2$—.

(B4-12) A compound according to any one of (B4-3) to (B4-11), wherein —R$^{Y4}$, if present, is independently saturated aliphatic C$_{1-4}$alkyl, saturated C$_{3-6}$cycloalkyl, -Ph, or —CH$_2$-Ph, wherein each of said C$_{3-6}$cycloalkyl, and -Ph is optionally substituted.

(B4-13) A compound according to any one of (B4-3) to (B4-11), wherein —R$^{Y4}$, if present, is independently saturated aliphatic C$_{1-4}$alkyl, -Ph, or —CH$_2$-Ph, wherein said -Ph is optionally substituted.

(B4-14) A compound according to any one of (B4-3) to (B4-11), wherein —R$^{Y4}$, if present, is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph, wherein each of said C$_{3-6}$cycloalkyl, C$_{5-6}$heteroaryl, and -Ph is optionally substituted with one or more groups selected from:
—F, —Cl, —Br, —I,
—R$^{Y4A}$, —CF$_3$,
—OH, —OR$^{Y4A}$, —OCF$_3$,
—NH$_2$, —NHR$^{Y4A}$, —NR$^{Y4A}$$_2$, pyrrolidino piperidino, morpholino, piperizino, (N—C$_{1-4}$alkyl)-piperizino,
—C(=O)OH, —C(=O)OR$^{Y4A}$,
—C(=O)R$^{Y4A}$,
—OC(=O)R$^{Y4A}$,
—C(=O)NH$_2$, —C(=O)NHR$^{Y4A}$, —C(=O)NR$^{Y4A}$$_2$,
—C(=O)-pyrrolidino, —C(=O)-piperidino, —C(=O)-morpholino, —C(=O)-piperizino,
—C(=O)—(N—C$_{1-4}$alkyl)-piperizino,
—NHC(=O)R$^{Y4A}$, —NR$^{Y4A}$C(=O)R$^{Y4A}$, and
—CN.

(B4-15) A compound according to any one of (B4-3) to (B4-11), wherein —R$^{Y4}$, if present, is independently saturated aliphatic C$_{1-4}$alkyl, saturated C$_{3-6}$cycloalkyl, -Ph, or —CH$_2$-Ph, wherein each of said C$_{3-6}$cycloalkyl, and -Ph is optionally substituted with one or more groups selected from:
—F, —Cl, —Br, —I,
—R$^{Y4A}$, —CF$_3$,
—OH, —OR$^{Y4A}$, —OCF$_3$,
—NH$_2$, —NHR$^{Y4A}$, —NR$^{Y4A}{}_2$, pyrrolidino piperidino, morpholino, piperizino, (N—C$_{1-4}$alkyl)-piperizino,
—C(=O)OH, —C(=O)OR$^{Y4A}$,
—C(=O)R$^{Y4A}$,
—OC(=O)R$^{Y4A}$,
—C(=O)NH$_2$, —C(=O)NHR$^{Y4A}$, —C(=O)NR$^{Y4A}{}_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Y4A}$, —NR$^{Y4A}$C(=O)R$^{Y4A}$, and
—CN.

(B4-16) A compound according to any one of (B4-3) to (B4-11), wherein —R$^{Y4}$, if present, is independently saturated aliphatic C$_{1-4}$alkyl, -Ph, or —CH$_2$-Ph, wherein said -Ph is optionally substituted with one or more groups selected from:
—F, —Cl, —Br, —I,
—R$^{Y4A}$, —CF$_3$,
—OH, —OR$^{Y4A}$, —OCF$_3$,
—NH$_2$, —NHR$^{Y4A}$, —NR$^{Y4A}{}_2$, pyrrolidino piperidino, morpholino, piperizino, (N—C$_{1-4}$alkyl)-piperizino,
—C(=O)OH, —C(=O)OR$^{Y4A}$,
—C(=O)R$^{Y4A}$,
—OC(=O)R$^{Y4A}$,
—C(=O)NH$_2$, —C(=O)NHR$^{Y4A}$, —C(=O)NR$^{Y4A}{}_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Y4A}$, —NR$^{Y4A}$C(=O)R$^{Y4A}$, and
—CN.

(B4-17) A compound according to any one of (B4-3) to (B4-11), wherein —R$^{Y4}$, if present, is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph, wherein each of said C$_{3-6}$cycloalkyl, C$_{5-6}$heteroaryl, and -Ph is optionally substituted with one or more groups selected from: —F, —Cl, —Br, —I, —R$^{Y4A}$, —CF$_3$, —OH, —OR$^{Y4A}$, and —OCF$_3$.

(B4-18) A compound according to any one of (B4-3) to (B4-11), wherein —R$^{Y4}$, if present, is independently saturated aliphatic C$_{1-4}$alkyl, saturated C$_{3-6}$cycloalkyl, -Ph, or —CH$_2$-Ph, wherein each of said C$_{3-6}$cycloalkyl, and -Ph is optionally substituted with one or more groups selected from: —F, —Cl, —Br, —I, —R$^{Y4A}$, —CF$_3$, —OH, —OR$^{Y4A}$, and —OCF$_3$.

(B4-19) A compound according to any one of (B4-3) to (B4-11), wherein —R$^{Y4}$, if present, is independently saturated aliphatic C$_{1-4}$alkyl, -Ph, or —CH$_2$-Ph, wherein said -Ph is optionally substituted with one or more groups selected from: —F, —Cl, —Br, —I, —R$^{Y4A}$, —CF$_3$, —OH, —OR$^{Y4A}$, and —OCF$_3$.

(B4-20) A compound according to any one of (B4-3) to (B4-11), wherein —R$^{Y4}$, if present, is independently saturated aliphatic C$_{1-4}$alkyl.

(B4-21) A compound according to any one of (B4-3) to (B4-11), wherein —R$^{Y4}$, if present, is independently -Me, -Et, -nPr, -iPr, -nBu, -sBu, -iBu, or -tBu.

(B4-22) A compound according to any one of (B4-3) to (B4-11), wherein —R$^{Y4}$, if present, is independently -Me, -Et, -nPr, or -iPr.

(B4-23) A compound according to any one of (B4-3) to (B4-11), wherein —R$^{Y4}$, if present, is independently -Me or -Et.

(B4-24) A compound according to any one of (B4-3) to (B4-11), wherein —R$^{Y4}$, if present, is independently -Me.

(B4-25) A compound according to (B4-3), wherein —B$^4$ is independently —CH$_2$—O-Me.

B5. 3-Aryl-Alkyl Compounds (B5-1) A compound according to any one of (1), (A1-1) to (A1-75), (A2-1) to (A2-19), (A3-1) to (A3-18), (A4-1) to (A4-17), (A5-1) to (A5-19), and (A6-1) to (A6-23), wherein —B is independently —B$^5$.

(B5-2) A compound according to (B5-1), wherein —B$^5$ is independently phenyl-C$_{1-6}$alkyl or C$_{5-6}$heteroaryl-C$_{1-6}$alkyl, and is optionally substituted.

(B5-3) A compound according to (B5-1), wherein —B$^5$ is independently -L$^{Y5}$-Ar$^{Y5}$,
wherein:
-L$^{Y5}$- is independently saturated aliphatic C$_{1-4}$alkylene, and
—Ar$^{Y5}$ is independently C$_{5-6}$heteroaryl or -Ph,
wherein each of said C$_{5-6}$heteroaryl and -Ph is optionally substituted, for example, with one or more groups selected from:
—F, —Cl, —Br, —I,
—R$^{Y5A}$, —CF$_3$,
—OH, —OR$^{Y5A}$, —OCF$_3$,
—SR$^{Y5A}$,
—NH$_2$, —NHR$^{Y5A}$, —NR$^{Y5A}{}_2$, pyrrolidino, piperidino, morpholino, piperizino, (N—C$_{1-4}$alkyl)-piperizino,
—C(=O)OH, —C(=O)OR$^{Y5A}$,
—C(=O)R$^{Y5A}$,
—OC(=O)R$^{Y5A}$,
—C(=O)NH$_2$, —C(=O)NHR$^{Y5A}$, —C(=O)NR$^{Y5A}{}_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Y5A}$, —NR$^{Y5A}$C(=O)R$^{Y5A}$,
OC(=O)NH$_2$, —OC(=O)NHR$^{Y5A}$, —OC(=O)NR$^{Y5A}{}_2$,
—OC(=O)-pyrrolidino, —OC(=O)-piperidino,
—OC(=O)-morpholino, —OC(=O)-piperizino,
(N—C$_{1-4}$alkyl)-piperizino,
—NHC(=O)OH, —NHC(=O)OR$^{Y5A}$, —NR$^{Y5A}$C(=O)OR$^{Y5A}$,
—NHC(=O)NH$_2$, —NHC(=O)NHR$^{Y5A}$, —NHC(=O)NR$^{Y5A}{}_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino,
—NO$_2$, and —CN,
wherein each —R$^{Y5A}$ is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more substituents selected from —F, —Cl, —Br, —I, —R$^{Y5B}$, —CF$_3$, —OH, —OR$^{Y5B}$, and —OCF$_3$, wherein each —R$^{Y5B}$ is independently saturated aliphatic C$_{1-4}$alkyl.

(B5-4) A compound according to any one of (B5-3) to (B5-5), wherein -L$^{Y5}$- is independently saturated aliphatic C$_{1-3}$alkylene.

(B5-5) A compound according to any one of (B5-3) to (B5-5), wherein -L$^{Y5}$- is independently saturated aliphatic C$_{2-4}$alkylene.

(B5-6) A compound according to any one of (B5-3) to (B5-5), wherein -L$^{Y5}$- is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

(B5-7) A compound according to any one of (B5-3) to (B5-5), wherein -L$^{Y5}$- is independently —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

(B5-8) A compound according to any one of (B5-3) to (B5-5), wherein -L$^{Y5}$- is independently —CH$_2$—, —CH(CH$_3$)—, or —CH(CH$_2$CH$_3$)—.

(B5-9) A compound according to any one of (B5-3) to (B5-5), wherein -L$^{Y5}$- is independently —CH(CH$_3$)— or —CH(CH$_2$CH$_3$)—.

(B5-10) A compound according to any one of (B5-3) to (B5-5), wherein -L$^{Y5}$- is independently —CH(CH$_3$)—.

(B5-11) A compound according to any one of (B5-3) to (B5-5), wherein -L$^{Y5}$- is independently —CH(CH$_2$CH$_3$)—.

(B5-12) A compound according to any one of (B5-3) to (B5-5), wherein -L$^{Y5}$- is independently —CH$_2$CH$_2$—, —CH(CH$_3$)CH$_2$—, or —CH$_2$CH(CH$_3$)—.

(B5-13) A compound according to any one of (B5-3) to (B5-5), wherein -L$^{Y5}$- is independently —CH$_2$CH$_2$—.

(B5-14) A compound according to any one of (B5-3) to (B5-13), wherein —Ar$^{Y5}$ is independently furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, or -Ph,
wherein each of said furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, and -Ph is optionally substituted.

(B5-15) A compound according to any one of (B5-3) to (B5-13), wherein —Ar$^{Y5}$ is independently -Ph, wherein said -Ph is optionally substituted.

(B5-16) A compound according to any one of (B5-3) to (B5-13), wherein —Ar$^{Y5}$ is independently C$_{5-6}$heteroaryl or -Ph, wherein each of said C$_{5-6}$heteroaryl and -Ph is optionally substituted with one or more groups selected from:
—F, —Cl, —Br, —I,
—R$^{Y5A}$, —CF$_3$,
—OH, —OR$^{Y5A}$, —OCF$_3$,
—NH$_2$, —NHR$^{Y5A}$, —NR$^{Y5A}_2$, pyrrolidino piperidino, morpholino, piperizino, (N—C$_{1-4}$alkyl)-piperizino,
—C(=O)OH, —C(=O)OR$^{Y5A}$,
—C(=O)R$^{Y5A}$,
—OC(=O)R$^{Y5A}$,
—C(=O)NH$_2$, —C(=O)NHR$^{Y5A}$, —C(=O)NR$^{Y5A}_2$,
—C(=O)-pyrrolidino, —C(=O)-piperidino,
—C(=O)-morpholino, —C(=O)-piperizino,
—C(=O(N—C$_{1-4}$alkyl)-piperizino,
—NHC(=O)R$^{Y5A}$, —NR$^{Y5A}$C(=O)R$^{Y5A}$, and
—CN.

(B5-17) A compound according to any one of (B5-3) to (B5-13), wherein —Ar$^{Y5}$ is independently furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, or -Ph,
wherein each of said furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, and -Ph is optionally substituted with one or more groups selected from:
—F, —Cl, —Br, —I,
—R$^{Y5A}$, —CF$_3$,
—OH, —OR$^{Y5A}$, —OCF$_3$,
—NH$_2$, —NHR$^{Y5A}$, —NR$^{Y5A}_2$, pyrrolidino piperidino, morpholino, piperizino, (N—C$_{1-4}$alkyl)-piperizino,
—C(=O)OH, —C(=O)OR$^{Y5A}$,
—C(=O)R$^{Y5A}$,
—OC(=O)R$^{Y5A}$,
—C(=O)NH$_2$, —C(=O)NHR$^{Y5A}$, —C(=O)NR$^{Y5A}_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Y5A}$, —NR$^{Y5A}$C(=O)R$^{Y5A}$, and
—CN.

(B5-18) A compound according to any one of (B5-3) to (B5-13), wherein —Ar$^{Y5}$ is independently -Ph, wherein said -Ph is optionally substituted with one or more groups selected from:
—F, —Cl, —Br, —I,
—R$^{Y5A}$, —CF$_3$,
—OH, —OR$^{Y5A}$, —OCF$_3$,
—NH$_2$, —NHR$^{Y5A}$, —NR$^{Y5A}_2$, pyrrolidino piperidino, morpholino, piperizino, (N—C$_{1-4}$alkyl-piperizino,
—C(=O)OH, —C(=O)OR$^{Y5A}$,
—C(=O)R$^{Y5A}$,
—OC(=O)R$^{Y5A}$,
—C(=O)NH$_2$, —C(=O)NHR$^{Y5A}$, —C(=O)NR$^{Y5A}_2$,
—C(=O)-pyrrolidino, —C(=O)-piperidino,
—C(=O)-morpholino, —C(=O)-piperizino,
—C(=O(N—C$_{1-4}$alkyl)-piperizino,
—NHC(=O)R$^{Y5A}$, —NR$^{Y5A}$C(=O)R$^{Y5A}$, and
—CN.

(B5-19) A compound according to any one of (B5-3) to (B5-13), wherein —Ar$^{Y5}$ is independently C$_{5-6}$heteroaryl, or -Ph, wherein each of said C$_{5-6}$heteroaryl and -Ph is optionally substituted with one or more groups selected from:
—F, —Cl, —Br, —I, —R$^{Y5A}$, —CF$_3$, —OH, —OR$^{Y5A}$, and —OCF$_3$.

(B5-20) A compound according to any one of (B5-3) to (B5-13), wherein —Ar$^{Y5}$ is independently -Ph, wherein said -Ph is optionally substituted with one or more groups selected from: —F, —Cl, —Br, —I, —R$^{Y5A}$, —CF$_3$, —OH, —OR$^{Y5A}$, and —OCF$_3$.

(B5-21) A compound according to any one of (B5-3) to (B5-13), wherein —Ar$^{Y5}$ is independently -Ph, wherein said -Ph is optionally substituted with one or more groups selected from: —F, —Cl, —Br, —I, and —OR$^{Y5A}$.

(B5-22) A compound according to any one of (B5-3) to (B5-13), wherein —Ar$^{Y5}$ is independently -Ph, wherein said -Ph is optionally substituted with one or more groups selected from: —Br and —OMe.

(B5-23) A compound according to (B5-3), wherein —B$^5$ is —CH$_2$-Ph.

B6. 8-Acyl-Alkyl, 8-Acid-Alkyl, and 8-Ester-Alkyl Compounds (B6-1) A compound according to any one of (1), (A1-1) to (A1-75), (A2-1) to (A2-19), (A3-1) to (A3-18), (A4-1) to (A4-17), (A5-1) to (A5-19), and (A6-1) to (A6-23), wherein —B is independently —B$^6$.

(B6-2) A compound according to (B6-1), wherein —B$^6$ is independently acyl-C$_{1-6}$alkyl, carboxy-C$_{1-6}$alkyl, oxacyl-C$_{1-6}$alkyl, or acyloxy-C$_{1-6}$alkyl.

(B6-3) A compound according to (B6-1), wherein —B$^6$ is independently:
-L$^{Y6}$-C(=O)R$^{Y6}$, -L$^{Y6}$-C(=O)OH, -L$^{Y6}$-C(=O)OR$^{Y6}$, or -L$^{Y6}$-O—C(=O)R$^{Y6}$,
wherein:
-L$^{Y6}$- is independently saturated aliphatic C$_{1-4}$alkylene, and —$R^{Y6}$ is independently saturated aliphatic $C_{1-4}$alkyl, saturated $C_{3-6}$cycloalkyl, $C_{5-6}$heteroaryl, —$CH_2$—$C_{5-6}$heteroaryl, -Ph, or —$CH_2$-Ph,
wherein each of said $C_{3-6}$cycloalkyl, $C_{5-6}$heteroaryl, and -Ph is optionally substituted, for example, with one or more groups selected from:
—F, —Cl, —Br, —I,
—$R^{Y6A}$, —$CF_3$,
—OH, —$OR^{Y6A}$, —$OCF_3$,
—$SR^{Y6A}$,
—$NH_2$, —$NHR^{Y6A}$, —$NR^{Y6A}{}_2$, pyrrolidino, piperidino, morpholino, piperizino, (N—$C_{1-4}$alkyl)-piperizino,
—C(=O)OH, —C(=O)$OR^{Y6A}$,
—C(=O)$R^{Y6A}$,
—OC(=O)$R^{Y6A}$,
—C(=O)$NH_2$, —C(=O)$NHR^{Y6A}$, —C(=O)$NR^{Y6A}{}_2$, —C(=O)-pyrrolidino, —C(=O)-piperidino, —C(=O)-morpholino, —C(=O)-piperizino, —C(=O)—(N—$C_{1-4}$alkyl)-piperizino,
—NHC(=O)$R^{Y6A}$, —$NR^{Y6A}$C(=O)$R^{Y6A}$,
—OC(=O)$NH_2$, —OC(=O)$NHR^{Y6A}$, —OC(=O)$NR^{Y6A}{}_2$, —OC(=O)-pyrrolidino, —OC(=O)-piperidino, —OC(=O)-morpholino, —OC(=O)-piperizino, (N—$C_{1-4}$alkyl)-piperizino,
—NHC(=O)OH, —NHC(=O)$OR^{Y6A}$, —$NR^{Y6A}$C(=O)$OR^{Y6A}$,
—NHC(=O)$NH_2$, —NHC(=O)$NHR^{Y6A}$, —NHC(=O)$NR^{Y6A}{}_2$, —NHC(=O)-pyrrolidino, —NHC(=O)-piperidino, —NHC(=O)-morpholino, —NHC(=O)-piperizino, —NHC(=O)—(N—$C_{1-4}$alkyl)-piperizino,
—$NO_2$, and —CN,
wherein each —$R^{Y6A}$ is independently saturated aliphatic $C_{1-4}$alkyl, saturated $C_{3-6}$cycloalkyl, -Ph, or —$CH_2$-Ph, wherein each of said $C_{3-6}$cycloalkyl and -Ph is optionally substituted with one or more substituents selected from —F, —Cl, —Br, —I, —$R^{Y6B}$, —$CF_3$, —OH, —$OR^{Y6B}$, and —$OCF_3$, wherein each —$R^{Y6B}$ is independently saturated aliphatic $C_{1-4}$alkyl.

(B6-4) A compound according to (B6-3), wherein —$B^6$ is independently -$L^{Y6}$-C(=O)$R^{Y6}$.

(B6-5) A compound according to (B6-3), wherein —$B^6$ is independently -$L^{Y6}$-C(=O)OH, -$L^{Y6}$-C(=O)$OR^{Y6}$, or -$L^{Y6}$-O—C(=O)$R^{Y6}$.

(B6-6) A compound according to (B6-3), wherein —$B^6$ is independently -$L^{Y6}$-C(=O)OH or -$L^{Y6}$-C(=O)$OR^{Y6}$.

(B6-7) A compound according to (B6-3), wherein —$B^6$ is independently -$L^{Y6}$-C(=O)OH.

(B6-8) A compound according to (B6-3), wherein —$B^6$ is independently -$L^{Y6}$-C(=O)$OR^{Y6}$.

(B6-9) A compound according to (B6-3), wherein —$B^6$ is independently -$L^{Y6}$-O—C(=O)$R^{Y6}$.

(B6-10) A compound according to any one of (B6-3) to (B6-9), wherein -$L^{Y6}$- is independently saturated aliphatic $C_{1-3}$alkylene.

(B6-11) A compound according to any one of (B6-3) to (B6-9), wherein -$L^{Y6}$- is independently —$CH_2$—, —$CH_2CH_2$—, —$CH_2CH_2CH_2$—, —CH($CH_3$)—, —CH($CH_3$)$CH_2$—, —$CH_2$CH($CH_3$)—, or —CH($CH_2CH_3$)—.

(B6-12) A compound according to any one of (B6-3) to (B6-9), wherein -$L^{Y6}$- is independently —$CH_2$—, —$CH_2CH_2$—, or —$CH_2CH_2CH_2$—.

(B6-13) A compound according to any one of (B6-3) to (B6-9), wherein -$L^{Y6}$- is independently —$CH_2$— or —$CH_2CH_2$—.

(B6-14) A compound according to any one of (B6-3) to (B6-9), wherein -$L^{Y6}$- is independently —$CH_2CH_2$—.

(B6-15) A compound according to any one of (B6-3) to (B6-9), wherein -$L^{Y5}$- is independently —$CH_2$—.

(B6-16) A compound according to any one of (B6-3) to (B6-15), wherein —$R^{Y6}$, if present, is independently saturated aliphatic $C_{1-4}$alkyl, saturated $C_{3-6}$cycloalkyl, -Ph, or —$CH_2$-Ph, wherein each of said $C_{3-6}$cycloalkyl and -Ph is optionally substituted.

(B6-17) A compound according to any one of (B6-3) to (B6-15), wherein —$R^{Y6}$, if present, is independently saturated aliphatic $C_{1-4}$alkyl, -Ph, or —$CH_2$-Ph, wherein said -Ph is optionally substituted.

(B6-18) A compound according to any one of (B6-3) to (B6-15), wherein —$R^{Y6}$, if present, is independently saturated aliphatic $C_{1-4}$alkyl, saturated $C_{3-6}$cycloalkyl, $C_{5-6}$heteroaryl, —$CH_2$—$C_{5-6}$heteroaryl, -Ph, or —$CH_2$-Ph, wherein each of said $C_{3-6}$cycloalkyl, $C_{5-6}$heteroaryl, and -Ph is optionally substituted with one or more groups selected from:
—F, —Cl, —Br, —I,
—$IR^{Y6A}$, —$CF_3$,
—OH, —$OR^{Y6A}$, —$OCF_3$,
—$NH_2$, —$NHR^{Y6A}$, —$NR^{Y6A}{}_2$, pyrrolidino piperidino, morpholino, piperizino, (N—$C_{1-4}$alkyl)-piperizino,
—C(=O)OH, —C(=O)$OR^{Y6A}$,
—C(=O)$R^{Y6A}$,
—OC(=O)$R^{Y6A}$,
—C(=O)$NH_2$, —C(=O)$NHR^{Y6A}$, —C(=O)$NR^{Y6A}{}_2$, —C(=O)-pyrrolidino, —C(=O)-piperidino, —C(=O)-morpholino, —C(=O)-piperizino, —C(=O(N—$C_{1-4}$alkyl)-piperizino,
—NHC(=O)$R^{Y6A}$, —$NR^{Y6A}$C(=O)$R^{Y6A}$, and —CN.

(B6-19) A compound according to any one of (B6-3) to (B6-15), wherein —$R^{Y6}$, if present, is independently saturated aliphatic $C_{1-4}$alkyl, saturated $C_{3-6}$cycloalkyl, -Ph, or —$CH_2$-Ph, wherein each of said $C_{3-6}$cycloalkyl and -Ph is optionally substituted with one or more groups selected from:
—F, —Cl, —Br, —I,
—$R^{Y6A}$, —$CF_3$,
—OH, —$OR^{Y6A}$, —$OCF_3$,
—$NH_2$, —$NHR^{Y6A}$, —$NR^{Y6A}{}_2$, pyrrolidino piperidino, morpholino, piperizino, (N—$C_{1-4}$alkyl)-piperizino,
—C(=O)OH, —C(=O)$OR^{Y6A}$,
—C(=O)$R^{Y6A}$,
—OC(=O)$R^{Y6A}$,
—C(=O)$NH_2$, —C(=O)$NHR^{Y6A}$, —C(=O)$NR^{Y6A}{}_2$, —C(=O)-pyrrolidino, —C(=O)-piperidino, —C(=O)-morpholino, —C(=O)-piperizino, —C(=O(N—$C_{1-4}$alkylypiperizino,
—NHC(=O)$R^{Y6A}$, —$NR^{Y6A}$C(=O)$R^{Y6A}$, and —CN.

(B6-20) A compound according to any one of (B6-3) to (B6-15), wherein —$R^{Y6}$, if present, is independently saturated aliphatic $C_{1-4}$alkyl, -Ph, or —$CH_2$-Ph, wherein said -Ph is optionally substituted with one or more groups selected from:
—F, —Cl, —Br, —I,
—$R^{Y6A}$, —$CF_3$,
—OH, —$OR^{Y6A}$, —$OCF_3$,
—$NH_2$, —$NHR^{Y6A}$, —$NR^{Y6A}{}_2$, pyrrolidino piperidino, morpholino, piperizino, (N—$C_{1-4}$alkyl)-piperizino,
—C(=O)OH, —C(=O)$OR^{Y6A}$,
—C(=O)$R^{Y6A}$,
—OC(=O)$R^{Y6A}$,
—C(=O)$NH_2$, —C(=O)$NHR^{Y6A}$, —C(=O)$NR^{Y6A}{}_2$, —C(=O)-pyrrolidino, —C(=O)-piperidino, —C(=O)-morpholino, —C(=O)-piperizino, —C(=O(N—C$_{1-4}$alkyl)-piperizino, —NHC(=O)R$^{Y6A}$, —NR$^{Y6A}$C(=O)R$^{Y6A}$, and —CN.

(B6-21) A compound according to any one of (B6-3) to (B6-15), wherein —R$^{Y6}$, if present, is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph, wherein each of said C$_{3-6}$cycloalkyl, C$_{5-6}$heteroaryl, and -Ph is optionally substituted with one or more groups selected from: —F, —Cl, —Br, —I, —R$^{Y6A}$, —CF$_3$, —OH, —OR$^{Y6A}$, and —OCF$_3$.

(B6-22) A compound according to any one of (B6-3) to (B6-15), wherein —R$^{Y6}$, if present, is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more groups selected from: —F, —Cl, —Br, —I, —R$^{Y6A}$, —CF$_3$, —OH, —OR$^{Y6A}$, and —OCF$_3$.

(B6-23) A compound according to any one of (B6-3) to (B6-15), wherein —R$^{Y6}$, if present, is independently saturated aliphatic C$_{1-4}$alkyl, -Ph, or —CH$_2$-Ph, wherein said -Ph is optionally substituted with one or more groups selected from: —F, —Cl, —Br, —I, —R$^{Y6A}$, —CF$_3$, —OH, —OR$^{Y6A}$, and —OCF$_3$.

(B6-24) A compound according to any one of (B6-3) to (B6-15), wherein —R$^{Y6}$, if present, is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph.

(B6-25) A compound according to any one of (B6-3) to (B6-15), wherein —R$^{Y6}$, if present, is independently saturated aliphatic C$_{1-4}$alkyl, saturated C$_{3-6}$cycloalkyl, -Ph, or —CH$_2$-Ph.

(B6-26) A compound according to any one of (B6-3) to (B6-15), wherein —R$^{Y6}$, if present, is independently saturated aliphatic C$_{1-4}$alkyl, -Ph, or —CH$_2$-Ph.

(B6-27) A compound according to any one of (B6-3) to (B6-15), wherein —R$^{Y6}$, if present, is independently saturated aliphatic C$_{1-4}$alkyl.

(B6-28) A compound according to any one of (B6-3) to (B6-15), wherein —R$^{Y6}$, if present, is independently -Me, -Et, -nPr, -iPr, -nBu, -sBu, -iBu, or -tBu.

(B6-29) A compound according to (B6-3), wherein —B$^6$ is independently —CH$_2$—C(=O)—O-Et.

B7. 3-Amido-Alkyl Compounds (B7-1) A compound according to any one of (1), (A1-1) to (A1-75), (A2-1) to (A2-19), (A3-1) to (A3-18), (A4-1) to (A4-17), (A5-1) to (A5-19), and (A6-1) to (A6-23), wherein —B is independently —B$^7$.

(B7-2) A compound according to (B7-1), wherein —B$^7$ is independently amido-C$_{1-4}$alkyl or substituted amido-C$_{1-4}$alkyl.

(B7-3) A compound according to (B7-1), wherein —B$^7$ is independently:
-L$^{Y7}$-C(=O)NH$_2$, -L$^{Y7}$-C(=O)NHR$^{Y7}$, -L$^{Y7}$-(=O)NR$^{Y7}$$_2$, -L$^{Y7}$-C(=O)-pyrrolidino, -L$^{Y7}$-C(=O)-piperidino, -L$^{Y7}$-C(=O)-morpholino, -L$^{Y7}$-C(=O)-piperizino, or -L$^{Y7}$-C(=O)—(N—C$_{1-4}$alkyl)-piperizino,
wherein:
-L$^{Y7}$- is independently saturated aliphatic C$_{1-4}$alkylene, and —R$^{Y7}$ is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph,
wherein each of said C$_{3-6}$cycloalkyl, C$_{5-6}$heteroaryl, and -Ph is optionally substituted, for example, with one or more groups selected from:

—F, —Cl, —Br, —I,
—R$^{Y7A}$, —CF$_3$,
—OH, —OR$^{Y7A}$, —OCF$_3$,
—SR$^{Y7A}$,
—NH$_2$, —NHR$^{Y7A}$, —NR$^{Y7A}$$_2$, pyrrolidino, piperidino, morpholino, piperizino, (N—C$_{1-4}$alkyl)-piperizino,
—C(=O)OH, —C(=O)OR$^{Y7A}$,
—C(=O)R$^{Y7A}$,
—OC(=O)R$^{Y7A}$,
—C(=O)NH$_2$, —C(=O)NHR$^{Y7A}$, —C(=O)NR$^{Y7A}$$_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Y7A}$, —NR$^{Y7A}$C(=O)R$^{Y7A}$,
—OC(=O)NH$_2$, —OC(=O)NHR$^{Y7A}$, —OC(=O)NR$^{Y7A}$$_2$, —OC(=O)-pyrrolidino, —OC(=O)-piperidino, —OC(=O)-morpholino, —OC(=O)-piperizino, (N—C$_{1-4}$alkyl)-piperizino,
—NHC(=O)OH, —NHC(=O)OR$^{Y7A}$, —NR$^{Y7A}$C(=O)OR$^{Y7A}$,
—NHC(=O)NH$_2$, —NHC(=O)NHR$^{Y7A}$, —NHC(=O)NR$^{Y7A}$$_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino,
—NO$_2$, and —CN,
wherein each —R$^{Y7A}$ is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more substituents selected from —F, —Cl, —Br, —I, —R$^{Y7B}$, —CF$_3$, —OH, —OR$^{Y7B}$, and —OCF$_3$, wherein each —R$^{Y7B}$ is independently saturated aliphatic C$_{1-4}$alkyl.

(B7-4) A compound according to (B7-3), wherein —B$^7$ is independently -L$^{Y7}$-C(=O)NH$_2$, -L$^{Y7}$-C(=O)NHR$^{Y7}$, or -L$^{Y7}$-C(=O)NR$^{Y7}$$_2$.

(B7-5) A compound according to (B7-3), wherein —B$^7$ is independently -L$^{Y7}$-C(=O)NH$_2$.

(B7-6) A compound according to (B7-3), wherein —B$^7$ is independently -L$^{Y7}$-C(=O)-pyrrolidino, -L$^{Y7}$-C(=O)-piperidino, -L$^{Y7}$-C(=O)-morpholino, -L$^{Y7}$-C(=O)-piperizino, or -L$^{Y7}$-C(=O)—(N—C$_{1-4}$alkyl)-piperizino.

(B7-7) A compound according to any one of (B7-3) to (B7-6), wherein -L$^{Y7}$- is independently saturated aliphatic C$_{1-3}$alkylene.

(B7-8) A compound according to any one of (B7-3) to (B7-6), wherein -L$^{Y7}$- is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

(B7-9) A compound according to any one of (B7-3) to (B7-6), wherein -L$^{Y7}$ is independently —CH$_2$—, —CH$_2$CH$_2$—, or —CH$_2$CH$_2$CH$_2$—.

(B7-10) A compound according to any one of (B7-3) to (B7-6), wherein -L$^{Y7}$ is independently —CH$_2$— or —CH$_2$CH$_2$—.

(B7-11) A compound according to any one of (B7-3) to (B7-6), wherein -L$^{Y7}$ is independently —CH$_2$CH$_2$—.

(B7-12) A compound according to any one of (B7-3) to (B7-6), wherein -L$^{Y7}$ is independently —CH$_2$—.

(B7-13) A compound according to any one of (B7-3) to (B7-12), wherein —R$^{Y7}$, if present, is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted.

(B7-14) A compound according to any one of (B7-3) to (B7-12), wherein —IR$^{Y7}$, if present, is independently saturated aliphatic C$_{1-4}$alkyl, -Ph, or —CH$_2$-Ph, wherein said -Ph is optionally substituted.

(B7-15) A compound according to any one of (B7-3) to (B7-12), wherein —$R^{Y7}$, if present, is independently saturated aliphatic $C_{1-4}$alkyl, saturated $C_{3-6}$cycloalkyl, $C_{5-6}$heteroaryl, —$CH_2$—$C_{5-6}$heteroaryl, -Ph, or —$CH_2$-Ph, wherein each of said $C_{3-6}$cycloalkyl, $C_{5-6}$heteroaryl, and -Ph is optionally substituted with one or more groups selected from:
—F, —Cl, —Br, —I,
—$R^{Y7A}$, —$CF_3$,
—OH, —$OR^{Y7A}$, —$OCF_3$,
—$NH_2$, —$NHR^{Y7A}$, —$NR^{Y7A}{}_2$, pyrrolidino piperidino, morpholino, piperizino, (N—$C_{1-4}$alkyl)-piperizino,
—C(=O)OH, —C(=O)$OR^{Y7A}$,
—C(=O)$R^{Y7A}$,
—OC(=O)$R^{Y7A}$,
—C(=O)$NH_2$, —C(=O)$NHR^{Y7A}$, —C(=O)$NR^{Y7A}{}_2$,
—C(=O)-pyrrolidino, —C(=O)-piperidino,
—C(=O)-morpholino, —C(=O)-piperizino,
—C(=O)—(N—$C_{1-4}$alkyl)-piperizino,
—NHC(=O)$R^{Y7A}$, —$NR^{Y7A}$C(=O)$R^{Y7A}$, and
—CN.

(B7-16) A compound according to any one of (B7-3) to (B7-12), wherein —$R^{Y7}$, if present, is independently saturated aliphatic $C_{1-4}$alkyl, saturated $C_{3-6}$cycloalkyl, -Ph, or —$CH_2$-Ph, wherein each of said $C_{3-6}$cycloalkyl and -Ph is optionally substituted with one or more groups selected from:
—F, —Cl, —Br, —I,
—$R^{Y7A}$, —$CF_3$,
—OH, —$OR^{Y7A}$, —$OCF_3$,
—$NH_2$, —$NHR^{Y7A}$, —$NR^{Y7A}{}_2$, pyrrolidino piperidino, morpholino, piperizino, (N—$C_{1-4}$alkyl)-piperizino,
—C(=O)OH, —C(=O)$OR^{Y7A}$,
—C(=O)$R^{Y7A}$,
—OC(=O)$R^{Y7A}$,
—C(=O)$NH_2$, —C(=O)$NHR^{Y7A}$, —C(=O)$NR^{Y7A}{}_2$,
—C(=O)-pyrrolidino, —C(=O)-piperidino,
—C(=O)-morpholino, —C(=O)-piperizino,
—C(=O)—(N—$C_{1-4}$alkyl)-piperizino,
—NHC(=O)$R^{Y7A}$, —$NR^{Y7A}$C(=O)$R^{Y7A}$, and
—CN.

(B7-17) A compound according to any one of (B7-3) to (B7-12), wherein —$R^{Y7}$, if present, is independently saturated aliphatic $C_{1-4}$alkyl, -Ph, or —$CH_2$-Ph, wherein said -Ph is optionally substituted with one or more groups selected from:
—F, —Cl, —Br, —I,
—$R^{Y7A}$, —$CF_3$,
—OH, —$OR^{Y7A}$, —$OCF_3$,
—$NH_2$, —$NHR^{Y7A}$, —$NR^{Y7A}{}_2$, pyrrolidino piperidino, morpholino, piperizino, (N—$C_{1-4}$alkyl)-piperizino,
—C(=O)OH, —C(=O)$OR^{Y7A}$,
—C(=O)$R^{Y7A}$,
—OC(=O)$R^{Y7A}$,
—C(=O)$NH_2$, —C(=O)$NHR^{Y7A}$, —C(=O)$NR^{Y7A}{}_2$,
—C(=O)-pyrrolidino, —C(=O)-piperidino,
—C(=O)-morpholino, —C(=O)-piperizino,
—C(=O(N—$C_{1-4}$alkylypiperizino,
—NHC(=O)$R^{Y7A}$, —$NR^{Y7A}$C(=O)$R^{Y7A}$, and
—CN.

(B7-18) A compound according to any one of (B7-3) to (B7-12), wherein —$R^{Y7}$, if present, is independently saturated aliphatic $C_{1-4}$alkyl, saturated $C_{3-6}$cycloalkyl, $C_{5-6}$heteroaryl, —$CH_2$—$C_{5-6}$heteroaryl, -Ph, or —$CH_2$-Ph, wherein each of said $C_{3-6}$cycloalkyl, $C_{5-6}$heteroaryl, and -Ph is optionally substituted with one or more groups selected from: —F, —Cl, —Br, —I, —$R^{Y7A}$, —$CF_3$, —OH, —$OR^{Y7A}$, and —$OCF_3$.

(B7-19) A compound according to any one of (B7-3) to (B7-12), wherein —$R^{Y7}$, if present, is independently saturated aliphatic $C_{1-4}$alkyl, saturated $C_{3-6}$cycloalkyl, -Ph, or —$CH_2$-Ph, wherein each of said $C_{3-6}$cycloalkyl and -Ph is optionally substituted with one or more groups selected from: —F, —Cl, —Br, —I, —$R^{Y7A}$, —$CF_3$, —OH, —$OR^{Y7A}$, and —$OCF_3$.

(B7-20) A compound according to any one of (B7-3) to (B7-12), wherein —Rn, if present, is independently saturated aliphatic $C_{1-4}$alkyl, -Ph, or —$CH_2$-Ph, wherein said -Ph is optionally substituted with one or more groups selected from: —F, —Cl, —Br, —I, —$R^{Y7A}$, —$CF_3$, —OH, —$OR^{Y7A}$, and —$OCF_3$.

(B7-21) A compound according to any one of (B7-3) to (B7-12), wherein —Rn, if present, is independently saturated aliphatic $C_{1-4}$alkyl, -Ph, or —$CH_2$-Ph.

(B7-22) A compound according to any one of (B7-3) to (B7-12), wherein —$R^{Y7}$, if present, is independently saturated aliphatic $C_{1-4}$alkyl.

(B7-23) A compound according to any one of (B7-3) to (B7-12), wherein —$R^{Y7}$, if present, is independently -Me, -Et, -nPr, -iPr, -nBu, -sBu, -iBu, or -tBu.

(B7-24) A compound according to any one of (B7-3) to (B7-12), wherein —$R^{Y7}$, if present, is independently -Me, -Et, -nPr, or -iPr.

(B7-25) A compound according to any one of (B7-3) to (B7-12), wherein —$R^{Y7}$, if present, is independently -Me or -Et.

(B7-26) A compound according to any one of (B7-3) to (B7-12), wherein —Rn, if present, is independently -Me.

(B7-27) A compound according to (B7-3), wherein —$B^7$, if present, is independently:
—$CH_2$—C(=O)$NH_2$, —$CH_2$—C(=O)NHMe, —$CH_2$—C(=O)$NMe_2$,
—$CH_2CH_2$—C(=O)$NH_2$, —$CH_2CH_2$—C(=O)NHMe, —$CH_2CH_2$—C(=O)$NMe_2$,
—$CH_2$—C(=O)-piperidino, or —$CH_2CH_2$—C(=O)-piperidino.

B8. 3-Cyclic and 3-Cyclic-Alkyl Compounds (B8-1) A compound according to any one of (1), (A1-1) to (A1-75), (A2-1) to (A2-19), (A3-1) to (A3-18), (A4-1) to (A4-17), (A5-1) to (A5-19), and (A6-1) to (A6-23), wherein —B is independently —$B^8$.

(B8-2) A compound according to (B8-1), wherein —$B^8$ is independently $C_{3-6}$cycloalkyl, $C_{3-6}$cycloalkyl-$C_{1-4}$alkyl, $C_{3-6}$heterocyclyl, or $C_{3-6}$heterocyclyl-$C_{1-4}$alkyl, and is optionally substituted.

(B8-3) A compound according to (B8-1), wherein —$B^8$ is independently:
—$R^{Y8}$ or -$L^{Y8}$-$R^{Y8}$,
wherein:
-$L^{Y8}$- is independently saturated aliphatic $C_{1-4}$alkylene, and —$R^{Y8}$ is independently saturated $C_{3-6}$cycloalkyl or saturated $C_{3-6}$heterocyclyl,
wherein each of said $C_{3-6}$cycloalkyl and $C_{3-6}$heterocyclyl is optionally substituted, for example, with one or more groups selected from:
—F, —Cl, —Br, —I,
—$R^{Y8A}$, —$CF_3$,
—OH, —$OR^{Y8A}$, —$OCF_3$,
—$NH_2$, —$NHR^{Y8A}$, —$NR^{Y8A}{}_2$, pyrrolidino piperidino, morpholino, piperizino, (N—$C_{1-4}$alkyl)-piperizino,
—C(=O)OH, —C(=O)$OR^{Y8A}$,
—C(=O)$R^{Y8A}$,
—OC(=O)$R^{Y8A}$, —C(=O)NH$_2$, —C(=O)NHR$^{Y8A}$, —C(=O)NR$^{Y8A}$$_2$, —C(=O)-pyrrolidino, —C(=O)-piperidino, —C(=O)-morpholino, —C(=O)-piperizino, —C(=O)—(N—C$_{1-4}$alkyl)-piperizino, —NHC(=O)R$^{Y8A}$, —NR$^{Y8A}$C(=O)R$^{Y8A}$, and —CN;
  wherein each —R$^{Y8A}$ is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more substituents selected from —F, —Cl, —Br, —I, —R$^{Y8B}$, —CF$_3$, —OH, —OR$^{Y8B}$, and —OCF$_3$, wherein each —R$^{Y8B}$ is independently saturated aliphatic C$_{1-4}$alkyl.

(B8-4) A compound according to (B8-3), wherein —B$^8$ is independently -1:2$^{Y8}$.

(B8-5) A compound according to (B8-3), wherein —B$^8$ is independently -L$^{Y8}$-R$^{Y8}$.

(B8-6) A compound according to any one of (B8-3) to (B8-5), wherein -L$^{Y8}$-, if present, is independently saturated aliphatic C$_{1-3}$alkylene.

(B8-7) A compound according to any one of (B8-3) to (B8-5), wherein -L$^{Y8}$-, if present, is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

(B8-8) A compound according to any one of (B8-3) to (B8-5), wherein -L$^{Y8}$-, if present, is independently —CH$_2$—, —CH$_2$CH$_2$—, or —CH$_2$CH$_2$CH$_2$—.

(B8-9) A compound according to any one of (B8-3) to (B8-5), wherein -L$^{Y8}$-, if present, is independently —CH$_2$— or —CH$_2$CH$_2$—.

(B8-10) A compound according to any one of (B8-3) to (B8-5), wherein -L$^{Y8}$-, if present, is independently —CH$_2$CH$_2$—.

(B8-11) A compound according to any one of (B8-3) to (B8-5), wherein -L$^{Y8}$-, if present, is independently —CH$_2$—.

(B8-12) A compound according to any one of (B8-3) to (B8-11), wherein —R$^{Y8}$ is independently saturated C$_{3-6}$cycloalkyl, and is optionally substituted.

(B8-13) A compound according to any one of (B8-3) to (B8-11), wherein —R$^{Y8}$ is independently saturated C$_{3-6}$heterocyclyl, and is optionally substituted.

(B8-14) A compound according to any one of (B8-3) to (B8-11), wherein —R$^{Y8}$ is independently saturated pyrrolidinyl, piperidinyl, piperizinyl, or morpholinyl, and is optionally substituted.

(B8-15) A compound according to any one of (B8-3) to (B8-11), wherein and —R$^{Y8}$ is independently saturated C$_{3-6}$cycloalkyl or saturated C$_{3-6}$heterocyclyl, wherein each of said C$_{3-6}$cycloalkyl and C$_{3-6}$heterocyclyl is optionally substituted, for example, with one or more groups selected from: —F, —Cl, —Br, —I, —R$^{Y8A}$, —CF$_3$, —OH, —OR$^{Y8A}$, and —OCF$_3$.

(B8-16) A compound according to any one of (B8-3) to (B8-11), wherein and —R$^{Y8}$ is independently saturated C$_{3-6}$cycloalkyl, wherein said C$_{3-6}$cycloalkyl is optionally substituted, for example, with one or more groups selected from: —F, —Cl, —Br, —I, —R$^{Y8A}$, —CF$_3$, —OH, —OR$^{Y8A}$, and —OCF$_3$.

(B8-17) A compound according to any one of (B8-3) to (B8-11), wherein and —R$^{Y8}$ is independently saturated C$_{3-6}$heterocyclyl, wherein said C$_{3-6}$heterocyclyl is optionally substituted, for example, with one or more groups selected from: —F, —Cl, —Br, —I, —R$^{Y8A}$, —CF$_3$, —OH, —OV$^A$, and —OCF$_3$.

(B8-18) A compound according to any one of (B8-3) to (B8-11), wherein and R$^{Y8}$ is independently saturated pyrrolidinyl, piperidinyl, piperizinyl, or morpholinyl, wherein each of said pyrrolidinyl, piperidinyl, piperizinyl, and morpholinyl is optionally substituted with one or more groups selected from: —F, —Cl, —Br, —I, —R$^{Y8A}$, —CF$_3$, —OH, —OR$^{Y8A}$, and —OCF$_3$.

(B8-19) A compound according to any one of (B8-3) to (B8-11), wherein and —R$^{Y8}$ is independently cyclopropyl, cyclobutyl, cyclopentyl, or cyclohexyl.

(B8-20) A compound according to any one of (B8-3) to (B8-11), wherein and —R$^{Y8}$ is independently saturated C$_{3-6}$heterocyclyl.

(B8-21) A compound according to any one of (B8-3) to (B8-11), wherein and —R$^{Y8}$ is independently pyrrolidinyl, piperidinyl, piperizinyl, or morpholinyl.

B9. 8-Halo-Alkyl Compounds (B9-1) A compound according to any one of (1), (A1-1) to (A1-75), (A2-1) to (A2-19), (A3-1) to (A3-18), (A4-1) to (A4-17), (A5-1) to (A5-19), and (A6-1) to (A6-23), wherein —B is independently —B$^9$.

(B9-2) A compound according to (B9-1), wherein —B$^9$ is independently halo-C$_{1-6}$alkyl.

As used herein, the term "haloalkyl" relates to a saturated aliphatic alkyl group in which one or more hydrogen atoms has been replaced with a halogen atom selected from —F, —Cl, —Br, and —I.

(B9-3) A compound according to (B9-2), wherein —B$^9$ is independently halo-C$_{1-4}$alkyl.

(B9-4) A compound according to (B9-2), wherein —B$^9$ is independently selected from:
  —CH$_2$F, —CH$_2$CH$_2$F, —CH$_2$CH$_2$CH$_2$F,
  —CH$_2$Cl, —CH$_2$CH$_2$Cl, —CH$_2$CH$_2$CH$_2$Cl,
  —CH$_2$Br, —CH$_2$CH$_2$Br, —CH$_2$CH$_2$CH$_2$Br,
  —CH$_2$I, —CH$_2$CH$_2$I, —CH$_2$CH$_2$CH$_2$I,
  —CHF$_2$, —CH$_2$CHF$_2$, —CH$_2$CH$_2$CHF$_2$,
  —CF$_3$, —CH$_2$CF$_3$, and —CH$_2$CH$_2$CF$_3$.

(B9-5) A compound according to (B9-2), wherein —B$^9$ is independently selected from:
  —CH$_2$F, —CH$_2$CH$_2$F, —CH$_2$CH$_2$CH$_2$F,
  —CH$_2$Cl, —CH$_2$CH$_2$Cl, —CH$_2$CH$_2$CH$_2$Cl,
  —CH$_2$Br, —CH$_2$CH$_2$Br, —CH$_2$CH$_2$CH$_2$Br,
  —CHF$_2$, —CH$_2$CHF$_2$, —CH$_2$CH$_2$CHF$_2$,
  —CF$_3$, —CH$_2$CF$_3$, and —CH$_2$CH$_2$CF$_3$.

(B9-6) A compound according to (B9-2), wherein —B$^9$ is independently selected from:
  —CH$_2$F, —CH$_2$CH$_2$F,
  —CH$_2$Cl, —CH$_2$CH$_2$Cl,
  —CH$_2$Br, —CH$_2$CH$_2$Br,
  —CHF$_2$, —CH$_2$CHF$_2$,
  —CF$_3$, and —CH$_2$CF$_3$.

(B9-7) A compound according to (B9-2), wherein —B$^9$ is independently selected from:
  —CH$_2$F, —CH$_2$CH$_2$F, —CHF$_2$, —CH$_2$CHF$_2$, —CF$_3$, and —CH$_2$CF$_3$.

(B9-8) A compound according to (B9-2), wherein —B$^9$ is independently selected from:
  —CH$_2$CH$_2$F, —CH$_2$CHF$_2$, and —CH$_2$CF$_3$.

B10. 8-Nitro-Alkyl Compounds (B10-1) A compound according to any one of (1), (A1-1) to (A1-75), (A2-1) to (A2-19), (A3-1) to (A3-18), (A4-1) to (A4-17), (A5-1) to (A5-19), and (A6-1) to (A6-23), wherein —B is independently —B$^{10}$.

(B10-2) A compound according to (B10-1), wherein —B$^{10}$ is independently nitro-C$_{1-6}$alkyl.

(B10-3) A compound according to (B10-1), wherein —B$^{10}$ is independently -L$^{Y10}$-NO$_2$, wherein -L$^{Y10}$- is independently saturated aliphatic C$_{1-4}$alkylene.

(B10-4) A compound according to (B10-3), wherein -L$^{Y10}$- is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

(B10-5) A compound according to (B10-3), wherein -L$^{Y10}$- is independently —CH$_2$—, —CH$_2$CH$_2$— or —CH$_2$CH$_2$CH$_2$—.

(B10-6) A compound according to (B10-3), wherein -L$^{Y10}$- is independently —CH$_2$—.

(B10-7) A compound according to (B10-3), wherein —B$^{10}$ is independently —CH$_2$—NO$_2$.

B11. 8-Cyano-Alkyl Compounds (B11-1) A compound according to any one of (1), (A1-1) to (A1-75), (A2-1) to (A2-19), (A3-1) to (A3-18), (A4-1) to (A4-17), (A5-1) to (A5-19), and (A6-1) to (A6-23), wherein —B is independently —B$^{11}$.

(B11-2) A compound according to (B11-1), wherein —B$^{11}$ is independently cyano-C$_{1-6}$alkyl.

(B11-3) A compound according to (B11-1), wherein —B$^{11}$ is independently -L$^{Y11}$-CN, wherein -L$^{Y11}$- is independently saturated aliphatic C$_{1-4}$alkylene.

(B11-4) A compound according to (B11-3), wherein -L$^{Y11}$- is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

(B11-5) A compound according to (B11-3), wherein -L$^{Y11}$- is independently —CH$_2$—, —CH$_2$CH$_2$— or —CH$_2$CH$_2$CH$_2$—.

(B11-6) A compound according to (B11-3), wherein -L$^{Y11}$- is independently —CH$_2$— or —CH$_2$CH$_2$—.

(B11-7) A compound according to (B11-3), wherein —B$^{11}$ is independently —CH$_2$—CN.

B12. 8-Phosphate-Alkyl Compounds (B12-1) A compound according to any one of (1), (A1-1) to (A1-75), (A2-1) to (A2-19), (A3-1) to (A3-18), (A4-1) to (A4-17), (A5-1) to (A5-19), and (A6-1) to (A6-23), wherein —B is independently —B$^{12}$.

(B12-2) A compound according to (B12-1), wherein —B$^{12}$ is independently phosphate-C$_{1-6}$alkyl.

(B12-3) A compound according to (B12-1), wherein —B$^{12}$ is independently:
-L$^{Y12}$-P(=O)(OH)$_2$, -L$^{Y12}$-P(=O)(OH)(OR$^{Y12}$), or -L$^{Y12}$-P(=O)(OR$^{Y12}$)$_2$,
wherein:
-L$^{Y12}$- is independently saturated aliphatic C$_{1-4}$alkylene, and
each —R$^{Y12}$ is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph,
wherein each of said C$_{3-6}$cycloalkyl, C$_{5-6}$heteroaryl, and -Ph is optionally substituted, for example, with one or more groups selected from:
—F, —Cl, —Br, —I,
—R$^{Y12A}$, —CF$_3$,
—OH, —OR$^{Y12A}$, —OCF$_3$,
—NH$_2$, —NHR$^{Y12A}$, —NR$^{Y12A}$$_2$, pyrrolidino piperidino, morpholino, piperizino, (N—C$_{1-4}$alkyl)-piperizino,
—C(=O)OH, —C(=O)OR$^{Y12A}$,
—C(=O)R$^{Y12A}$,
—OC(=O)R$^{Y12A}$,
—C(=O)NH$_2$, —C(=O)NHR$^{Y12A}$, —C(=O)NR$^{Y12A}$$_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Y12A}$, —NR$^{Y12A}$C(=O)R$^{Y12A}$, and
—CN;
wherein each —R$^{Y12A}$ is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more substituents selected from —F, —Cl, —Br, —I, —R$^{Y12B}$, —CF$_3$, —OH, —OR$^{Y12B}$, and —OCF$_3$, wherein each —R$^{Y12B}$ is independently saturated aliphatic C$_{1-4}$alkyl.

(B12-4) A compound according to (B12-3), wherein —B$^{12}$ is independently -L$^{Y12}$-P(=O)(OH)$_2$.

(B12-5) A compound according to (B12-3), wherein —B$^{12}$ is independently -L$^{Y12}$-P(=O)(OH)(OR$^{Y12}$).

(B12-6) A compound according to (B12-3), wherein —B$^{12}$ is independently -L$^{Y12}$-P(=O)(OR$^{Y12}$)$_2$.

(B12-7) A compound according to any one of (B12-3) to (B12-6), wherein -L$^{Y12}$- is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

(B12-8) A compound according to any one of (B12-3) to (B12-6), wherein -L$^{Y12}$- is independently —CH$_2$— or —CH$_2$CH$_2$—.

(B12-9) A compound according to any one of (B12-3) to (B12-6), wherein -L$^{Y12}$- is independently —CH$_2$—.

(B12-10) A compound according to any one of (612-3) to (B12-6), wherein -L$^{Y12}$- is independently —CH$_2$CH$_2$—.

(B12-11) A compound according to any one of (B12-3) to (B12-10), wherein each —R$^{Y12}$, if present, is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted.

(B12-12) A compound according to any one of (B12-3) to (B12-10), wherein each —R$^{Y12}$, if present, is independently saturated aliphatic C$_{1-4}$alkyl, -Ph, or —CH$_2$-Ph, wherein said -Ph is optionally substituted.

(B12-13) A compound according to any one of (B12-3) to (B12-10), wherein each —R$^{Y12}$, if present, is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph, wherein each of said C$_{3-6}$cycloalkyl, C$_{5-6}$heteroaryl, and -Ph is optionally substituted with one or more groups selected from: —F, —Cl, —Br, —I, —R$^{Y12A}$, —CF$_3$, —OH, —OR$^{Y12A}$, and —OCF$_3$.

(B12-14) A compound according to any one of (B12-3) to (B12-10), wherein each —R$^{Y12}$, if present, is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more groups selected from: —F, —Cl, —Br, —I, —R$^{Y12A}$, —CF$_3$, —OH, —OR$^{Y12A}$, and —OCF$_3$.

(B12-15) A compound according to any one of (B12-3) to (B12-10), wherein each —R$^{Y12}$, if present, is independently saturated aliphatic C$_{1-4}$alkyl, -Ph, or —CH$_2$-Ph, wherein said -Ph is optionally substituted with one or more groups selected from: —F, —Cl, —Br, —I, —R$^{Y12A}$, —CF$_3$, —OH, —OR$^{Y12A}$, and —OCF$_3$.

(B12-16) A compound according to any one of (B12-3) to (B12-10), wherein each —R$^{Y12}$, if present, is independently saturated aliphatic C$_{1-4}$alkyl, -Ph, or —CH$_2$-Ph.

(B12-17) A compound according to any one of (B12-3) to (B12-10), wherein each —R$^{Y12}$, if present, is independently saturated aliphatic C$_{1-4}$alkyl.

(B12-18) A compound according to any one of (B12-3) to (B12-10), wherein each —R$^{Y12}$, if present, is independently -Me, -Et, -nPr, -iPr, -nBu, -sBu, -iBu, or -tBu.

(B12-19) A compound according to any one of (B12-3) to (B12-10), wherein each —R$^{Y12}$, if present, is independently -Me, -Et, -nPr, or -iPr.

(B12-20) A compound according to any one of (B12-3) to (B12-10), wherein each —R$^{Y12}$, if present, is independently -Me or -Et.

(B12-21) A compound according to any one of (B12-3) to (B12-10), wherein each —$R^{Y12}$, if present, is independently -Et.

(B12-22) A compound according to (B12-3), wherein each —$B^{12}$ is —$CH_2$—P(=O)(OEt)$_2$.

B13. 8-Carbamate-Alkyl Compounds (B13-1) A compound according to any one of (1), (A1-1) to (A1-75), (A2-1) to (A2-19), (A3-1) to (A3-18), (A4-1) to (A4-17), (A5-1) to (A5-19), and (A6-1) to (A6-23), wherein —B is independently —$B^{13}$.

(B13-2) A compound according to (B13-1), wherein —$B^{13}$ is independently carbamate-$C_{1-6}$alkyl.

(B13-3) A compound according to (B13-1), wherein —$B^{13}$ is independently:
-$L^{Y13}$-NH—C(=O)OH,     -$L^{Y13}$-NH—C(=O)—$R^{Y13}$,
-$L^{Y13}$-N$R^{Y13}$—C(=O)OH,     or     -$L^{Y13}$-N$R^{Y13}$—C(=O)—$R^{Y13}$,
wherein:
-$L^{Y13}$- is independently saturated aliphatic $C_{1-4}$alkylene, and
each —$R^{Y13}$ is independently saturated aliphatic $C_{1-4}$alkyl, saturated $C_{3-6}$cycloalkyl, $C_{5-6}$heteroaryl, —$CH_2$—$C_{5-6}$heteroaryl, fluorenyl, —$CH_2$-fluorenyl, -Ph, or —$CH_2$-Ph,
wherein each of said $C_{3-6}$cycloalkyl, $C_{5-6}$heteroaryl, fluorenyl and -Ph is optionally substituted, for example, with one or more groups selected from:
—F, —Cl, —Br, —I,
—$R^{Y13A}$, —$CF_3$,
—OH, —O$R^{Y13A}$, —OCF$_3$,
—NH$_2$, —NHR$^{Y13A}$, —NR$^{Y13A}$$_2$, pyrrolidino piperidino, morpholino, piperizino, (N—$C_{1-4}$alkyl)-piperizino,
—C(=O)OH, —C(=O)O$R^{Y13A}$,
—C(=O)$R^{Y13A}$,
—OC(=O)$R^{Y13A}$,
—C(=O)NH$_2$, —C(=O)NHR$^{Y13A}$, —C(=O)NR$^{Y13A}$$_2$,
—C(=O)-pyrrolidino,     —C(=O)-piperidino,
—C(=O)-morpholino,     —C(=O)-piperizino,
—C(=O)—(N—$C_{1-4}$alkyl)-piperizino,
—NHC(=O)$R^{Y13A}$, —NR$^{Y13A}$C(=O)$R^{Y13A}$, and
—CN;
wherein each —$R^{Y13A}$ is independently saturated aliphatic $C_{1-4}$alkyl, saturated $C_{3-6}$cycloalkyl, -Ph, or —$CH_2$-Ph, wherein each of said $C_{3-6}$cycloalkyl and -Ph is optionally substituted with one or more substituents selected from —F, —Cl, —Br, —I, —$R^{Y13B}$, —$CF_3$, —OH, —O$R^{Y13B}$, and —OCF$_3$, wherein each —$R^{Y13B}$ is independently saturated aliphatic $C_{1-4}$alkyl.

(B13-4) A compound according to (B13-3), wherein —$B^{13}$ is independently -$L^{Y13}$-NH—C(=O)OH, or -$L^{Y13}$-NH—C(=O)—$R^{Y13}$.

(B13-5) A compound according to (B13-3), wherein —$B^{13}$ is independently -$L^{Y13}$-NH—C(=O)OH.

(B13-6) A compound according to (B13-3), wherein —$B^{13}$ is independently -$L^{Y13}$-NH—C(=O)—$R^{Y13}$.

(B13-7) A compound according to any one of (B13-3) to (B13-6), wherein -$L^{Y13}$- is independently —$CH_2$—, —$CH_2CH_2$—, —$CH_2CH_2CH_2$—, —CH(CH$_3$)—, —CH(CH$_3$)CH$_2$—, —$CH_2$CH(CH$_3$)—, or —CH(CH$_2$CH$_3$)—.

(B13-8) A compound according to (B13-3) to (B13-6), wherein -$L^{Y13}$- is independently —$CH_2$— or —$CH_2CH_2$—.

(B13-9) A compound according to (B13-3) to (B13-6), wherein -$L^{Y13}$- is independently —$CH_2$—.

(B13-10) A compound according to (B13-3) to (B13-6), wherein -$L^{Y13}$- is independently —$CH_2CH_2$—.

(B13-11) A compound according to any one of (B13-3) to (B13-10), wherein each —$R^{Y13}$, if present, is independently saturated aliphatic $C_{1-4}$alkyl, saturated $C_{3-6}$cycloalkyl, fluorenyl, —$CH_2$-fluorenyl, -Ph, or —$CH_2$-Ph, wherein each of said $C_{3-6}$cycloalkyl, fluorenyl and -Ph is optionally substituted.

(B13-12) A compound according to any one of (B13-3) to (B13-10), wherein each —$R^{Y13}$, if present, is independently fluorenyl or —$CH_2$-fluorenyl, wherein said fluorenyl is optionally substituted.

(B13-13) A compound according to any one of (B13-3) to (B13-10), wherein each —$R^{Y13}$, if present, is independently saturated aliphatic $C_{1-4}$alkyl, -Ph, or —$CH_2$-Ph, wherein said -Ph is optionally substituted.

(B13-14) A compound according to any one of (B13-3) to (B13-10), wherein each —$R^{Y13}$, if present, is independently saturated aliphatic $C_{1-4}$alkyl, saturated $C_{3-6}$cycloalkyl, fluorenyl, —$CH_2$-fluorenyl, -Ph, or —$CH_2$-Ph, wherein each of said $C_{3-6}$cycloalkyl, $C_{5-6}$heteroaryl, fluorenyl and -Ph is optionally substituted with one or more groups selected from: —F, —Cl, —Br, —I, —$R^{Y12A}$, —$CF_3$, —OH, —O$R^{Y12A}$, and —OCF$_3$.

(B13-15) A compound according to any one of (B13-3) to (B13-10), wherein each —$R^{Y13}$, if present, is independently fluorenyl or —$CH_2$-fluorenyl, wherein said fluorenyl is optionally substituted with one or more groups selected from: —F, —Cl, —Br, —I, —$R^{Y12A}$, —$CF_3$, —OH, —O$R^{Y12A}$, and —OCF$_3$.

(B13-16) A compound according to any one of (B13-3) to (B13-10), wherein each —$R^{Y13}$, if present, is independently saturated aliphatic $C_{1-4}$alkyl, -Ph, or —$CH_2$-Ph, wherein said -Ph is optionally substituted with one or more groups selected from: —F, —Cl, —Br, —I, —$R^{Y12A}$, —$CF_3$, —OH, —O$R^{Y12A}$, and —OCF$_3$.

(B13-17) A compound according to any one of (B13-3) to (B13-10), wherein each —$R^{Y13}$, if present, is independently saturated aliphatic $C_{1-4}$alkyl, -Ph, or —$CH_2$-Ph.

(B13-18) A compound according to any one of (B13-3) to (B13-10), wherein each —$R^{Y13}$, if present, is independently saturated aliphatic $C_{1-4}$alkyl.

(B13-19) A compound according to any one of (B13-3) to (B13-10), wherein —$R^{Y13}$ is fluorenyl or —$CH_2$-fluorenyl.

B14. 8-Oxime-Alkyl Compounds (B14-1) A compound according to any one of (1), (A1-1) to (A1-75), (A2-1) to (A2-19), (A3-1) to (A3-18), (A4-1) to (A4-17), (A5-1) to (A5-19), and (A6-1) to (A6-23), wherein —B is independently —$B^{14}$.

(B14-2) A compound according to (B14-1), wherein —$B^{14}$ is independently oxime-$C_{1-6}$alkyl.

(B14-3) A compound according to (B14-1), wherein —$B^{14}$ is independently:
-$L^{Y14}$-CH(=N—O—H),     -$L^{Y14}$-CH(=N—O—$R^{Y14}$),
-$L^{Y14}$-CR$^{Y14}$(=N—O—H),     or     -$L^{Y14}$-CR$^{Y14}$(=N—O—$R^{Y14}$),
wherein:
-$L^{Y14}$- is independently saturated aliphatic $C_{1-4}$alkylene, and
each —$R^{Y14}$ is independently saturated aliphatic $C_{1-4}$alkyl, saturated $C_{3-6}$cycloalkyl, $C_{5-6}$heteroaryl, —$CH_2$—$C_{5-6}$heteroaryl, -Ph, or —$CH_2$-Ph,
wherein each of said $C_{3-6}$cycloalkyl, $C_{5-6}$heteroaryl, and -Ph is optionally substituted, for example, with one or more groups selected from:
—F, —Cl, —Br, —I,
—$R^{Y14A}$, —$CF_3$,
—OH, —O$R^{Y14A}$, —OCF$_3$, —NH$_2$, —NHR$^{Y14A}$, —NR$^{Y14A}{}_2$, pyrrolidino piperidino, morpholino, piperizino, (N—C$_{1-4}$alkyl)-piperizino,
—C(=O)OH, —C(=O)OR$^{Y14A}$,
—C(=O)R$^{Y14A}$,
—OC(=O)R$^{Y14A}$,
—C(=O)NH$_2$, —C(=O)NHR$^{Y14A}$, —C(=O)NR$^{Y14A}{}_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Y14A}$, —NR$^{Y14A}$C(=O)R$^{Y14A}$, and
—CN;
  wherein each —R$^{Y14A}$ is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more substituents selected from —F, —Cl, —Br, —I, —R$^{Y14B}$, —CF$_3$, —OH, —OR$^{Y14B}$, and —OCF$_3$, wherein each —R$^{Y14B}$ is independently saturated aliphatic C$_{1-4}$alkyl.

(B14-4) A compound according to (B14-3), wherein —B$^{14}$ is independently -L$^{Y14}$-CH(=N—O—R$^{Y14}$) or -L$^{Y5}$-CR$^{Y5}$(=N—O—R$^{Y5}$).

(B14-5) A compound according to (B14-3), wherein —B$^{14}$ is independently -L$^{Y14}$-CR$^{Y14}$(=N—O—R$^{Y14}$).

(B14-6) A compound according to any one of (B14-3) to (B14-5), wherein -L$^{Y14}$- is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

(B14-7) A compound according to any one of (B14-3) to (B14-5), wherein -L$^{Y14}$- is independently —CH$_2$— or —CH$_2$CH$_2$—.

(B14-8) A compound according to any one of (B14-3) to (B14-5), wherein -L$^{Y14}$- is independently —CH$_2$—.

(B14-9) A compound according to any one of (B14-3) to (B14-5), wherein -L$^{Y14}$- is independently —CH$_2$CH$_2$—.

(B14-10) A compound according to any one of (B14-3) to (B14-9), wherein each —R$^{Y14}$, if present, is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted.

(B14-11) A compound according to any one of (B14-3) to (B14-9), wherein each —R$^{Y14}$, if present, is independently saturated aliphatic C$_{1-4}$alkyl, -Ph, or —CH$_2$-Ph, wherein said -Ph is optionally substituted.

(B14-12) A compound according to any one of (B14-3) to (B14-9), wherein each —R$^{Y14}$, if present, is independently saturated aliphatic C$_{1-4}$alkyl, saturated C$_{3-6}$cycloalkyl, C$_{5-6}$heteroaryl, —CH$_2$-C$_{5-6}$heteroaryl, -Ph, or —CH$_2$-Ph, wherein each of said C$_{3-6}$cycloalkyl, C$_{5-6}$heteroaryl, and -Ph is optionally substituted with one or more groups selected from: —F, —Cl, —Br, —I, —R$^{Y14A}$, —CF$_3$, —OH, —OR$^{Y14A}$, and —OCF$_3$.

(B14-13) A compound according to any one of (B14-3) to (B14-9), wherein each —R$^{Y14}$, if present, is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more groups selected from: —F, —Cl, —Br, —I, —R$^{Y14A}$, —CF$_3$, —OH, —OR$^{Y14A}$, and —OCF$_3$.

(B14-14) A compound according to any one of (B14-3) to (B14-9), wherein each —R$^{Y14}$, if present, is independently saturated aliphatic C$_{1-4}$alkyl, -Ph, or —CH$_2$-Ph, wherein said -Ph is optionally substituted with one or more groups selected from: —F, —Cl, —Br, —I, —R$^{Y14A}$, —CF$_3$, —OH, —OR$^{Y14A}$, and —OCF$_3$.

(B14-15) A compound according to any one of (B14-3) to (B14-9), wherein each —R$^{Y14}$, if present, is independently saturated aliphatic C$_{1-4}$alkyl, -Ph, or —CH$_2$-Ph.

(B14-16) A compound according to any one of (B14-3) to (B14-9), wherein each —R$^{Y14}$, if present, is independently saturated aliphatic C$_{1-4}$alkyl.

(B14-17) A compound according to any one of (B14-3) to (B14-9), wherein each —R$^{Y14}$, if present, is independently -Me, -Et, -nPr, -iPr, -nBu, -sBu, -iBu, or -tBu.

(B14-18) A compound according to any one of (B14-3) to (B14-9), wherein each —R$^{Y14}$, if present, is independently -Me, -Et, -nPr, or -iPr.

(B14-19) A compound according to any one of (B14-3) to (B14-9), wherein each —R$^{Y14}$, if present, is independently -Me or -Et.

(B14-20) A compound according to (B14-3), wherein —B$^{14}$ is independently —CH$_2$—C(Et)(=N—O-Me).

Certain Preferred Embodiments (C1) A compound according to (1), wherein:
  -A is independently:
    -A$^1$, for example, as set out in any one of (A1-1) to (A1-75); and
  —B is independently:
    —B$^1$, for example, as set out in any one of (B1-1) to (B1-12);
    —B$^2$, for example, as set out in any one of (B2-1) to (B2-5);
    —B$^3$, for example, as set out in any one of (B3-1) to (B3-32);
    —B$^4$, for example, as set out in any one of (B4-1) to (B4-25);
    —B$^5$, for example, as set out in any one of (B5-1) to (B5-23); or
    —B$^6$, for example, as set out in any one of (B6-1) to (B6-29).

(C2) A compound according to (1), wherein:
  -A is independently:
    -A$^1$, for example, as set out in any one of (A1-1) to (A1-75); and
  —B is independently:
    —B$^1$, for example, as set out in any one of (B1-1) to (B1-12);
    —B$^2$, for example, as set out in any one of (B2-1) to (B2-5);
    —B$^3$, for example, as set out in any one of (B3-1) to (B3-32); or
    —B$^4$, for example, as set out in any one of (B4-1) to (B4-25).

(C3) A compound according to (1), wherein:
  -A is independently:
    -A$^1$, for example, as set out in any one of (A1-1) to (A1-75); and
  —B is independently:
    —B$^1$, for example, as set out in any one of (B1-1) to (B1-12).

(C4) A compound according to (1), wherein:
  -A is independently:
    -A$^1$, for example, as set out in any one of (A1-1) to (A1-75); and
  —B is independently:
    —B$^2$, for example, as set out in any one of (B2-1) to (B2-5).

(C5) A compound according to (1), wherein:
  -A is independently:
    -A$^1$, for example, as set out in any one of (A1-1) to (A1-75); and
  —B is independently:
    —B$^3$, for example, as set out in any one of (B3-1) to (B3-32).

(C6) A compound according to (1), wherein:
  -A is independently:
    -A$^1$, for example, as set out in any one of (A1-1) to (A1-75); and —B is independently:
—B⁴, for example, as set out in any one of (B4-1) to (B4-25).

Molecular Weight

In one embodiment, the 38TM compound has a molecular weight of from 200 to 1200.

In one embodiment, the bottom of range is from 210, 220, 225, 250, 275, 300, or 350.

In one embodiment, the top of range is 1100, 1000, 900, 800, 700, or 600.

In one embodiment, the range is 220 to 600.

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., -A¹, -A², -A³, -A⁴, -A⁵, -A⁶, —B¹, —B², —B³, —B⁴, —B⁵, —B⁶, —B⁷, —B⁸, —B⁹, —B¹⁰, —B¹¹, —B¹², —B¹³, —B¹⁴, —R^{Z1}, —R^{Z1A}, —R^{Z1B}, —R^{Z2}, —R^{Z2A}, R^{Z2B}, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to 38TM compounds, as described herein, in substantially purified form and/or in a form substantially free from contaminants.

In one embodiment, the compound is in a substantially purified form with a purity of least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the compound is in a substantially purified form with an optical purity of at least 60% (i.e., 60% of the compound, on a molar basis, is the desired enantiomer, and 40% is the undesired enantiomer), e.g., at least 70%, e.g., at least 80%, e.g., at least 90%, e.g., at least 95%, e.g., at least 97%, e.g., at least 98%, e.g., at least 99%.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

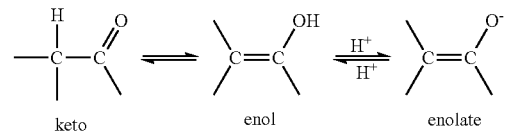

Note that specifically included in the term "isomer" are compounds with one or more isotopic substitutions. For example, H may be in any isotopic form, including ¹H, ²H (D), and ³H (T); C may be in any isotopic form, including ¹²C, ¹³C, and ¹⁴C; O may be in any isotopic form, including ¹⁶O and ¹⁸O; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci., Vol. 66*, pp. 1-19.

For example, if the compound is anionic, or has a functional group which may be anionic (e.g., —COON may be —COO⁻), then a salt may be formed with a suitable cation.

Examples of suitable inorganic cations include, but are not limited to, alkali metal ions such as Na⁺ and K⁺, alkaline earth cations such as Ca²⁺ and Mg²⁺, and other cations such as Al⁺³. Examples of suitable organic cations include, but are not limited to, ammonium ion (i.e., NH₄⁺) and substituted ammonium ions (e.g., NH₃R⁺, NH₂R₂⁺, NR₄⁺). Examples of some suitable substituted ammonium ions are those derived from ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

If the compound is cationic, or has a functional group which may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Hydrates and Solvates

It may be convenient or desirable to prepare, purify, and/or handle a corresponding hydrate or solvate of the compound (e.g., pharmaceutically acceptable hydrates or solvates of the compound). The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes hydrate and solvate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 4th Edition; John Wiley and Sons, 2006).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl(diphenylmethyl), or trityl(triphenylmethyl)ether; a trimethylsilyl or t-butyldimethylsilyl ether; or an acetyl ester (—OC(=O)CH₃, —OAc).

For example, an aldehyde or ketone group may be protected as an acetal (R—CH(OR)₂) or ketal (R₂C(OR)₂), respectively, in which the carbonyl group (>C=O) is converted to a diether (>C(OR)₂), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH₃); a benzyloxy amide (—NHCO—OCH₂C₆H₅, —NH-Cbz); as a t-butoxy amide (—NHCO—OC(CH₃)₃, —NH-Boc); a 2-biphenyl-2-propoxy amide (—NHCO—OC(CH₃)₂C₆H₄C₆H₅, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O•).

For example, a carboxylic acid group may be protected as an ester for example, as: an C₁₋₇alkyl ester (e.g., a methyl ester; a t-butyl ester); a C₁₋₇haloalkyl ester (e.g., a C₁₋₇trihaloalkyl ester); a triC₁₋₇alkylsilyl-C₁₋₇alkyl ester; or a C₅₋₂₀aryl-C₁₋₇alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH₂NHC(=O)CH₃).

For example, a carbonyl group may be protected as an oxime (—C(=NOH)—) or a substituted oxime (—C(=NOR)—), for example, where R is saturated aliphatic C₁₋₄alkyl.

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(═O)OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of 38TM compounds of the present invention are described herein. These and/or other well known methods may be modified and/or adapted in known ways in order to facilitate the synthesis of additional compounds within the scope of the present invention.

In one approach, a suitable isocyanate is reacted with 5-diazoimidazole-4-carboxamide (a well-known reagent) to give the corresponding 3-substituted imidazotetrazine, for example as illustrated in the following scheme.

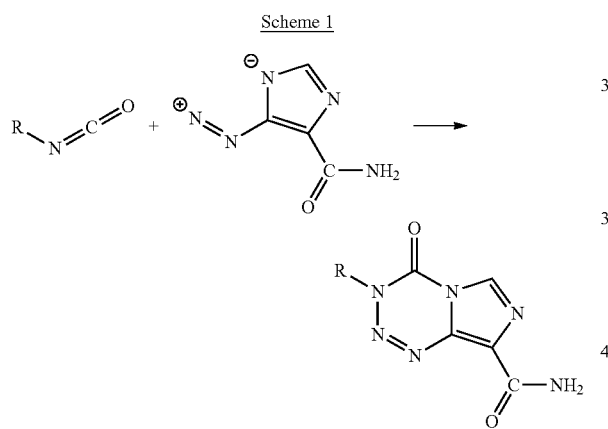

See, for example, Wang, Y., et al., 1998, "Antitumour imidazotetrazines. Part 36. Conversion of 5-amino-imidazole-4-carboxamide to imidazo[5,1-d][1,2,3,5]tetrazin-4(3H)-ones and imidazo[1,5-a][1,3,5]triazin-4(3H)-ones related in structure to the antitumour agents temozolomide and mitozolomide," *J. Chem. Soc., Perkin Trans* 1, Vol. 10, pp. 1669-1675;

Stevens, M. F. G., et al., 1984, "Antitumour imidazotetrazines. Part 1. Synthesis and chemistry of 8-carbamoyl-3-(2-chloroethypimidazo[1,5-d]-1,2,3,5-tetrazin-4(3H)-one, a novel broad spectrum antitumour agent", *J. Med. Chem.*, Vol. 27, pp. 196-201.

Suitable isocyanates may be obtained from commercial sources, or prepared using known methods, or by adapting known methods in known ways. For example, methods for preparing certain isocyanates are described in WO 96/27588.

The classical routes to isocyanates are treatment of a primary amine with phosgene, or a phosgene equivalent, and the Curtius rearrangement of an acyl azide (see, e.g., Ozaki, S., 1972, *Chem. Rev.*, Vol. 72, pp. 457-496; Saunders, J. H., et al., 1948, *Chem. Rev.*, Vol. 43, pp. 203-218). Acyl azides are commonly prepared by the treatment of an acid chloride with sodium azide or, more conveniently, are prepared directly from the carboxylic acid using diphenylphosphoryl azide (dppa) (see, e.g., Shioiri, T., et al., 1972, *J. Am. Chem. Soc.*, Vol. 94, pp. 6203-6205) and are not normally isolated.

In another approach, the 3-(hydroxymethyl) compound (3-hydroxymethyl-4-oxo-3,4-dihydro-imidazo[5,1-d][1,2,3,5]tetrazine-8-carboxylic acid amide) is used as a key intermediate. This key intermediate may be prepared by methods described here, and illustrated, for example, in the following scheme.

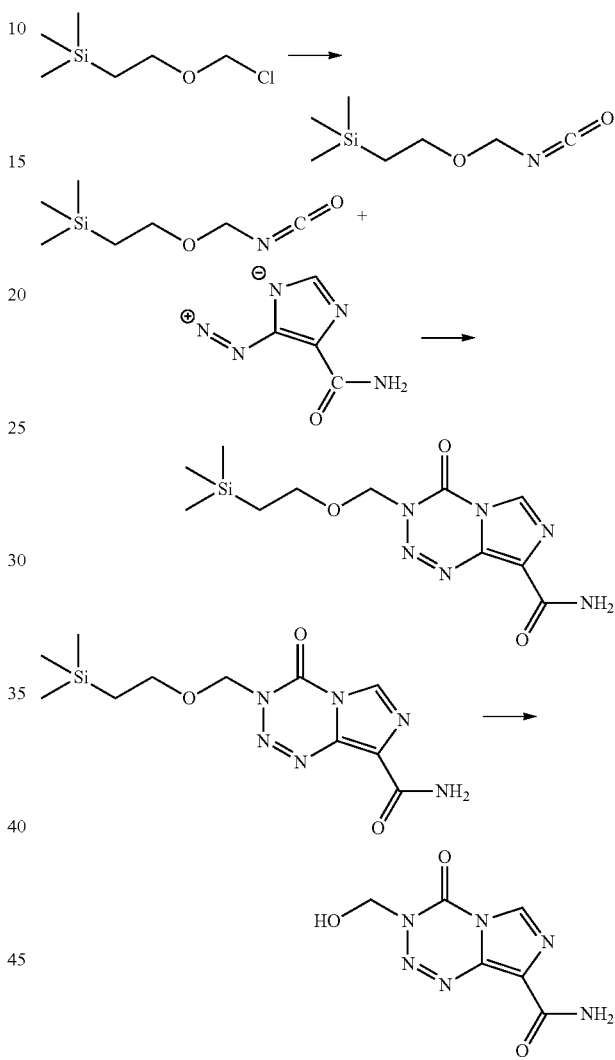

This key intermediate may then be used to prepare a range of other 3-substituted compounds by reaction with a suitable halide (e.g., R—X, where X is, for example, —I), for example, in the presence of a suitable base. An example of this method is illustrated in the following scheme.

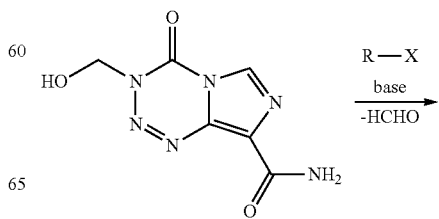

-continued

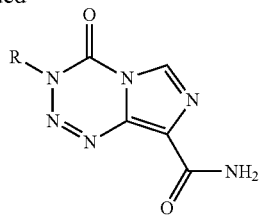

This approach has the particular advantage that is employs halides (e.g., R—X) instead of isocyanates (e.g., R—N=C=O). A wider variety of halides is known and/or can be relatively easily prepared, as compared to the corresponding isocyanates. (Of course, an isocyanate is used in the preparation of the key intermediate, but it is an isocyanate that is known and relatively easy to prepare and handle.)

Modifications at the 8-position may be made, for example, by starting from the corresponding carboxamide. Suitable methods for modification at the 8-position are described in the Examples below.

Isotopically labelled compounds (for example, labelled at the 3-position) may be prepared, for example, using methods illustrated in the following scheme, where R* denotes an isotopically labelled group.

Scheme 4

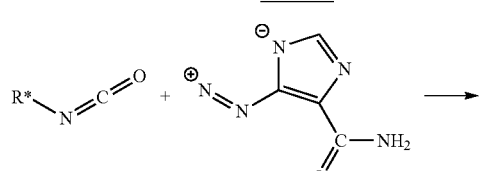

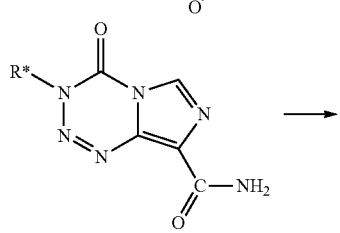

A specific example of such a method, where the isotopically labelled fragment is incorporated at the N-3 position early in the syntheses of the target compound, is illustrated in the following scheme.

Scheme 5

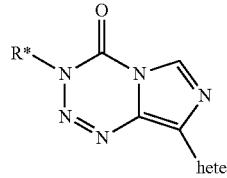

-continued

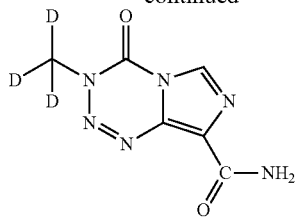

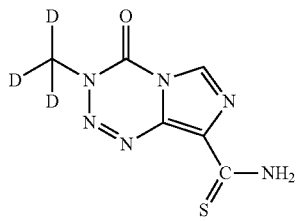

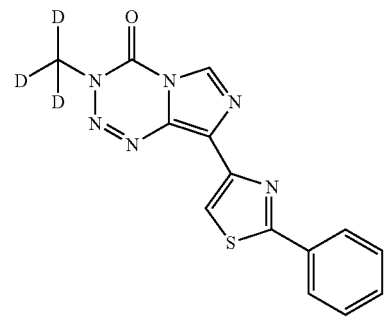

Alternatively, an isotopically labelled group may be introduced at the 8-position, later in the synthesis of the target compound, for example, using methods illustrated in the following scheme, where R* denotes an isotopically labelled group.

Scheme 6

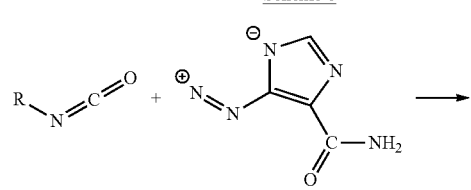

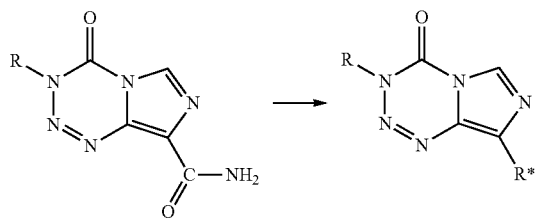

A specific example of such a method, where the isotopically labelled fragment is incorporated at the C-8 position early in the syntheses of the target compound, is illustrated in the following scheme.

Scheme 7

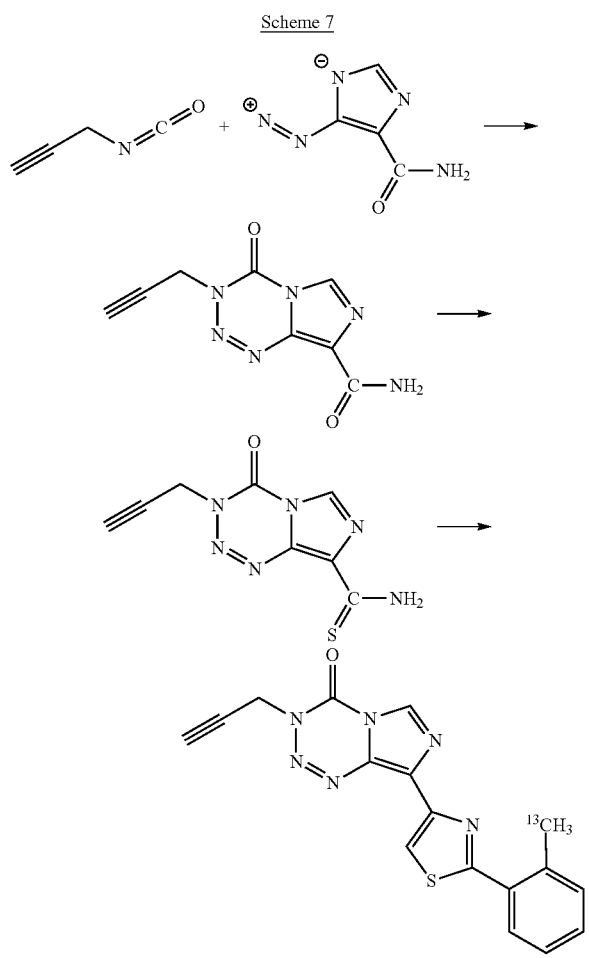

Compositions

One aspect of the present invention pertains to a composition (e.g., a pharmaceutical composition) comprising a 38TM compound, as described herein, and a pharmaceutically acceptable carrier, diluent, or excipient.

Another aspect of the present invention pertains to a method of preparing a composition (e.g., a pharmaceutical composition) comprising admixing a 38TM compound, as described herein, and a pharmaceutically acceptable carrier, diluent, or excipient.

Uses

The 38TM compounds described herein are useful, for example, in the treatment of proliferative disorders, such as, for example, cancer, etc.

Use in Methods of Inhibiting Cell Proliferation, Etc.

The 38TM compounds described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a 38TM compound, as described herein.

In one embodiment, the method is a method of regulating (e.g., inhibiting) cell proliferation (e.g., proliferation of a cell), in vitro or in vivo, comprising contacting a cell with an effective amount of a 38TM compound, as described herein.

In one embodiment, the method is performed in vitro.

In one embodiment, the method is performed in vivo.

In one embodiment, the 38TM compound is provided in the form of a pharmaceutically acceptable composition.

Any type of cell may be treated, including but not limited to, cancer cells derived from tumours or the lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a 38TM compound, as described herein, for use in a method of treatment of the human or animal body by therapy.

Use in the Manufacture of Medicaments

Another aspect of the present invention pertains to use of a 38TM compound, as described herein, in the manufacture of a medicament for use in treatment.

In one embodiment, the medicament comprises the 38TM compound.

Methods of Treatment

Another aspect of the present invention pertains to a method of treatment comprising administering to a patient in need of treatment a therapeutically effective amount of a 38TM compound, as described herein, preferably in the form of a pharmaceutical composition.

Conditions Treated-Proliferative Disorders and Cancer

In one embodiment (e.g., of use in methods of therapy, of use in the manufacture of medicaments, of methods of treatment), the treatment is treatment of a proliferative disorder.

The term "proliferative condition," as used herein, pertains to an unwanted or uncontrolled cellular proliferation of excessive or abnormal cells which is undesired, such as, neoplastic or hyperplastic growth.

In one embodiment, the treatment is treatment of: a proliferative condition characterised by benign, pre-malignant, or malignant cellular proliferation, including but not limited to, neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

In one embodiment, the treatment is treatment of: cancer.

In one embodiment, the treatment is treatment of: lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, nasopharyngeal cancer, squamous carcinoma of the head or neck, skin cancer, squamous cancer, Kaposi's sarcoma, melanoma, malignant melanoma, lymphoma, or leukemia.

In one embodiment, the treatment is treatment of:
a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);
a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;
a hematopoietic tumor of myeloid lineage, for example acute and chronic myelogenous leukemias, myelodysplastic syndrome, or promyelocytic leukemia;
a tumour of mesenchymal origin, for example fibrosarcoma or habdomyosarcoma;
a tumor of the central or peripheral nervous system, for example astrocytoma, neuroblastoma, glioma or schwannoma;
melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of solid tumour cancer.

In one embodiment, the treatment is treatment of haematological cancer.

In one embodiment, the treatment is treatment of: lung cancer, breast cancer, ovarian cancer, colorectal cancer, melanoma, renal cancer, prostate cancer, esophageal cancer, squamous carcinoma of the head or neck, or glioma.

In one embodiment, the treatment is treatment of glioma.

In one embodiment, the cancer is characterised by, or further characterised by, cancer stem cells.

In one embodiment, the cancer is MGMT− cancer.
In one embodiment, the cancer is MGMT+ cancer.
In one embodiment, the cancer is MMR proficient cancer.
In one embodiment, the cancer is MMR deficient cancer.
In one embodiment, the cancer is temozolomide resistant or temozolomide refractory.

In one embodiment, the cancer is inherently temozolomide resistant or inherently temozolomide refractory.

In one embodiment, the cancer is temozolomide resistant or temozolomide refractory following exposure to (e.g., treatment with) temozolomide.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death). The compounds of the present invention may be used in the treatment of the cancers described herein, independent of the mechanisms discussed herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, cytotoxic agents, anticancer agents, molecularly-targeted agents, etc. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a 38TM compound as described herein with one or more other (e.g., 1, 2, 3, 4) agents or therapies that regulates cell growth or survival or differentiation via a different mechanism, thus treating several characteristic features of cancer development.

One aspect of the present invention pertains to a 38TM compound as described herein, in combination with one or more additional therapeutic agents, as described below.

The particular combination would be at the discretion of the physician who would select dosages using his common general knowledge and dosing regimens known to a skilled practitioner.

The agents (i.e., the 38TM compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the 38TM compound described here, plus one or more other agents) may be formulated together in a single dosage form, or alternatively, the individual agents may be formulated separately and presented together in the form of a kit, optionally with instructions for their use.

Other Uses

The 38TM compounds described herein may also be used as cell culture additives to inhibit cell proliferation, etc.

The 38TM compounds described herein may also be used as part of an in vitro assay, for example, in order to determine whether a candidate host is likely to benefit from treatment with the compound in question.

The 38TM compounds described herein may also be used as a standard, for example, in an assay, in order to identify other compounds, other anti-proliferative agents, other anticancer agents, etc.

Kits

One aspect of the invention pertains to a kit comprising (a) a 38TM compound as described herein, or a composition comprising a 38TM compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The 38TM compound or pharmaceutical composition comprising the 38TM compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the 38TM compound to be administered alone, it is preferable to present it as a pharmaceutical formulation (e.g., composition, preparation, medicament) comprising at least one 38TM compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one 38TM compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the 38TM compounds, and compositions comprising the 38TM compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular 38TM compound, the route of administration, the time of administration, the rate of excretion of the 38TM compound, the duration of the treatment, other drugs, compounds, and/or materials used in combination, the severity of the condition, and the species, sex, age, weight, condition, general health, and prior medical history of the patient. The amount of 38TM compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the 38TM compound is in the range of about 10 μg to about 250 mg (more typically about 100 μg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

(I) Preparation of C8-Carboxylic Acids

To a solution (or near solution) of the appropriate carboxamide in trifluoroacetic acid (1 mL/mmol carboxamide) in a water bath at room temperature was added a solution of sodium nitrite (0.25 g/mmol carboxamide) in water (0.5 mL/mmol carboxamide) over 30-60 minutes. The mixture was then heated for 3 hours at 35° C. (during which time the mixture lightened considerably in colour) and was then allowed to cool, before pouring onto ice. The resulting precipitate was filtered and dried in the vacuum oven.

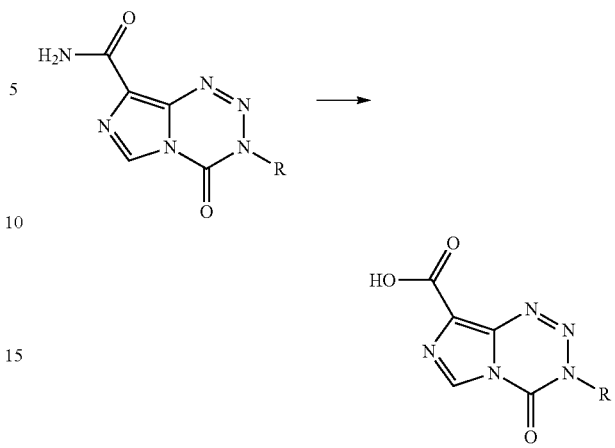

Synthesis 1

3-(Methoxymethyl)-4-oxo-3,4-dihydroimidazo[5,1-d][1,2,3,5]tetrazine-8-carboxylic acid

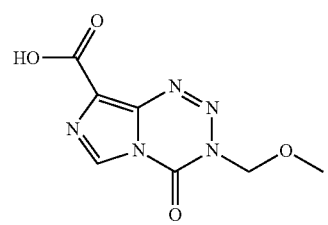

Using the general method, the title compound was obtained as a beige powder (78%). $\delta_H$(DMSO-$d_6$) 13.39 (1H, bs), 8.86 (1H, s), 5.62 (2H, s), 3.42 (3H, s). IR (cm$^{-1}$) 1753, 1711, 1560.

Synthesis 2

4-oxo-3-(prop-2-ynyl)-3,4-dihydroimidazo[5,1-d][1,2,3,5]tetrazine-8-carboxylic acid

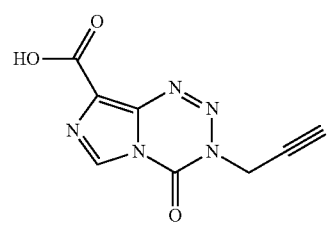 [SMILES: C#CCn1nnc2c(C(=O)O)ncn2c1=O]

Using the general method, the title compound was obtained as an off-white powder (60%). $\delta_H$(DMSO-$d_6$) 13.39 (1H, bs), 8.85 (1H, s), 5.15 (2H, d, J=2.5), 3.53 (1H, t, J=2.5). IR (cm$^{-1}$) 1742, 1709, 1452.

Synthesis 3

3-(Methylthiomethyl)-4-oxo-3,4-dihydroimidazo[5,1-d][1,2,3,5]tetrazine-8-carboxylic acid

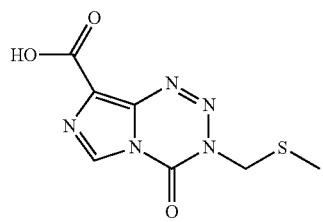 [SMILES: CSCn1nnc2c(C(=O)O)ncn2c1=O]

Using the general method, the title compound was obtained as pale cream powder (66%). $\delta_H$ (DMSO-d$_6$) 13.37 (1H, bs), 8.85 (1H, s), 5.44 (2H, s), 2.26 (3H, s). IR (cm$^{-1}$) 1749, 1716, 1458.

(II) Preparation of C8-Thioamides

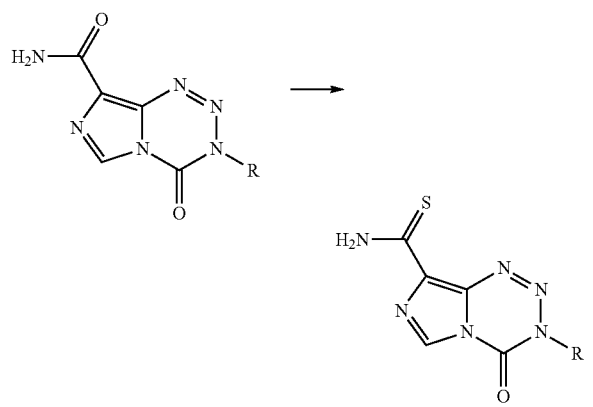

Synthesis 4

3-methyl-4-oxo-3,4-dihydroimidazo[5,1-d][1,2,3,5]tetrazine-8-carbothioamide

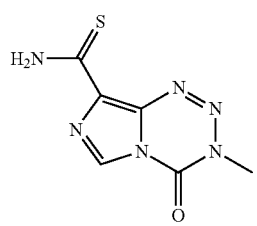

A mixture of temozolomide (3 g, 15.5 mmol) and Belleau's reagent (4.49 g, 8.5 mmol) was refluxed in DCM (80 mL) overnight. The reaction was quenched with water and the precipitate was filtered and washed with diethyl ether to give the pure title compound as an orange solid. (2.75 g, 84%). $\delta_H$ (DMSO-d$_6$): 9.92 (1H, s), 9.45 (1H, s), 8.81 (1H, s), 3.85 (3H, s).

Synthesis 5

4-oxo-3-(prop-2-ynyl)-3,4-dihydroimidazo[5,1-d][1,2,3,5]tetrazine-8-carbothioamide (TT-001)

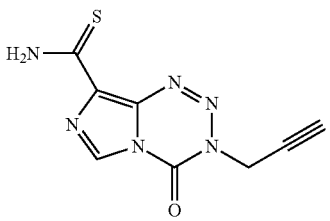 [SMILES: C#CCn1nnc2c(C(N)=S)ncn2c1=O]

4-oxo-3-(prop-2-ynyl)-3,4-dihydroimidazo[5,1-d][1,2,3,5]tetrazine-8-carboxamide (13.75 mmol), phosphorous pentasulphide (10.98 mmol) and hexamethyldisiloxane (32.93 mmol) were stirred in DCM at 40° C. for 5 hours. The crude reaction mixture was poured directly onto a column, and purified by chromatography, eluting with 10% MeCN/DCM. Yield=56%. $\delta_H$ (DMSO-d$_6$) 9.97 (1H, bs), 9.48 (1H, bs), 8.85 (1H, s), 5.14 (2H, d, J=2.5), 3.53 (1H, t, J=2.5).

Synthesis 6

3-(Methylthiomethyl)-4-oxo-3,4-dihydroimidazo[5,1-d][1,2,3,5]tetrazine-8-carbothioamide

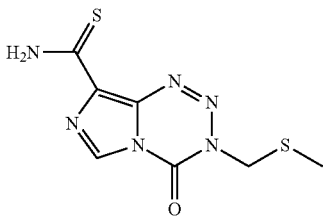 [SMILES: CSCn1nnc2c(C(N)=S)ncn2c1=O]

Phosphorus pentasulfide (25 mg, 0.11 mmol) was added in one portion to a suspension of 3-(methylthiomethyl)-4-oxo-3,4-dihydroimidazo[5,1-d][1,2,3,5]tetrazine-8-carboxamide and hexamethyldisiloxane (85 mg; 0.112 mL, 0.525 mmol) in DCM (5 mL) and the mixture was refluxed overnight. The crude product was absorbed on silica and purified by flash chromatography using DCM:MeOH (95:5) as eluent to give 39 mg of the title compound as an orange solid (36% yield). $\delta_H$ (DMSO d$_6$): 9.95 (1H, s), 9.47 (1H, s), 8.85 (1H, s), 5.43 (2H, s), 2.26 (3H, s).

Synthesis 7

3-(Methoxymethyl)-4-oxo-3,4-dihydroimidazo[5,1-d][1,2,3,5]tetrazine-8-carbothioamide

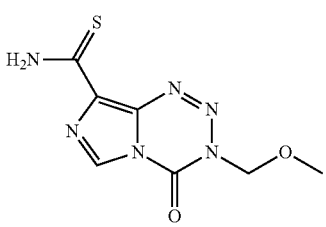 [SMILES: COCn1nnc2c(C(N)=S)ncn2c1=O]

3-(Methoxymethyl)-4-oxo-3,4-dihydroimidazo[5,1-d][1,2,3,5]tetrazine-8-carboxamide (0.100 g, 0.446 mmol), phosphorus pentasulfide (27 mg; 0.06 mmol), and hexamethyldisiloxane (87 mg; 0.114 mL; 0.535 mmol) were stirred in DCM under reflux for 24 hours. After 24 hours, a second portion of $P_2S_5$ (27 mg; 0.06 mmol) was added, and reflux continued for a further 24 hours, after which time the reaction mixture was filtered, and the precipitate was washed with EtOAc, $Et_2O$ and air dried to yield the title compound as an orange solid (67% yield). $^1H$ NMR (400 MHz, $d_6$-DMSO) δ ppm 9.95 (1H, bs), 9.47 (1H, bs), 8.85 (1H, s), 5.74 (2H, s) and 3.40 (3H, s).

(III) Preparation of C8-Thiazoles

To a solution of the appropriate C-8 thioamide (1 eq.) in acetonitrile (15 mL/mmol) was added the appropriate α-bromo ketone (1 eq.), and the solution stirred at room temperature overnight. If a solid precipitate was present, it was filtered; otherwise the reaction mixture was either added directly onto a column, or it was concentrated, and the solid washed, and purified by column chromatography (5-10% MeCN/DCM) where necessary.

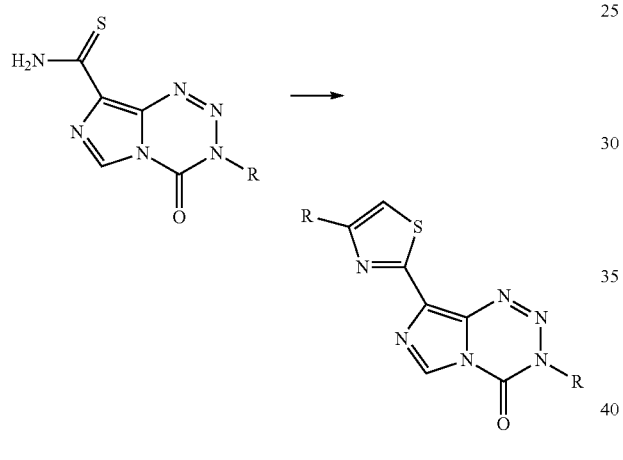

Synthesis 8

8-(4-(4-Fluorophenyl)thiazol-2-yl)-3-methylimidazo[5,1-d][1,2,3,5]tetrazin-4(3H)-one (WW-001)

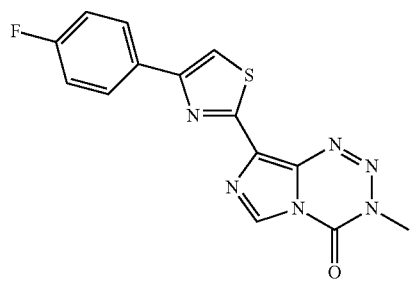 [SMILES: Cn1nnc2c(-c3nc(-c4ccc(F)cc4)cs3)ncn2c1=O]

Using the general method for 8-thiazoles, the title compound was obtained with addition of water to reaction mixture on completion. The precipitate was filtered and dried. Yield 90%. $δ_H$ (DMSO-$d_6$) 8.91 (1H, s), 8.30 (1H, s) 8.13 (2H, dd, J=8.9, 5.5), 7.34 (2H, t, J=8.9), 3.89 (3H, s).

Synthesis 9

3-Methyl-8-(4-phenylthiazol-2-yl)imidazo[5,1-d][1,2,3,5]tetrazin-4(3H)-one (WW-002)

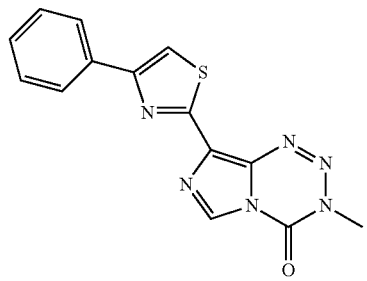 [SMILES: Cn1nnc2c(-c3nc(-c4ccccc4)cs3)ncn2c1=O]

Using the general method for 8-thiazoles, where the reaction mixture was heated for 4 hours, and water was added on cooling, the title compound was obtained as a bright yellow powder, which was filtered, washed with water and dried under vacuum. m.p. 180-182° C. Yield 78%. $δ_H$ (DMSO-$d_6$) 8.92 (1H, s), 8.32 (1H, s), 8.09 (2H, d, J=7.1), 7.52 (2H, t, J=7.6), 7.39-7.43 (1H, m), 3.89 (3H, s).

Synthesis 10

8-(4-Ethylthiazol-2-yl)-3-methylimidazo[5,1-d][1,2,3,5]tetrazin-4(3H)-one (WW-003)

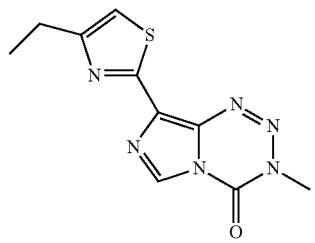 [SMILES: CCc1csc(-c2ncn3c(=O)n(C)nnc23)n1]

Using the general method for 8-thiazoles, the title compound was obtained on addition of water to reaction mixture. The precipitate was filtered, washed with diethyl ether, and dried. Yield 56%.

Synthesis 11

8-(4-phenylthiazol-2-yl)-3-(prop-2-ynyl)imidazo[5,1-d][1,2,3,5]tetrazin-4(3H)-one (WW-004)

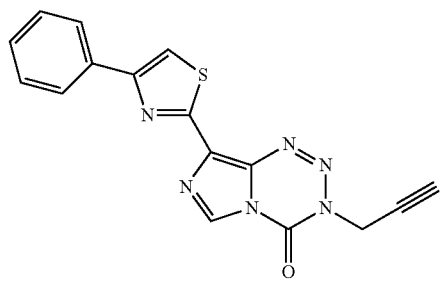 [SMILES: C#CCn1nnc2c(-c3nc(-c4ccccc4)cs3)ncn2c1=O]

Using the general method for 8-thiazoles, the crude reaction mixture was evaporated to dryness and purified by column chromatography, eluting with 1/5 MeCN/DCM to give the title compound. Yield 83%. $\delta_H$ (DMSO-d$_6$) 8.96 (1h, s), 8.34 (1H, s), 8.90 (2H, d, J=7.2), 7.51 (2H, t, J=7.6), 7.42 (1H, t, J=7.2), 5.16 (2H, d, J=2.5), 3.54 (1H, t, J=2.5).

Synthesis 12

8-(4-tert-Butylthiazol-2-yl)-3-(prop-2-ynyl)imidazo[5,1-d][1,2,3,5]tetrazin-4(3H)-one (WW-020)

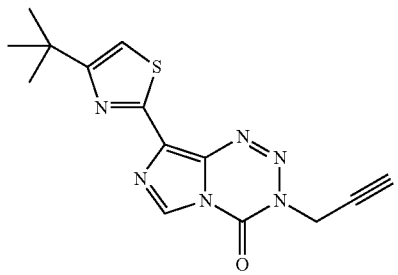 [SMILES: C#CCn1nnc2c(-c3nc(C(C)(C)C)cs3)ncn2c1=O]

Using the general method for 8-thiazoles, a crude reaction mixture was obtained and evaporated to dryness and purified by column chromatography, eluting with 2% MeCN/DCM, to give the title compound. Yield 90%. $\delta_H$ (DMSO-d$_6$) 8.48 (1h, s), 7.12 (1H, s), 5.13 (2H, d, J=2.4), 2.44 (1H, t, J=2.4), 1.44 (9H, s).

Synthesis 13

8-(4-(4-(Methylsulfonyl)phenypthiazol-2-yl)-3-(prop-2-ynyl)imidazo[5,1-d][1,2,3,5]tetrazin-4(3H)-one (WW-025)

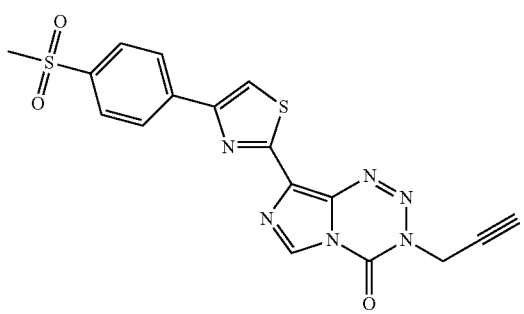 [SMILES: C#CCn1nnc2c(-c3nc(-c4ccc(S(C)(=O)=O)cc4)cs3)ncn2c1=O]

Using the general method for 8-thiazoles, a crude reaction mixture was obtained and evaporated to dryness and purified by column chromatography, eluting with 10% MeCN/DCM, to give the title compound. Yield 48%. $\delta_H$ (DMSO-d$_6$) 8.98 (1H, s), 8.61 (1H, s), 8.34 (2H, dt, J=8.8, 1.6), 8.06 (2H, dt, J=8.8, 1.6), 5.16 (2H, d, J=2.4), 3.55 (1H, t, J=2.8), 3.28 (3H, s).

Synthesis 14

3-Methyl-8-(4-(pyridin-4-yl)thiazol-2-ypimidazo[5,1-d][1, 2, 3, 5]tetrazin-4(3H)-one (WW-013)

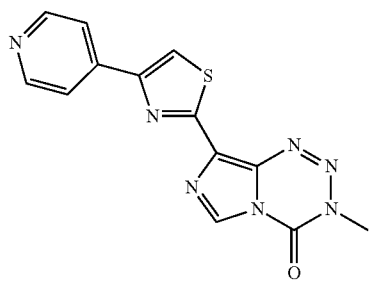 [SMILES: Cn1nnc2c(-c3nc(-c4ccncc4)cs3)ncn2c1=O]

3-Methyl-4-oxo-3,4-dihydroimidazo[5,1-d][1,2,3,5]tetrazine-8-carbothioamide (0.48 mmol), 2-bromo-1-(4-pyridyl)-1-ethanone (0.48 mmol) and DBU (2 drops) were stirred in MeGN (2 mL) overnight at room temperature. The resulting precipitate was filtered, dissolved in saturated sodium bicarbonate solution and extracted with DCM (3×5 mL). The organic layers were evaporated to dryness to give the title compound. Yield 7%. $\delta_H$ (DMSO-d$_6$) 8.73 (2H, dd, J=4.8, 1.6), 8.52 (1H, s), 7.95 (2H, dd, J=4.4, 1.6), 7.91 (1H, s), 4.10 (3H, s).

Synthesis 15

8-(4-(3-Chlorophenyl)thiazol-2-yl)-3-(prop-2-ynyl)imidazo[5,1-d][1,2,3,5]tetrazin-4(3H)-one (WW-023)

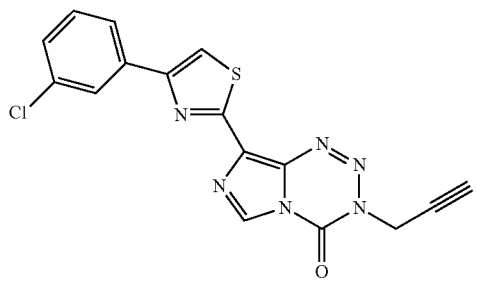 [SMILES: C#CCn1nnc2c(-c3nc(-c4cccc(Cl)c4)cs3)ncn2c1=O]

4-oxo-3-(prop-2-ynyl)-3,4-dihydroimidazo[5,1-d][1,2,3,5]tetrazine-8-carbothioamide (0.43 mmol) and 3'-chlorophenacyl chloride (0.43 mmol) were stirred in MeCN (2 mL) for 60 hours. The reaction mixture was then evaporated to dryness and purified by column chromatography, eluting with 10% MeCN/DCM, to give the title compound. Yield 48%. $\delta_H$ (DMSO-d$_6$) 8.98 (1H, s), 8.50 (1H, s), 8.14 (1H, t, J=1.6), 8.06 (1H, dt, J=8.0, 1.2), 7.55 (1H, t, J=8.0), 7.47 (1H, ddd, J=8.0, 2.0, 1.2), 5.16 (2H, d, J=2.4), 3.56 (1H, t, J=2.4).

Synthesis 16

8-(4-(Benzo[d][1,3]dioxol-5-yl)thiazol-2-yl)-3-(prop-2-ynyl)imidazo[5,1-d][1,2,3,5]tetrazin-4(3H)-one (WW-026)

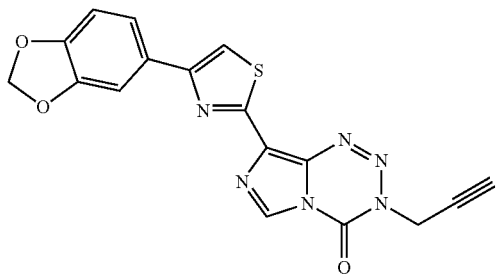 [SMILES: C#CCn1nnc2c(-c3nc(-c4ccc5c(c4)OCO5)cs3)ncn2c1=O]

4-oxo-3-(prop-2-ynyl)-3,4-dihydroimidazo[5,1-d][1,2,3,5]tetrazine-8-carbothioamide (0.22 mmol), 1-(1,3-benzodioxol-5-yl)-2-bromoethan-1-one (0.22 mmol) and triethylamine (0.22 mmol) were stirred in MeCN (2 mL) at room temperature overnight. The reaction mixture was then evaporated to dryness and purified by column chromatography eluting with 3→5% MeCN/DCM, to give the title compound. Yield 59%. $\delta_H$ (DMSO-$d_6$) 9.01 (1H, s), 8.27 (1H, s), 7.70 (1H, dd, J=8.4, 2.0) 7.67 (1H, d, J=1.6), 7.10 (1H, d, J=8.4), 6.16 (2H, s), 5.21 (2H, d, J=2.4), 3.60 (1H, t, J=2.4).

Synthesis 17

3-(Prop-2-ynyl)-8-(4-(thiophen-2-yl)thiazol-2-yl)imidazo[5,1-d][1,2,3,5]tetrazin-4(3H)-one (WW-029)

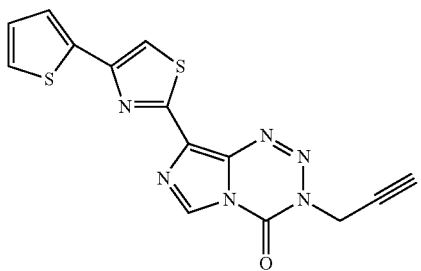 [SMILES: C#CCn1nnc2c(-c3nc(-c4cccs4)cs3)ncn2c1=O]

4-Oxo-3-(prop-2-ynyl)-3,4-dihydroimidazo[5,1-d][1,2,3,5]tetrazine-8-carbothioamide (0.43 mmol) and 2-bromo-1-(2-thienyl)-1-ethanone (0.43 mmol) were stirred in dry MeCN (2 mL) at room temperature overnight. A precipitate formed which was filtered off and treated with basic ion exchange resin. After removal of the resin, the liquor was recombined with the original filtrate and evaporated to dryness before being purified by column chromatography eluting with 5% MeCN/DCM to give the title compound. Yield 73%. $\delta_H$ (DMSO-$d_6$) 8.95 (1H, s), 8.16 (1H, s) 7.67 (1H, dd, J=3.6, 1.2), 7.58 (1H, dd, J=4.8, 1.2), 7.16 (1H, dd, J=4.8, 3.6), 5.14 (2H, d, J=2.4), 3.53 (1H, t, J=2.4).

Synthesis 18

8-(2,4'-Bithiazol-2'-yl)-3-(prop-2-ynyl)imidazo[5,1-d][1,2,3,5]tetrazin-4(3H)-one (WW-028)

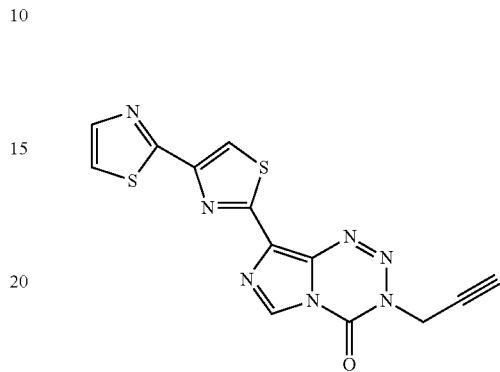

4-oxo-3-(prop-2-ynyl)-3,4-dihydroimidazo[5,1-d][1,2,3,5]tetrazine-8-carbothioamide (0.43 mmol) and 2-bromo-1-(1,3-thiazol-2-yl)ethanone (0.43 mmol) were stirred in MeCN (2 mL) overnight at room temperature. The reaction mixture containing a newly formed precipitate was then treated with sufficient triethylamine to solubilise before evaporating to dryness and purifying by column chromatography, eluting with 10% MeCN/DCM, to give the title compound. Yield 38%. $\delta_H$ (DMSO-$d_6$) 9.00 (1H, s) 8.44 (1H, s), 7.97 (1H, d, J=3.2), 7.85 (1H, d, J=2.8), 5.16 (2H, d, J=2.4), 3.55 (1H, t, J=2.4).

Synthesis 19

N-tert-Butyl-2-(3-methyl-4-oxo-3,4-dihydroimidazo[5,1-d][1,2,3,5]tetrazin-8-yl)thiazole-4-carboxamide (WW-009)

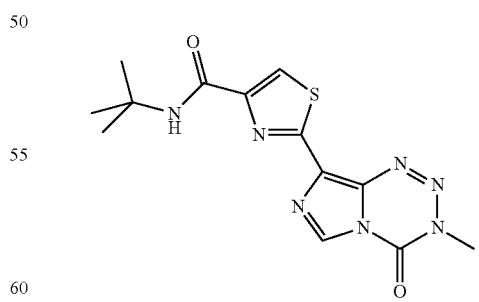

Using the general method for 8-thiazoles, and where a few drops of dichloromethane were added to the reaction mixture to dissolve the starting materials, the title compound was obtained and purified by column chromatography (CHCl₃/

MeCN 19/1→9/1). Yield 69%. $\delta_H$ (DMSO-d$_6$) 8.85 (1H, s), 7.45 (1H, s), 3.85 (3H, s), 1.36 (9H, s).

Synthesis 20

8-(2,4'-Bithiazol-2'-yl)-3-methylimidazo[5,1-d][1,2,3,5]tetrazin-4(3H)-one (WW-010)

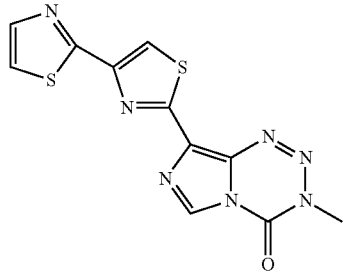 [SMILES: Cn1nnc2c(-c3nc(-c4nccs4)cs3)ncn2c1=O]

Using the general method for 8-thiazoles, the product precipitated from the reaction mixture and was washed with acetonitrile, to give the title compound. Yield 99%. $\delta_H$ (DMSO-d$_6$) 8.95 (1H, s); 8.42 (1H, s), 7.97 (1H, d, J=3.2), 7.85 (1H, d, J=3.2,), 3.90 (Me, s, 3H).

Synthesis 21

8-(4-(4-Bromophenyl)thiazol-2-yl)-3-methylimidazo[5,1-d][1,2,3,5]tetrazin-4(3H)-one (WW-022)

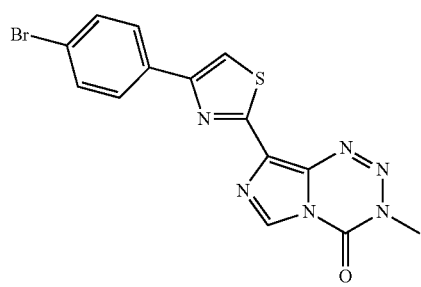 [SMILES: Cn1nnc2c(-c3nc(-c4ccc(Br)cc4)cs3)ncn2c1=O]

3-Methyl-4-oxo-3,4-dihydroimidazo[5,1-d][1,2,3,5]tetrazine-8-carbothioamide (0.48 mmol) and 2,4'-dibromoacetophenone (0.48 mmol) were stirred in MeCN overnight at room temperature. A slight yellow solid persisted which was filtered off before the remaining mixture was purified by preparative thin layer chromatography, eluting with 10% MeCN/DCM, to give the title compound. Yield=81%. $\delta_H$ (DMSO-d$_6$): 8.92 (1H, s), 8.39 (1H, s), 8.04 (2H, d, J=8.8), 7. (2H, d, J=8.8), 3.89 (3H, s).

Synthesis 22

8-(4-(4-Bromophenyl)thiazol-2-yl)-3-(prop-2-ynyl)imidazo[5,1-d][1,2,3,5]tetrazin-4(3H)-one (WW-021)

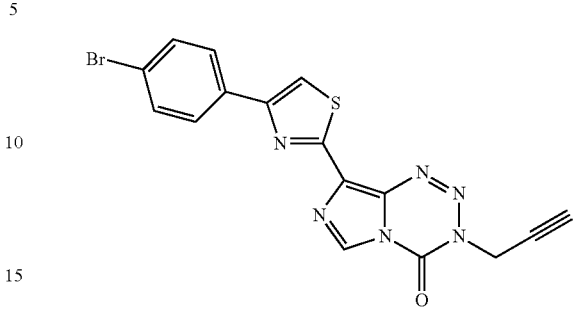

Using the general method for 8-thiazoles, a precipitate was obtained which was filtered and purified by column chromatography, eluting with 2.5% MeCN/DCM, to give the title compound as an off white solid. Yield 33%. $\delta_H$ (DMSO-d$_6$): 8.54 (1H, s), 7.95 (2H, d, J=8.4), 7.71 (1H, s), 7.60 (2H, d, J=8.4), 5.19 (2H, d, J=2.4), 2.49 (2H, t, J=2.8), 2.03 (1H, s).

Synthesis 23

3-Methyl-8-(4-(thiophen-3-yl)thiazol-2-yl)imidazo[5,1-d][1,2,3,5]tetrazin-4(3H)-one (WW-012)

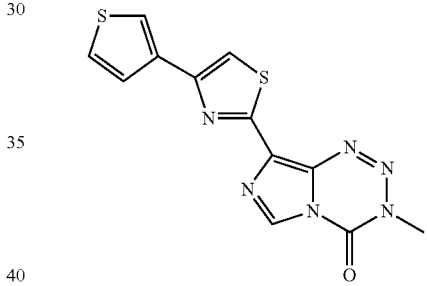

Using the general method for 8-thiazoles, a crude reaction mixture was obtained which was evaporated to dryness and purified by silica column chromatography eluting with 5→10% MeCN/DCM, to give the title compound. Yield=50%. $\delta_H$ (DMSO-d$_6$): 8.91 (1H, s), 8.14 (s, 1H), 8.01 (1H, dd, J=2.8, 1.1), 7.68 (2H, m) 3.89 (1H, s).

Synthesis 24

3-(Prop-2-ynyl)-8-(4-(thiophen-3-yl)thiazol-2-yl)imidazo[5,1-d][1,2,3,5]tetrazin-4(3H)-one (WW-024)

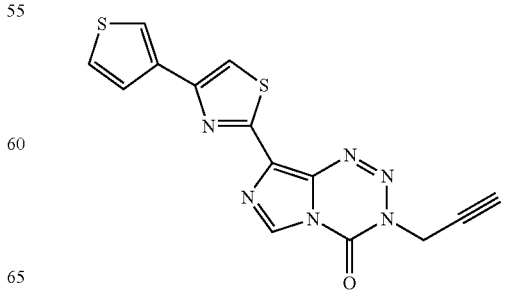

Using the general method for 8-thiazoles, a crude reaction mixture was obtained which was evaporated to dryness and purified by column chromatography eluting with 5→10% MeCN/DCM to give the title compound. Yield 39%. $\delta_H$ (DMSO-$d_6$): 8.95 (1H, s), 8.16 (1H, s), 8.02 (1H, dd, J=2.8, 1.6), 7.69 (2H, m), 5.15 (2H, d, J=2.4), 3.54 (1H, t, J=2.4).

Synthesis 25

3-Methyl-8-(4-(thiophen-2-yl)thiazol-2-yl)imidazo[5,1-d][1,2,3,5]tetrazin-4(3H)-one (WW-011)

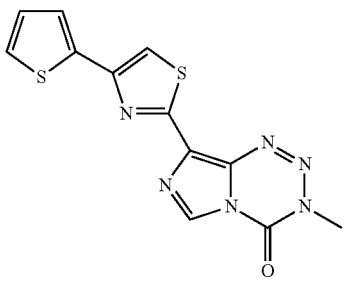 [SMILES: Cn1nnc2c(-c3nc(-c4cccs4)cs3)ncn2c1=O]

Using the general method for 8-thiazoles, a crude reaction mixture was obtained which was evaporated to dryness and purified by column chromatography, (CHCl$_3$/MeCN 19/1), to give the title compound. Yield 75%. $\delta_H$ (DMSO-$d_6$) 8.92 (1H, s), 8.15 (1H, s, 7.68 (1H, dd, J=3.6, 1.2), 7.67 (1H, dd, J=5.2, 1.2), 7.17 (1H, dd, J=4.8, 3.6), 3.89 (3H, s).

Synthesis 26

8-(4-tert-Butylthiazol-2-yl)-3-(methoxymethyl)imidazo[5,1-d][1,2,3,5]tetrazin-4(3H)-one (WW-014)

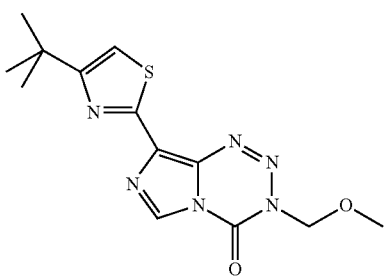 [SMILES: COCn1nnc2c(-c3nc(C(C)(C)C)cs3)ncn2c1=O]

Using the general method for 8-thiazoles, a crude reaction mixture was obtained which was evaporated to dryness and purified by column chromatography, eluting with DCM to DCM: MeOH, 10:1 to give the title compound as a yellow solid (yield 87%). $\delta_H$ (DMSO-$d_6$) 8.90 (1H, s), 7.47 (1H, s), 5.59 (2H, s), 3.42 (3H, s), 1.36 (9H, s).

Synthesis 27

8-(2,4'-Bithiazol-2'-yl)-3-(methoxymethyl)imidazo[5,1-d][1,2,3,5]tetrazin-4(3H)-one (WW-015)

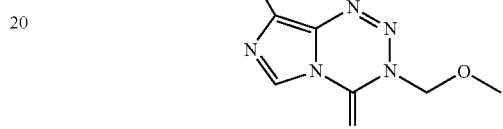

Using the general method for 8-thiazoles, a crude reaction mixture was obtained which was evaporated to dryness and purified by column chromatography, eluting with DCM to DCM: MeOH, 1:1, to yield the title compound as a yellow solid (yield 74%). $\delta_H$ (DMSO-$d_6$) 9.11 (1H, s), 8.59 (1H, s), 8.08 (1H, d, J=3.2), 7.97 (1H, d, J=3.2), 5.71 (2H, s), 3.56 (3H, s).

Synthesis 28

3-(Methoxymethyl)-8-(4-phenylthiazol-2-yl)imidazo[5,1-d][1,2,3,5]tetrazin-4(3H)-one (WW-016)

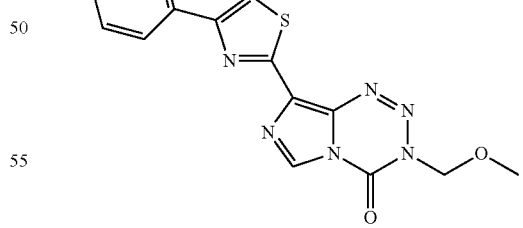

Using the general method for 8-thiazoles, a crude reaction mixture was obtained which was evaporated to dryness and purified by column chromatography, eluting with DCM to DCM: MeOH, 10:1, to yield the title compound as a yellow solid (yield 54%). $\delta_H$ (DMSO-$d_6$) 8.96 (1H, s), 8.33 (1H, s), 8.80 (2H, d, J=7), 7.52 (2H, t, J=7), 7.41 (1H, tt, J=1.2), 5.40 (2H, s), 3.43 (3H, s).

Synthesis 29

3-(Methoxymethyl)-8-(4-(thiophen-3-yl)thiazol-2-yl)imidazo[5,1-d][1,2,3,5]tetrazin-4(3H)-one (WW-017)

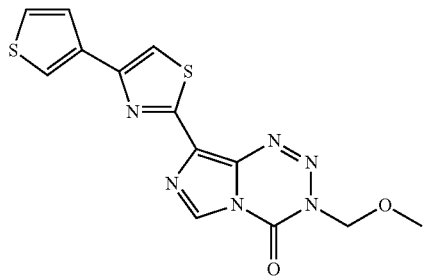 [SMILES: COCn1nnc2c(-c3nc(-c4ccsc4)cs3)ncn2c1=O]

Using the general method for 8-thiazoles, a crude reaction mixture was obtained which was evaporated to dryness and purified by column chromatography, eluting with DCM to DCM: MeOH, 10:1, to give the title compound (yield 37%). $\delta_H$(DMSO-$d_6$) 8.94 (1H, s), 8.14 (1H, s), 8.01 (1H, dd, J=3.2, 1.6), 7.68-7.64 (2H, m), 5.60 (2H, s), 3.42 (3H, s).

Synthesis 30

3-(Methoxymethyl)-8-(4-(thiophen-2-yl)thiazol-2-yl)imidazo[5,1-d][1, 2, 3, 5]tetrazin-4(3H)-one (WW-018)

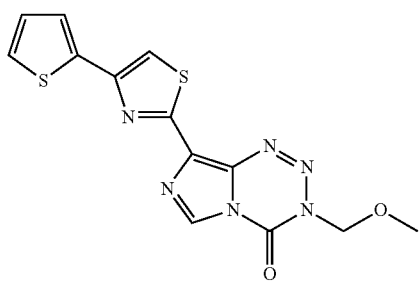 [SMILES: COCn1nnc2c(-c3nc(-c4cccs4)cs3)ncn2c1=O]

Using the general method for 8-thiazoles, a crude reaction mixture was obtained which was evaporated to dryness and purified by column chromatography, eluting with DCM to DCM: MeOH, 10:1, to give the title compound (yield 95%). $\delta_H$(DMSO-$d_6$) 8.95 (1H, s), 8.16 (1H, s), 7.68 (1H, dd, J=3.6, 1.2), 7.59 (1H, dd, J=4.8, 1.2), 7.17 (1H, dd, J=4.8, 3.6), 5.61 (2H, s), 3.43 (3H, s).

Synthesis 31

3-(Methoxymethyl)-8-(4-(pyridin-4-yl)thiazol-2-yl)imidazo[5,1-d][1,2,3,5]tetrazin-4(3H)-one (WW-019)

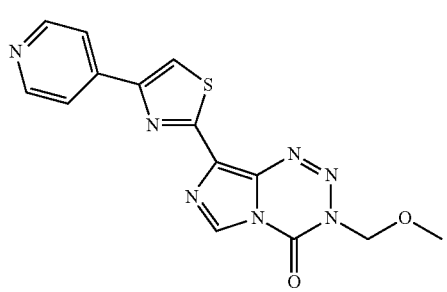 [SMILES: COCn1nnc2c(-c3nc(-c4ccncc4)cs3)ncn2c1=O]

3-(Methoxymethyl)-4-oxo-3,4-dihydroimidazo[5,1-d][1,2,3,5]tetrazine-8-carbothioamide (0.050 g, 0.208 mmol) was stirred in MeCN (2 mL) at room temperature under $N_2$ and then 2-bromo-1-(4-pyridinyl-1-thanone hydrochloride (0.064 g, 0.227 mmol) was added and the reaction mixture stirred overnight. The reaction mixture was then concentrated in vacuo and re-dissolved in EtOAc and washed with aq. NaHCO$_3$ (10 mL). The aqueous layer was extracted with EtOAc (3×10 mL) and the organic fractions combined, dried (MgSO$_4$) and concentrated in vacuo to yield an orange solid (0.036 g). The solid was then purified by flash chromatography (silica gel, gradient elution, DCM (100%) to DCM: MeCN, 10:1 to 1:1) to give the title compound as a yellow solid (0.029 g, 41%); $\delta_H$ (DMSO-$d_6$) 9.06 (1H, s), 8.77-8.76 (2H, m), 8.74 (1H, s), 8.10-8.08 (2H, m), 5.82 (2H, s), 3.51 (3H s).

Synthesis 32

3-(Methoxymethyl)-8-(4-(4-(methylsulfonyl)phenyl)thiazol-2-yl)imidazo[5,1-d][1,2,3,5]tetrazin-4(3H)-one (WW-027)

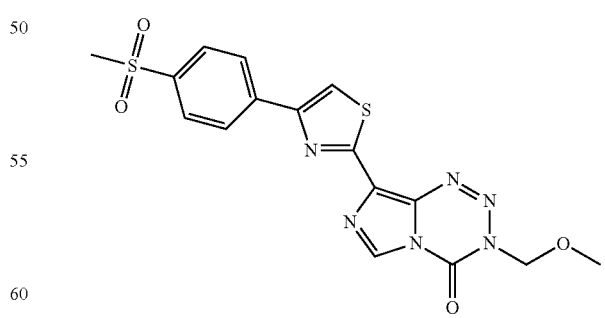

Using the general method for 8-thiazoles, a crude reaction mixture was obtained which was evaporated to dryness and purified by column chromatography, eluting with DCM to DCM: MeCN, 10:1, to give the title compound (yield 70%).

δ$_H$(DMSO-d$_6$) 9.00 (1H, s), 8.62 (1H, s), 8.36 (2H, d, J=8.8), 8.07 (2H, d, J=8.4), 5.64 (2H, s), 3.45 (3H, s), 3.27 (3H, s).

Synthesis 33

(Methoxymethyl)-8-(4-(4-(methylsulfonyl)phenyl)thiazol-2-yl)imidazo[5,1-d][1,2,3,5]tetrazin-4(3H)-one (WW-032)

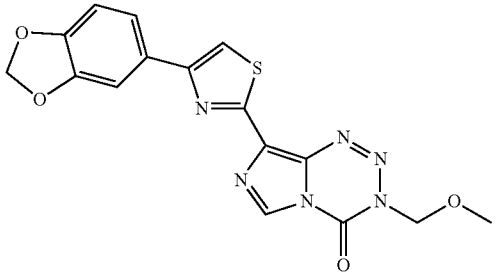 [SMILES: COCn1nnc2c(-c3nc(-c4ccc5c(c4)OCO5)cs3)ncn2c1=O]

Using the general method for 8-thiazoles, and after stirring the reaction mixture for 6 days, the crude reaction mixture was evaporated to dryness and purified by column chromatography, eluting with DCM to DCM: MeCN, 10:1, to give the title compound (yield 55%). δ$_H$ (DMSO-d$_6$) 9.02 (1H, s), 8.27 (1H, s), 7.85-7.67 (2H, m), 7.12 (1H, d, J=8.0), 6.15 (2H, s), 5.69 (2H, s), 3.68 (3H, s).

(IV) Preparation of 8-Thiazole-4-Carboxamides

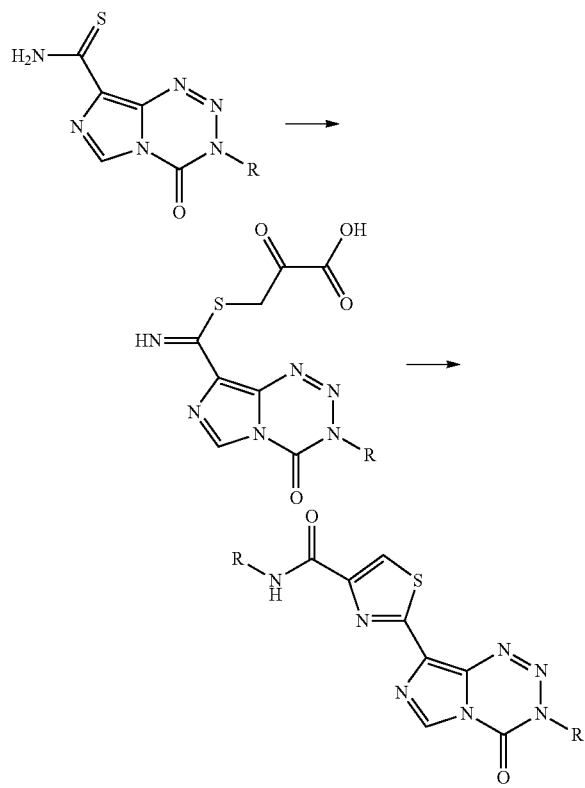

Synthesis 34

3-(Imino(3-methyl-4-oxo-3,4-dihydroimidazo[5,1-d][1,2,3,5]tetrazin-8-yl)methylthio)-2-oxopropanoic acid

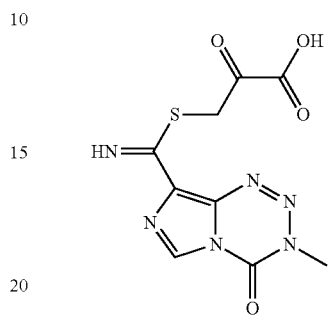

To a solution of 3-bromopyruvic acid (1.388 g; 8.3 mmol) in dry acetonitrile (20 mL) was added 3-methyl-4-oxo-3,4-dihydroimidazo[5,1-d][1,2,3,5]tetrazine-8-carbothioamide (1.000 g; 4.8 mmol). The mixture was stirred at room temperature overnight, and then concentrated under reduced pressure. The residue was washed with DCM (3×15 mL) and diethyl ether (2×20 mL) and the pale yellow solid (1.20 g; 84%) was used without further purification.

Synthesis 35

2-(3-Methyl-4-oxo-3,4-dihydroimidazo[5,1-d][1,2,3,5]tetrazin-8-yl)-N-(prop-2-ynyl)thiazole-4-carboxamide (WW-005)

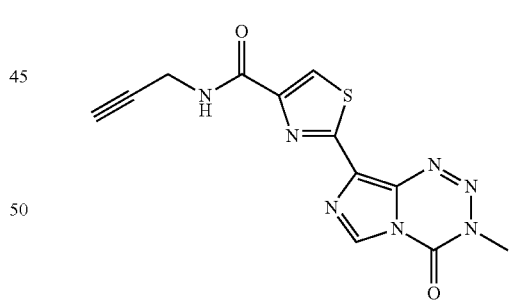

To a solution of 3-(imino(3-methyl-4-oxo-3,4-dihydroimidazo[5,1-d][1,2,3,5]tetrazin-8-yl)methylthio)-2-oxopropanoic acid (0.65 g; 2.2 mmol) in dry THF (30 mL) under nitrogen was added isobutyl chloroformate (0.60 mL; 4.4 mmol), followed by triethylamine (0.62 mL; 4.4 mmol). The mixture was stirred for 1 hour, and then propargylamine (0.28 mL; 4.4 mmol) was added, and stirring continued for a further 3 hours. The precipitate was washed with water (5×15 mL) and diethyl ether (2×15 mL) to yield the title compound as a pale yellow solid (0.250 g; 36%). δ$_H$ (DMSO-d$_6$) 3.13 (1H, m), 3.89 (3H, s), 4.10 (2H, m), 8.47 (1H, s), 8.68 (1H, t, J=5.9), 8.95 (1H, s).

Synthesis 36

2-(3-Methyl-4-oxo-3,4-dihydroimidazo[5,1-d][1, 2, 3, 5]tetrazin-8-yl)thiazole-4-carboxamide (WW-007)

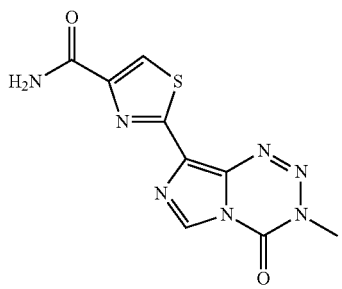 [SMILES: Cn1nnc2c(-c3nc(C(N)=O)cs3)ncn2c1=O]

To a solution of 3-(imino(3-methyl-4-oxo-3,4-dihydroimidazo[5,1-d][1,2,3,5]tetrazin-8-yl)methylthio)-2-oxopropanoic acid (0.700 g; 2.5 mmol) in dry THF (30 mL) under nitrogen was added isobutyl chloroformate (0.50 mL; 3.8 mmol), followed by triethylamine (0.53 mL; 3.8 mmol). The mixture was stirred for 1 hour, and then ammonia solution (0.5 M in dioxane; 20 mL) was added, and stirring continued for a further 3 hours. The precipitate was filtered, washed with water (5×20 mL) and diethyl ether (2×15 mL) to yield the title compound as a pale yellow solid (0.223 g; 40%). $\delta_H$ (DMSO-$d_6$) 8.94 (1H, s), 8.42 (1H, s), 7.74 (1H, bs), 7.59 (1H, bs), 3.89 (3H, s).

Synthesis 37

N-Cyclopropyl-2-(3-methyl-4-oxo-3,4-dihydroimidazo[5,1-d][1, 2, 3, 5]tetrazin-8-yl)thiazole-4-carboxamide (WW-008)

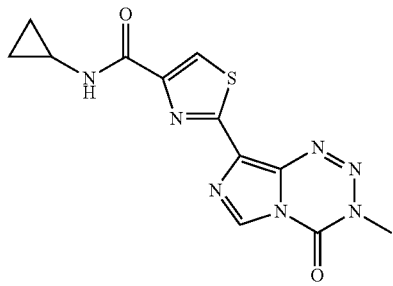 [SMILES: Cn1nnc2c(-c3nc(C(=O)NC4CC4)cs3)ncn2c1=O]

To a solution of 3-(imino(3-methyl-4-oxo-3,4-dihydroimidazo[5,1-d][1,2,3,5]tetrazin-8-yl)methylthio)-2-oxopropanoic acid (0.500 g; 1.8 mmol) in dry THF (30 mL) under nitrogen was added isobutyl chloroformate (0.47 mL; 3.6 mmol), followed by triethylamine (0.51 mL; 3.6 mmol). The mixture was stirred for 1 hours, and then cyclopropylamine (0.206 g; 3.6 mmol) was added, and stirring continued for a further 3 hours. The precipitate was filtered, washed with water (5×20 mL) and diethyl ether (2×15 mL) to yield the title compound as a pale yellow solid (0.278 g; 49%). $\delta_H$ (DMSO-$d_6$) 8.94 (1H, s), 8.41 (1H, s), 8.22 (1H, d, J=4.3), 3.89 (3H, s), 2.88 (1H, m), 0.66-0.76 (4H, m).

Synthesis 38

2-(3-Methyl-4-oxo-3,4-dihydroimidazo[5,1-d][1,2,3,5]tetrazin-8-yl)thiazole-4-carbonitrile (WW-006)

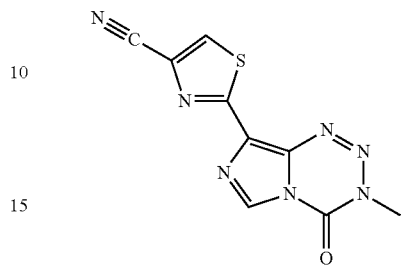

3-methyl-4-oxo-3,4-dihydroimidazo[5,1-d][1,2,3,5]tetrazine-8-carbothioamide: To trimethylsilylcyanide (0.744 g; 7.5 mmol) was added 2-bromoacetyl bromide (1.010 g; 5 mmol). The reaction mixture was stirred for 0.5 hours, and then heated to 70° for 3 hours. Unreacted starting materials were removed under reduced pressure at 120° C. The crude mixture was used without further purification.

To 3-methyl-4-oxo-3,4-dihydroimidazo[5,1-d][1,2,3,5]tetrazine-8-carbothioamide (0.100 g; 0.48 mmol) in acetonitrile (20 mL) was added 2-bromoacetyl cyanide (0.070 g; 0.48 mmol) and the mixture stirred for 8 hours, and then concentrated under reduced pressure. The residue was purified using column chromatography (5:1 DCM:CH$_3$CN) to give the title compound as a pale yellow powder (0.070 mg; 57%). $\delta_H$ (DMSO-$d_6$) 3.90 (3H, s), 8.98 (1H, s), 9.02 (1H, s).

(V) Preparation of C8-Thiazoles N3-Sulfides/Sulfoxides

A mixture of the appropriate α-bromoketone (1 eq.) and 3-(methylthiomethyl)-4-oxo-3,4-dihydroimidazo[5,1-d][1,2,3,5]tetrazine-8-carbothioamide in acetonitrile (~1 mL/0.1 mmol) was stirred at room temperature overnight. The crude product was absorbed on silica and was purified by flash chromatography using a gradient elution from DCM:hexane (50:50) to DCM:MeOH (95:5) to give the target compounds in 62-86% yield.

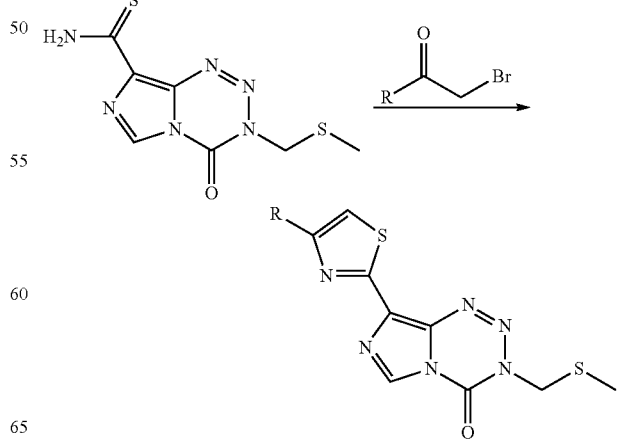

An aqueous solution of Oxone™ (2.2 eq.) was added dropwise to a solution of the appropriate sulfide in DMF (4 mL 100 mg) and the reaction was monitored by TLC (reaction time: 5 to 20 hours). The resulting suspension was poured into ice and the precipitate was filtered and washed successively with water, ethyl acetate and diethyl ether. The crude product was analysed by NMR to detect any remaining starting material. If required, the crude product was suspended in DMF and an aqueous solution of Oxone™ (0.5 eq.) was added. The product was worked-up as above and the process was repeated until a suitable conversion (>95%) was obtained (37-67% yield).

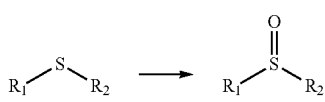

Synthesis 39

3-(Methylthiomethyl)-8-(4-phenylthiazol-2-yl)imidazo[5,1-d][1,2,3,5]tetrazin-4(3H)-one (WW-030)

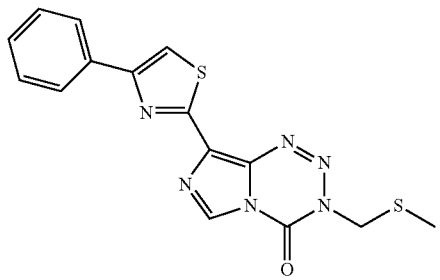

Using the general method, the title compound was obtained. $\delta_H$ (DMSO $d_6$): 8.96 (1H, s), 8.34 (1H, s), 8.10-8.08 (2H, m), 7.53-7.49 (2H, m), 7.39-7.43 (1H, m), 5.45 (2H, s), 2.29 (3H, s).

Synthesis 40

3-(methylthiomethyl)-8-(4-(thiophen-3-yl)thiazol-2-1/1)imidazo[5,1-d][1,2,3,5]tetrazin-4(3H)-one (WW-035)

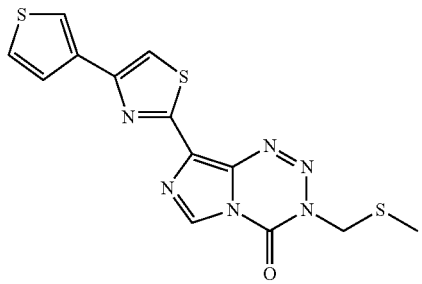 [SMILES: CSCn1nnc2c(-c3nc(-c4ccsc4)cs3)ncn2c1=O]

Using the general method, the title compound was obtained. $\delta_H$ (DMSO $d_6$): 8.95 (1H, s), 8.16 (1H, s), 8.03 (1H, dd, J=2.8, 1.3), 7.70 (1H, dd, J=5.0, 1.3), 7.68 (1H, dd, J=5.0, 2.8), 5.45 (2H, s), 2.29 (3H, s).

Synthesis 41

3-(methylthiomethyl)-8-(4-(thiophen-2-yl)thiazol-2-yl)imidazo[5,1-d][1,2,3,5]tetrazin-4(3H)-one (WW-034)

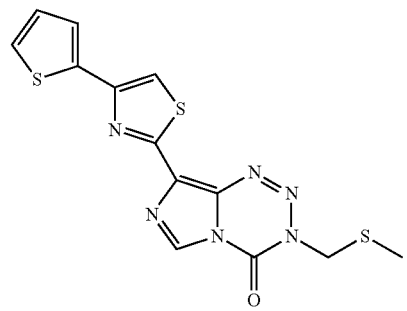 [SMILES: CSCn1nnc2c(-c3nc(-c4cccs4)cs3)ncn2c1=O]

Using the general method, the title compound was obtained. $\delta_H$ (DMSO $d_6$): 8.95 (1H, s), 8.17 (1H, s), 7.68 (1H, dd, J=3.6, 1.2), 7.60 (1H, dd, J=5.0, 1.2), 7.17 (1H, dd, J=5.0, 3.6), 5.44 (2H, s), 2.29 (3H, s).

Synthesis 42

3-(methylsulfinylmethyl)-8-(4-phenylthiazol-2-yl)imidazo[5,1-d][1,2,3,5]tetrazin-4(3H)-one (WW-031)

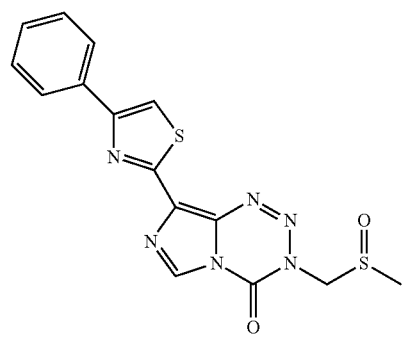 [SMILES: CS(=O)Cn1nnc2c(-c3nc(-c4ccccc4)cs3)ncn2c1=O]

Using the general method, the title compound was obtained. $\delta_H$ (DMSO $d_6$): 9.06 (1H, s), 8.40 (1H, s), 8.14-8.12 (2H, m), 7.57-7.53 (2H, m), 7.47-7.45 (1H, m), 5.65 (1H, d, J=13.2), 5.52 (1H, d, J=13.2), 2.83 (3H, s).

Synthesis 43

3-(methylsulfinylmethyl)-8-(4-(thiophen-3-yl)thiazol-2-yl)imidazo[5,1-d][1,2,3,5]tetrazin-4(3H)-one (WW-033)

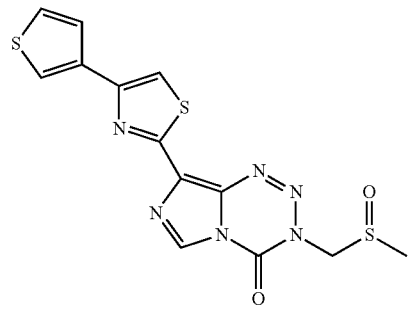 [SMILES: CS(=O)Cn1nnc2c(-c3nc(-c4ccsc4)cs3)ncn2c1=O]

Using the general method, the title compound was obtained. δ$_H$ (DMSO d$_6$): 9.01 (1H, s), 8.18 (1H, s), 8.03 (1H, dd, J=2.8, 1.3), 7.70 (1H, dd, J=5.0, 1.3), 7.68 (1H, dd, J=5.0, 2.8), 5.61 (1H, d, J=13.2), 5.48 (1H, dd, J=13.2), 2.79 (3H, s).

Synthesis 44

3-(methylsulfinylmethyl)-8-(4-(thiophen-2-yl)thiazol-2-yl)imidazo[5,1-d][1,2,3,5]tetrazin-4(3H)-one (WW-036)

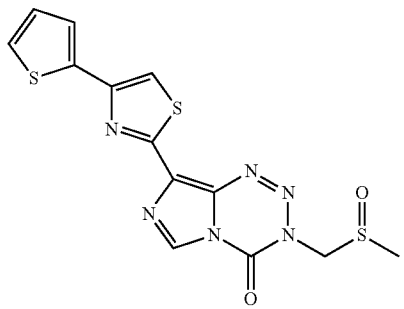 [SMILES: CS(=O)Cn1nnc2c(-c3nc(-c4cccs4)cs3)ncn2c1=O]

Using the general method, the title compound was obtained. δ$_H$ (DMSO d$_6$): 9.00 (1H, s), 8.18 (1H, s), 7.67 (1H, dd, J=3.6, 1.2), 7.59 (1H, dd, J=5.0, 1.2), 7.16 (1H, dd, J=5.0, 3.6), 5.59 (1H, d, J=13.2), 5.46 (1H, d, J=13.2), 2.78 (3H, s).

(VI) Preparation of C8-Oxazoles

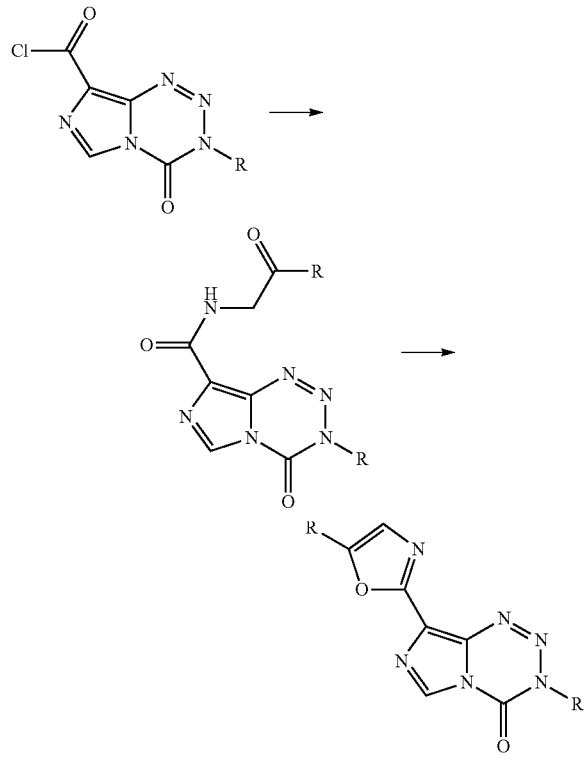

Synthesis 45

3-Methyl-4-oxo-N-(2-oxo-2-phenylethyl)-3,4-dihydroimidazo[5,1-d][1,2,3,5]tetrazine-8-carboxamide

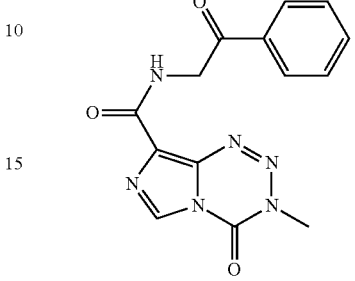

To 3-methyl-4-oxo-3,4-dihydroimidazo[5,1-d][1,2,3,5]tetrazine-8-carbonyl chloride (0.620 g; 2.90 mmol) and 2-aminoacetophenone hydrochloride (0.500 g; 2.90 mmol) was added DMF (6 mL) and pyridine (1.2 mL). The reaction mixture was stirred for 16 hours at room temperature, and then poured onto water. The precipitate was filtered, washed with water, and dried in the vacuum oven, and used without further purification. δ$_H$ (DMSO-d$_6$) 8.89 (1H, s), 8.68 (1H, t, J=5.6), 8.06 (2H, dd, J=8.3, 1.2), (1H, tt, J=7.4, 1.8), 7.58 (2H, m), 4.86 (1H, d, J=5.6), 3.89 (3H, s).

Synthesis 46

N-(2-(4-Bromophenyl)-2-oxoethyl)-3-(methoxymethyl)-4-oxo-3,4-dihydroimidazo[5,1-d][1,2,3,5]tetrazine-8-carboxamide

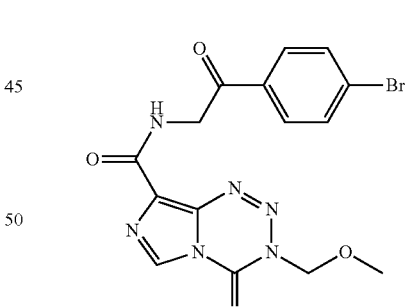

To a solution of the appropriate carboxylic acid (1 eq.) in DMF (2 mL/mmol) was added HBTU (1.05 eq.) and the mixture stirred for 20 minutes. The appropriate amine hydrochloride (1.1 eq.) was added, followed by DIPEA (4 eq.). The mixture was stirred for 2 hours, and then poured onto ice, and the precipitate purified by column chromatography (CHCl$_3$: CH$_3$CN 7:3) to give the title compound as a yellow powder (yield 56%). δ$_H$ (DMSO-d$_6$) 8.94 (1H, s), 8.74 (1H, t, J=5.6), 8.00 (2H, d, J=8.6), 7.79 (2H, d, J=8.6), 5.63 (2H, s), 4.84 (2H, d, J=5.6), 3.43 (3H, s).

Synthesis 47

4-oxo-N-(2-oxo-2-phenylethyl)-3-(prop-2-ynyl)-3,4-dihydroimidazo[5,1-d][1,2,3,5]tetrazine-8-carboxamide

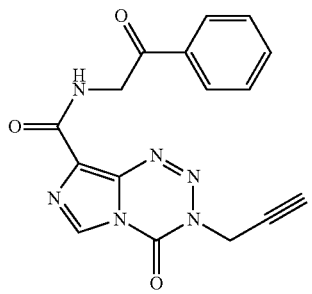 [SMILES: C#CCn1nnc2c(C(=O)NCC(=O)c3ccccc3)ncn2c1=O]

To a solution of the appropriate carboxylic acid (1 eq.) in DMF (2 mL/mmol) was added HBTU (1.05 eq.) and the mixture stirred for 20 minutes. The appropriate amine hydrochloride (1.1 eq.) was added, followed by DIPEA (4 eq.). The mixture was stirred for 2 hours, and then poured onto ice, and the precipitate purified by column chromatography (CHCl$_3$: MeOH 19:1) to give the title compound as a white solid (yield 64%). $\delta_H$ (DMSO-d$_6$) 8.93 (1H, s), 8.71 (1H, t, J=5.5), 8.04-8.02 (2H, m), 7.72-7.68 (1H, m), 7.60-7.56 (2H, m).

Synthesis 48

3-Methyl-8-(4-phenyloxazol-2-yl)imidazo[5,1-d][1,2,3,5]tetrazin-4(3H)-one (WW-037)

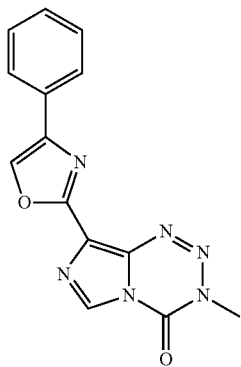 [SMILES: Cn1nnc2c(-c3nc(-c4ccccc4)co3)ncn2c1=O]

Temozolomide (0.200 g; 1.03 mmol) and 2-bromoacetophenone (0.246 g; 1.24 mmol) were stirred in a sealed tube under nitrogen, and heated to 130° C. for 1 hour. The mixture was cooled, and then concentrated in vacuo before being applied directly to the head of a chromatography column (SiO$_2$) and purified by column chromatography (DCM: MeOH, 5:1), to give the title compound as a yellow powder (0.003 g; 1%). $\delta_H$ (DMSO-d$_6$) 8.97 (1H, s), 8.88 (1H, s), 7.91 (2H, t, J=7.4), 7.50 (2H, t, J=7.4), 7.39 (1H, t, J=7.4), 3.90 (3H, s).

Synthesis 49

3-Methyl-8-(5-phenyloxazol-2-yl)imidazo[5,1-d][1,2,3,5]tetrazin-4(3H)-one (WW-038)

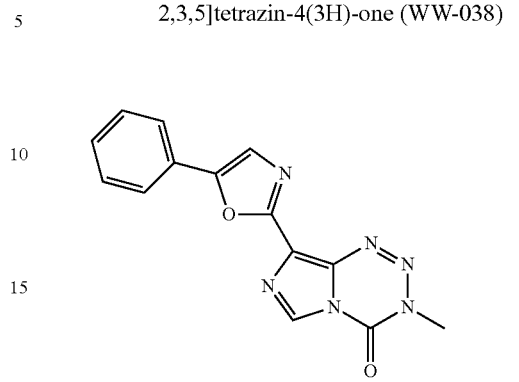

3-Methyl-4-oxo-N-(2-oxo-2-phenylethyl)-3,4-dihydroimidazo[5,1-d][1,2,3,5]tetrazine-8-carboxamide (0.180 g; 0.58 mmol) was added to phosphorus oxychloride (3.6 mL) and the stirred mixture heated at 110° C. for 1.5 hours. The mixture was cooled and poured onto ice, and allowed to stand for 3 hour. The solid was filtered and extracted with chloroform on Soxhlet apparatus. Concentration under reduced pressure yielded pure title compound as a bright yellow powder (55 mg; 32%). $\delta_H$ (DMSO-d$_6$) 8.94 (1H, s), 7.99 (1H, s), 7.85 (2H, m), 7.55 (2H, m), 7.44 (1H, tt, J=7.8, 1.1), 3.90 (3H, s).

Synthesis 50

8-(5-(4-Bromophenyl)oxazol-2-yl)-3-(methoxymethyl)imidazo[5,1-d][1, 2, 3, 5]tetrazin-4(3H)-one (WW-039)

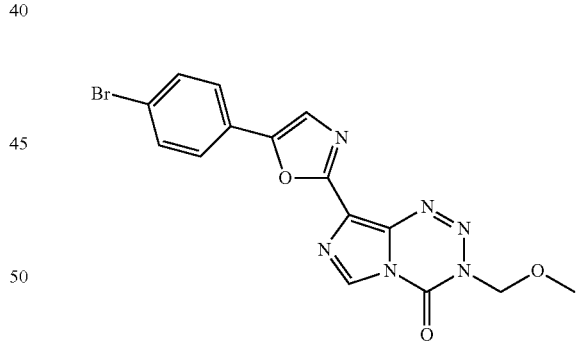

Nitrogen gas was bubbled through N-(2-(4-bromophenyl)-2-oxoethyl)-3-(methoxymethyl)-4-oxo-3,4-dihydroimidazo[5,1-d][1,2,3,5]tetrazine-8-carboxamide (0.252 g; 0.6 mmol) in tetrahydrofuran (6 mL) and Burgess reagent (0.285 g; 1.2 mmol) was added. The reaction was heated at 60° C. under microwave irradiation for 10 minutes, then the reaction analysed by LC/MS, which indicated some product had formed. Further batches of Burgess reagent were added, and microwave irradiation repeated, until all the starting material had been consumed—a total of 6 mmol Burgess reagent used. The product was purified by column chromatography (CHCl$_3$: MeOH 98:2) followed by a second column (Hexane:EtOAc 2:1→1:1), to give the title compound as a pale yellow powder (36 mg; 15%). $\delta_H$ (DMSO-$d_6$) 3.60 (3H, s), 5.78 (2H, s), 7.63 (2H, d, J=8.7), 7.67 (1H, s), 7.72 (2H, d, J=8.7), 8.59 (1H, s).

Synthesis 51

8-(5-Phenyloxazol-2-yl)-3-(prop-2-ynyl)imidazo[5,1-d][1, 2, 3, 5]tetrazin-4(3H)-one (WW-040)

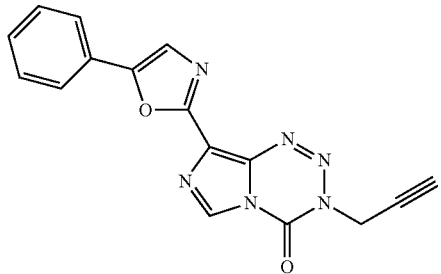 [SMILES: C#CCn1nnc2c(-c3ncc(-c4ccccc4)o3)ncn2c1=O]

Nitrogen gas was bubbled through 4-oxo-N-(2-oxo-2-phenylethyl)-3-(prop-2-ynyl)-3,4-dihydroimidazo[5,1-d][1,2,3,5]tetrazine-8-carboxamide (0.067 g; 0.2 mmol) in tetrahydrofuran (1.5 mL) and Burgess reagent (0.190 g; 0.8 mmol) was added. The reaction was heated at 60° C. under microwave irradiation for 10 minutes, then the reaction analysed by LC/MS, which indicated that the reaction was incomplete. Further Burgess reagent (0.190 g; 0.8 mmol) was adding, and the mixture again heated at 60° C. under microwave irradiation for 10 minutes. The reaction mixture was cooled, filtered, and washed with tetrahydrofuran, and purified by column chromatography (Hexane:ethyl acetate 1:1) to give the title compound as a bright yellow powder (0.005 g; 8%). $\delta_H$ (CDCl$_3$), 8.58 (1H, s), (2H, d, J=8.3, 1.2), 7.66 (1H, s), 7.39-7.43 (1H, m), 5.20 (2H, d, J=2.5), 2.49 (1H, t, J=2.5).

(VII) Preparation of C8-Oxadiazoles

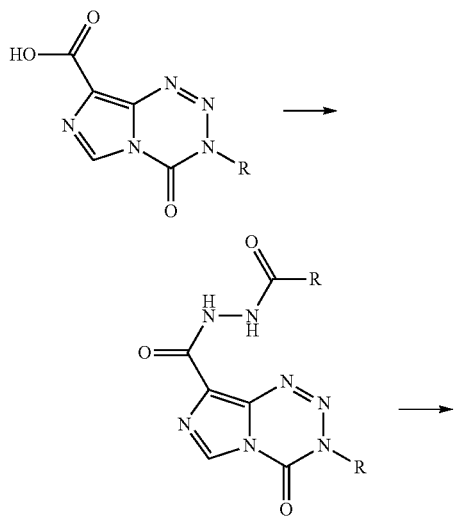

-continued

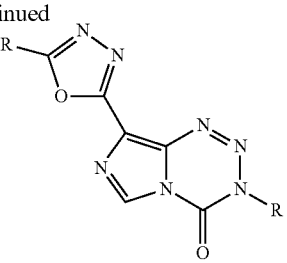

Synthesis 52

3-Methyl-8-(5-phenyl-1,3,4-oxadiazol-2-yl)imidazo[5,1-d][1,2,3,5]tetrazin-4(3H)-one (WW-041)

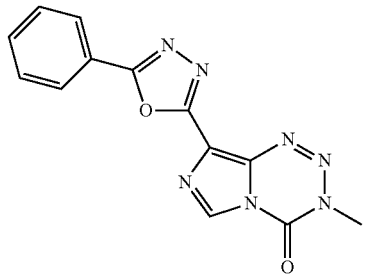 [SMILES: Cn1nnc2c(-c3nnc(-c4ccccc4)o3)ncn2c1=O]

3-Methyl-4-oxo-3,4-dihydroimidazo[5,1-d][1,2,3,5]tetrazine-8-carboxylic acid (0.26 mmol), EDCI (0.26 mmol) and benzoyl hydrazide (0.26 mmol) were stirred in MeCN (1.5 mL) for 36 hours. The yellow precipitate which formed was filtered, washed with diethyl ether and dried to give N'-benzoyl-3-methyl-4-oxo-3,4-dihydroimidazo[5,1-d][1,2,3,5]tetrazine-8-carbohydrazide (72%). $\delta_H$ (DMSO-$d_6$): 10.54 (1H, s), 10.42 (1H, s), 8.91 (1H, s), 7.93 (2H, dd, J=5.2 & 7.2), 7.59 (3H, m), 3.89 (3H, s).

N'-Benzoyl-3-methyl-4-oxo-3,4-dihydroimidazo[5,1-d][1,2,3,5]tetrazine-8-carbohydrazide (0.03 mmol), carbon tetrabromide (0.06 mmol) and triphenylphosphine (0.06 mmol) were stirred in DCM (0.5 mL) for 3 hours. The crude reaction mixture was purified by column chromatography, eluting with 10% MeCN/DCM, to give the title compound. $\delta_H$ (DMSO-$d_6$) 9.06 (1H, s), 8.11 (2H, m), 7.67 (3H, m), 3.93 (3H, s).

Synthesis 53

8-(5-Phenyl-1,3,4-oxadiazol-2-yl)-3-(prop-2-ynyl)imidazo[5,1-d][1,2,3,5]tetrazin-4(3H)-one (WW-042)

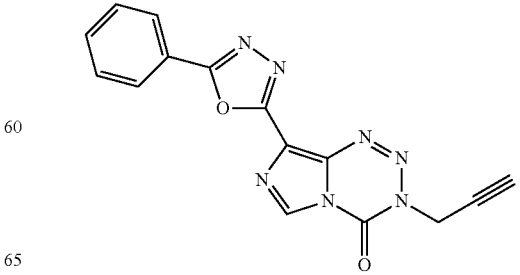

4-oxo-3-(prop-2-ynyl)-3,4-dihydroimidazo[5,1-d][1,2,3,5]tetrazine-8-carboxylic acid (0.23 mmol), EDCI (0.23 mmol) and benzoyl hydrazide (0.23 mmol) were stirred in MeCN (1.5 mL) at room temperature for 24 hours. The reaction was then poured into ice-water, filtered and dried to give N'-benzoyl-4-oxo-3-(prop-2-ynyl)-3,4-dihydroimidazo[5,1-d][1,2,3,5]tetrazine-8-carbohydrazide (74%). $\delta_H$ (DMSO-$d_6$): 10.49 (2H, bs), 8.95 (1H, s), 7.93 (2H, dd, J=6.8, 5.2), 7.60 (3H, m), 5.16 (2H, d, J=2.4), 3.34 (1H, t, J=2.4).

N'-Benzoyl-4-oxo-3-(prop-2-ynyl)-3,4-dihydroimidazo[5,1-d][1,2,3,5]tetrazine-8-carbohydrazide (0.15 mmol) and Burgess reagent (0.30 mmol) were heated under microwave irradiation in THF (1 mL) at 60° C. for 2 minutes (Max Power 100 W). The precipitate was filtered and washed with DCM to give the title compound. $\delta_H$ (DMSO-$d_6$) 9.10 (1H, s), 8.13 (2H, m), 7.70 (3H, m), 5.20 (2H, d, J=2.8), 3.57 (1H, t, J=2.8).

Synthesis 54

3-(Methylthiomethyl)-4-oxo-3,4-dihydroimidazo[5,1-d][1,2,3,5]tetrazine-8-carboxylic acid

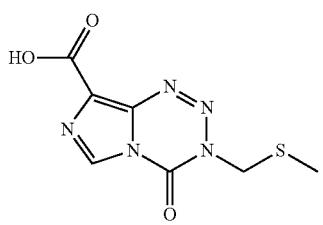

To a solution of 3-(methylthiomethyl)-4-oxo-3,4-dihydroimidazo[5,1-d][1,2,3,5]tetrazine-8-carboxamide (12.43 mmol, 3 g, 1 eq.) in TFA (12 mL) was added sodium nitrite (43.5 mmol, 3 g, 3.5 eq.) dissolved in water (6 mL) portionwise keeping exothermic effervescence under control and the mixture was stirred at room temperature for over 3 hours. The reaction mixture was poured into ice and it was gently stirred until the ice melted. The resulted suspension was filtered, washed with water and ether and dried under vacuum to give the title compound. Yield=61%. $\delta_H$ (DMSO-$d_6$) 8.85 (1H, s), 5.44 (2H, s), 2.25 (3H, s).

Synthesis 55

N'-Benzoyl-3-(methylthiomethyl)-4-oxo-3,4-dihydroimidazo[5,1-d][1,2,3,5]tetrazine-8-carbohydrazide

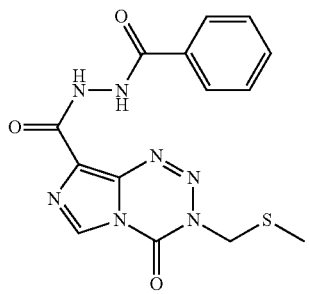 [SMILES: CSCn1nnc2c(C(=O)NNC(=O)c3ccccc3)ncn2c1=O]

3-(Methylthiomethyl)-4-oxo-3,4-dihydroimidazo[5,1-d][1,2,3,5]tetrazine-8-carboxylic acid (0.73 mmol, 175 mg, 1 eq.), 1-ethyl-3-(3'-dimethylaminopropyl)carbodiimide (EDCI) (0.76 mmol, 146 mg, 1.05 eq.) and benzohydrazide (0.76 mmol, 104 mg, 1.05 eq.) were placed in a round bottom flask and dissolved in acetonitrile (3 mL). A suspension developed 1 minute after starting room temperature stirring and it was stirred for further 90 minutes. The reaction mixture was filtered and the obtained solid washed with water, acetonitrile and ether, and dried under vacuum. The filtrate was poured into ice/water and the filtration, washing and drying steps were repeated. Yield 65%. $\delta_H$ (DMSO-$d_6$) 10.35 (1H, bs), 10.28 (1H, bs), 8.75 (1H, bs), 7.74 (2H, m), 7.37 (3H, m), 5.25 (2H, bs), 2.07 (3H, bs).

Synthesis 56

3-(Methylthiomethyl)-8-(5-phenyl-1,3,4-oxadiazol-2-yl)imidazo[5,1-d][1,2,3,5]tetrazin-4(3H)-one

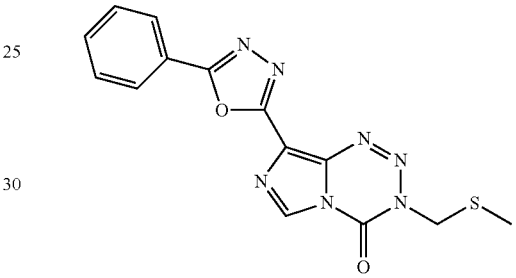

N'-benzoyl-3-(methylthiomethyl)-4-oxo-3,4-dihydroimidazo[5,1-d][1,2,3,5]tetrazine-8-carbohydrazide (0.47 mmol, 170 mg, 1 eq.) and 1-methoxy-N-triethylammoniosulfonyl-methanimidate (Burgess Reagent) (1.61 mmol, 383 mg, 3.4 eq.) were dissolved in THF (8 mL). Microwave energy was applied to the solution for 5 minutes, keeping reaction temperature at 60° C. The reaction mixture was poured into ice/water and the formed solid was filtered and washed with water, acetonitrile and ether, and dried under vacuum to give the title compound. Yield 71%. $\delta_H$ (DMSO-$d_6$) 8.90 (1H, bs), 7.92 (2H, bs), 7.49 (3H, bs), 5.29 (2H, bs), 2.09 (3H, bs).

Synthesis 57

3-(Methylsulfinylmethyl)-8-(5-phenyl-1,3,4-oxadiazol-2-yl)imidazo[5,1-d][1,2,3,5]tetrazin-4(3H)-one
(WW-043)

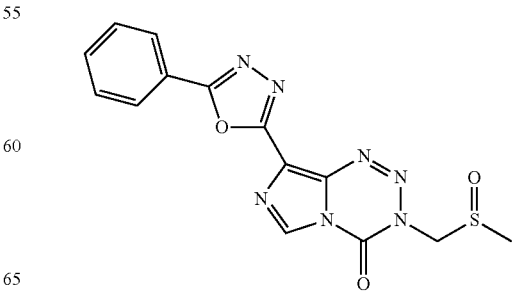

To a 0° C. solution of 3-(methylthiomethyl)-8-(5-phenyl-1,3,4-oxadiazol-2-yl)imidazo[5,1-d][1,2,3,5]tetrazin-4(3H)-one (0.337 mmol, 115 mg, 1 eq.) in DMF (6 mL) was added potassium peroxymonosulfate (Oxone™) (0.37 mmol, 114 mg, 1.1 eq.) dissolved in water (1.2 mL) drop wise. The formed suspension was stirred at 0° C. and stepwise additions of Oxone™ in water were made until reaction completion. The reaction mixture was filtered and the obtained solid was washed with water, acetonitrile and ether, and dried under vacuum to give the title compound. Yield 90%. $\delta_H$ (DMSO-$d_6$) 9.15 (1H, s), 8.13 (2H, dd, J: 7.96, 2.25), 7.70 (3H, m), 5.67 (1H, d, J: 13.06), 5.52 (1H, d, J: 13.06), 2.81 (3H, s).

(VIII) Preparation of C8-Imidazoles

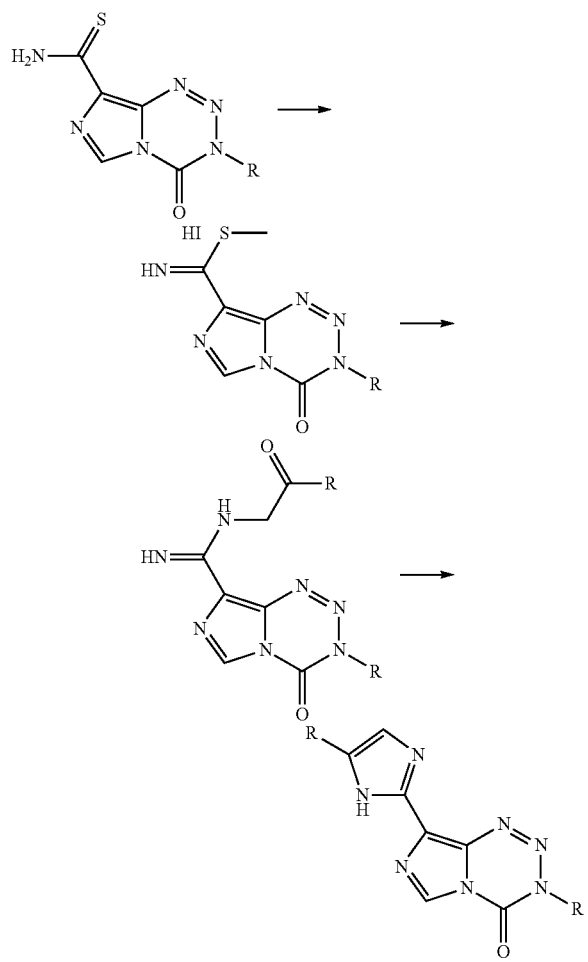

Synthesis 58

Methyl 3-methyl-4-oxo-3,4-dihydroimidazo[5,1-d][1,2,3,5]tetrazine-8-carbimidothioate hydroiodide

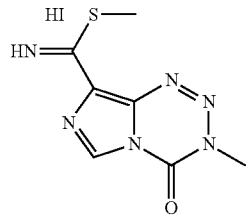

A solution of 3-methyl-4-oxo-3,4-dihydroimidazo[5,1-d][1,2,3,5]tetrazine-8-carbothioamide (2.75 g, 13.1 mmol) and methyl iodide (8.2 mL, 131 mmol) in acetonitrile (900 mL) was stirred at room temperature for 3 days. The mixture was concentrated under vacuum and the solid was suspended in diethyl ether. The precipitate was filtered and washed with diethyl ether to give the pure title compound as an orange solid (4.03 g, 88% yield). $\delta_H$ (DMSO-$d_6$): 11.6 (1H, bs), 9.18 (1H, s) 3.94 (3H, s), 2.82 (3H, s).

Synthesis 59

Methyl-4-oxo-3-(prop-2-ynyl)-3,4-dihydroimidazo[5,1-d][1,2,3,5]tetrazine-8-carbimidothioate hydroiodide

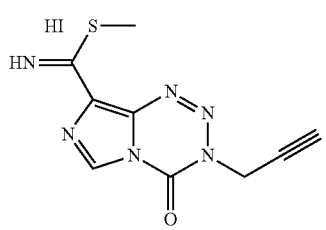

4-oxo-3-(prop-2-ynyl)-3,4-dihydroimidazo[5,1-d][1,2,3,5]tetrazine-8-carbothioamide (0.323 g; 0.86 mmol) was dissolved in dry MeCN (1 mL) and iodomethane (1.220 g; 8.6 mmol) was added and the reaction mixture stirred at room temperature overnight.

A yellow precipitate was filtered, washed with diethyl ether and dried to give the title compound (90%). $\delta_H$ (DMSO-$d_6$): 9.23 (1H, s), 5.24 (2H, d, J=2.6), 3.61 (1H, t, J=2.6), 2.87 (3H, s).

C8-Substituted Amidines: Triethylamine (1.1 eq.) was added to a suspension of the appropriate aminoketone hydrochloride in acetonitrile (4 mL/100 mg of S-methylthioimidate hydroiodide) and the mixture was stirred for 5 minutes (10 minutes in the case of aminoacetophenone) at room temperature before the addition of the appropriate 8-substituted S-methylthioimidate hydroiodide derivative. The mixture was stirred for the reaction time specified for each compound and the precipitate, which formed during the reaction, was filtered, washed successively with cold water, acetonitrile, ethyl acetate and diethyl ether to give the 8-substituted amidine hydroiodide derivative as an off-white solid. The product was used crude for the next step. (The NMR spectra of the crude amidines showed that these were obtained as a mixture with the 8-subsitituted imidazole hydroiodides.)

Synthesis 60

3-Methyl-4-oxo-N-(2-oxo-2-phenylethyl)-3,4-dihydroimidazo[5,1-d][1,2,3,5]tetrazine-8-carboximidamide hydroiodide

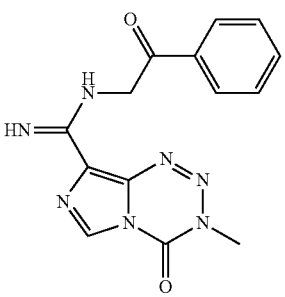 [SMILES: Cn1nnc2c(C(=N)NCC(=O)c3ccccc3)ncn2c1=O]

Using the general procedure, the title compound was synthesized from methyl 3-methyl-4-oxo-3,4-dihydroimidazo[5,1-d][1,2,3,5]tetrazine-8-carbimidothioate hydroiodide and aminoacetophenone, using a reaction time for the amidine formation of 3.5 hours. Yield 34%. $\delta_H$ (DMSO-$d_6$): 9.69 (2H, m), 9.51 (1H, bs), 9.22 (1H, s), 8.07-8.05 (2H, m), 7.78-7.73 (1H, m), 7.65-7.61 (2H, m), 5.24 (2H, d, J=6.0), 4.06 (3H, s).

Synthesis 61

3-Methyl-4-oxo-N-(2-oxo-2-(thiophen-2-yl)ethyl)-3,4-dihydroimidazo[5,1-d][1,2,3,5]tetrazine-8-carboximidamide hydroiodide

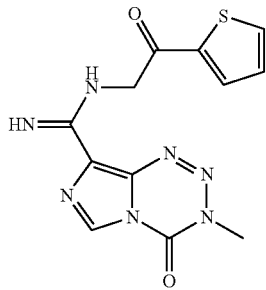 [SMILES: Cn1nnc2c(C(=N)NCC(=O)c3cccs3)ncn2c1=O]

Using the general procedure, the title compound was synthesized from methyl 3-methyl-4-oxo-3,4-dihydroimidazo[5,1-d][1,2,3,5]tetrazine-8-carbimidothioate hydroiodide and 2-amino-1-(thiophen-2-yl)ethanone hydrochloride, using a reaction time of 16 hours for the amidine formation. Yield 66%. $\delta_H$ (DMSO-$d_6$): 9.76-9.73 (1H, m), 9.69 (1H, s), 9.49 (1H, bs), 9.22 (1H, s), 8.16 (1H, dd, J=4.9, 1.1), 8.12 (1H, dd, J=3.8, 1.1), 7.37 (1H, dd, J=4.9, 3.8), 5.17 (2H, d, J=6.3), 4.06 (3H, s).

Synthesis 62

4-oxo-N-(2-oxo-2-phenylethyl)-3-(prop-2-ynyl)-3,4-dihydroimidazo[5,1-d][1,2,3,5]tetrazine-8-carboximidamide hydroiodide

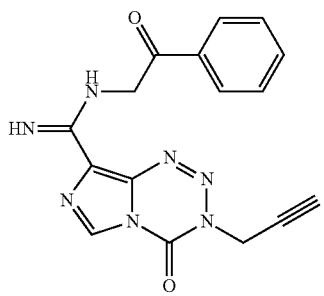 [SMILES: C#CCn1nnc2c(C(=N)NCC(=O)c3ccccc3)ncn2c1=O]

Using the general procedure, the title compound was synthesized from methyl 4-oxo-3-(prop-2-ynyl)-3,4-dihydroimidazo[5,1-d][1,2,3,5]tetrazine-8-carbimidothioate hydroiodide and aminoacetophenone hydrochloride, using a reaction time of 5 hours and 30 minutes for the amidine formation. Yield 29%. $\delta_H$ (DMSO-$d_6$): 9.74 (2H, m), 9.54 (1H, bs), 9.25 (1H, s), 8.07-8.05 (2H, m), 7.78-7.73 (1H, m), 7.65-7.61 (2H, m), 5.27-5.24 (4H, m), 3.62 (1H, t, J=2.5).

Synthesis 63

3-Methyl-8-(4-phenyl-1H-imidazol-2-yl)imidazo[5,1-d][1,2,3,5]tetrazin-4(3H)-one (WW-049)

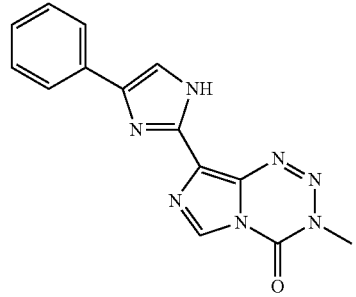 [SMILES: Cn1nnc2c(-c3nc(-c4ccccc4)c[nH]3)ncn2c1=O]

A mixture of crude 3-methyl-4-oxo-N-(2-oxo-2-phenylethyl)-3,4-dihydroimidazo[5,1-d][1,2,3,5]tetrazine-8-carboximidamide hydroiodide (250 mg) in 3N HCl (17 mL) was heated at 80° C. overnight. After being cooled to room temperature, the mixture was left at 4° C. for 1 hour and the precipitate was filtered and washed successively with cold water, ethyl acetate and diethyl ether to give a 97:3 mixture of hydrochloride and hydroiodide salt (elemental analysis) of the title compound.

The salt (50 mg) was dissolved in MeCN:MeOH and triethylamine (23 µL) was added and a precipitate formed almost immediately. The resulting suspension was stirred for 5 minutes and methanol was added. The precipitate was filtered and washed successively with water, ethyl acetate and diethyl ether to give pure title compound as a bright yellow solid (26 mg, 50%). $\delta_H$ (DMSO-$d_6$): 12.9 (1H, bs), 8.89 (1H, s), 7.92-7.89 (2H, m), 7.80 (1H, bs), 7.40 (2H, t, J=7.6), 7.24 (1H, t, J=7.2), 3.86 (3H, s).

Synthesis 64

3-Methyl-8-(4-(thiophen-2-yl)-1H-imidazol-2-yl)imidazo[5,1-d][1,2,3,5]tetrazin-4(3H)-one (WW-048)

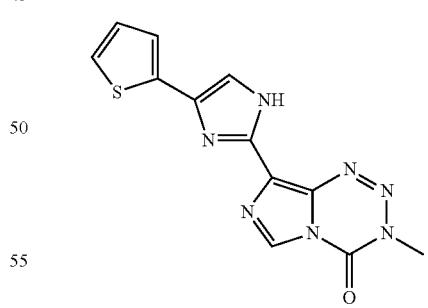

A mixture of crude 3-methyl-4-oxo-N-(2-oxo-2-(thiophen-2-yl)ethyl)-3,4-dihydroimidazo[5,1-d][1,2,3,5]tetrazine-8-carboximidamide hydroiodide (40 mg) in 3N HCl (3 mL) was heated at 80° C. overnight. After being cooled to room temperature, the mixture was left at 4° C. for 2 hours and the precipitate was filtered and washed successively with cold water, ethyl acetate and diethyl ether to give the a mixture of the hydrochloride and hydroiodide salts of the title compound (24 mg).

The salt (24 mg) was dissolved in MeCN:MeOH and triethylamine (10 μL) was added. The mixture was stirred for 5-10 minutes and concentrated under vacuum. The resulting solid was suspended in ethyl acetate and the product was filtered and washed successively with water, ethyl acetate and diethyl ether to give pure title compound as a bright yellow solid (10 mg, 49%). $\delta_H$ (DMSO-$d_6$): 12.9 (1H, bs), 8.89 (1H, s), 7.67 (1H, bs), 7.44-7.39 (2H, m), 7.08 (1H, dd, J=4.7, 3.9), 3.86 (3H, s).

Synthesis 65

8-(4-Phenyl-1H-imidazol-2-yl)-3-(prop-2-ynyl)imidazo[5,1-d][1,2,3,5]tetrazin-4(3H)-one (WW-050)

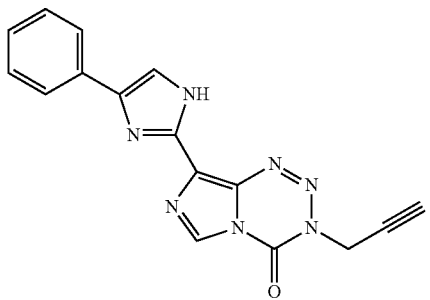 [SMILES: C#CCn1nnc2c(-c3nc(-c4ccccc4)c[nH]3)ncn2c1=O]

A mixture of crude 4-oxo-N-(2-oxo-2-phenylethyl)-3-(prop-2-ynyl)-3,4-dihydroimidazo[5,1-d][1,2,3,5]tetrazine-8-carboximidamide hydroiodide (45 mg) in 3N HCl (4 mL) was heated at 80° C. overnight. After being cooled to room temperature, the mixture was left at 4° C. for 2 hours and the precipitate was filtered and washed successively with cold water, ethyl acetate and diethyl ether to give a mixture of the hydrochloride and hydroiodide salts of the title compound.

The product was dissolved in MeCN:MeOH and triethylamine (30 μL) was added. The mixture was stirred for 10 minutes and concentrated under vacuum. The resulting solid was suspended in ethyl acetate and the product was filtered and washed successively with water, ethyl acetate and diethyl ether to give pure title compound as a bright yellow solid (18 mg, 34%). $\delta_H$ (DMSO-$d_6$): 12.9 (1H, bs), 8.93 (1H, s), 7.90-7.88 (2H, m), 7.82 (1H, d, J=2.3), 7.43-7.36 (2H, m), 7.21-7.25 (1H, m), 5.11 (2H, d, J=2.5), 3.51 (1H, d, J=2.5). (The NMR spectrum showed that the product contained ~15% of the regioisomer.)

Synthesis 66

N-(2,2-Dimethoxyethyl)-3-methyl-4-oxo-3,4-dihydroimidazo[5,1-d][1,2,3,5]tetrazine-8-carboximidamide hydroidide

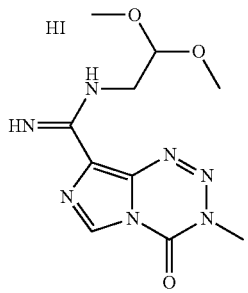

Aminoacetaldehyde dimethyl acetal (68 μL, 0.624 mmol) was added to a suspension of methyl 3-methyl-4-oxo-3,4-dihydroimidazo[5,1-d][1,2,3,5]tetrazine-8-carbimidothioate hydroiodide (200 mg, 0.568 mmol) in acetonitrile (8 mL) and the mixture was stirred overnight. The precipitate, which formed during the reaction, was filtered and washed successively with water, acetonitrile, ethyl acetate and diethyl ether to give the title product as a bright yellow solid (92 mg, 58%). $\delta_H$ (DMSO-$d_6$): 9.50 (3H, bs), 9.17 (1H, s), 4.69-4.71 (1H, t, J=5.3), 3.95 (3H, s), 3.70-3.72 (2H, d, J=5.3), 3.37 (6H, s).

(In some cases, concentration of the filtrate, suspension of the resulting solid in ether and filtration of the product could give the amidine in suitable purity to be used, without further manipulation, for the next step.)

Synthesis 67

8-(1H-Imidazol-2-yl)-3-methylimidazo[5,1-d][1,2,3,5]tetrazin-4(3H)-one (WW-047)

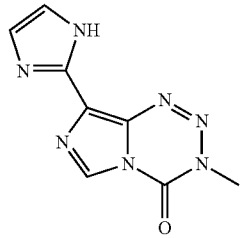 [SMILES: Cn1nnc2c(-c3ncc[nH]3)ncn2c1=O]

A solution of N-(2,2-dimethoxyethyl)-3-methyl-4-oxo-3,4-dihydroimidazo[5,1-d][1,2,3,5]tetrazine-8-carboximidamide hydroiodide (60 mg; 0.147 mmol) in 3N HCl (4.5 mL) was stirred at 80° C. overnight and was then allowed to cool to room temperature. The solution was concentrated under high vacuum and the residue was dissolved in MeCN:MeOH. Triethylamine (1.2 eq.) was added and the mixture was stirred for 5 minutes. The mixture was absorbed on silica and the product was purified by flash chromatography using DCM:MeOH (90:10) as eluent to give a yellow/green solid (22 mg). The NMR spectrum of the product showed contamination with triethylamine hydrochloride, so the product was suspended in diethyl ether, filtered and washed successively with water, ethyl acetate and diethyl ether to give the pure title product as a yellow/green solid (16 mg, 39%). $\delta_H$ (DMSO-$d_6$): 12.8 (1H, bs), 8.86 (1H, s), 7.22 (1H, s), 3.85 (3H, s).

(IX) Preparation of C8-Alkylated Imidazoles

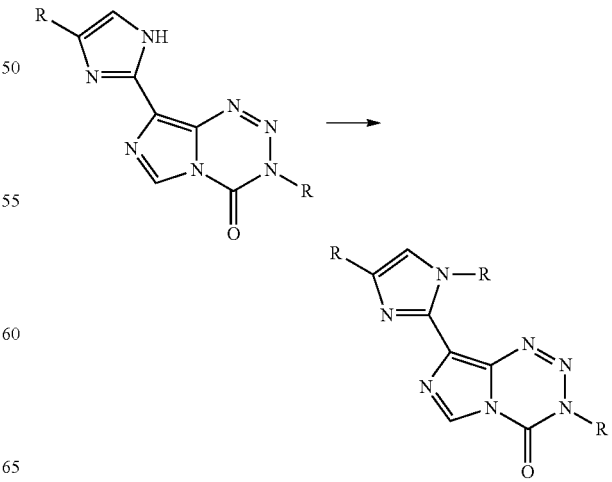

Synthesis 68

3-Methyl-8-(1-methyl-4-phenyl-1H-imidazol-2-yl) imidazo[5,1-d][1,2,3,5]tetrazin-4(3H)-one (WW-051)

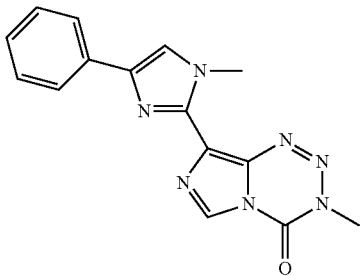 [SMILES: Cn1cc(-c2ccccc2)nc1-c1ncn2c(=O)n(C)nnc12]

Sodium hydride (60% in mineral oil, 19 mg, 0.467 mmol) was added in portions to a solution of 8-(4-phenyl-1H-imidazol-2-yl)-3-(prop-2-ynyl)imidazo[5,1-d][1,2,3,5]tetrazin-4(3H)-one hydrochloride (70 mg) in DMF (3 mL) and the mixture was sonicated several times until hydrogen evolution ceased. Methyl iodide (66 µL, 1.065 mmol) was added and the mixture was stirred overnight. The resulting solution was poured into ice and was then left at 4° C. for 5 hours. The precipitate was filtered and washed successively with water and diethyl ether. 10 mg of crude product obtained from a previous experiment was combined, and the crude mixture was absorbed on silica. The crude product was purified by flash chromatography using DCM:MeOH (95:5) as eluent to give the title compound as a bright yellow solid (25 mg, 23%). The NMR spectrum of the product showed that it contained ~5/6% of either starting material or the regioisomer of the product. $\delta_H$ (DMSO-$d_6$): 8.92 (1H, s), 7.89 (1H, s), 7.89-7.92 (2H, m), 7.38-7.42 (2H, m), 7.22-7.26 (1H, m), 3.98 (3H, s), 3.87 (3H, s).

Synthesis 69

8-(1-Methyl-4-(thiophen-2-yl)-1H-imidazol-2-yl)-3-(prop-2-ynyl)imidazo[5,1-d][1,2,3,5]tetrazin-4(3H)-one (WW-053)

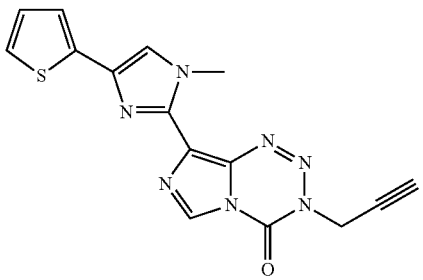 [SMILES: C#CCn1nnc2c(-c3nc(-c4cccs4)cn3C)ncn2c1=O]

3-(Prop-2-ynyl)-8-(5-(thiophen-2-yl)-1H-imidazol-2-yl)imidazo[5,1-d][1,2,3,5]tetrazin-4(3H)-one (0.15 mmol) was dissolved in dry DMF (1 mL) and cooled in ice under a nitrogen atmosphere. A 60% suspension of sodium hydride in mineral oil (0.17 mmol) was added in one portion and the reaction stirred on ice for 10 minutes. Methyl iodide (0.30 mmol) was then added dropwise to the reaction and the mixture stirred at room temperature for 24 hours. Solvent was then removed under vacuum and product isolated by preparative thin layer chromatography eluting with 2.5% MeOH/DCM. Yield 90%. $\delta_H$ (DMSO-$d_6$) 8.97 (1H, s), 7.78 (1H, s), 7.40 (1H, dd, J=5.2, 1.2), 7.33 (1H, dd, J=3.6, 1.2), 7.08 (1H, m), 5.13 (2H, d, J=2.4), 3.96 (3H, s), 3.52 (1H, t, J=2.4).

Synthesis 70

8-(1-Methyl-4-phenyl-1H-imidazol-2-yl)-3-(prop-2-ynyl)imidazo[5,1-d][1,2,3,5]tetrazin-4(3H)-one (WW-052)

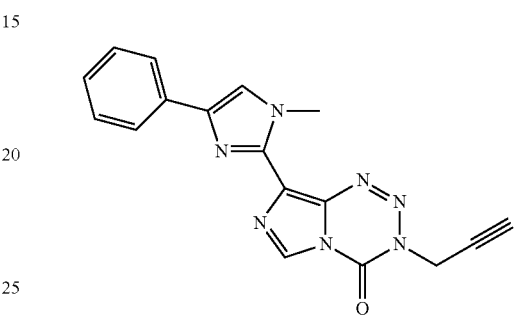

8-(4-Phenyl-1H-imidazol-2-yl)-3-(prop-2-ynyl)imidazo [5,1-d][1,2,3,5]tetrazin-4(3H)-one (1.07 mmol) was dissolved in dry DMF (35 mL) and cooled in ice under a nitrogen atmosphere. A 60% suspension of sodium hydride in mineral oil (1.18 mmol) was added in one portion and the reaction stirred on ice for 10 minutes. Methyl iodide (2.14 mmol) was then added dropwise to the reaction and the mixture stirred at room temperature for 48 hours. The mixture was poured onto ice water (140 mL) and the precipitate was filtered, washed with water, ethyl acetate, and diethyl ether, and purified by column chromatography (hexane:ethyl acetate 4:3) to give the title compound (0.030 g; 89%). $\delta_H$ (DMSO-$d_6$) 8.97 (1H, s), 7.90 (1H, s), 7.83 (2H, d, J=7.2), 7.40 (2H, t, J=7.6), 7.25 (1H, t, J=7.2), 5.13 (2H, d, J=2.0), 3.99 (3H, s), 3.52 (1H, J=2.0).

(X) Preparation of C8-Imidamides

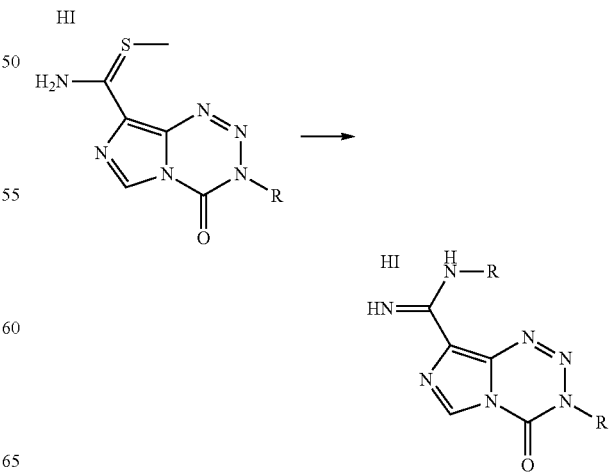

Synthesis 71

Methyl-2-(4-oxo-3-(prop-2-ynyl)-3,4-dihydroimidazo[5,1-d][1,2,3,5]tetrazine-8-carboximidamido)acetate hydroiodide (SS-001)

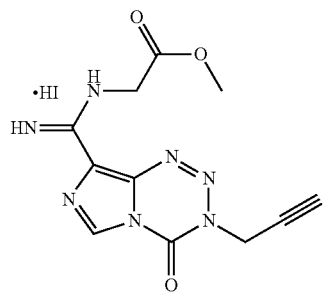

Glycine methyl ester (0.14 mmol) was suspended in dry MeCN (1 mL). Triethylamine (0.14 mmol) was added and the solution stirred for 10 minutes. Methyl 4-oxo-3-(prop-2-ynyl)-3,4-dihydroimidazo[5,1-d][1,2,3,5]tetrazine-8-carbimidothioate hydroiodide (0.13 mmol) was then added and the reaction stirred at room temperature for 2 hours. The resulting precipitate was then filtered and washed with MeCN and ether. $\delta_H$ (DMSO-$d_6$) 9.70 (2H, bs), 9.22 (1H, s), 5.76 (1H, s), 5.24 (2H, d, J=2.4), 4.45 (2H, s), 3.74 (3H, s), 3.60 (1H, t, J=2.4).

(XI) Preparation of C8-Benzoxazoles

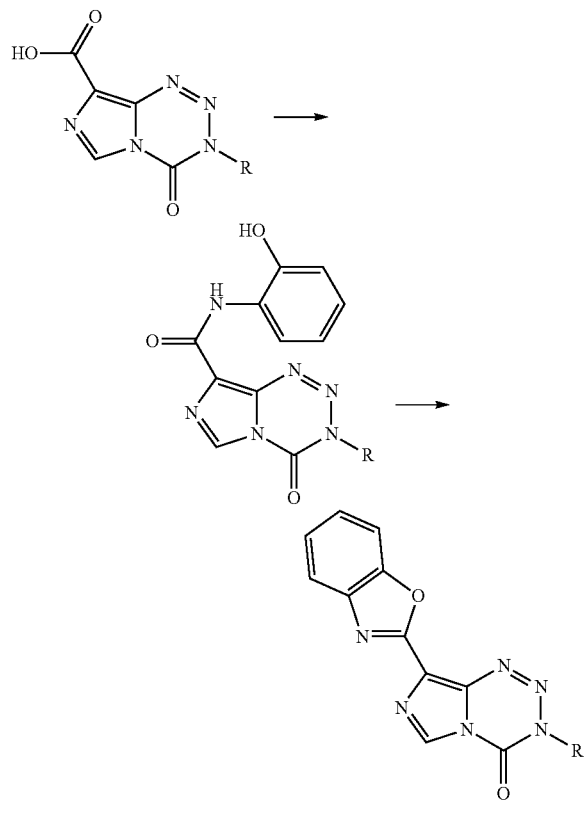

Synthesis 72

8-(Benzo[d]oxazol-2-yl)-3-methylimidazo[5,1-d][1,2,3,5]tetrazin-4(3H)-one (WW-054)

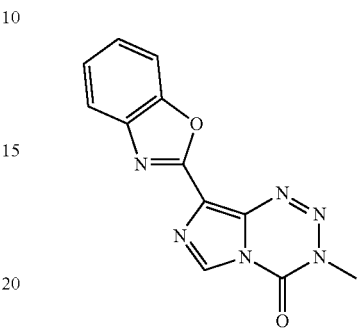

Isobutyl chloroformate (350 mL, 2.69 mmol, 1.05 eq.) followed by triethylamine (375 mL, 2.69 mmol, 1.05 eq.) were added to a solution of 3-methyl-4-oxo-3,4-dihydroimidazo[5,1-d][1,2,3,5]tetrazine-8-carboxylic acid (500 mg, 2.56 mmol) in THF (150 mL) and the mixture was stirred for 2 hours at room temperature. The precipitate of triethylamine hydrochloride, which formed during the reaction, was removed by filtration, and 2-aminophenol (294 mg, 2.69 mmol, 1.05 eq.) was added to the filtrate. The resulting mixture was stirred at room temperature under nitrogen overnight. The precipitate, which formed overnight, was filtered and the solid was washed successively with ethyl acetate and diethyl ether.

The crude product was suspended in ethyl acetate and the resulting suspension was filtered. The solid was washed successively with water, ethyl acetate and diethyl ether to give 415 mg of N-(2-hydroxyphenyl)-3-methyl-4-oxo-3,4-dihydroimidazo[5,1-d][1,2,3,5]tetrazine-8-carboxamide as a bright yellow solid (57% yield). The product was used without further purification for the next step. $\delta_H$ (DMSO $d_6$): 10.3 (1H, s), 9.79 (1H, s), 8.93 (1H, s), 8.33 (1H, dd, J=8.0, 1.2), 6.94-7.00 (2H, m), 6.86 (1H, ddd, J=8.0, 6.5, 2.0), 3.91 (3H, s).

Diisopropyl azodicarboxylate (0.688 mL, 3.49 mmol) was added dropwise to a suspension of the crude N-hydroxyphenyl carboxamide (200 mg, 0.70 mmol) and triphenylphosphine (916 mg, 3.49 mmol) in THF (8 mL) at room temperature. The mixture, which became a solution and then a thick suspension, was stirred overnight. The mixture was diluted with a small amount of THF and the precipitate was filtered and washed with THF and diethyl ether to give 470 mg of the crude title compound as a bright yellow green solid. 235 mg of the crude product was absorbed on silica and the product was purified by flash chromatography using DCM:MeOH (98:2) as eluent to give 65 mg of the pure title compound as a bright yellow/green solid (69% yield). $\delta_H$ (DMSO $d_6$): 9.01 (1H, s), 7.87-7.91 (2H, m), 7.48 (2H, m), 3.91 (3H, s).

Synthesis 73

8-(Benzo[d]oxazol-2-yl)-3-(methylsulfinylmethyl)imidazo[5,1-d][1,2,3,5]tetrazin-4(3H)-one (WW-056)

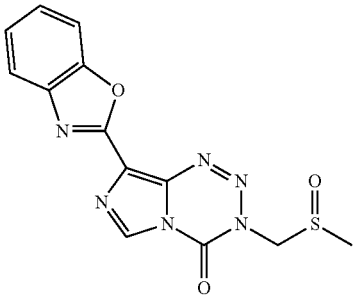 [SMILES: CS(=O)Cn1nnc2c(-c3nc4ccccc4o3)ncn2c1=O]

Isobutyl chloroformate (141 µL, 1.09 mmol) followed by triethylamine (152 µL, 1.09 mmol) were added to a solution of 3-(methylthiomethyl)-4-oxo-3,4-dihydroimidazo[5,1-d][1,2,3,5]tetrazine-8-carboxylic acid (250 mg, 1.04 mmol) in THF (60 mL) and the mixture was stirred for 2 hours at room temperature. The precipitate of triethylamine hydrochloride, which formed during the reaction, was removed by filtration, and 2-aminophenol (119 mg, 1.09 mmol) was added to the filtrate. The resulting mixture was stirred at room temperature under nitrogen for three days and was concentrated under vacuum. The crude product was absorbed on silica and purified by flash chromatography using a gradient elution of DCM:MeOH (97:3 to 90:10) to give 167 mg of N-(2-hydroxyphenyl)-3-(methylthiomethyl)-4-oxo-3,4-dihydroimidazo[5,1-d][1,2,3,5]tetrazine-8-carboxamide as a yellow/green solid (49% yield). The product was contaminated with around 10% of an uncharacterized impurity and was used without further purification. $\delta_H$ (DMSO d$_6$): 10.3 (1H, s), 9.80 (1H, s), 8.96 (1H, s), 8.33 (1H, dd, J=8.0, 1.2), 6.95-6.99 (2H, m), 6.85-6.89 (1H, ddd, J=8.0, 6.5, 2.2), 5.47 (1H, s), 2.26 (3H, s).

Diisopropyl azodicarboxylate (206 µL, 1.09 mmol) was added dropwise to a suspension of the crude N-hydroxyphenyl-carboxamide (165 mg, 0.50 mmol) and triphenylphosphine (286 mg, 1.09 mmol) in THF (6 mL) at room temperature. The mixture became homogeneous and was stirred overnight. The precipitate, which formed overnight, was filtered and washed with diethyl ether. The filtrate, which contained mainly 8-(benzo[d]oxazol-2-yl)-3-(methylthiomethyl)imidazo[5,1-d][1, 2, 3, 5]tetrazin-4(3H)-one, was combined with the precipitate for purification by flash chromatography using DCM:MeOH (98:2) as eluent to give 50 mg of 8-(benzo[d]oxazol-2-yl)-3-(methylthiomethypimidazo[5,1-d][1,2,3,5]tetrazin-4(3H)-one as a bright yellow/green solid. $\delta_H$ (DMSO d$_6$): 9.05 (1H, s), 7.88-7.93 (2H, m), 7.46-7.54 (2H, m), 5.48 (2H, s), 2.29 (3H, s). The NMR spectrum also showed that the product contained 5-10% of triphenylphosphine oxide. The product was used without further purification for the next step.

An aqueous solution (250 µL) of Oxone™ (54 mg, 0.195 mmol) was added to a stirred solution of 8-(benzo[d]oxazol-2-yl)-3-(methylthiomethyl)imidazo[5,1-d][1,2,3,5]tetrazin-4(3H)-one (25 mg, 0.0795 mmol) in DMF (1 mL) and the resulting suspension was stirred overnight. The mixture was poured into ice (10 g) and the precipitate was filtered and washed successively with water, ethyl acetate and diethyl ether to give 19 mg of the title compound as a bright yellow solid (73% yield). $\delta_H$ (DMSO d$_6$): 9.12 (1H, s), 7.89-7.94 (2H, m), 7.47-7.55 (2H, m), 5.66 (1H, d, J=13.2), 5.53 (1H, d, J=13.2), 2.80 (3H, s). LCMS: 97% pure at 4.63 min., m/z (ES$^+$): 331.1 (MH$^+$).

Synthesis 74

8-(Benzo[d]oxazol-2-yl)-3-(prop-2-ynyl)imidazo[5,1-d][1,2,3,5]tetrazin-4(3H)-one (WW-055)

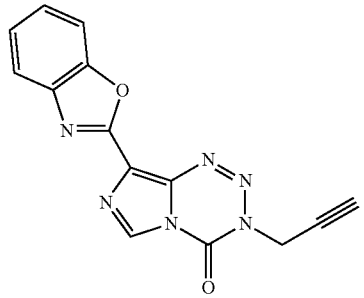 [SMILES: C#CCn1nnc2c(-c3nc4ccccc4o3)ncn2c1=O]

Isobutyl chloroformate (156 µL, 1.20 mmol) followed by triethylamine (167 µL, 1.20 mmol) were added to a solution of 4-oxo-3-(prop-2-ynyl)-3,4-dihydroimidazo[5,1-d][1,2,3,5]tetrazine-8-carboxylic acid (250 mg, 1.14 mmol) in THF (100 mL) and the mixture was stirred for 2 hours at room temperature. The precipitate of triethylamine hydrochloride, which formed during the reaction, was removed by filtration, and 2-aminophenol (131 mg, 1.20 mmol) was added to the filtrate. The resulting mixture was stirred at room temperature under nitrogen for three days and was concentrated under vacuum. The crude product was absorbed on silica and purified by flash chromatography using DCM:MeOH (98:2) as eluent to give 156 mg of N-(2-hydroxyphenyl)-4-oxo-3-(prop-2-ynyl)-3,4-dihydroimidazo[5,1-d][1,2,3,5]tetrazine-8-carboxamide as a yellow solid (44% yield). $\delta_H$ (DMSO d$_6$) 10.3 (1H, s), 9.79 (1H, s), 8.97 (1H, s), 8.33 (1H, dd, J=8.0, 1.3), 6.95-6.99 (2H, m), 6.85-6.89 (1H, ddd, J=8.0, 6.5, 2.0), 5.18 (1H, d, J=2.5), 3.55 (1H, t, J=2.5).

Diisopropyl azodicarboxylate (98 µL, 0.518 mmol) was added dropwise to a suspension of the crude N-hydroxyphenylcarboxamide (74 mg, 0.238 mmol) and triphenylphosphine (136 mg, 0.518 mmol, 2.2) in THF (3 mL) at room temperature. The mixture became homogeneous and was stirred overnight. The precipitate, which formed overnight, was filtered and washed with a small amount of DCM to give 39 mg of crude product. 19 mg of crude mixture obtained from a previous synthesis was combined for purification by flash chromatography using DCM:MeOH (98:2) as eluent to give 34 mg of the title compound as a bright yellow/green solid (29% yield). $\delta_H$ (DMSO d$_6$) 9.06 (1H, s, CH), 7.88-7.93 (2H, m), 7.48-7.52 (2H, m), 5.19 (2H, d, J=2.5), 3.56 (1H, t, J=2.5).

Synthesis 75

8-(Benzo[d]oxazole-2-carbonyl)-3-(methoxymethyl)imidazo[5,1-d][1,2,3,5]tetrazin-4(3H)-one (WW-057)

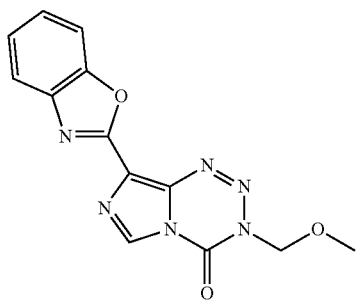

To 3-(methoxymethyl)-4-oxo-3,4-dihydroimidazo[5,1-d][1,2,3,5]tetrazine-8-carboxylic acid (0.256 g; 1.14 mmol) in DMF (2.5 mL) was added HBTU (0.454 g; 1.20 mmol), and the mixture stirred for 20 minutes. 2-Aminophenol (0.187 g; 1.71 mmol) was added, followed immediately by DIPEA (400 µL). The mixture was stirred for 6 hours, then poured onto ice. Once the ice had melted, the orange/brown solid was filtered, and used without further purification. $\delta_H$ (DMSO d$_6$): 10.36 (1H, s), 9.80 (1H, s), 8.98 (1H, s), 8.34 (1H, m), 6.96-7.01 (2H, m), 6.85-6.89 (1H, m), 5.65 (2H, s), 3.44 (3H, s).

To a suspension of the N-(2-hydroxyphenyl)-3-(methoxymethyl)-4-oxo-3,4-dihydroimidazo[5,1-d][1,2,3,5]tetrazine-8-carboxamide (0.102 g; 0.322 mmol) and triphenylphosphine (0.184 mg; 0.700 mmol) in tetrahydrofuran (4 mL) was added diisopropyl azodicarboxylate (132 µL; 0.700 mmol). The suspension immediately disappeared and the reaction mixture turned red. After stirring for a short time, a precipitate reappeared. Stirring continued overnight. The solid was filtered, and washed with DCM to give the title compound as a yellow solid (0.037 mg; 39%).

(XII) Preparation of C8-Benzothiazoles

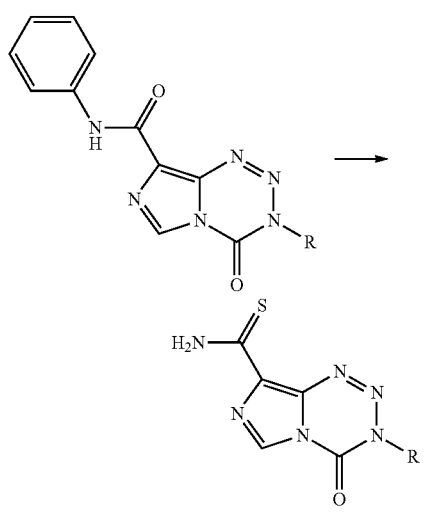

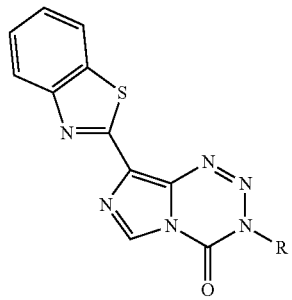

Synthesis 76

8-(Benzo[d]thiazol-2-yl)-3-methylimidazo[5,1-d][1,2,3,5]tetrazin-4(3H)-one (WW-058)

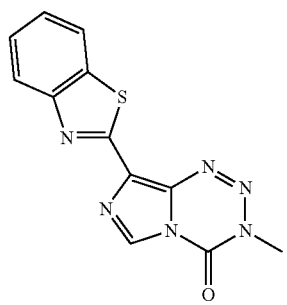

A. A mixture of 3-methyl-4-oxo-N-phenyl-3,4-dihydroimidazo[5,1-d][1,2,3,5]tetrazine-8-carboxamide (430 mg, 1.59 mmol), phosphorus pentasulfide (212 mg, 0.48 mmol) and hexamethyldisiloxane (680 µL, 3.18 mmol) in DCM (20 mL) was refluxed overnight. The crude product was absorbed on silica and was purified by flash chromatography using a gradient elution of DCM:MeOH (100:0 to 98:2) to give 372 mg of 3-methyl-4-oxo-N-phenyl-3,4-dihydroimidazo[5,1-d][1,2,3,5]tetrazine-8-carbothioamide as a 1.5:1 inseparable mixture with the starting material.

B. Dess Martin periodinane (202 mg, 0.477 mmol) was added in small portions to a solution of 3-methyl-4-oxo-N-phenyl-3,4-dihydroimidazo[5,1-d][1,2,3,5]tetrazine-8-carbothioamide (300 mg (as 3:2 mixture with carboxamide), 0.434 mmol) in chloroform (60 mL) and the reaction was monitored by thin layer chromatography. The mixture was stirred for 1 hour and 20 mg of Dess Martin periodinane was added. The mixture was stirred for 30 minutes and the crude product was absorbed on silica and purified by flash chromatography using DCM:MeOH (98:2) as eluent to give the pure title compound as a bright yellow solid (12 mg, 10%). $\delta_H$ (DMSO d$_6$): 8.96 (1H, s), 8.20 (1H, d, J=8.0), 8.15 (1H, d, J=8.0), 7.58 (1H, td, J=7.6, 1.3), 7.50 (1H, td, J=7.6, 1.2), 3.90 (3H, s).

125

Synthesis 77

8-(Benzo[d]thiazol-2-yl)-3-(prop-2-ynyl)imidazo[5,1-d][1, 2, 3, 5]tetrazin-4(3H)-one (WW-059)

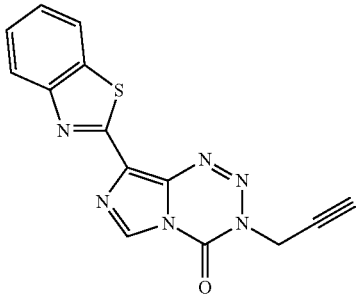 [SMILES: C#CCn1nnc2c(-c3nc4ccccc4s3)ncn2c1=O]

Isobutyl chloroformate (187 μL, 1.43 mmol) followed by triethylamine (200 μL, 1.43 mmol) were added to a solution of 4-oxo-3-(prop-2-ynyl)-3,4-dihydroimidazo[5,1-d][1,2,3,5]tetrazine-8-carboxylic acid (300 mg, 1.37 mmol) in THF (100 mL) and the mixture was stirred for 75 minutes at room temperature. The precipitate of triethylamine hydrochloride, which formed during the reaction, was filtered, and 2-aminothiophenol (153 μL, 1.43 mmol) was added to the filtrate. The resulting mixture was stirred at room temperature under nitrogen overnight and the suspension was filtered. The precipitate was characterised as triethylamine hydrochloride. The filtrate was concentrated under vacuum and the residue was suspended in diethyl ether. The precipitate was filtered and washed successively with water and ethyl acetate. The product was soluble in ethyl acetate so the filtrate was concentrated under vacuum. The residue was suspended in diethyl ether and filtered to give crude N-(2-mercaptophenyl)-4-oxo-3-(prop-2-ynyl)-3,4-dihydroimidazo[5,1-d][1,2,3,5]tetrazine-8-carboxamide (254 mg). The NMR spectrum of the crude product showed that a complex mixture containing the N-mercaptophenyl carboxamide, the title compound and other uncharacterized impurities, was obtained. Diisopropyl azodicarboxylate (127 μL, 0.674 mmol) was added dropwise to a suspension of the mixture (100 mg) and triphenylphosphine (178 mg, 0.674 mmol) in THF (4 mL) at room temperature. The mixture was stirred overnight and was diluted in dichloromethane and methanol. The crude product was absorbed on silica and purified by flash chromatography using DCM:MeOH (98:2) as eluent to give 44 mg of a sticky solid. The solid was suspended in diethyl ether. The precipitate was filtered and washed with diethyl ether to give the pure title compound as a bright yellow solid (12%). $\delta_H$ (DMSO $d_6$): 9.02 (1H, s, CH), 8.21-8.23 (1H, ddd, J=8.0, 1.3, 0.6), 8.18-8.16 (1H, ddd, J=8.0, 1.3, 0.6), 7.63-7.55 (1H, m), 7.54-7.51 (1H, m), 5.19 (2H, d, J=2.5), 3.56 (1H, t, J=2.5).

126

Synthesis 78

8-(Benzo[d]thiazol-2-yl)-3-(methoxymethyl)imidazo[5,1-d][1,2,3,5]tetrazin-4(3H)-one (WW-060)

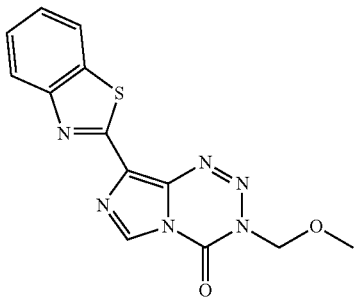

To a mixture of polyphosphate ester (see, e.g., Yalpn et al., Eur. J. Med. Chem., 1992, Vol. 27, pp. 401-406) (1 g) and chloroform (3 mL) was added 3-(methoxymethyl)-4-oxo-3,4-dihydroimidazo[5,1-d][1,2,3,5]tetrazine-8-carboxylic acid (225 mg; 1 mmol) and 2-aminothiophenol (107 μL; 1 mmol). The mixture was carefully heated to 70° C. for 3.5 hours, then cooled and the chloroform removed under reduced pressure. The residue was added to water (100 mL), which was extracted with ethyl acetate (×3). The combined organic fractions were dried (MgSO$_4$) and concentrated. The crude product was washed with ether/hexane, and purified by column chromatography to give a pale yellow powder (0.007 g; 3%). $\delta_H$ (DMSO d$_6$): 9.03 (1H, s), 8.22 (1H, d, J=7.9), 8.17 (1H, d, J=7.9), 7.61 (1H, td, J=7.7, 1.3), 7.53 (1H, td, J=7.6, 1.2), 5.65 (2H, s), 3.46 (3H, s).

Synthesis 79

8-(Benzo[d]thiazol-2-yl)-3-(methylthiomethyl)imidazo[5,1-d][1,2,3,5]tetrazin-4(3H)-one

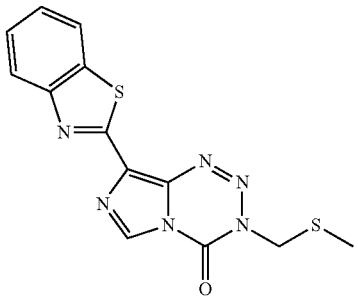 [SMILES: CSCn1nnc2c(-c3nc4ccccc4s3)ncn2c1=O]

To a solution of 3-(methylthiomethyl)-4-oxo-3,4-dihydroimidazo[5,1-d][1,2,3,5]tetrazine-8-carboxylic acid (2.07 mmol, 0.5 g, 1 eq.) in THF (166 mL) was added isobutyl chloroformate (2.18 mmol, 285 μL, 1.05 eq.) and triethylamine (2.18 mmol, 302 μL, 1.05 eq.). The mixture was stirred at room temperature for 90 minutes and then 2-aminobenzenethiol (2.18 mmol, 233 μL, 1.05 eq.) was added in once and the solution was stirred at room temperature overnight. The reaction mixture volume was reduced to dryness and the solid residue was triturated in ethyl acetate, filtered, washed with water and ether and dried under vacuum. The obtained solid was purified by absorbing into silica and loading into a column for flash chromatography, and eluted using 200:1 DCM:MeOH to give the title compound. Yield=26%. $\delta_H$ (DMSO-$d_6$) 9.01 (1H, s), 8.21 (1H, m), 8.15 (1H, m), 7.60 (1H, m), 7.53 (1H, m), 5.47 (2H, s), 2.29 (3H, s).

Synthesis 80

8-(Benzo[d]thiazol-2-yl)-3-(methylsulfinylmethyl)imidazo[5,1-d][1,2,3,5]tetrazin-4(3H)-one (WW-061)

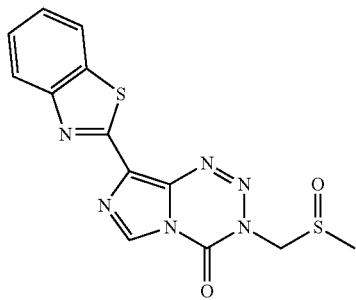 [SMILES: CS(=O)Cn1nnc2c(-c3nc4ccccc4s3)ncn2c1=O]

To a 0° C. solution of 8-(benzo[d]thiazol-2-yl)-3-(methylthiomethyl)imidazo[5,1-d][1,2,3,5]tetrazin-4(3H)-one (0.23 mmol, 75 mg, 1 eq.) in DMF (4.5 mL) was added slowly drop wise Oxone™ (0.25 mmol, 77 mg, 1.1 eq.) dissolved in water (0.75 mL). The formed suspension was stirred at 0° C. and stepwise additions of Oxone™ in water were made until reaction completion. The reaction mixture was filtered and the obtained solid washed with water, acetonitrile, ethyl acetate and ether, and dried under vacuum to give the title compound. Yield: 98%. $\delta_H$ (DMSO-$d_6$) 9.07 (1H, s), 8.22 (1H, m), 8.16 (1H, m), 7.60 (1H, m), 7.52 (1H, m), 5.63 (1H, d, J=13.2), 5.50 (1H, d, J=13.2), 2.79 (3H, s).

(XIII) Preparation of C8-Benzimidazoles

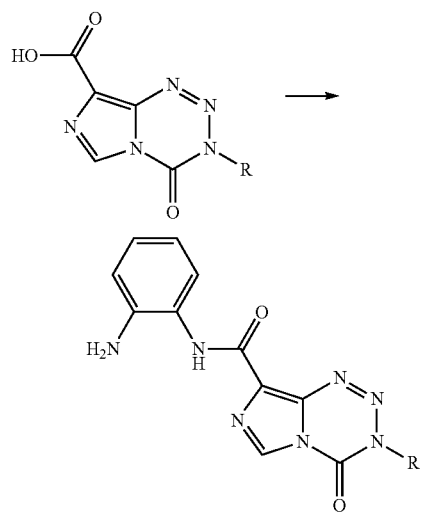

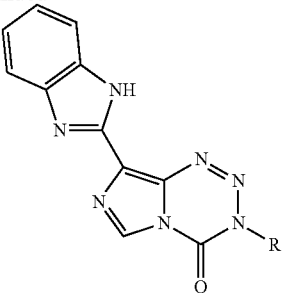

Synthesis 81

N-(2-Aminophenyl)-3-methyl-4-oxo-3,4-dihydroimidazo[5,1-d][1,2,3,5]tetrazine-8-carboxamide

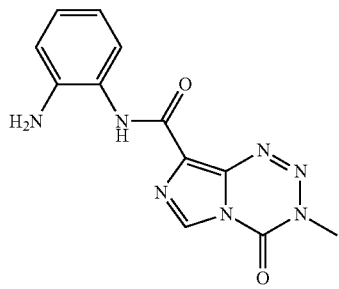 [SMILES: Cn1nnc2c(C(=O)Nc3ccccc3N)ncn2c1=O]

The title compound was synthesized following the general procedure for the synthesis of N-phenyl-8-carboxamide derivatives using phenylenediamine instead of aniline and DCM:MeOH (98:2) as eluent during the purification by flash chromatography (38% yield). $\delta_H$ (DMSO $d_6$): 9.72 (1H, s), 8.94 (1H, s), 7.43-7.45 (1H, dd, J=7.8, J2=1.3), 6.96-7.00 (1H, ddd, J=7.5, 7.3, 1.6), 6.83-6.85 (1H, dd, J=8.0, 1.3), 6.64-6.66 (1H, m), 4.91 (2H, s), 3.90 (3H, s).

Synthesis 82

8-(1H-Benzo[d]imidazol-2-yl)-3-methylimidazo[5,1-d][1,2,3,5]tetrazin-4(3H)-one (WW-062)

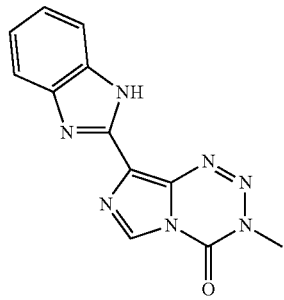 [SMILES: Cn1nnc2c(-c3nc4ccccc4[nH]3)ncn2c1=O]

A solution of N-(2-aminophenyl)-3-methyl-4-oxo-3,4-dihydroimidazo[5,1-d][1,2,3,5]tetrazine-8-carboxamide (300 mg) in 3N HCl (15 mL) was heated at 90° C. overnight. After cooling to room temperature, the mixture was concentrated to dryness under high vacuum and the residue was dissolved in MeCN:MeOH. Triethylamine (170 μL) was added to the solution and the crude product was absorbed on silica and purified by flash chromatography using DCM:MeOH (95:5) as eluent to give 8 mg of the pure title compound as a green solid (3% yield). $δ_H$ (DMSO $d_6$): 13.0 (1H, s), 8.99 (1H, s), 7.73-7.75 (1H, d, J=7.5), 7.56-7.58 (1H, d, J=7.5), 7.23-7.27 (2H, m), 3.90 (3H, s).

Synthesis 83

3-Methyl-8-(1-methyl-1H-benzo[d]imidazol-2-yl)imidazo[5,1-d][1,2,3,5]tetrazin-4(3H)-one (WW-066)

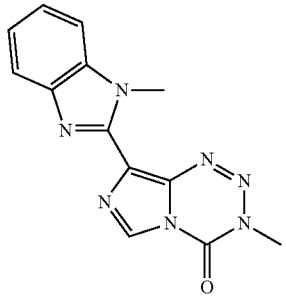 [SMILES: Cn1nnc2c(-c3nc4ccccc4n3C)ncn2c1=O]

To a 0° C. solution of 8-(1H-benzo[d]imidazol-2-yl)-3-methylimidazo[5,1-d][1,2,3,5]tetrazin-4(3H)-one (0.54 mmol, 0.144 grams, 1 eq.) in anhydrous DMF (2.5 mL) was added sodium hydride 60% in mineral oil (0.59 mmol, 24 mg, 1.1 eq.) portion-wise. The formed suspension was stirred at low temperature for 10 minutes and methyl iodide (1.07 mmol, 67 μL, 2 eq.) was added into it in one portion. The suspension was stirred over night at room temperature. The reaction mixture was filtered and the obtained solid was washed with water, acetonitrile and ethyl acetate, and dried under vacuum to give the title compound. Yield: 55%. $δ_H$ (DMSO-$d_6$) 9.02 (1H, s), 7.77 (1H, d, J: 8.09), 7.68 (1H, d, J: 8.12), 7.36 (1H, m), 7.32 (1H, m), 4.14 (3H, s), 3.90 (3H, s).

Synthesis 84

8-(1H-Benzo[d]imidazol-2-yl)-3-(prop-2-ynyl)imidazo[5,1-d][1,2,3,5]tetrazin-4(3H)-one (WW-063)

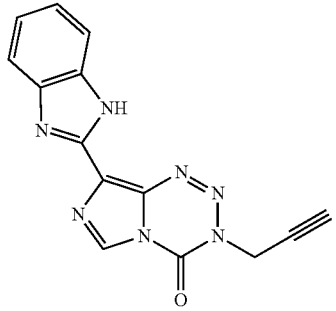 [SMILES: C#CCn1nnc2c(-c3nc4ccccc4[nH]3)ncn2c1=O]

Step A. O-(Benzotriazol-1-yl)-N,N,N',N'-tetramethyluronium hexafluorophosphate (908 mg, 2.40 mmol) was added to a solution of 4-oxo-3-(prop-2-ynyl)-3,4-dihydroimidazo[5,1-d][1,2,3,5]tetrazine-8-carboxylic acid (500 mg, 2.28 mmol) in DMF (5 mL) and the mixture was stirred 20 minutes before being added slowly dropwise to a solution of phenylenediamine (370 mg, 3.42 mmol) in DMF (5 mL). The mixture was stirred overnight and was poured into ice. The resulting precipitate was filtered and was washed successively with water, ethyl acetate and diethyl ether to give 629 mg of an orange solid. The crude product was absorbed on silica and purified by flash chromatography using DCM:MeOH (98:2) as eluent to give 344 mg (49%) of N-(2-aminophenyl)-4-oxo-3-(prop-2-ynyl)-3,4-dihydroimidazo[5,1-d][1,2,3,5]tetrazine-8-carboxamide as an orange solid. $δ_H$ (DMSO $d_6$): 9.74 (1H, s), 8.98 (1H, s), 7.42-7.44 (1H, dd, J=8.0, 1.3), 6.96-7.00 (1H, ddd, J=8.0, 7.3, 1.6), 6.82-6.85 (1H, dd, J=8.0, 1.4), 6.64-6.68 (1H, m), 5.17 (2H, d, J=2.5), 4.91 (2H, s), 3.54 (1H, t, J=2.5).

Step B. Triflic anhydride (82 μL, 0.485 mmol) was added dropwise at 0° C. under nitrogen to a solution of triphenylphosphine oxide (135 mg, 0.485 mmol) in DCM (1.5 mL) and the mixture was stirred at 0° C. for 20 minutes. The resulting solution was then added dropwise at 0° C. under nitrogen to a stirred suspension of N-(2-aminophenyl)-4-oxo-3-(prop-2-ynyl)-3,4-dihydroimidazo[5,1-d][1,2,3,5]tetrazine-8-carboxamide (50 mg, 0.162 mmol) in DCM (1.5 mL). The resulting dark brown mixture was stirred for 3 days and the precipitate, which formed during the reaction, was filtered. The solid was dissolved in MeCN:MeOH and triethylamine (75 μL) was added. The mixture was stirred for about 5 minutes and was then concentrated under vacuum. The crude product was suspended in ethyl acetate and the resulting suspension was filtered. The solid was washed with ethyl acetate to give the pure title compound as a bright yellow solid (22 mg, 47%). (Less triethylamine (100 μL/250 mg starting material) was used during the neutralization on larger scale preparations.) $δ_H$ (DMSO $d_6$): 13.1 (1H, s), 9.02 (1H, s), 7.73-7.75 (1H, m), 7.56-7.58 (1H, m), 7.22-7.27 (2H, m), 5.15 (2H, d, J=2.5), 3.53 (1H, t, J=2.5).

Synthesis 85

8-(1-Methyl-1H-benzo[d]imidazol-2-yl)-3-(prop-2-ynyl)imidazo[5,1-d][1,2,3,5]tetrazin-4(3H)-one (WW-065)

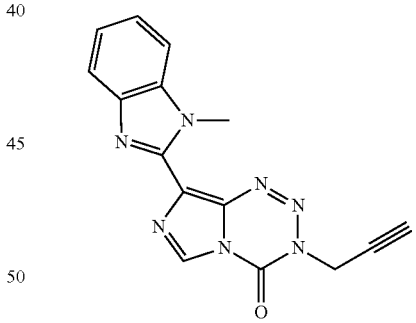

Sodium hydride (60% in mineral oil, 8 mg, 0.189 mmol, 1.1 eq.) was added in one portion to a slurry of 8-(1H-benzo[d]imidazol-2-yl)-3-(prop-2-ynyl)imidazo[5,1-d][1,2,3,5]tetrazin-4(3H)-one (50 mg, 0.172 mmol) in DMF (4.5 mL) at 0° C. and the mixture, which became red, was stirred for 5 minutes before the addition of MeI (21 μL, 0.344 mmol, 2 eq.). The mixture was then stirred overnight and concentrated under high vacuum. The product was absorbed on silica and purified by flash chromatography using DCM:MeCN (80:20) as eluent to give the title compound as a bright yellow/green solid (33 mg, 62% yield). The product was then suspended in ethyl acetate, filtered and washed successively with water, ethyl acetate and diethyl ether to remove any trace of DMF. $δ_H$ (DMSO-$d_6$): 9.07 (1H, s), 7.76-7.79 (1H, m), 7.67-7.70 (1H, m), 7.35-7.39 (1H, m), 7.29-7.33 (1H, m), 5.17 (2H, d, J=2.5), 4.14 (3H, s), 3.53-3.54 (1H, t, J=2.5).

Synthesis 86

8-(1H-Benzo[d]imidazol-2-yl)-3-(methoxymethyl) imidazo[5,1-d][1,2,3,5]tetrazin-4(3H)-one (WW-064)

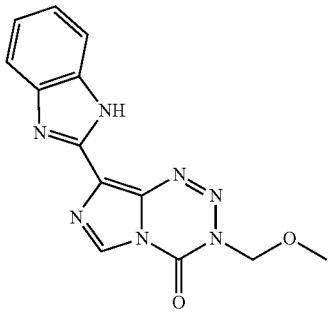 [SMILES: COCn1nnc2c(-c3nc4ccccc4[nH]3)ncn2c1=O]

To a solution of 3-(methoxymethyl)-4-oxo-3,4-dihydroimidazo[5,1-d][1,2,3,5]tetrazine-8-carboxylic acid (512 mg; 2.28 mmol) in DMF (50 mL) was added HBTU (908 mg; 2.40 mmol). The solution was stirred for 20 minutes, then added dropwise over 20 minutes to a solution of phenylenediamine (370 mg; 6.84 mmol) in DMF (50 mL). The reaction mixture was stirred for 24 hours, then poured onto ice (1 kg), and allowed to stand until the ice had melted. The resulting orange solid was filtered, and purified by column chromatography (DCM:MeOH 98:2) to give N-(2-aminophenyl)-3-(methoxymethyl)-4-oxo-3,4-dihydroimidazo[5,1-d][1,2,3,5]tetrazine-8-carboxamide as an orange solid. (474 mg; 70%). $\delta_H$ (DMSO d$_6$): 9.76 (1H, s), 8.99 (1H, s), 7.43 (1H, dd, J=7.9, 1.0), 6.99 (1H, td, J=7.6, 1.5), 6.84 (1H, dd, J=8.0, 1.3), 6.67 (1H, dd, J=7.6, 1.3), 5.64 (2H, s), 4.91 (2H, s), 3.44 (3H, s).

Triflic anhydride (820 µL; 4.85 mmol) was added to a solution of triphenylphosphine oxide (1.35 g; 4.85 mmol) in DCM (15 mL) at 0° C. and the mixture stirred for 20 minutes, then added to a suspension of N-(2-aminophenyl)-3-(methoxymethyl)-4-oxo-3,4-dihydroimidazo[5,1-d][1,2,3,5]tetrazine-8-carboxamide (0.500 g; 1.61 mmol—combined batches) in DCM (15 mL). The solution was stirred for 6 hours, and the precipitate filtered. This was the triflate salt of the desired product (550 mg). This salt was dissolved in a mixture of MeCN (19 mL) and MeOH (1 mL) and triethylamine (750 µL) added. The resulting precipitate was filtered, and washed with ethyl acetate to give the title compound as a yellow powder (269 mg; 56%). Concentration of the filtrate, and washing the residue with ethyl acetate yielded a further 48 mg of pure material. $\delta_H$ (DMSO d$_6$): 13.09 (1H, s), 7.75 (1H, d, J=7.5), 7.58 (1H, d, J=7.1), 7.30-7.22 (2H, m), 5.64 (2H, s), 3.45 (3H, s).

(XIV) Preparation of C8-Amino Oxadiazoles

The appropriate carboxylic acid (1.03 mmol), thiosemicarbazide (1.03 mmol), and EDCI (0.592 g, 3.09 mmol) were stirred in DCM (30 mL) at room temperature for 48-144 hours. The mixture was filtered, and the resulting 'gum' was re-dissolved in MeOH, sonicated and concentrated in vacuo to yield an orange/yellow material. The 'gum' was adsorbed onto silica and purified by flash chromatography to yield the target amino-oxadiazole.

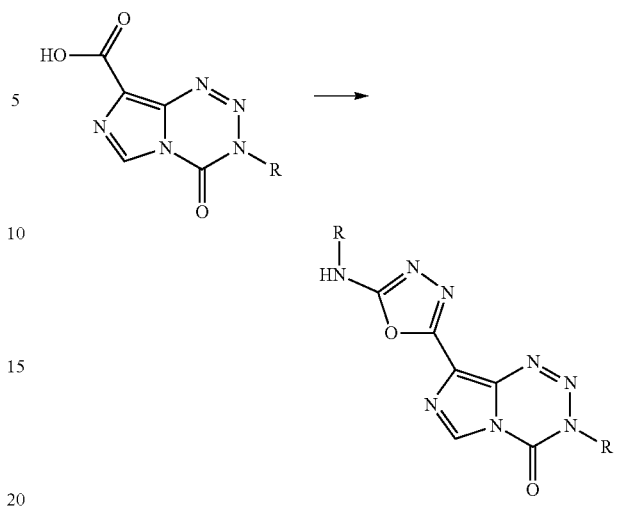

Synthesis 87

3-Methyl-8-(5-(methylamino)-1,3,4-oxadiazol-2-yl) imidazo[5,1-d][1,2,3,5]tetrazin-4(3H)-one (WW-045)

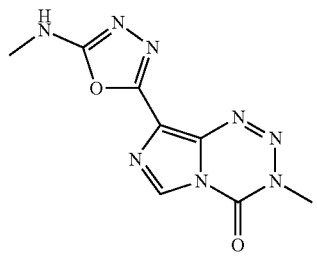

Using the general procedure, the title compound was prepared and then purified by flash chromatography (DCM→DCM: MeOH, 10:3) to yield a yellow solid (0.027 g; %). $\delta_H$ (DMSO-d$_6$) 8.90 (1H, s), 7.91 (1H, q, J=10), 3.85 (3H, s) and 2.89 (3H, d, J=5).

Synthesis 88

3-Methyl-8-(5-(phenylamino)-1,3,4-oxadiazol-2-yl) imidazo[5,1-d][1,2,3,5]tetrazin-4(3H)-one (WW-044)

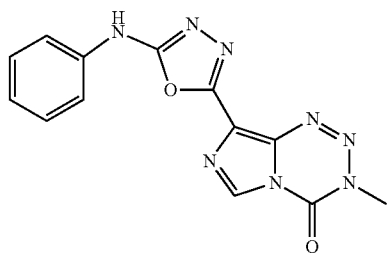 [SMILES: Cn1nnc2c(-c3nnc(Nc4ccccc4)o3)ncn2c1=O]

Using the general procedure, the title compound was prepared and then purified by flash chromatography (silica gel, gradient elution, DCM (100%) to DCM: MeOH, 10:1) to yield a yellow solid (0.050 g, 0.161 mmol, 16%). $\delta_H$ (DMSO-d$_6$) 10.90 (1H, s), 8.96 (1H, s), 7.66 (2H, d, J=8.0), 7.39 (2H, t, J=7.2), 7.05 (1H, t, J=7.2), 3.82 (3H, s).

Synthesis 89

8-(5-(Benzylamino)-1,3,4-oxadiazol-2-yl)-3-(methoxymethyl)imidazo[5,1-d][1,2,3,5]tetrazin-4(3H)-one (WW-046)

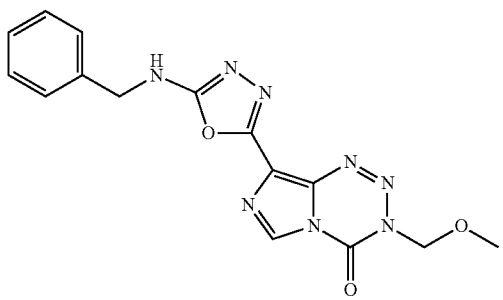 [SMILES: COCn1nnc2c(-c3nnc(NCc4ccccc4)o3)ncn2c1=O]

Using the general procedure, the title compound was prepared and then purified by flash chromatography (DCM) to yield a pale green solid. Yield 20%. $\delta_H$ (DMSO-$d_6$) 8.97 (1H, s), 8.64 (1H, t, J=6.8), 7.42-7.34 (4H, m), 7.30-7.28 (1H, m), 5.61 (1H, s), 4.50 (2H, d, J=4), 3.43 (3H, s).

(XV) Preparation of C8-Alkenes

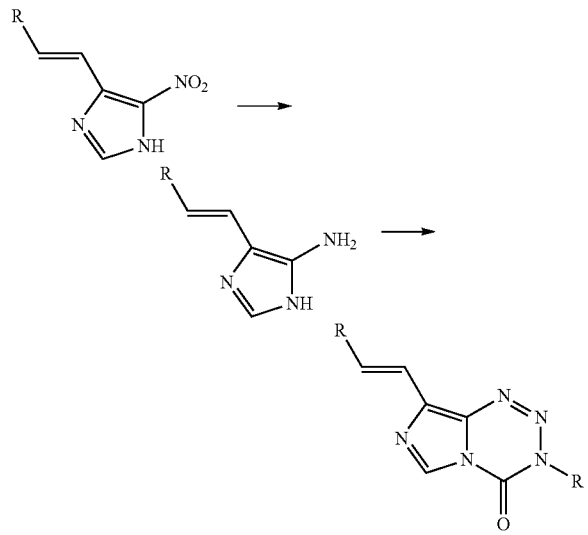

Synthesis 90

(E)-4-(2-(5-Nitro-1H-imidazol-4-yl)vinyl)benzonitrile

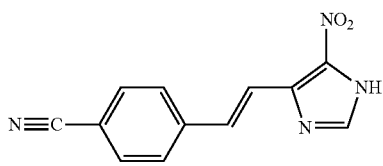

4-Cyanobenzaldehyde (75 g, 0.57 mol) was heated to 110° C. Once melted, 4-methyl-5-nitroimidazole (15 g, 0.12 mol) and piperidine (5 g, 0.06 mol) were added and heating continued for a further 24 hours. DMF (15 mL) and IPA (150 mL) were then added and the precipitate filtered from solution and washed with IPA (50 mL) to leave the product as a yellow solid (13.8 g, 49%). mp>300° C. $\delta_H$ (DMSO-$d_6$) 7.95 (1H, s), 7.88 (2H, d, J=6.8), 7.78 (2H, d, J=6.8), 7.78 (1H, d, J=16.8), 7.50 (1H, d, J=16.8); IR (cm$^{-1}$) 2239 (C≡N), 1502, 1348 (NO$_2$); MS (m/z) 241.1 ($C_{12}H_9N_4O_2$ (M+1)).

Synthesis 91

(E)-4-(2-(5-Amino-1H-imidazol-4-yl)vinyl)benzonitrile

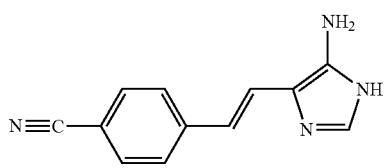 [SMILES: N#Cc1ccc(/C=C/c2nc[nH]c2[N+](=O)[O-])cc1]

5% Palladium on carbon (0.5 g) was added to a solution of (E)-4-(2-(5-nitro-1H-imidazol-4-yl)vinyl)benzonitrile (10 g, 0.04 mol) in methanol (500 mL) and the resulting mixture hydrogenated at atmospheric pressure for 24 hours. The catalyst was removed by filtering through a short bed of Celite™, and the Celite™ washed with 10% MeOH/DCM (200 mL). The filtrate was evaporated to dryness and purified by column chromatography (10% MeOH/DCM) to leave the product as a yellow/brown solid (6 g, 69%). $\delta_H$ (DMSO-$d_6$) 11.76 (1H, bs, NH), 7.70 (2H, d, J=8.4), 7.50 (2H, d, J=8.4), 7.44 (1H, d, J=16.0), 7.36 (1H, s), 6.42 (1H, d, J=16.0), 5.17 (2H, bs, NH$_2$); IR (cm$^{-1}$) 2220 (CEN), 1629 (C=C); MS (m/z) 211.0969 ($C_{12}H_{11}N_4$ (M+1)) requires 211.0984.

Synthesis 92

(E)-4-(2-(3-(Methoxymethyl)-4-oxo-3,4-dihydroimidazo[5,1-d][1,2,3,5]tetrazin-8-yl)vinyl)benzonitrile (MM-001)

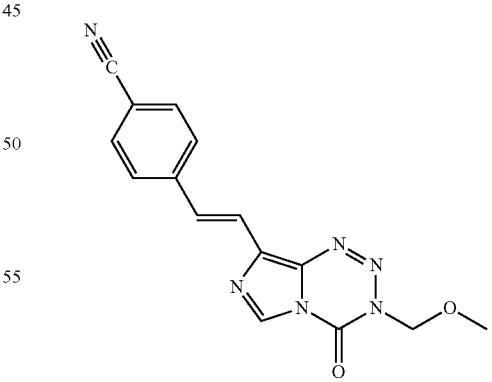

Sodium nitrite (40 mg, 0.57 mmol) in water (0.5 mL) was added to a suspension of (E)-4-(2-(5-amino-1H-imidazol-4-yl)vinyl)benzonitrile (100 mg, 0.47 mmol) in 50% HBF$_4$ (2 mL) at 0° C. After stirring at 0° C. for 20 minutes, the precipitate was filtered from solution and dried over P$_2$O$_5$. This diazo compound was used without further purification. Methoxymethyl isocyanate (150 mg, 1.8 mmol) was added to a solution of (E)-4-(2-(4-diazo-4H-imidazol-5-yl)vinyl)benzonitrile (80 mg, 0.36 mmol) in dry DMSO (1 mL) under nitrogen. The resulting solution was stirred at room temperature for 24 hours, then purified by column chromatography (5% MeCN/DCM) to give the title compound as a yellow solid (42 mg, 38%). $\delta_H$ (DMSO-$d_6$) 8.48 (1H, s), 7.81 (1H, d, J=16.0), 7.71 (4H, m), 7.60 (1H, d, J=16.0) 5.72 (2H, s), 3.58 (3H, s); IR (cm$^{-1}$) 2222 (C≡N), 1631 (C≡N); MS (m/z) 309.1121 ($C_{15}H_{13}N_6O_2$ (M+1)) requires 309.1100.

Synthesis 93

(E)-5-Nitro-4-(2-(thiophen-2-yl)vinyl)-1H-imidazole

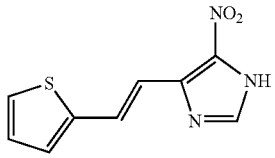

Piperidine (1.7 g, 0.02 mol) was added to a suspension of 4-methyl-5-nitroimidazole (5 g, 0.04 mol) and 2-thiophenecarboxaldehyde (22 g, 0.2 mol) and heated at 100° C. for 15 hours. After cooling, DMF (5 mL) and IPA (15 mL) were added and the precipitate filtered from solution and washed with IPA (50 mL) to leave the product as a yellow solid (6.0 g, 69%). $\delta_H$ (DMSO-$d_6$) 13.56 (1H, bs, NH), 7.90 (1H, s), 7.66 (1H, d, J=16.4), 7.66 (1H, d, J=5.0), 7.40 (1H, d, J=16.4), 7.35 (1H, d, J=3.6), 7.15 (1H, dd, J=3.6, 5.0).

Synthesis 94

(E)-4-(2-(Thiophen-2-yl)vinyl)-1H-imidazol-5-amine

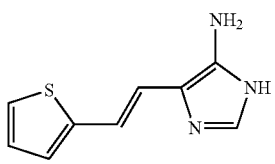 [SMILES: O=[N+]([O-])c1[nH]cnc1/C=C/c1cccs1]

5% Palladium on carbon (0.5 g) was added to a solution of (E)-5-nitro-4-(2-(thiophen-2-yl)vinyl)-1H-imidazole (4.5 g, 0.02 mol) in methanol (500 mL) and the resulting mixture hydrogenated at atmospheric pressure for 24 hours. The catalyst was removed by filtering through a short bed of Celite™, and the Celite™ washed with 10% MeOH/DCM (200 mL). The filtrate was evaporated to dryness and purified by column chromatography (5-10% MeOH/DCM) to leave the product as a pale brown solid (2.75 g, 71%). $\delta_H$ (DMSO-$d_6$) 11.58 (1H, bs, NH), 7.25 (2H, m), 6.95 (3H, m), 6.62 (1H, d, J=16.0), 4.86 (2H, bs, NH$_2$).

Synthesis 95

(E)-3-(Methoxymethyl)-8-(2-(thiophen-2-yl)vinyl) imidazo[5,1-d][1,2,3,5]tetrazin-4(3H)-one (MM-004)

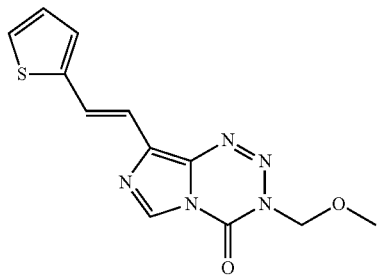 [SMILES: COCn1nnc2c(/C=C/c3cccs3)ncn2c1=O]

Sodium nitrite (150 mg, 2.1 mmol) in water (1 mL) was added to a suspension of (E)-4-(2-(thiophen-2-yl)vinyl)-1H-imidazol-5-amine (0.35 g, 1.8 mmol) in 10% HBF$_4$ (4 mL) at 0° C. After stirring at 0° C. for 60 minutes, the precipitate was filtered from solution and dried over P$_2$O$_5$. This diazo compound (IR stretch 2193 cm$^{-1}$) was used without further purification. Methoxymethyl isocyanate (0.43 g, 4.9 mmol) was added to a solution of (E)-4-diazo-5-(2-(thiophen-2-yl)vinyl)-4H-imidazole (0.3 g, 1.47 mmol) in dry DMSO (2 mL) under nitrogen. The resulting solution was stirred at room temperature for 48 hours, then purified by column chromatography (DCM) to give the title compound as a yellow solid (50 mg, 12%). $\delta_H$ (CDCl$_3$) 8.44 (1H, s), 7.95 (1H, d, J=15.6), 7.34 (1H, d, J=5.1), 7.31 (1H, d, J=15.6), 7.26 (1H, d, J=3.6), 7.08 (1H, dd, J=5.1, 3.6), 5.69 (2H, s), 3.57 (3H, s).

Synthesis 96

(E)-4-(2-(3-(Methylthiomethyl)-4-oxo-3,4-dihydroimidazo[5,1-d][1,2,3,5]tetrazin-8-yl)vinyl)benzonitrile (MM-002)

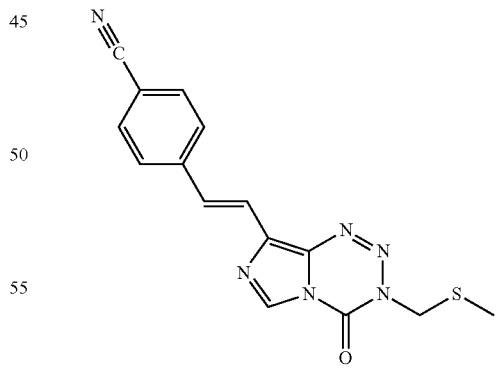

A solution of (isocyanatomethyl)(methyl)sulfane (337 mg, 3.27 mmol) in dry DMSO (1 mL) was added dropwise in the dark under nitrogen to a stirred suspension of (E)-4-(2-(4-diazo-4H-imidazol-5-yl)vinyl)benzonitrile (600 mg, 2.71 mmol) in DMSO (6 mL) and the mixture was stirred overnight. The resulting solution was poured into ice and the precipitate was filtered and washed successively with water and diethyl ether. The crude product was dried under vacuum and was absorbed on silica and purified by flash chromatography using DCM:MeCN (95:5) as eluent to give the pure title compound as a bright yellow solid (71 mg, 8%). δ$_H$ (DMSO d$_6$): 8.87 (1H, s), 7.94-7.97 (2H, d, J=8.6), 7.85-7.87 (2H, d, J=8.6), 7.73 (2H, s), 5.40 (2H, s), 2.27 (3H, s).

Synthesis 97

(E)-4-(2-(3-(Methylsulfonylmethyl)-4-oxo-3,4-dihydroimidazo[5,1-d][1,2,3,5]tetrazin-8-yl)vinyl)benzonitrile (MM-003)

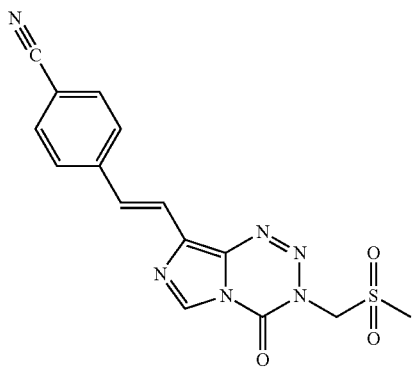 [SMILES: CS(=O)(=O)Cn1nnc2c(/C=C/c3ccc(C#N)cc3)ncn2c1=O]

Isocyanato(methylsulfonyl)methane (440 mg, 3.25 mmol) was added dropwise in the dark under nitrogen to a stirred suspension of E)-4-(2-(4-diazo-4H-imidazol-5-yl)vinyl)benzonitrile (600 mg, 2.71 mmol) in DMSO (6 mL) and the mixture was stirred overnight. The resulting solution was poured into ice and the precipitate was filtered and washed successively with water, ethyl acetate and diethyl ether. The crude product was dried under vacuum and was absorbed on silica and purified by flash chromatography using DCM:MeCN (90:10) as eluent to give the pure title compound as a bright yellow solid (31 mg, 3% yield). δ$_H$ (DMSO d$_6$): 8.95 (1H, s), 7.95-7.97 (2H, d, J=8.6), 7.84-7.87 (2H, d, J=8.6), 7.75 (2H, s), 5.76 (2H, s), 3.16 (3H, s).

(XVI) Preparation of C8-Carboxamides

Isobutyl chloroformate (1.05 eq.) followed by triethylamine (1.05 eq.) were added to a solution of the appropriate 8-carboxylic acid derivative in THF and the mixture was stirred for 1 hour at room temperature. The precipitate of triethylamine hydrochloride, which formed during the reaction, was removed by filtration, and aniline (1.05 eq.) was added to the filtrate. The resulting mixture was stirred at room temperature under nitrogen overnight and was concentrated under vacuum. The crude product was absorbed on silica and purified by flash chromatography using DCM:MeOH (95:5) as eluent to give the target compounds (57%-68% yield).

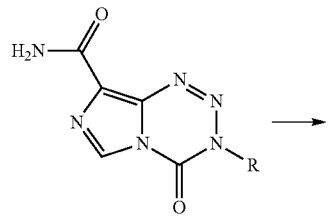

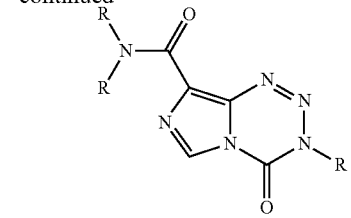

Synthesis 98

3-Methyl-4-oxo-N-phenyl-3,4-dihydroimidazo[5,1-d][1,2,3,5]tetrazine-8-carboxamide (LL-001)

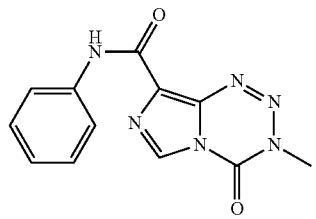 [SMILES: Cn1nnc2c(C(=O)Nc3ccccc3)ncn2c1=O]

Using the general procedure, the title compound was obtained. δ$_H$ (DMSO d$_6$): 10.40 (1H, s), 8.95 (1H, s), 7.87-7.89 (2H, m), 7.35-7.39 (2H, m), 7.13-7.15 (1H, m), 3.90 (3H, s).

Synthesis 99

3-(Methoxymethyl)-4-oxo-N-phenyl-3,4-dihydroimidazo[5,1-d][1,2,3,5]tetrazine-8-carboxamide (LL-002)

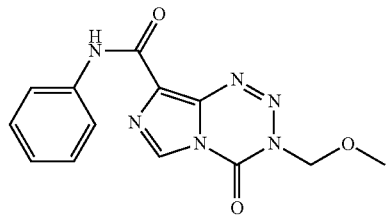 [SMILES: COCn1nnc2c(C(=O)Nc3ccccc3)ncn2c1=O]

Using the general procedure, the title compound was obtained. δ$_H$ (DMSO d$_6$): 10.4 (1H, s), 9.01 (1H, s), 7.87-7.89 (2H, m), 7.35-7.39 (2H, m), 7.11-7.16 (1H, m), 5.65 (2H, s), 3.44 (3H, s).

(XVII) Preparation of C8-Hydroxamates

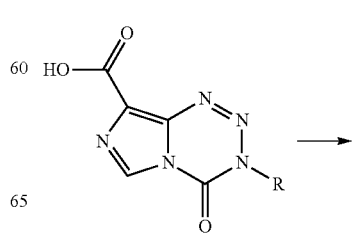

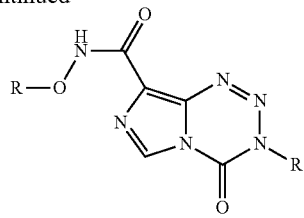

Synthesis 100

N-(Benzyloxy)-4-oxo-3-(prop-2-ynyl)-3,4-dihydroimidazo[5,1-d][1,2,3,5]tetrazine-8-carboxamide (RR-003)

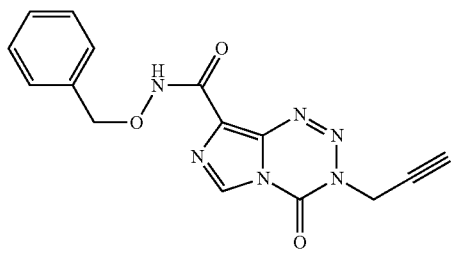 [SMILES: C#CCn1nnc2c(C(=O)NOCc3ccccc3)ncn2c1=O]

4-oxo-3-(prop-2-ynyl)-3,4-dihydroimidazo[5,1-d][1,2,3,5]tetrazine-8-carboxylic acid (0.46 mmol, 100 mg, 1 eq.), O-Benzotriazole-N,N,N',N'-tetramethyl-uronium-hexafluoro-phosphate (HBTU) (0.55 mmol, 208 mg, 1.2 eq.) and triethylamine (0.55 mmol, 77 μL, 1.2 eq.) were dissolved in THF (30 mL) and DMF (1 mL). The mixture was stirred at room temperature for 1 hour before adding O-benzylhydroxylamine (0.55 mmol, 68 mg, 1.2 eq.) in one portion. After 24 hours of room temperature stirring, the volume of the solution was reduced to 5 mL and poured into ice/water. The formed solid was filtered and washed with water, ethyl acetate and ether, and dried under vacuum. Yield: 72%. $\delta_H$ (DMSO-$d_6$) 11.93 (1H, bs), 8.89 (1H, s), 7.48 (2H, m), 7.40 (3H, m), 5.15 (2H, d, J: 1.84), 4.97 (2H, s), 3.53 (1H, bs).

Synthesis 101

N-(Benzyloxy)-3-methyl-4-oxo-3,4-dihydroimidazo[5,1-d][1,2,3,5]tetrazine-8-carboxamide (RR-002)

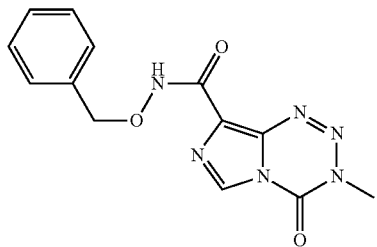 [SMILES: Cn1nnc2c(C(=O)NOCc3ccccc3)ncn2c1=O]

O-benzylhydroxylamine (195 μL, 1.68 mmol, 2 eq.) was added to a solution of crude 3-methyl-4-oxo-3,4-dihydroimidazo[5,1-d][1,2,3,5]tetrazine-8-carbonyl chloride (200 mg, 0.84 mmol; see Arrowsmith et al., J. Med. Chem., 2002, Vol. 45, No. 25, p. 5458) in THF (6 mL) and a precipitate formed instantly. The resulting suspension was stirred for 1 hour and 30 minutes and was then poured into ice. The suspension was diluted with water and the precipitate was filtered and washed successively with water, ethyl acetate and diethyl ether to give 158 mg of the pure title compound as an off-white solid (63% yield). $\delta_H$ (DMSO-$d_6$): 11.9 (1H, s), 8.85 (1H, s), 7.42-7.50 (2H, m), 7.36-7.42 (3H, m), 4.96 (2H, s), 3.88 (3H, s).

Synthesis 102

N-Hydroxy-3-methyl-4-oxo-3,4-dihydroimidazo[5,1-d][1,2,3,5]tetrazine-8-carboxamide (RR-001)

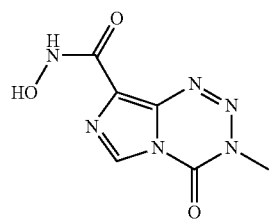

A solution of N-(benzyloxy)-3-methyl-4-oxo-3,4-dihydroimidazo[5,1-d][1,2,3,5]tetrazine-8-carboxamide (200 mg, 0.67 mmol) and 10% Pd/C (20 mg) in ethyl acetate:DMF (5:1) (36 mL) was put under an atmosphere of hydrogen for 3 days. The mixture was filtered through a pad of Celite™ and the filtrate was concentrated under vacuum. The residue was suspended in ethyl acetate and the precipitate was filtered and washed successively with water, ethyl acetate and diethyl ether to give the pure title compound as a pale orange solid (35 mg, 25% yield). $\delta_H$ (DMSO-$d_6$): 11.2 (1H, s), 9.18 (1H, s), 8.82 (1H, s), 3.86 (3H, s).

Biological Methods

General Cell Culture Methods

The cell culture techniques were carried out in a Class II microbiological safety cabinet which was swabbed with 70% IMS in distilled water before each use. Glioma cells were routinely cultured in Costar tissue culture flasks in RPMI 1640 liquid medium (containing 0.3 g/L L-glutamine and 2 g/L sodium bicarbonate) supplemented with 10% heat inactivated FBS (55-59° C.) for 1 hour to denature complement proteins which would otherwise evoke a cellular immune response resulting in cell lysis, 1% non-essential amino acids, 50 μg/mL gentamicin and 400 μg/mL G418 (vector selection reagent). Colorectal and melanoma cells were maintained in RPMI 1640 supplemented with 10% FBS. MRC-5 cells were cultured in EMEM+10% FBS, 1% pen/strep, 1% non-essential amino acids, 1% HEPES (1M) and 1% sodium bicarbonate.

Cells were grown at 37° C. in a humidified incubator in an atmosphere comprising 95% air/5% $CO_2$. Cells were subcultured when growth exceeded approximately 80% confluence, normally twice weekly. The medium was aspirated from the flask and approximately 0.8 mL trypsin-EDTA 1× solution added. The cells were re-incubated at 37° C. until they had visibly detached from the flask. The cells were re-suspended in 5 mL medium and 0.5-1 mL was transferred to a new flask (25 cm²) with 7 mL culture medium. The cells were further incubated at 37° C. To minimize phenotypic drift, cells were disposed of once they had been subcultured 30 times. New batches of cells were thawed rapidly in 37° C. water bath once taken from liquid nitrogen storage and re-suspended in 10 mL of culture medium in a 25 cm² flask. Cells were passaged twice to allow normal growth to resume prior to use in experiments.

For cryopreservation, viable cells at 60-80% confluence were detached by minimum amount of trypsin/EDTA and re-suspended in sterile filtered freezing medium (95% FBS, 5% DMSO), transferred to sterile cryogenic vials, and frozen overnight at −20° C. followed by −80° C. for 1-2 days and stored in liquid nitrogen for long term storage.

Drug Solutions

Most test compounds, including temozolomide, were prepared as 100 mM stock solutions in DMSO and stored at −20° C. for not more than 6 months.

MTT Assay for 7-Day Toxicity Assay

This assay was first described in Mosmann, T., 1983, "Rapid colorimetric assay for cellular growth and survival: Application to proliferation and cytotoxicity assays", *Journal of Immunological Methods*, Vol. 65, Nos. 1-2, pp. 55-63.

Glioma cell lines, SNB19 and U373, both stably transfected with MGMT (i.e., SNB19M and U373M) or their respective vector controls (i.e., SNB19V and U373V); colorectal carcinoma cell lines, HCT116, HT29, and DLD1; melanoma cell line, SKMEL-28; breast cell line, MCF-7; and normal human fetal lung fibroblast cell line, MRC-5; were used at 60-80% confluence, during the logarithmic phase of growth.

Following harvesting with trypsin/EDTA, cells in suspension were gently syringed through a 23 gauge needle to obtain a near-single cell suspension. Cells were then seeded into 96-well plates at the desired density in 180 μL culture medium if only one test compound was to be added, or in 160 μL if two test compounds were to be added in combination. Cells were allowed to attach overnight by incubation at 37° C. in 95% air/5% $CO_2$. For the 7 day assay, the cell seeding densities for the different cell lines were as follows: SNB19V, SNB19M: 650 cells/well; U373V, U373M: 650 cells/well; SNB19VR, U373VR: 650 cells/well; HCT116, DLD-1, SKMEL-28, MRC-5, MCF-7: 400 cells/well.

The two peripheral lanes of each plate were used as blank wells (cell free) and filled with 200 μL of medium in order to minimise medium evaporation from the plate. A separate time zero ($T_0$) plate was set up alongside other plates. Serial dilutions in tissue culture medium of a 100 mM stock of test compound were prepared immediately before each assay to ten times the final concentrations required. 20 μL was added to each well (200 μL total media per well) to achieve final concentrations of 0.5 μM, 1 μM, 5 μM, 10 μM, 50 μM, 100 μM, 500 μM, and 1000 μM. A minimum of four wells received the same test compound concentration. To control wells, including those in the $T_0$ plate, 20 μL of medium was added. Previous assays had been carried out to verify that cell viability was not affected by the amount of DMSO added into the test compound-treated wells. A separate plate treated in the same way, but free of test compound, was used as a measure of cell viability at the time of drug addition ($T_0$).

After incubation at 37° C., 95% air/5% $CO_2$ for 7 days (or immediately for the day 0 plate), cell viability was quantified using the MTT assay. 50 μL of sterile filtered MTT (3-(4,5-dimethylthiazol-2-yl)-2,5-diphenyltetrazolium bromide) (2 mg/mL in phosphate buffered saline) were added to each well (final concentration 0.4 mg/mL) and the plates were re-incubated for 4 hours to allow metabolic conversion of MTT by dehydrogenases in viable cells to insoluble formazan crystals. The medium and any unconverted MTT was aspirated, 150 μL of DMSO was added to each well, and the plates were shaken on a plate shaker (Stuart Scientific 503) to ensure complete formazan solubilisation. Absorbance was then read at 550 nm on an Anthos Labtec Systems plate reader and Deltasoft 3™ software, where the absorbance readings (corrected for background absorbance) were recorded.

The absorbance at 550 nm is directly proportional to viable cell number. A linear relationship exists between cell number and the amount of formazan so the mean absorbance determined for all wells of the same concentration can be used as a quantitative measure of viable cells compared to the controls. A graph of absorbance against drug concentration was plotted and the test compound concentration causing 50% inhibition ($GI_{50}$) of control cell growth (absorbance increase from $T_0$) was calculated by interpolation.

Generation of TMZ Resistant Cell Lines

SNB19V and U373V cell lines were cultured in the presence of incremental concentrations of TMZ (1, 2, 5, 10, 20, 50, 100 μM) (and up to 150 μM for U373V) to generate corresponding TMZ acquired resistant cell lines (i.e., SNB19VR and U373VR). At each step of selection, cells were exposed to a higher TMZ concentration when the re-growth was apparent and labelled as SNB19VR and U373VR, respectively, to distinguish them from the parental cell lines.

Clonogenic Survival Assay

A clonogenic assay, which measures tumour cell survival and subsequent proliferative ability following drug exposure, was used to verify that the cells remaining metabolically active following treatment with TMZ and test compounds. See, e.g., Brown, J. M., et al., 1999, "Apoptosis, p 53, and tumor cell sensitivity to anticancer agents", *Cancer Research*, Vol. 59, No. 7, pp. 1391-1399.

Exponentially growing cells were seeded in triplicate at a density of 200 cells/well in 6 well plates, allowed to attach overnight and then exposed to increasing concentrations of TMZ or test compounds (0, 5, 10, 100, 500, 1000 μM). After 18 hours, the media was changed to drug free media and cells left to grow in the 37° C., 95% air/5% $CO_2$ incubator. After 14 days, the plates were rinsed in PBS and fixed with pre-chilled methanol at room temperature for 20 minutes, stained with 0.5% methylene blue in 1:1 methanol/$H_2O$ (v/v) for 10 minutes, thoroughly washed in distilled water and air dried. Cell colonies containing >30 cells were counted. Growth inhibition by TMZ and test compounds was estimated by expressing the mean number of colonies for TMZ or test compound treated wells as a percentage of the mean number of colonies in control.

Biological Data

As shown in the data in the following table (representing more than 80 replicates), the parent compound, Temozolomide (TMZ), is demonstrably more active in the glioma lines which are MGMT− (SNB 19V and U373V) than those which express MGMT (MGMT+lines SNB 19M and U373M).

TABLE 1

| $GI_{50}$ Values for Temozolomide (TMZ) | | | | |
|---|---|---|---|---|
| | SNB19V $GI_{50}$ (μM) | SNB19M $GI_{50}$ (μM) | U373V $GI_{50}$ (μM) | U373M $GI_{50}$ (μM) |
| TMZ | 45.6 | 526.3 | 72.9 | 394.8 |

Each of compounds WW-001 through WW-066 (i.e., -A is -A¹) where has a SNB19V $GI_{50}$ of less than 65 μM, and most have a SNB19V $GI_{50}$ of less than 45 μM.

Specifically, each of the following compounds has a SNB19V $GI_{50}$ of less than 45 μM: WW-001, WW-002, WW-003, WW-004, WW-005, WW-006, WW-007, WW-008, WW-009, WW-010, WW-011, WW-012, WW-017, WW-018, WW-019, WW-022, WW-023, WW-024, WW-025, WW-026, WW-027, WW-029, WW-031, WW-033, WW-036, WW-037, WW-038, WW-041, WW-042, WW-043, WW-045, WW-047, WW-048, WW-049, WW-050, WW-051, WW-052, WW-053, WW-054, WW-055, WW-056, WW-057, WW-058, WW-059, WW-060, WW-061, WW-062, WW-063, WW-064, WW-065, WW-066.

In this way, these compounds have a SNB19V activity that is similar to, if not better than, that of TMZ (45.6 µM).

Additionally, whereas TMZ has a SNB19M $GI_{50}$ of 526.3 µM, each of compounds WW-001 through WW-066 has a SNB19M $GI_{50}$ of less than 100 µM, and many have a SNB19M $GI_{50}$ of less than 70 µM.

Specifically, each of the following compounds has a SNB19M $GI_{50}$ of less than 70 µM: WW-001, WW-002, WW-003, WW-004, WW-005, WW-007, WW-008, WW-010, WW-011, WW-012, WW-013, WW-014, WW-015, WW-016, WW-017, WW-018, WW-019, WW-020, WW-021, WW-022, WW-023, WW-024, WW-025, WW-026, WW-027, WW-028, WW-029, WW-030, WW-031, WW-032, WW-033, WW-034, WW-035, WW-036, WW-037, WW-038, WW-039, WW-040, WW-042, WW-043, WW-046, WW-047, WW-048, WW-049, WW-050, WW-051, WW-052, WW-053, WW-055, WW-056, WW-057, WW-058, WW-059, WW-060, WW-061, WW-062, WW-063, WW-064, WW-065, WW-066.

In this way, these compounds have a SNB19M activity that is very much better than that of TMZ (526.3 µM).

These results were echoed in similar studies in the U373 cell line.

Specifically, each of the following compounds has a U373V $GI_{50}$ of less than 75 µM: WW-001, WW-002, WW-003, WW-004, WW-005, WW-006, WW-007, WW-008, WW-009, WW-011, WW-012, WW-013, WW-014, WW-015, WW-016, WW-021, WW-023, WW-024, WW-025, WW-026, WW-027, WW-028, WW-029, WW-030, WW-031, WW-032, WW-033, WW-034, WW-035, WW-036, WW-037, WW-038, WW-039, WW-040, WW-041, WW-042, WW-044, WW-045, WW-046, WW-047, WW-048, WW-049, WW-050, WW-051, WW-052, WW-054, WW-055, WW-058, WW-062, WW-063.

In this way, these compounds have a U373V activity that is similar to, if not better than, that of TMZ (72.9 µM).

Similarly, each of the following compounds has a U373M $GI_{50}$ of less than 60 µM: WW-001, WW-002, WW-003, WW-004, WW-005, WW-006, WW-007, WW-008, WW-009, WW-012, WW-013, WW-014, WW-015, WW-016, WW-021, WW-023, WW-024, WW-025, WW-026, WW-027, WW-028, WW-029, WW-030, WW-031, WW-032, WW-033, WW-034, WW-035, WW-036, WW-037, WW-038, WW-039, WW-040, WW-042, WW-046, WW-047, WW-048, WW-049, WW-050, WW-051, WW-052, WW-055, WW-058, WW-062, WW-063.

In this way, these compounds have a U373M activity that is very much better than that of TMZ (394.8 µM).

Data for a few particular compounds are summarised in the following table.

TABLE 2

| | $GI_{50}$ Values | | | |
|---|---|---|---|---|
| | SNB19V $GI_{50}$ (µM) | SNB19M $GI_{50}$ (µM) | U373V $GI_{50}$ (µM) | U373M $GI_{50}$ (µM) |
| TMZ | 45.6 | 526.3 | 72.9 | 394.8 |
| MM-004 | 4.5 | 5.1 | 4.4 | 6.5 |
| WW-028 | 54.0 | 56.5 | 50.0 | 35.1 |
| WW-027 | 22.0 | 33.8 | 9.3 | 33.1 |

As shown by the data discussed above, and unlike TMZ, these compounds have good activity against tumour cell lines regardless of the MGMT and MMR (Mis-Match Repair) status of the cell line.

In addition, several of the compounds have also been tested and found to be active in other cells lines, including HCT116, DLD-1, SKMEL-28, MRC-5, MCF-7, and HT29.

Similar results were obtained for compounds where -A is $-A^2$, $-A^3$, $-A^4$, $-A^5$, or $-A^6$. Data for examples of each of these classes are summarised in the following table.

TABLE 1

| | $GI_{50}$ Values for Temozolomide (TMZ) | | | |
|---|---|---|---|---|
| | SNB19V $GI_{50}$ (µM) | SNB19M $GI_{50}$ (µM) | U373V $GI_{50}$ (µM) | U373M $GI_{50}$ (µM) |
| TMZ | 45.6 | 526.3 | 72.9 | 394.8 |
| TT-001 | 63.2 | 54.7 | 42.3 | 53.4 |
| SS-001 | 59.0 | 52.7 | 51.2 | 55.1 |
| RR-001 | 41.0 | 87.1 | — | — |
| LL-002 | 55.3 | 43.8 | 36.3 | 52.3 |
| MM-001 | 9.1 | 8.9 | 7.7 | 8.8 |

Again, these compounds have a SNB19V activity that is similar to, if not better than, that of TMZ (45.6 µM).

Again, these compounds have a SNB19M activity that is very much better than that of TMZ (526.3 µM).

Again, these compounds have a U373V activity that is similar to, if not better than, that of TMZ (72.9 µM).

Again, these compounds have a U373M activity that is very much better than that of TMZ (394.8 µM).

Again, several of the compounds have also been tested and found to be active in other cells lines, including HCT116, DLD-1, SKMEL-28, MRC-5, MCF-7, and HT29.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

The invention claimed is:

1. A compound of the following formula or a pharmaceutically acceptable salt thereof:

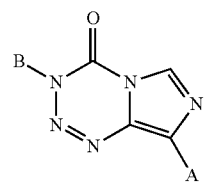

wherein:
-A is independently -$A^1$, -$A^3$, or -$A^6$; and
—B is independently —$B^1$, —$B^2$, —$B^3$, —$B^4$, —$B^5$, —$B^6$, —$B^7$, —$B^8$, —$B^9$, —$B^{10}$, —$B^{11}$, $B^{12}$, —$B^{13}$, or —$B^{14}$;
wherein:
-$A^1$ is independently $C_{5-12}$heteroaryl, and is optionally substituted with one or more groups selected from:
—F, —Cl, —Br, —I,
—$R^{Z1}$, —$CF_3$,
—OH, —$OR^{Z1}$, —$OCF_3$,
—$SR^{Z1}$,
—$NH_2$, —$NHR^{Z1}$, —$NR^{Z1}_2$, pyrrolidino, piperidino, morpholino, piperizino, (N—$C_{1-4}$alkyl)-piperizino,
—C(=O)OH, —C(=O)$OR^{Z1}$,
—C(=O)$R^{Z1}$,
—OC(=O)$R^{Z1}$,
—C(=O)$NH_2$, —C(=O)$NHR^{Z1}$, —C(=O)$NR^{Z1}_2$,
—C(=O)-pyrrolidino, —C(=O)-piperidino,
—C(=O)-morpholino, —C(=O)-piperizino,
—C(=O)—(N—$C_{1-4}$alkyl)-piperizino,
—NHC(=O)$R^{Z1}$, —$NR^{Z1}$C(=O)$R^{Z1}$,
—OC(=O)$NH_2$, —OC(=O)$NHR^{Z1}$, —OC(=O)$NR^{Z1}_2$,
—OC(=O)-pyrrolidino, —OC(=O)-piperidino,
—OC(=O)-morpholino, —OC(=O)-piperizino,
(N—$C_{1-4}$alkyl)-piperizino,
—NHC(=O)$OR^{Z1}$, —$NR^{Z1}$C(=O)$OR^{Z1}$,
—NHC(=O)$NH_2$, —NHC(=O)$NHR^{Z1}$, —NHC(=O)$NR^{Z1}_2$, —NHC(=O)-pyrrolidino, —NHC(=O)-piperidino, —NHC(=O)-morpholino, —NHC(=O)-piperizino, —NHC(=O)—(N—$C_{1-4}$alkyl)-piperizino,
—$NO_2$, and —CN;
wherein each —$R^{Z1}$ is independently saturated aliphatic $C_{1-4}$alkyl, aliphatic $C_{3-6}$alkynyl, saturated $C_{3-6}$cycloalkyl, $C_{5-6}$heteroaryl, -Ph, or —$CH_2$-Ph,
wherein each of said $C_{3-6}$cycloalkyl, $C_{5-6}$heteroaryl, and -Ph is optionally substituted with one or more substituents selected from —F, —Cl, —Br, —I, —$R^{Z1A}$, —$CF_3$, —OH, —$OR^{Z1A}$, and —$OCF_3$,
wherein each —$R^{Z1A}$ is independently saturated aliphatic $C_{1-4}$alkyl;
and additionally wherein two adjacent substituents may together form —O—$CH_2$—O— or —O—$CH_2CH_2$—O—;
-$A^3$ is independently imidamido or substituted imidamido;
-$A^6$ is independently aliphatic $C_{2-6}$alkenyl, and is optionally substituted with one or more groups selected from:
—F, —Cl, —Br, —I,
—$R^{Z6A}$, —$CF_3$,
—OH, —$OR^{Z6A}$, —$OCF_3$,
—$SR^{Z6A}$,
—$NH_2$, —$NHR^{Z6A}$, —$NR^{Z6A}_2$, pyrrolidino, piperidino, morpholino, piperizino, (N—$C_{1-4}$alkyl)-piperizino,
—C(=O)OH, —C(=O)$OR^{Z6A}$,
—C(=O)$R^{Z6A}$,
—OC(=O)$R^{Z6A}$,
—C(=O)$NH_2$, —C(=O)$NHR^{Z6A}$, —C(=O)$NR^{Z6A}_2$,
—C(=O)-pyrrolidino, —C(=O)-piperidino,
—C(=O)-morpholino, —C(=O)-piperizino,
—C(=O)—(N—$C_{1-4}$alkyl)-piperizino,
—NHC(=O)$R^{Z6A}$, —$NR^{Z6A}$C(=O)$R^{Z6A}$,
—OC(=O)$NH_2$, —OC(=O)$NHR^{Z6A}$, —OC(=O)$NR^{Z6A}_2$, —OC(=O)-pyrrolidino, —OC(=O)-piperidino, —OC(=O)-morpholino, —OC(=O)-piperizino, (N—$C_{1-4}$alkyl)-piperizino,
—NHC(=O)$OR^{Z6A}$, —$NR^{Z6A}$C(=O)$OR^{Z6A}$,
—NHC(=O)$NH_2$, —NHC(=O)$NHR^{Z6A}$, —NHC(=O)$NR^{Z6A2}$, —NHC(=O)-pyrrolidino, —NHC(=O)-piperidino, —NHC(=O)-morpholino, —NHC(=O)-piperizino, —NHC(=O)—(N—$C_{1-4}$alkyl)-piperizino,
—$NO_2$, and —CN,
wherein each —$R^{Z6A}$ is independently saturated aliphatic $C_{1-4}$alkyl, saturated $C_{3-6}$cycloalkyl, -Ph, or —$CH_2$-Ph,
wherein each $C_{3-6}$cycloalkyl and -Ph is optionally substituted with one or more substituents selected from —F, —Cl, —Br, —I, —$R^{Z6B}$, —$CF_3$, —OH, —$OR^{Z6B}$, and —$OCF_3$,
wherein each —$R^{Z6B}$ is independently saturated aliphatic $C_{1-4}$alkyl;
and wherein:
—$B^1$ is independently saturated aliphatic $C_{1-6}$alkyl;
—$B^2$ is independently aliphatic $C_{2-6}$alkynyl;
—$B^3$ is independently mercapto-$C_{1-4}$alkyl, sulfanyl-$C_{1-4}$ alkyl, sulfinyl-$C_{1-4}$alkyl, or sulfonyl-$C_{1-4}$alkyl;
—$B^4$ is independently hydroxy-$C_{1-4}$alkyl or ether-$C_{1-4}$ alkyl;
—$B^5$ is independently phenyl-$C_{1-6}$alkyl or $C_{5-6}$heteroaryl-$C_{1-6}$alkyl, and is optionally substituted with one or more groups selected from:
—F, —Cl, —Br, —I,
—$R^{Y5A}$, —$CF_3$,
—OH, —$OR^{Y5A}$, —$OCF_3$,
—$SR^{Y5A}$,
—$NH_2$, —$NHR^{Y5A}$, —$NR^{Y5A}_2$, pyrrolidino, piperidino, morpholino, piperizino, (N—$C_{1-4}$alkyl)-piperizino,
—C(=O)OH, —C(=O)$OR^{Y5A}$,
—C(=O)$R^{Y5A}$,
—OC(=O)$R^{Y5A}$,
—C(=O)$NH_2$, —C(=O)$NHR^{Y5A}$, —C(=O)$NR^{Y5A}_2$,
—C(=O)-pyrrolidino, —C(=O)-piperidino,
—C(=O)-morpholino, —C(=O)-piperizino,
—C(=O)—(N—$C_{1-4}$alkyl)-piperizino,
—NHC(=O)$R^{Y5A}$, —$NR^{Y5A}$C(=O)$R^{Y5A}$,
—OC(=O)$NH_2$, —OC(=O)$NHR^{Y5A}$, —OC(=O)$NR^{Y5A}_2$, —OC(=O)-pyrrolidino, —OC(=O)-piperidino, —OC(=O)-morpholino, —OC(=O)-piperizino, (N—$C_{1-4}$ alkyl)-piperizino,
—NHC(=O)$OR^{Y5A}$, —$NR^{Y5A}$C(=O)$OR^{Y5A}$,
—NHC(=O)$NH_2$, —NHC(=O)$NHR^{Y5A}$, —NHC(=O)$NR^{Y5A}_2$, —NHC(=O)-pyrrolidino, —NHC(=O)-piperidino, —NHC(=O)-morpholino, —NHC(=O)-piperizino, —NHC(=O)—(N—$C_{1-4}$alkyl)-piperizino,
—$NO_2$, and —CN,
wherein each —$R^{Y5A}$ is independently saturated aliphatic $C_{1-4}$alkyl, saturated $C_{3-6}$cycloalkyl, -Ph, or —$CH_2$-Ph,
wherein each of said $C_{3-6}$cycloalkyl and -Ph is optionally substituted with one or more substituents selected from —F, —Cl, —Br, —I, —$R^{Y5B}$, —$CF_3$, —OH, —$OR^{Y5B}$, and —$OCF_3$,
wherein each —$R^{Y5B}$ is independently saturated aliphatic $C_{1-4}$alkyl;
—$B^6$ is independently acyl-$C_{1-6}$alkyl, carboxy-$C_{1-6}$ alkyl, oxyacyl-$C_{1-6}$alkyl, or acyloxy-$C_{1-6}$alkyl;
—$B^7$ is independently amido-$C_{1-4}$alkyl or substituted amido-$C_{1-4}$alkyl;
—$B^8$ is independently $C_{3-6}$cycloalkyl, $C_{3-6}$cycloalkyl-$C_{1-4}$alkyl, $C_{3-6}$heterocyclyl, or $C_{3-6}$heterocyclyl-$C_{1-4}$ alkyl, and is optionally substituted with one or more groups selected from:
—F, —Cl, —Br, —I, —R$^{Y8A}$, —CF$_3$,
—OH, —OR$^{Y8A}$, —OCF$_3$,
—NH$_2$, —NHR$^{Y8A}$, —NR$^{Y8A}_2$, pyrrolidino piperidino, morpholino, piperizino, (N—C$_{1-4}$alkyl)-piperizino,
—C(=O)OH, —C(=O)OR$^{Y8A}$,
—C(=O)R$^{Y8A}$,
—OC(=O)R$^{Y8A}$,
—C(=O)NH$_2$, —C(=O)NHR$^{Y8A}$, —C(=O)NR$^{Y8A}_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Y8A}$, —NR$^{Y8A}$C(=O)R$^{Y8A}$, and
—CN;
    wherein each —R$^{Y8A}$ is independently saturated aliphatic C$_{1-4}$alkyl, saturated C$_{3-6}$cycloalkyl, -Ph, or —CH$_2$-Ph,
    wherein each of said C$_{3-6}$cycloalkyl and -Ph is optionally substituted with one or more substituents selected from —F, —Cl, —Br, —I, —R$^{Y8B}$, —CF$_3$, —OH, —OR$^{Y8B}$, and —OCF$_3$,
    wherein each —R$^{Y8B}$ is independently saturated aliphatic C$_{1-4}$alkyl;
—B$^9$ is independently halo-C$_{1-6}$alkyl;
—B$^{10}$ is independently nitro-C$_{1-6}$alkyl;
—B$^{11}$ is independently cyano-C$_{1-6}$alkyl;
—B$^{12}$ is independently phosphate-C$_{1-6}$alkyl;
—B$^{13}$ is independently carbamate-C$_{1-6}$alkyl; and
—B$^{14}$ is independently oxime-C$_{1-6}$alkyl.

2. A compound according to claim 1, wherein -A is independently -A$^1$; and -A$^1$ is independently:
furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, indolyl, isoindolyl, benzofuranyl, isobenzofuranyl, benzothienyl, isobenzothienyl, indazolyl, benzimidazolyl, benzothiazolyl, benzoisothiazolyl, benzoxazolyl, benzoisoxazolyl, quinolinyl, isoquinolinyl, cinnolinyl, or quinazolinyl;
and is optionally substituted with one or more groups selected from:
—F, —Cl, —Br, —I,
—R$^{Z1}$, —CF$_3$,
—OH, —OR$^{Z1}$, —OCF$_3$,
—SR$^{Z1}$,
—NH$_2$, —NHR$^{Z1}$, —NR$^{Z1}_2$, pyrrolidino, piperidino, morpholino, piperizino, (N—C$_{1-4}$alkyl)-piperizino,
—C(=O)OH, —C(=O)OR$^{Z1}$,
—C(=O)R$^{Z1}$,
—OC(=O)R$^{Z1}$,
—C(=O)NH$_2$, —C(=O)NHR$^{Z1}$, —C(=O)NR$^{Z1}_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Z1}$, —NR$^{Z1}$C(=O)R$^{Z1}$,
—OC(=O)NH$_2$, —OC(=O)NHR$^{Z1}$, —OC(=O)NR$^{Z1}_2$, —OC(=O)-pyrrolidino, —OC(=O)-piperidino, —OC(=O)-morpholino, —OC(=O)-piperizino, (N—C$_{1-4}$alkyl)-piperizino, NHC(=O)OH, NHC(=O)OR$^{Z1}$, —NR$^{Z1}$C(=O)OR$^{Z1}$,
—NHC(=O)NH$_2$, —NHC(=O)NHR$^{Z1}$, —NHC(=O)NR$^{Z1}_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino,
—NO$_2$, and —CN;
    wherein each —R$^{Z1}$ is independently saturated aliphatic C$_{1-4}$alkyl, aliphatic C$_{3-6}$alkynyl, saturated C$_{3-6}$cycloalkyl, C$_{5-6}$heteroaryl, -Ph, or —CH$_2$-Ph,
    wherein each of said C$_{3-6}$cycloalkyl, C$_{5-6}$heteroaryl, and -Ph is optionally substituted with one or more substituents selected from —F, —Cl, —Br, —I, —R$^{Z1A}$, —CF$_3$, —OH, —OR$^{Z1A}$, and —OCF$_3$,
    wherein each —R$^{Z1A}$ is independently saturated aliphatic C$_{1-4}$alkyl;
    and additionally wherein two adjacent substituents may together form —O—CH$_2$—O— or —O—CH$_2$CH$_2$—O—.

3. A compound according to claim 2, wherein -A$^1$ is independently oxazolyl, thiazolyl, imidazolyl, or oxadiazolyl, and is optionally substituted with one or more groups selected from:
—F, —Cl, —Br, —I,
—R$^{Z1}$, —CF$_3$,
—OH, —OR$^{Z1}$, —OCF$_3$,
—SR$^{Z1}$,
—NH$_2$, —NHR$^{Z1}$, —NR$^{Z1}_2$, pyrrolidino, piperidino, morpholino, piperizino, (N—C$_{1-4}$alkyl)-piperizino,
—C(=O)OH, —C(=O)OR$^{Z1}$,
—C(=O)R$^{Z1}$,
—OC(=O)R$^{Z1}$,
—C(=O)NH$_2$, —C(=O)NHR$^{Z1}$, —C(=O)NR$^{Z1}_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Z1}$, —NR$^{Z1}$C(=O)R$^{Z1}$,
—OC(=O)NH$_2$, —OC(=O)NHR$^{Z1}$, —OC(=O)NR$^{Z1}_2$, —OC(=O)-pyrrolidino, —OC(=O)-piperidino, —OC(=O)-morpholino, —OC(=O)-piperizino, (N—C$_{1-4}$alkyl)-piperizino,
—NHC(=O)OR$^{Z1}$, —NR$^{Z1}$C(=O)OR$^{Z1}$,
—NHC(=O)NH$_2$, —NHC(=O)NHR$^{Z1}$, —NHC(=O)NR$^{Z1}_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino,
—NO$_2$, and —CN;
    wherein each —R$^{Z1}$ is independently saturated aliphatic C$_{1-4}$alkyl, aliphatic C$_{3-6}$alkynyl, saturated C$_{3-6}$cycloalkyl, C$_{5-6}$heteroaryl, -Ph, or —CH$_2$-Ph,
    wherein each of said C$_{3-6}$cycloalkyl, C$_{5-6}$heteroaryl, and -Ph is optionally substituted with one or more substituents selected from —F, —Cl, —Br, —I, —R$^{Z1A}$, —CF$_3$, —OH, —OR$^{Z1A}$, and —OCF$_3$,
    wherein each —R$^{Z1A}$ is independently saturated aliphatic C$_{1-4}$alkyl;
    and additionally wherein two adjacent substituents may together form —O—CH$_2$—O— or —O—CH$_2$CH$_2$—O—.

4. A compound according to claim 2, wherein -A$^1$ is independently imidazolyl, and is optionally substituted with one or more groups selected from:
—F, —Cl, —Br, —I,
—R$^{Z1}$, —CF$_3$,
—OH, —OR$^{Z1}$, —OCF$_3$,
—SR$^{Z1}$,
—NH$_2$, —NHR$^{Z1}$, —NR$^{Z1}_2$, pyrrolidino, piperidino, morpholino, piperizino, (N—C$_{1-4}$alkyl)-piperizino,
—C(=O)OH, —C(=O)OR$^{Z1}$,
—C(=O)R$^{Z1}$,
—OC(=O)R$^{Z1}$,
—C(=O)NH$_2$, —C(=O)NHR$^{Z1}$, —C(=O)NR$^{Z1}_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Z1}$, —NR$^{Z1}$C(=O)R$^{Z1}$, —OC(=O)NH$_2$, —OC(=O)NHR$^{Z1}$, —OC(=O)NR$^{Z1}_2$, —OC(=O)-pyrrolidino, —OC(=O)-piperidino, —OC(=O)-morpholino, —OC(=O)-piperizino, (N—C$_{1-4}$alkyl)-piperizino,

—NHC(=O)OR$^{Z1}$, —NR$^{Z1}$C(=O)OR$^{Z1}$,

—NHC(=O)NH$_2$, —NHC(=O)NHR$^{Z1}$, —NHC(=O)NR$^{Z1}_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino, —NO$_2$, and —CN;

wherein each —R$^{Z1}$ is independently saturated aliphatic C$_{1-4}$alkyl, aliphatic C$_{3-6}$alkynyl, saturated C$_{3-6}$cycloalkyl, C$_{5-6}$heteroaryl, -Ph, or —CH$_2$-Ph, wherein each of said C$_{3-6}$cycloalkyl, C$_{5-6}$heteroaryl, and -Ph is optionally substituted with one or more substituents selected from —F, —Cl, —Br, —I, —R$^{Z1A}$, —CF$_3$, —OH, —OR$^{Z1A}$, and —OCF$_3$, wherein each —R$^{Z1A}$ is independently saturated aliphatic C$_{1-4}$alkyl;

and additionally wherein two adjacent substituents may together form —O—CH$_2$—O— or —O—CH$_2$CH$_2$—O—.

5. A compound according to claim 2, wherein -A$^1$ is independently imidazol-2-yl, and is optionally substituted with one or more groups selected from:

—F, —Cl, —Br, —I,

—R$^{Z1}$, —CF$_3$,

—OH, —OR$^{Z1}$, —OCF$_3$,

—SR$^{Z1}$,

—NH$_2$, —NHR$^{Z1}$, —NR$^{Z1}_2$, pyrrolidino, piperidino, morpholino, piperizino, (N—C$_{1-4}$alkyl)-piperizino,

—C(=O)OH, —C(=O)OR$^{Z1}$,

—C(=O)R$^{Z1}$,

—OC(=O)R$^{Z1}$,

—C(=O)NH$_2$, —C(=O)NHR$^{Z1}$, —C(=O)NR$^{Z1}_2$, —C(=O)-pyrrolidino, —C(=O)-piperidino, —C(=O)-morpholino, —C(=O)-piperizino, —C(=O)—(N—C$_{1-4}$alkyl)-piperizino,

—NHC(=O)R$^{Z1}$, —NR$^{Z1}$C(=O)R$^{Z1}$,

—OC(=O)NH$_2$, —OC(=O)NHR$^{Z1}$, —OC(=O)NR$^{Z1}_2$, —OC(=O)-pyrrolidino, —OC(=O)-piperidino, —OC(=O)-morpholino, —OC(=O)-piperizino, (N—C$_{1-4}$alkyl)-piperizino,

—NHC(=O)OR$^{Z1}$, —NR$^{Z1}$C(=O)OR$^{Z1}$,

—NHC(=O)NH$_2$, —NHC(=O)NHR$^{Z1}$, —NHC(=O)NR$^{Z1}_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino, —NO$_2$, and —CN;

wherein each —R$^{Z1}$ is independently saturated aliphatic C$_{1-4}$alkyl, aliphatic C$_{3-6}$alkynyl, saturated C$_{3-6}$cycloalkyl, C$_{5-6}$heteroaryl, -Ph, or —CH$_2$-Ph, wherein each of said C$_{3-6}$cycloalkyl, C$_{5-6}$heteroaryl, and -Ph is optionally substituted with one or more substituents selected from —F, —Cl, —Br, —I, —R$^{Z1A}$, —CF$_3$, —OH, —OR$^{Z1A}$, and —OCF$_3$, wherein each —R$^{Z1A}$ is independently saturated aliphatic C$_{1-4}$alkyl;

and additionally wherein two adjacent substituents may together form —O—CH$_2$—O— or —O—CH$_2$CH$_2$—O—.

6. A compound according to claim 2, which is a compound selected from the following compounds:

| Code No. | Structure |
|---|---|
| WW-001 | 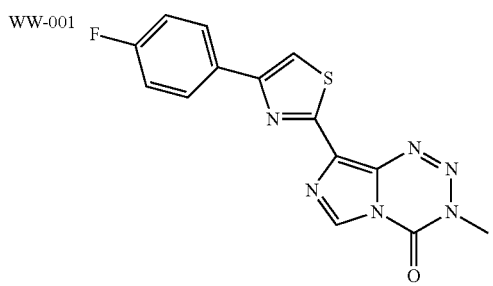 |
| WW-002 | 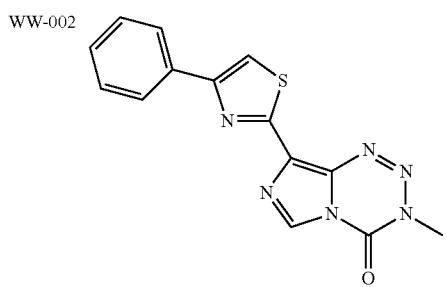 |
| WW-003 | 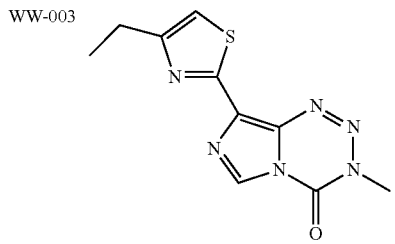 |
| WW-004 | 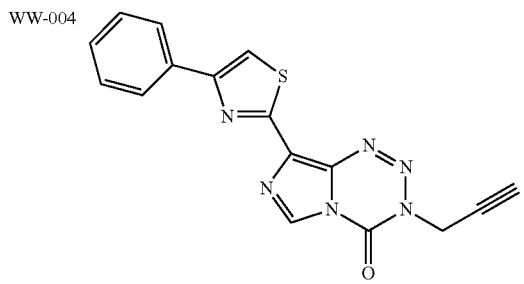 |
| WW-005 | 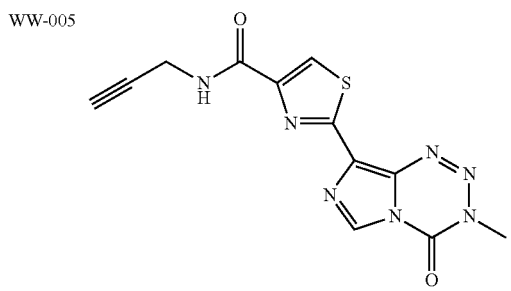 |

| Code No. | Structure |
|---|---|
| WW-006 | 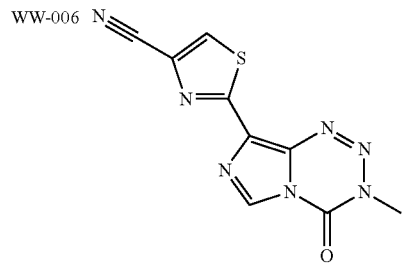 |
| WW-007 | 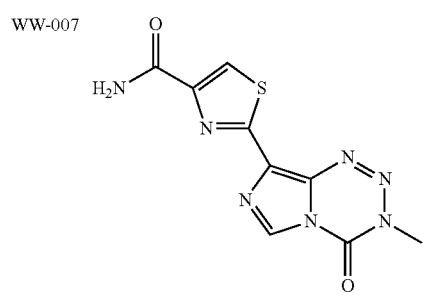 |
| WW-008 | 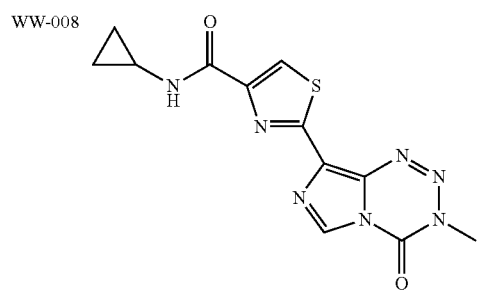 |
| WW-009 | 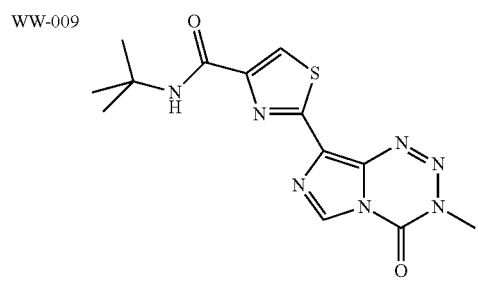 |
| WW-010 | 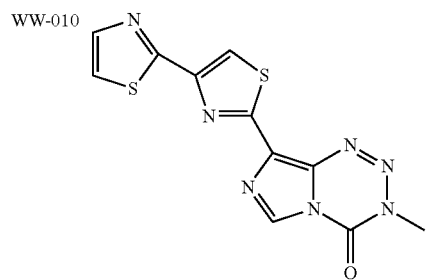 |
| Code No. | Structure |
|---|---|
| WW-011 | 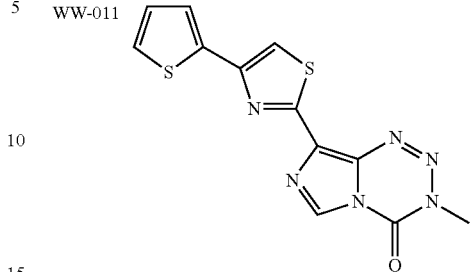 |
| WW-012 | 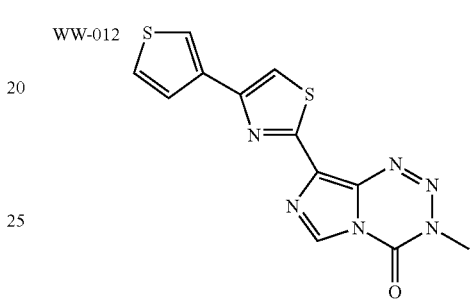 |
| WW-013 | 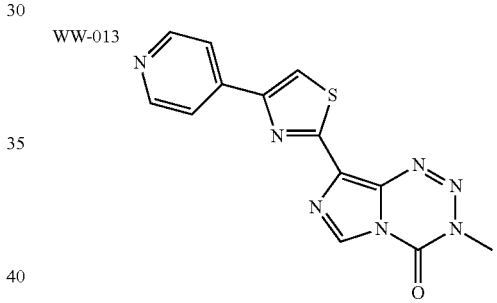 |
| WW-014 | 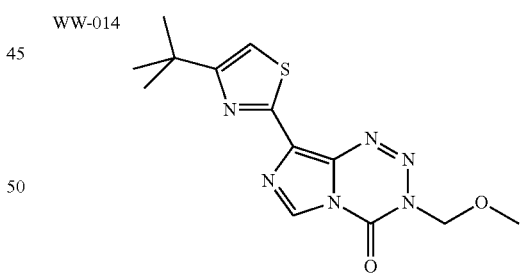 |
| WW-015 | 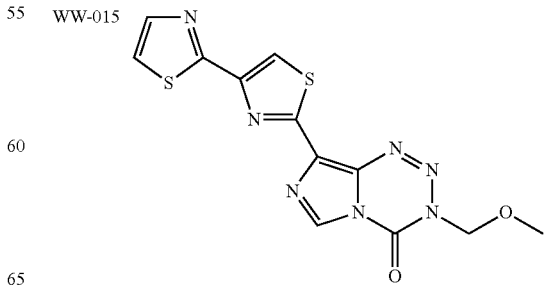 |

| Code No. | Structure |
|---|---|
| WW-016 | 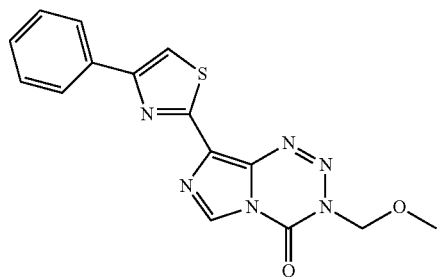 |
| WW-017 | 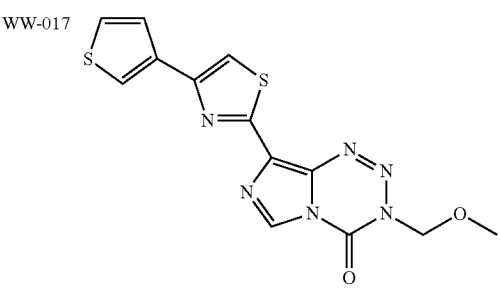 |
| WW-018 | 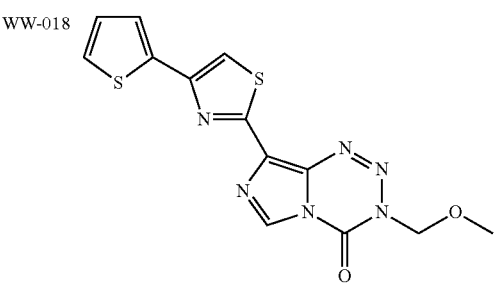 |
| WW-019 | 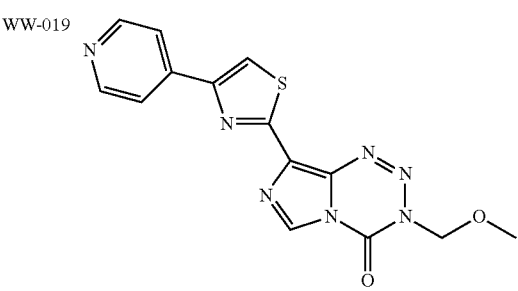 |
| WW-020 | 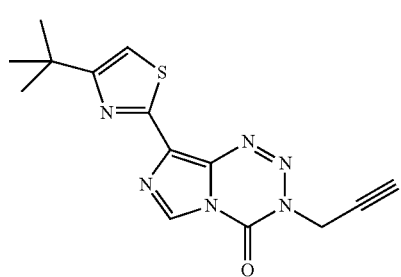 [SMILES: C#CCn1nnc2c(-c3nc(C(C)(C)C)cs3)ncn2c1=O] |
| WW-021 | 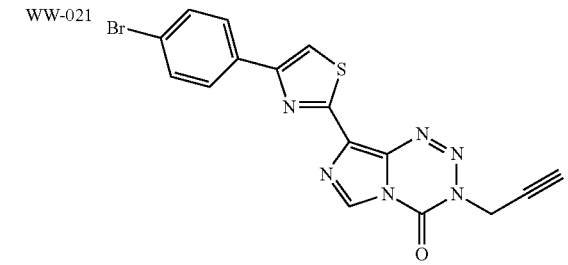 |
| WW-022 | 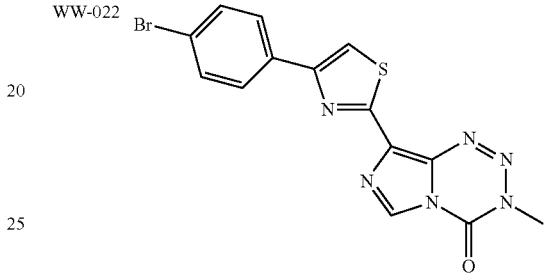 |
| WW-023 | 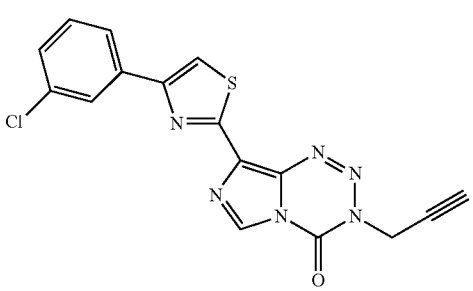 [SMILES: C#CCn1nnc2c(-c3nc(-c4cccc(Cl)c4)cs3)ncn2c1=O] |
| WW-024 | 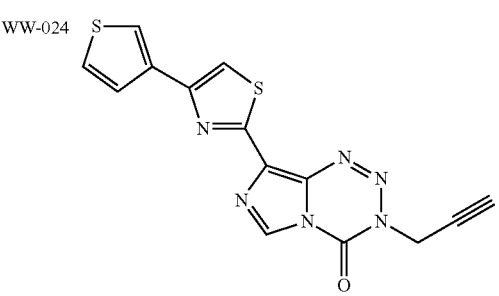 |
| WW-025 | 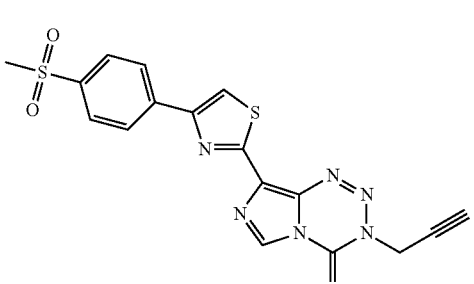 |

| Code No. | Structure |
|---|---|
| WW-026 | 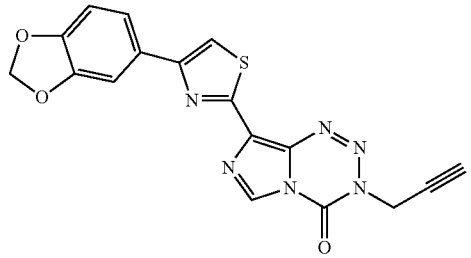 [SMILES: C#CCn1nnc2c(-c3nc(-c4ccc5c(c4)OCO5)cs3)ncn2c1=O] |
| WW-027 | 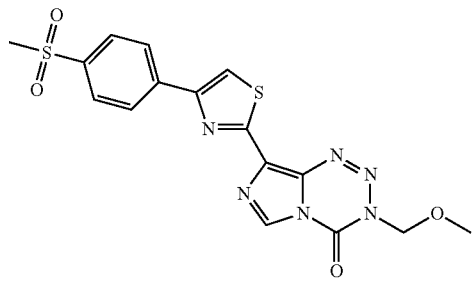 |
| WW-028 | 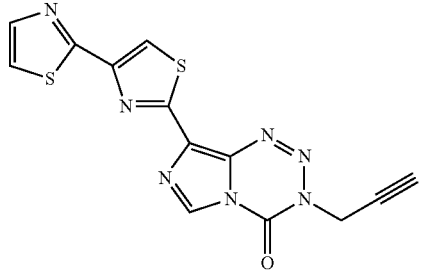 [SMILES: C#CCn1nnc2c(-c3nc(-c4nccs4)cs3)ncn2c1=O] |
| WW-029 | 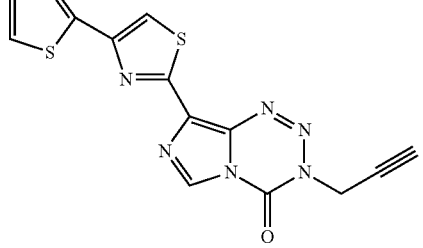 |
| WW-030 | 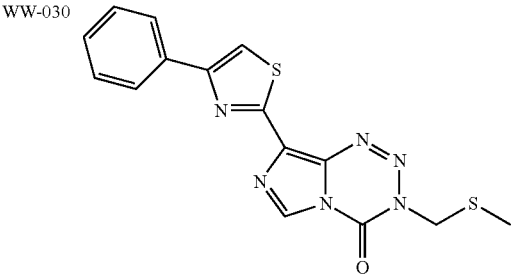 |
| WW-031 | 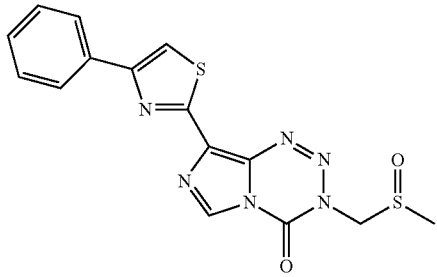 [SMILES: CS(=O)Cn1nnc2c(-c3nc(-c4ccccc4)cs3)ncn2c1=O] |
| WW-032 | 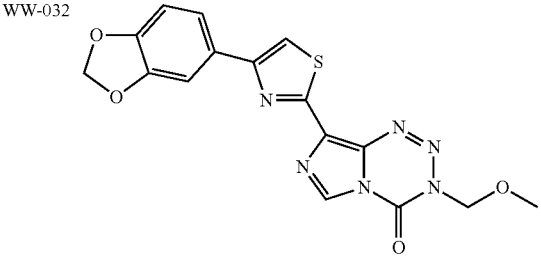 |
| WW-033 | 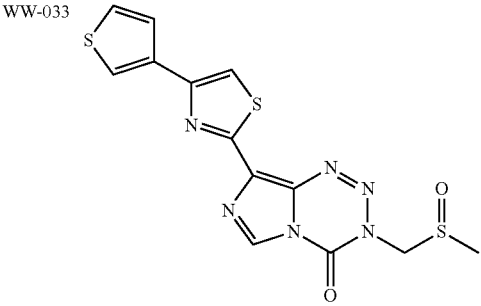 |
| WW-034 | 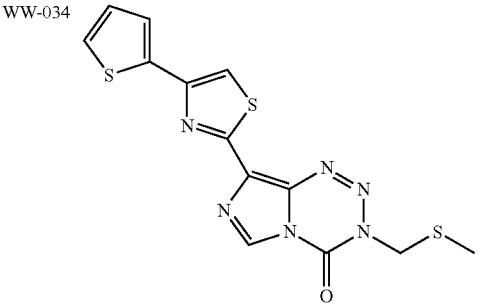 |
| WW-035 | 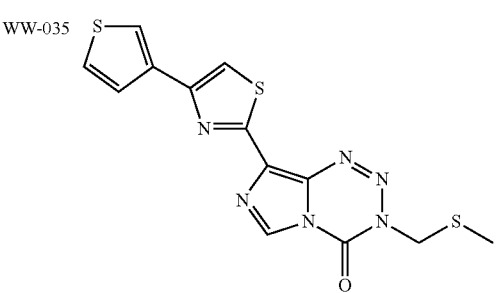 |

| Code No. | Structure |
|---|---|
| WW-036 | 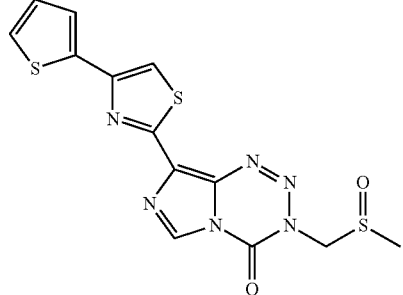 [SMILES: CS(=O)Cn1nnc2c(-c3nc(-c4cccs4)cs3)ncn2c1=O] |
| WW-037 | 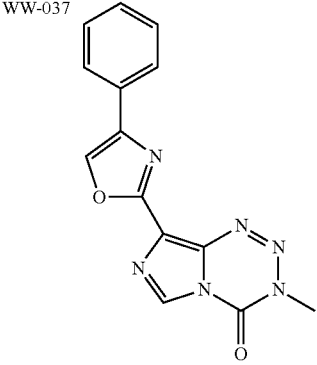 |
| WW-038 | 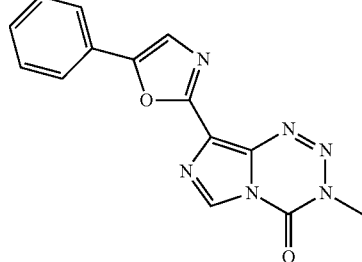 |
| WW-039 | 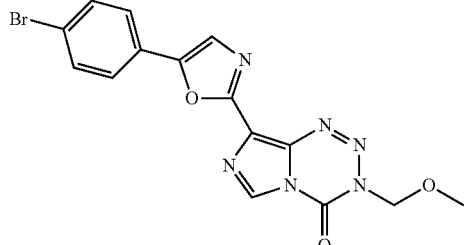 |
| WW-040 | 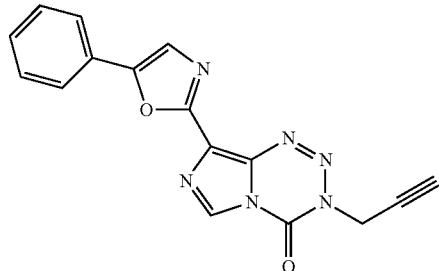 |
| WW-041 | 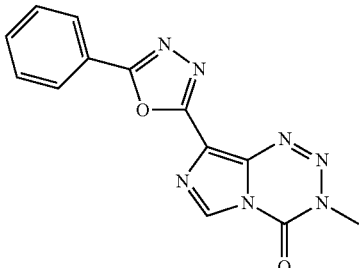 |
| WW-042 | 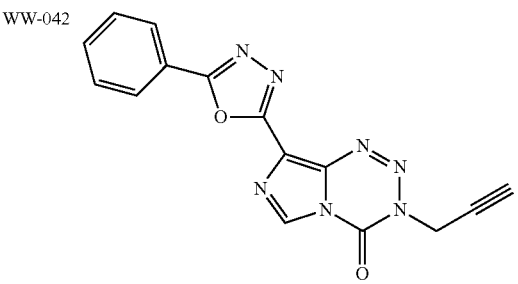 |
| WW-043 | 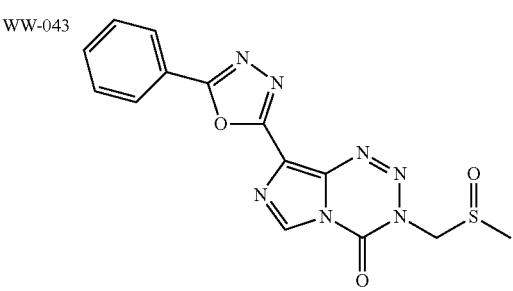 |
| WW-044 | 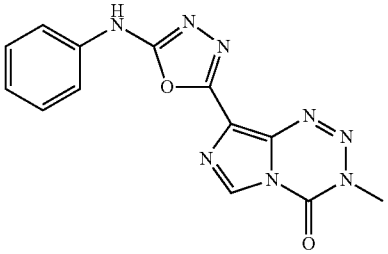 [SMILES: Cn1nnc2c(-c3nnc(Nc4ccccc4)o3)ncn2c1=O] |
| WW-045 | 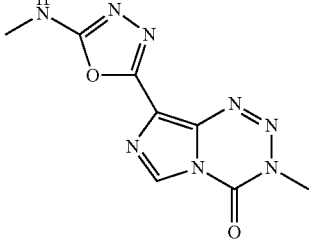 |

| Code No. | Structure |
|---|---|
| WW-046 | 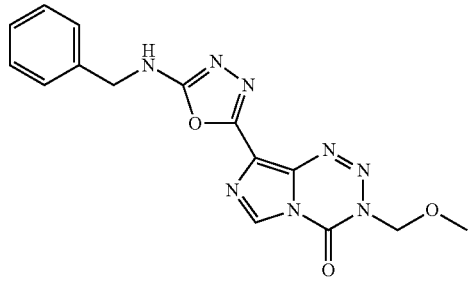 [SMILES: COCn1nnc2c(-c3nnc(NCc4ccccc4)o3)ncn2c1=O] |
| WW-047 | 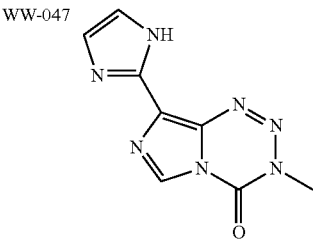 |
| WW-048 | 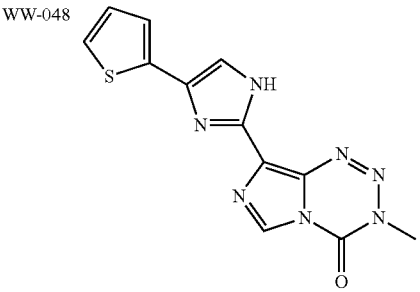 |
| WW-049 | 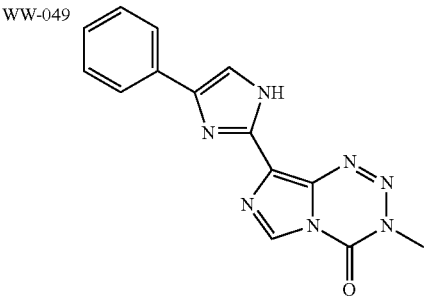 |
| WW-050 | 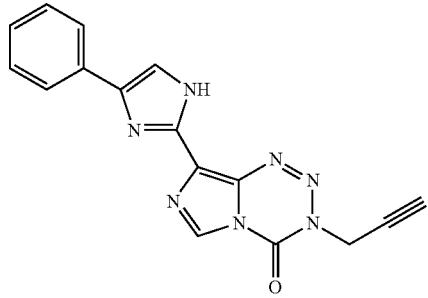 [SMILES: C#CCn1nnc2c(-c3nc(-c4ccccc4)c[nH]3)ncn2c1=O] |
| Code No. | Structure |
|---|---|
| WW-051 | 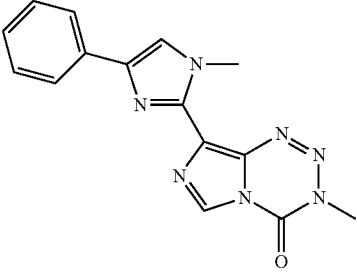 [SMILES: Cn1cc(-c2ccccc2)nc1-c1ncn2c(=O)n(C)nnc12] |
| WW-052 | 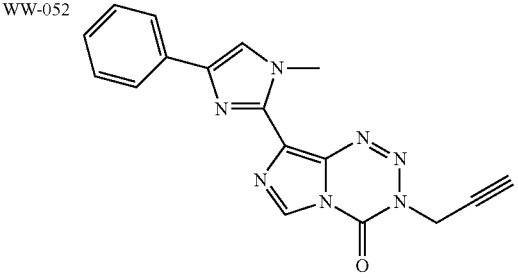 |
| WW-053 | 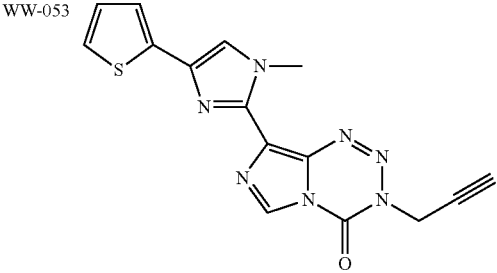 |
| WW-054 | 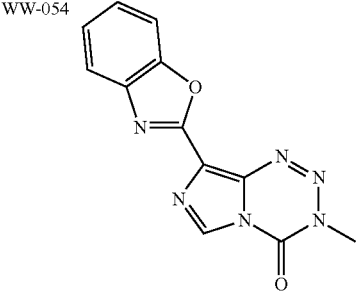 |
| WW-055 | 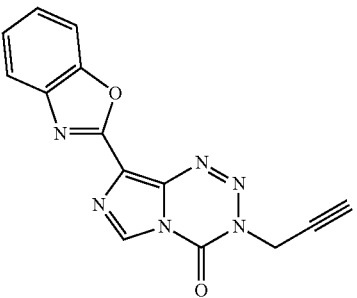 [SMILES: C#CCn1nnc2c(-c3nc4ccccc4o3)ncn2c1=O] |

| Code No. | Structure |
|---|---|
| WW-056 | 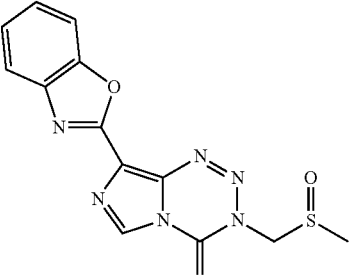 |
| WW-057 | 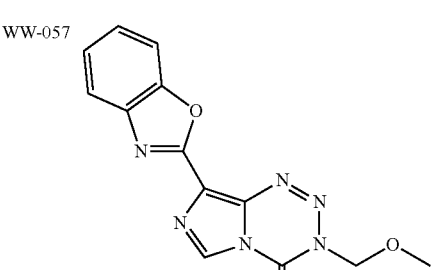 |
| WW-058 | 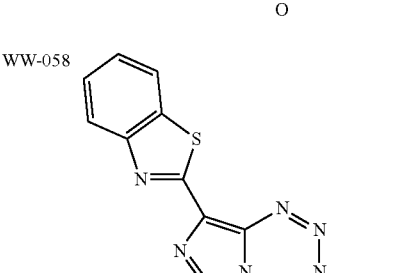 |
| WW-059 | 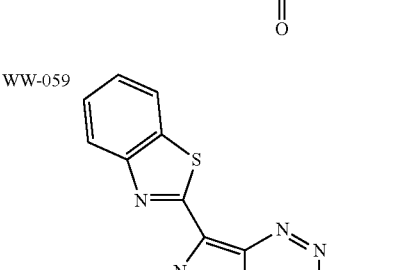 |
| WW-060 | 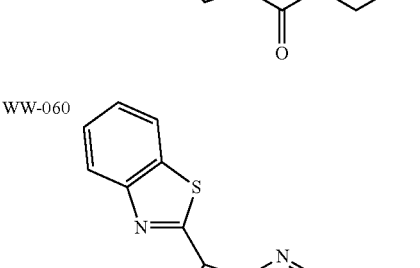 |
| WW-061 | 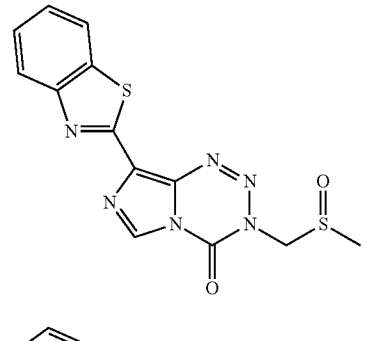 |
| WW-062 | 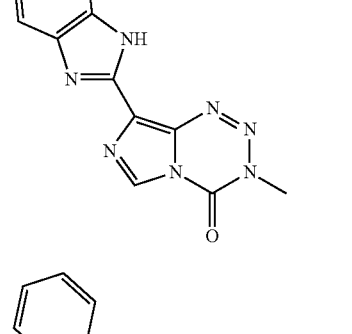 |
| WW-063 | 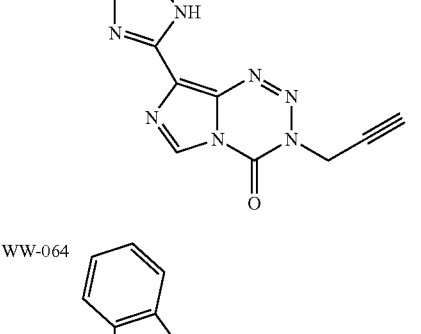 |
| WW-064 | 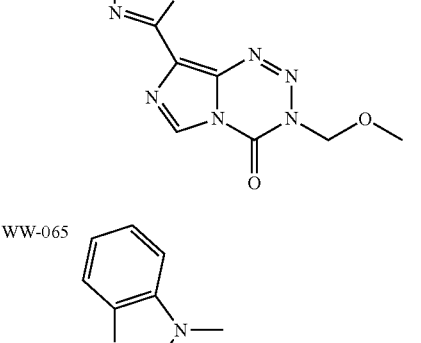 |
| WW-065 | 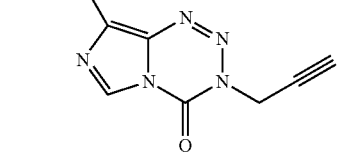 |

| Code No. | Structure |
|---|---|
| WW-066 | [structure] | or a pharmaceutically acceptable salt thereof.

7. A compound according to claim 1, wherein -A is independently -A³; and -A³ is independently:
—C(=NH)NH₂, —C(=NH)NHR^{Z3}, or —C(=NH) NR^{Z3}₂, —C(=NH)-pyrrolidino, —C(=NH)-piperidino, —C(=NH)-morpholino, —C(=NH)-piperizino, or —C(=NH)—N—C₁₋₄alkyl)-piperizino, wherein:
—R^{Z3} is independently saturated aliphatic C₁₋₄alkyl, saturated C₃₋₆cycloalkyl, C₅₋₆heteroaryl, —CH₂—C₅₋₆heteroaryl, -Ph, or —CH₂-Ph, wherein each of said C₁₋₄alkyl, C₃₋₆cycloalkyl, C₅₋₆heteroaryl, and -Ph is optionally substituted with one or more groups selected from:
—F, —Cl, —Br, —I,
—R^{Z3A}, —CF₃,
—OH, —OR^{Z3A}, —OCF₃,
—SR^{Z3A},
—NH₂, —NHR^{Z3A}, —NR^{Z3A}₂, pyrrolidino, piperidino, morpholino, piperizino, (N—C₁₋₄alkyl)-piperizino,
—C(=O)OH, —C(=O)OR^{Z3A},
—C(=O)R^{Z3A},
—OC(=O)R^{Z3A},
—C(=O)NH₂, —C(=O)NHR^{Z3A}, —C(=O)NR^{Z3A}₂, —C(=O)-pyrrolidino, —C(=O)-piperidino, —C(=O)-morpholino, —C(=O)-piperizino, —C(=O)—(N—C₁₋₄alkyl)-piperizino,
—NHC(=O)R^{Z3A}, —NR^{Z3A}C(=O)R^{Z3A},
—OC(=O)NH₂, —OC(=O)NHR^{Z3A}, —OC(=O) NR^{Z3A}₂, —OC(=O)-pyrrolidino, —OC(=O)-piperidino, —OC(=O)-morpholino, —OC(=O)-piperizino, (N—C₁₋₄alkyl)-piperizino,
—NHC(=O)OR^{Z3A}, —NR^{Z3A}C(=O)OR^{Z3A},
—NHC(=O)NH₂, —NHC(=O)NHR^{Z3A}, —NHC(=O) NR^{Z3A}₂, —NHC(=O)-pyrrolidino, —NHC(=O)-piperidino, —NHC(=O)-morpholino, —NHC(=O)-piperizino, —NHC(=O)—(N—C₁₋₄alkyl)-piperizino,
—NO₂, and —CN,
wherein each —R^{Z3A} is independently saturated aliphatic C₁₋₄alkyl, saturated C₃₋₆cycloalkyl, -Ph, or —CH₂-Ph,
wherein each of said C₃₋₆cycloalkyl and -Ph is optionally substituted with one or more substituents selected from —F, —Cl, —Br, —I, —R^{Z3B}, —CF₃, —OH, —OR^{Z3B}, and —OCF₃,
wherein each —R^{Z3B} is independently saturated aliphatic C₁₋₄alkyl.

8. A compound according to claim 7, which is the following compound:

| Code No. | Structure |
|---|---|
| SS-001 | [structure] | or a pharmaceutically acceptable salt thereof.

9. A compound according to claim 1, wherein -A is independently -A⁶; and -A⁶ is independently:
-L⁶-R^{Z6},
wherein:
-L⁶- is independently aliphatic C₂₋₆alkenyl, and
—R^{Z6} is independently C₅₋₆heteroaryl or -Ph,
wherein each of said C₅₋₆heteroaryl and -Ph is optionally substituted with one or more groups selected from:
—F, —Cl, —Br, —I,
—R^{Z6A}, —CF₃,
—OH, —OR^{Z6A}, —OCF₃,
—SR^{Z6A},
—NH₂, —NHR^{Z6A}, —NR^{Z6A}₂, pyrrolidino, piperidino, morpholino, piperizino, (N—C₁₋₄alkyl)-piperizino,
—C(=O)OH, —C(=O)OR^{Z6A},
—C(=O)R^{Z6A},
—OC(=O)R^{Z6A},
—C(=O)NH₂, —C(=O)NHR^{Z6A}, —C(=O)NR^{Z6A}₂, —C(=O)-pyrrolidino, —C(=O)-piperidino, —C(=O)-morpholino, —C(=O)-piperizino, —C(=O)—(N—C₁₋₄alkyl)-piperizino,
—NHC(=O)R^{Z6A}, —NR^{Z6A}C(=O)R^{Z6A},
—OC(=O)NH₂, —OC(=O)NHR^{Z6A}, —OC(=O) NR^{Z6A}₂, —OC(=O)-pyrrolidino, —OC(=O)-piperidino, —OC(=O)-morpholino, —OC(=O)-piperizino, (N—C₁₋₄alkyl)-piperizino,
—NHC(=O)OR^{Z6A}, —NR^{Z6A}C(=O)OR^{Z6A},
—NHC(=O)NH₂, —NHC(=O)NHR^{Z6A}, —NHC(=O) NR^{Z6A}₂, —NHC(=O)-pyrrolidino, —NHC(=O)-piperidino, —NHC(=O)-morpholino, —NHC(=O)-piperizino, —NHC(=O)—(N—C₁₋₄alkyl)-piperizino,
—NO₂, and —CN,
wherein each —R^{Z6A} is independently saturated aliphatic C₁₋₄alkyl, saturated C₃₋₆cycloalkyl, -Ph, or —CH₂-Ph,
wherein each C₃₋₆cycloalkyl and -Ph is optionally substituted with one or more substituents selected from —F, —Cl, —Br, —I, —R^{Z6B}, —CF₃, —OH, —OR^{Z6B}, and —OCF₃,
wherein each —R^{Z6B} is independently saturated aliphatic C₁₋₄alkyl.

10. A compound according to claim 9 which is a compound selected from the following compounds:

| Code No. | Structure |
|---|---|
| MM-001 | (4-cyanostyryl imidazo-tetrazinone with N—CH₂—OMe) |
| MM-002 | (4-cyanostyryl imidazo-tetrazinone with N—CH₂—SMe) |
| MM-003 | (4-cyanostyryl imidazo-tetrazinone with N—CH₂—S(=O)₂—Me) |
| MM-004 | (2-thienylvinyl imidazo-tetrazinone with N—CH₂—OMe) | or a pharmaceutically acceptable salt thereof.

11. A compound according to claim 1, wherein —B is independently —B$^1$.

12. A compound according to claim 11, wherein —B$^1$ is independently -Me.

13. A compound according to claim 1, wherein —B is independently —B$^2$.

14. A compound according to claim 13, wherein —B$^2$ is independently —CH$_2$—C≡CH.

15. A compound according to claim 1, wherein —B is independently —B$^3$; and —B$^3$ is independently:
 -L$^{Y3}$—SH, -L$^{Y3}$—S—R$^{Y3}$, -L$^{Y3}$-S(=O)—R$^{Y3}$, or L$^{Y3}$-S(=O)$_2$—R$^{Y3}$,
wherein:
 -L$^{Y3}$- is independently saturated aliphatic C$_{1-4}$alkylene, and
 —R$^{Y3}$ is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph,
 wherein each of said C$_{3-6}$cycloalkyl, C$_{5-6}$heteroaryl, and -Ph is optionally substituted with one or more groups selected from:
  —F, —Cl, —Br, —I,
  —R$^{Y3A}$, —CF$_3$,
  —OH, —OR$^{Y3A}$, —OCF$_3$,
  —SR$^{Y3A}$,
  —NH$_2$, —NHR$^{Y3A}$, —NR$^{Y3A}_2$, pyrrolidino, piperidino, morpholino, piperizino, (N—C$_{1-4}$alkyl)-piperizino,
  —C(=O)OH, —C(=O)OR$^{Y3A}$,
  —C(=O)R$^{Y3A}$,
  —OC(=O)R$^{Y3A}$,
  —C(=O)NH$_2$, —C(=O)NHR$^{Y3A}$, —C(=O)NR$^{Y3A}_2$, —C(=O)-pyrrolidino, —C(=O)-piperidino, —C(=O)-morpholino, —C(=O)-piperizino, —C(=O)—(N—C$_{1-4}$alkyl)-piperizino,
  —NHC(=O)R$^{Y3A}$, —NR$^{Y3A}$C(=O)R$^{Y3A}$,
  —OC(=O)NH$_2$, —OC(=O)NHR$^{Y3A}$, —OC(=O)NR$^{Y3A}_2$, —OC(=O)-pyrrolidino, —OC(=O)-piperidino, —OC(=O)-morpholino, —OC(=O)-piperizino, (N—C$_{1-4}$alkyl)-piperizino,
  —NHC(=O)OR$^{Y3A}$, —NR$^{Y3A}$C(=O)OR$^{Y3A}$,
  —NHC(=O)NH$_2$, —NHC(=O)NHR$^{Y3A}$, —NHC(=O)NR$^{Y3A}_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino,
  —NO$_2$, and —CN,
  wherein each —R$^{Y3A}$ is independently saturated aliphatic C$_{1-4}$alkyl, saturated C$_{3-6}$cycloalkyl, -Ph, or —CH$_2$-Ph,
   wherein each of said C$_{3-6}$cycloalkyl and -Ph is optionally substituted with one or more substituents selected from —F, —Cl, —Br, —I, —R$^{Y3B}$, —CF$_3$, —OH, —OR$^{Y3B}$, and —OCF$_3$,
  wherein each —R$^{Y3B}$ is independently saturated aliphatic C$_{1-4}$alkyl.

16. A compound according to claim 15, wherein —B$^3$ is independently —CH$_2$—S-Me, —CH$_2$—S(=O)-Me, or —CH$_2$—S(=O)$_2$-Me.

17. A compound according to claim 1, wherein —B is independently —B$^4$; and —B$^4$ is independently:
 -L$^{Y4}$-OH or -L$^{Y4}$-O—R$^{Y4}$,
wherein:
 -L$^{Y4}$- is independently saturated aliphatic C$_{1-4}$alkylene, and
 —R$^{Y4}$ is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph,
 wherein each of said C$_{3-6}$cycloalkyl, C$_{5-6}$heteroaryl, and -Ph is optionally substituted with one or more groups selected from:
  —F, —Cl, —Br, —I,
  —R$^{Y4A}$, —CF$_3$,
  —OH, —OR$^{Y4A}$, —OCF$_3$,
  —SR$^{Y4A}$,
  —NH$_2$, —NHR$^{Y4A}$, —NR$^{Y4A}_2$, pyrrolidino, piperidino, morpholino, piperizino, (N—C$_{1-4}$alkyl)-piperizino, —C(=O)OH, —C(=O)OR$^{Y4A}$,
—C(=O)R$^{Y4A}$,
—OC(=O)R$^{Y4A}$,
—C(=O)NH$_2$, —C(=O)NHR$^{Y4A}$, —C(=O)NR$^{Y4A}{}_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Y4A}$, —NR$^{Y4A}$C(=O)R$^{Y4A}$,
—OC(=O)NH$_2$, —OC(=O)NHR$^{Y4A}$, —OC(=O)NR$^{Y4A}{}_2$, —OC(=O)-pyrrolidino, —OC(=O)-piperidino, —OC(=O)-morpholino, —OC(=O)-piperizino, (N—C$_{1-4}$alkyl)-piperizino,
—NHC(=O)OR$^{Y4A}$, —NR$^{Y4A}$C(=O)OR$^{Y4A}$,
—NHC(=O)NH$_2$, —NHC(=O)NHR$^{Y4A}$, —NHC(=O)NR$^{Y4A}{}_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino,
—NO$_2$, and —CN, wherein each —R$^{Y4A}$ is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more substituents selected from —F, —Cl, —Br, —I, —R$^{Y4B}$, —CF$_3$, —OH, —OR$^{Y4B}$, and —OCF$_3$, wherein each —R$^{Y4B}$ is independently saturated aliphatic C$_{1-4}$alkyl.

18. A compound according to claim 17, wherein —B$^4$ is independently —CH$_2$—O-Me.

19. A compound according to claim 1, wherein —B is independently —B$^5$; and —B$^5$ is independently:
-L$^{Y5}$-Ar$^{Y5}$,
wherein:
-L$^{Y5}$- is independently saturated aliphatic C$_{1-4}$alkylene, and
-Ar$^{Y5}$ is independently C$_{5-6}$heteroaryl or -Ph,
wherein each of said C$_{5-6}$heteroaryl and -Ph is optionally substituted with one or more groups selected from:
—F, —Cl, —Br, —I,
—R$^{Y5A}$, —CF$_3$,
—OH, —OR$^{Y5A}$, —OCF$_3$,
—SR$^{Y5A}$,
—NH$_2$, —NHR$^{Y5A}$, —NR$^{Y5A}{}_2$, pyrrolidino, piperidino, morpholino, piperizino, (N—C$_{1-4}$alkyl)-piperizino,
—C(=O)OH, —C(=O)OR$^{Y5A}$,
—C(=O)R$^{Y5A}$,
—OC(=O)R$^{Y5A}$,
—C(=O)NH$_2$, —C(=O)NHR$^{Y5A}$, —C(=O)NR$^{Y5A}{}_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Y5A}$, —NR$^{Y5A}$C(=O)R$^{Y5A}$,
—OC(=O)NH$_2$, —OC(=O)NHR$^{Y5A}$, —OC(=O)NR$^{Y5A}{}_2$, —OC(=O)-pyrrolidino, —OC(=O)-piperidino, —OC(=O)-morpholino, —OC(=O)-piperizino, (N—C$_{1-4}$alkyl)-piperizino,
—NHC(=O)OR$^{Y5A}$, —NR$^{Y5A}$C(=O)OR$^{Y5A}$,
—NHC(=O)NH$_2$, —NHC(=O)NHR$^{Y5A}$, —NHC(=O)NR$^{Y5A}{}_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino,
—NO$_2$, and —CN, wherein each —R$^{Y5A}$ is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more substituents selected from —F, —Cl, —Br, —I, —R$^{Y5B}$, —CF$_3$, —OH, —OR$^{Y5B}$, and —OCF$_3$, wherein each —R$^{Y5B}$ is independently saturated aliphatic C$_{1-4}$alkyl.

20. A compound according to claim 19, wherein —B$^5$ is —CH$_2$-Ph.

21. A compound according to claim 1, wherein —B is independently —B$^6$; and —B$^6$ is independently:
-L$^{Y6}$-C(=O)R$^{Y6}$, -L$^{Y6}$-C(=O)OH, -L$^{Y6}$-C(=O)OR$^{Y6}$, or -L$^{Y6}$-O—C(=O)R$^{Y6}$,
wherein:
-L$^{Y6}$- is independently saturated aliphatic C$_{1-4}$alkylene, and
—R$^{Y6}$ is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph, wherein each of said C$_{3-6}$cycloalkyl, C$_{5-6}$heteroaryl, and -Ph is optionally substituted with one or more groups selected from:
—F, —Cl, —Br, —I,
—R$^{Y6A}$, —CF$_3$,
—OH, —OR$^{Y6A}$, —OCF$_3$,
—SR$^{Y6A}$,
—NH$_2$, —NHR$^{Y6A}$, —NR$^{Y6A}{}_2$, pyrrolidino, piperidino, morpholino, piperizino, (N—C$_{1-4}$alkyl)-piperizino,
—C(=O)OH, —C(=O)OR$^{Y6A}$,
—C(=O)R$^{Y6A}$,
—OC(=O)R$^{Y6A}$,
—C(=O)NH$_2$, —C(=O)NHR$^{Y6A}$, —C(=O)NR$^{Y6A}{}_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Y6A}$, —NR$^{Y6A}$C(=O)R$^{Y6A}$,
—OC(=O)NH$_2$, —OC(=O)NHR$^{Y6A}$, —OC(=O)NR$^{Y6A}{}_2$, —OC(=O)-pyrrolidino, —OC(=O)-piperidino, —OC(=O)-morpholino, —OC(=O)-piperizino, (N—C$_{1-4}$alkyl)-piperizino,
—NHC(=O)OR$^{Y6A}$, —NR$^{Y6A}$C(=O)OR$^{Y6A}$,
—NHC(=O)NH$_2$, —NHC(=O)NHR$^{Y6A}$, —NHC(=O)NR$^{Y6A}{}_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino,
—NO$_2$, and —CN, wherein each —R$^{Y6A}$ is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more substituents selected from —F, —Cl, —Br, —I, —R$^{Y6B}$, —CF$_3$, —OH, —OR$^{Y6B}$, and —OCF$_3$, wherein each —R$^{Y6B}$ is independently saturated aliphatic C$_{1-4}$alkyl.

22. A compound according to claim 21, wherein —B$^6$ is independently —CH$_2$—C(=O)—O-Et.

23. A compound according to claim 1, wherein —B is independently —B$^7$; and —B$^7$ is independently:
-L$^{Y7}$-C(=O)NH$_2$, -L$^{Y7}$-C(=O)NHR$^{Y7}$, -L$^{Y7}$-C(=O)NR$^{Y7}{}_2$, -L$^{Y7}$-C(=O)-pyrrolidino, -L$^{Y7}$-C(=O)-piperidino, -L$^{Y7}$-C(=O)-morpholino, -L$^{Y7}$-C(=O)-piperizino, or -L$^{Y7}$-C(=O)—(N—C$_{1-4}$alkyl)-piperizino,
wherein:
-L$^{Y7}$- is independently saturated aliphatic C$_{1-4}$alkylene, and —R$^{Y7}$ is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph,
wherein each of said C$_{3-6}$cycloalkyl, C$_{5-6}$heteroaryl, and -Ph is optionally substituted with one or more groups selected from:
—F, —Cl, —Br, —I,
—R$^{Y7A}$, —CF$_3$,
—OH, —OR$^{Y7A}$, —OCF$_3$,
—SR$^{Y7A}$,
—NH$_2$, —NHR$^{Y7A}$, —NR$^{Y7A}$$_2$, pyrrolidino, piperidino, morpholino, piperizino, (N—C$_{1-4}$alkyl)-piperizino,
—C(=O)OH, —C(=O)OR$^{Y7A}$,
—C(=O)R$^{Y7A}$,
—OC(=O)R$^{Y7A}$,
—C(=O)NH$_2$, —C(=O)NHR$^{Y7A}$, —C(=O)NR$^{Y7A}$$_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Y7A}$, —NR$^{Y7A}$C(=O)R$^{Y7A}$,
—OC(=O)NH$_2$, —OC(=O)NHR$^{Y7A}$, —OC(=O)NR$^{Y7A}$$_2$, —OC(=O)-pyrrolidino, —OC(=O)-piperidino, —OC(=O)-morpholino, —OC(=O)-piperizino, (N—C$_{1-4}$alkyl)-piperizino,
—NHC(=O)OR$^{Y7A}$, —NR$^{Y7A}$C(=O)OR$^{Y7A}$,
—NHC(=O)NH$_2$, —NHC(=O)NHR$^{Y7A}$, —NHC(=O)NR$^{Y7A}$$_2$, —NHC(=O)-pyrrolidino, —NHC(=O)-piperidino, —NHC(=O)-morpholino, —NHC(=O)-piperizino, —NHC(=O)—(N—C$_{1-4}$alkyl)-piperizino,
—NO$_2$, and —CN,
wherein each —R$^{Y7A}$ is independently saturated aliphatic C$_{1-4}$alkyl, saturated C$_{3-6}$cycloalkyl, -Ph, or —CH$_2$-Ph,
wherein each of said C$_{3-6}$cycloalkyl and -Ph is optionally substituted with one or more substituents selected from —F, —Cl, —Br, —I, —R$^{Y7B}$, —CF$_3$, —OH, —OR$^{Y7B}$, and —OCF$_3$,
wherein each —R$^{Y7B}$ is independently saturated aliphatic C$_{1-4}$alkyl.

24. A compound according to claim 23, wherein —B$^7$is independently: —CH$_2$—C(=O)NH$_2$, —CH$_2$—C(=O)NHMe, —CH$_2$—C(=O)NMe$_2$, —CH$_2$CH$_2$—C(=O)NH$_2$, —CH$_2$CH$_2$—C(=O)NHMe, —CH$_2$CH$_2$—C(=O)NMe$_2$, —CH$_2$—C(=O)-piperidino, or —CH$_2$CH$_2$—C(=O)-piperidino.

25. A compound according to claim 1, wherein —B is independently —B$^8$; and —B$^8$ is independently:
—R$^{Y8}$ or -L$^{Y8}$-R$^{Y8}$,
wherein:
-L$^{Y8}$- is independently saturated aliphatic C$_{1-4}$alkylene, and
—R$^{Y8}$ is independently saturated C$_{3-6}$cycloalkyl or saturated C$_{3-6}$heterocyclyl,
wherein each of said C$_{3-6}$cycloalkyl and C$_{3-6}$heterocyclyl is optionally substituted with one or more groups selected from:
—F, —Cl, —Br, —I,
—R$^{Y8A}$, —CF$_3$,
—OH, —OR$^{Y8A}$, —OCF$_3$,
—NH$_2$, —NHR$^{Y8A}$, —NR$^{Y8A}$$_2$, pyrrolidino piperidino, morpholino, piperizino, (N—C$_{1-4}$alkyl)-piperizino,
—C(=O)OH, —C(=O)OR$^{Y8A}$,
—C(=O)R$^{Y8A}$,
—OC(=O)R$^{Y8A}$,
—C(=O)NH$_2$, —C(=O)NHR$^{Y8A}$, —C(=O)NR$^{Y8A}$$_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Y8A}$, —NR$^{Y8A}$C(=O)R$^{Y8A}$, and
—CN;
wherein each —R$^{Y8A}$ is independently saturated aliphatic C$_{1-4}$alkyl, saturated C$_{3-6}$cycloalkyl, -Ph, or —CH$_2$-Ph,
wherein each of said C$_{3-6}$cycloalkyl and -Ph is optionally substituted with one or more substituents selected from —F, —Cl, —Br, —I, —R$^{Y8B}$, —CF$_3$, —OH, —OR$^{Y8B}$, and —OCF$_3$,
wherein each —R$^{Y8B}$ is independently saturated aliphatic C$_{1-4}$alkyl.

26. A compound according to claim 1, wherein —B is independently —B$^9$.

27. A compound according to claim 26, wherein —B$^9$ is independently selected from: —CH$_2$F, —CH$_2$CH$_2$F, —CHF$_2$, —CH$_2$CHF$_2$, —CF$_3$, and —CH$_2$CF$_3$.

28. A compound according to claim 1, wherein —B is independently —B$^{10}$.

29. A compound according to claim 28, wherein —B$^{10}$ is independently —CH$_2$—NO$_2$.

30. A compound according to claim 1, wherein —B is independently —B$^{11}$.

31. A compound according to claim 30, wherein —B$^{11}$ is independently —CH$_2$—CN.

32. A compound according to claim 1, wherein —B is independently —B$^{12}$; wherein —B$^{12}$ is independently:
-L$^{Y12}$-P(=O)(OH)$^2$, L$^{Y12}$ -P(OH)(OR$^{Y12}$), or -P(=O)(OR$^{Y12}$)$_2$,
wherein:
-L$^{Y12}$- is independently saturated aliphatic C$_{1-4}$alkylene, and
each —R$^{Y12}$ is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph,
wherein each of said C$_{3-6}$cycloalkyl, C$_{5-6}$heteroaryl, and -Ph is optionally substituted with one or more groups selected from:
—F, —Cl, —Br, —I,
—R$^{Y12A}$, —CF$_3$,
—OH, —OR$^{Y12A}$, —OCF$_3$,
—NH$_2$, —NHR$^{Y12A}$, —NR$^{Y12A}$$_2$, pyrrolidino piperidino, morpholino, piperizino, (N—C$_{1-4}$alkyl)-piperizino,
—C(=O)OH, —C(=O)OR$^{Y12A}$,
—C(=O)R$^{Y12A}$,
—OC(=O)R$^{Y12A}$,
—C(=O)NH$_2$, —C(=O)NHR$^{Y12A}$, —C(=O)NR$^{Y12A}$$_2$, —C(=O)-pyrrolidino, —C(=O)-piperidino, —C(=O)-morpholino, —C(=O)-piperizino, —C(=O)—(N—C$_{1-4}$alkyl)-piperizino,
—NHC(=O)R$^{Y12A}$, —NR$^{Y12A}$C(=O)R$^{Y12A}$, and
—CN;
wherein each —R$^{Y12A}$ is independently saturated aliphatic C$_{1-4}$alkyl, saturated C$_{3-6}$cycloalkyl, -Ph, or —CH$_2$-Ph,
wherein each of said C$_{3-6}$cycloalkyl and -Ph is optionally substituted with one or more substituents selected from —F, —Cl, —Br, —I, —R$^{Y12B}$, —CF$_3$, —OH, —OR$^{Y12B}$, and —OCF$_3$,
wherein each —R$^{Y12B}$ is independently saturated aliphatic C$_{1-4}$alkyl.

33. A compound according to claim 32, wherein —B$^{12}$ is —CH$_2$-P(=O)(OEt)$_2$.

34. A compound according to claim 1, wherein —B is independently —B$^{13}$; wherein —B$^{13}$ is independently:

-L$^{Y13}$-NH—C(=O)OH,    -L$^{Y13}$-NH—C(=O)—R$^{Y13}$, -L$^{Y13}$-NR$^{Y13}$—C(=O)OH,   or   -L$^{Y13}$-NR$^{Y13}$—C(=O)—R$^{Y13}$, wherein:

-L$^{Y13}$- is independently saturated aliphatic C$_{1-4}$alkylene, and each —R$^{Y13}$ is independently saturated aliphatic C$_{1-4}$alkyl, saturated C$_{3-6}$cycloalkyl, C$_{5-6}$heteroaryl, —CH$_2$—C$_{5-6}$heteroaryl, fluorenyl, —CH$_2$—Fluorenyl, -Ph, or —CH$_2$-Ph, wherein each of said C$_{3-6}$cycloalkyl, C$_{5-6}$heteroaryl, fluorenyl and -Ph is optionally substituted with one or more groups selected from:

—F, —Cl, —Br, —I,
—R$^{Y13A}$, —CF$_3$,
—OH, —OR$^{Y13A}$, —OCF$_3$,
—NH$_2$, —NHR$^{Y13A}$, —NR$^{Y13A}$$_2$, pyrrolidino piperidino, morpholino, piperizino, (N—C$_{1-4}$alkyl)-piperizino,
—C(=O)OH, —C(=O)OR$^{Y13A}$,
—C(=O)R$^{Y13A}$,
—OC(=O)R$^{Y13A}$,
—C(=O)NH$_2$, —C(=O)NHR$^{Y13A}$, —C(=O)NR$^{Y13A}$$_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Y13A}$, —NR$^{Y13A}$C(=O)R$^{Y13A}$, and
—CN;

wherein each —R$^{Y13A}$ is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more substituents selected from —F, —Cl, —Br, —I, —R$^{Y13B}$, —CF$_3$, —OH, —OR$^{Y13B}$, and —OCF$_3$, wherein each —R$^{Y13B}$ is independently saturated aliphatic C$_{1-4}$alkyl.

35. A compound according to claim 1, wherein —B is independently —B$^{14}$; wherein —B$^{14}$ is independently:

-L$^{Y14}$—CH(=N—O—H), -L$^{Y14}$-CH(=N—O—R$^{Y14}$), -L$^{Y14}$-CR$^{Y14}$(=N—O—H), or -L$^{Y14}$-CR$^{Y14}$(=N—O—R$^{Y14}$), wherein:

-L$^{Y14}$- is independently saturated aliphatic C$_{1-4}$alkylene, and each —R$^{Y14}$ is independently saturated aliphatic C$_{1-4}$alkyl, saturated C$_{3-6}$cycloalkyl, C$_{5-6}$heteroaryl, —CH$_2$—C$_{5-6}$heteroaryl, -Ph, or —CH$_2$-Ph, wherein each of said C$_{3-6}$cycloalkyl, C$_{5-6}$heteroaryl, and -Ph is optionally substituted with one or more groups selected from:

—F, —Cl, —Br, —I,
—R$^{Y14A}$, —CF$_3$,
—OH, —OR$^{Y14A}$, —OCF$_3$,
—NH$_2$, —NHR$^{Y14A}$, 13 NR$^{Y14A}$$_2$, pyrrolidino, piperidino, morpholino, piperizino, (N—C$_{1-4}$alkyl)-piperizino,
—C(=O)OH, —C(=O)OR$^{Y14A}$,
—C(=O)R$^{Y14A}$,
—OC(=O)R$^{Y14A}$,
—C(=O)NH$_2$, —C(=O)NHR$^{Y14A}$, —C(=O)NR$^{Y14A}$$_2$,
—C(=O)-pyrrolidino, —C(=O)-piperidino,
—C(=O)-morpholino, —C(=O)-piperizino,
—C(=O)—(N—C$_{1-4}$alkyl)-piperizino,
—NHC(=O)R$^{Y14A}$, NR$^{Y14A}$C(=O)R$^{Y14A}$, and
—CN;

wherein each —R$^{Y14A}$ is independently saturated aliphatic C$_{1-4}$alkyl, saturated C$_{3-6}$cycloalkyl, -Ph, or —CH$_2$-Ph, wherein each of said C$_{3-6}$cycloalkyl and -Ph is optionally substituted with one or more substituents selected from —F, —Cl, —Br, —I, —R$^{Y14B}$, —CF$_3$, —OH, —OR$^{Y14B}$, and —OCF$_3$, wherein each —R$^{Y14B}$ is independently saturated aliphatic C$_{1-4}$alkyl.

36. A compound according to claim 35, wherein —B$^{14}$ is independently —CH$_2$—C(Et)(=N—O-Me).

37. A pharmaceutical composition comprising a compound according to claim 1 and a pharmaceutically acceptable carrier or diluent.

38. A method of preparing a pharmaceutical composition comprising the step of admixing a compound according to claim 1, and a pharmaceutically acceptable carrier or diluent.

39. A method of treatment of glioma comprising administering to a subject in need of treatment a therapeutically-effective amount of a compound according to claim 1.

* * * * *